United States Patent
Runyon et al.

(10) Patent No.: US 10,377,718 B2
(45) Date of Patent: Aug. 13, 2019

(54) APELIN RECEPTOR (APJ) AGONISTS AND USES THEREOF

(71) Applicants: Research Triangle Institute, Research Triangle Park, NC (US); Scott P. Runyon, Research Triangle Park, NC (US); Rangan Maitra, Research Triangle Park, NC (US); Sanju Narayanan, Research Triangle Park, NC (US); James Barnwell Thomas, Research Triangle Park, NC (US)

(72) Inventors: Scott P. Runyon, Hillsborough, NC (US); Rangan Maitra, Cary, NC (US); Sanju Narayanan, Durham, NC (US); James Barnwell Thomas, Efland, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 15/023,510

(22) PCT Filed: Jun. 5, 2015

(86) PCT No.: PCT/US2015/034427
§ 371 (c)(1),
(2) Date: Mar. 21, 2016

(87) PCT Pub. No.: WO2015/188073
PCT Pub. Date: Dec. 10, 2015

(65) Prior Publication Data
US 2016/0207889 A1    Jul. 21, 2016

Related U.S. Application Data

(60) Provisional application No. 62/008,688, filed on Jun. 6, 2014.

(51) Int. Cl.
| | | |
|---|---|---|
| *C07D 231/14* | (2006.01) | |
| *A61K 45/06* | (2006.01) | |
| *A61K 31/415* | (2006.01) | |
| *C07D 405/12* | (2006.01) | |
| *A61K 31/422* | (2006.01) | |
| *A61K 31/454* | (2006.01) | |
| *A61K 31/4155* | (2006.01) | |
| *A61K 31/496* | (2006.01) | |
| *C07D 413/12* | (2006.01) | |
| *C07D 403/12* | (2006.01) | |
| *C07D 403/06* | (2006.01) | |
| *C07D 407/12* | (2006.01) | |

(52) U.S. Cl.
CPC .......... *C07D 231/14* (2013.01); *A61K 31/415* (2013.01); *A61K 31/4155* (2013.01); *A61K 31/422* (2013.01); *A61K 31/454* (2013.01); *A61K 31/496* (2013.01); *A61K 45/06* (2013.01); *C07D 403/06* (2013.01); *C07D 403/12* (2013.01); *C07D 405/12* (2013.01); *C07D 407/12* (2013.01); *C07D 413/12* (2013.01)

(58) Field of Classification Search
CPC .. C07D 231/14; C07D 403/06; C07D 403/12; C07D 405/12; C07D 407/12; C07D 413/12; A61K 31/415; A61K 31/4155; A61K 31/422; A61K 31/496; A61K 45/06; A61K 31/454
USPC .......................................................... 548/240
See application file for complete search history.

(56) References Cited

U.S. PATENT DOCUMENTS

| | | | |
|---|---|---|---|
| 5,420,141 A | 5/1995 | Boigegrain et al. | |
| 5,502,059 A | 3/1996 | Labeeuw et al. | |
| 5,523,455 A | 6/1996 | Labeeuw et al. | |
| 5,585,497 A | 12/1996 | Labeeuw et al. | |
| 5,624,941 A * | 4/1997 | Barth ................... | C07D 231/12 514/217.09 |
| 5,723,483 A | 3/1998 | Labeeuw et al. | |
| 5,925,661 A | 7/1999 | Labeeuw et al. | |
| 5,936,123 A | 8/1999 | Labeeuw et al. | |
| 5,939,449 A | 8/1999 | Labeeuw et al. | |
| 5,965,579 A | 10/1999 | Labeeuw et al. | |
| 6,028,084 A | 2/2000 | Barth et al. | |
| 6,172,239 B1 | 1/2001 | Labeeuw et al. | |
| 7,186,741 B2 | 3/2007 | Feenstra et al. | |
| 2014/0094450 A1 | 4/2014 | Hachtel et al. | |

FOREIGN PATENT DOCUMENTS

| | | | |
|---|---|---|---|
| EP | 0477049 A1 | 3/1992 | |
| EP | 1903052 A2 | 3/2008 | |
| WO | 2010053545 A1 | 5/2010 | |
| WO | WO-2011012630 A1 * | 2/2011 | ........... C07D 231/14 |
| WO | 2012166387 A1 | 12/2012 | |
| WO | 2013014204 A2 | 1/2013 | |
| WO | 2014044738 A1 | 3/2014 | |
| WO | 2015188073 A1 | 12/2015 | |

OTHER PUBLICATIONS

International Search Report and Written Opinion dated Sep. 25, 2015 for related International related application No. PCT/US2015/034427.
Anderson et al.; "Apelin and pulmonary hypertension", Pulm. Circ. Jul.-Sep. 2011, 1(3) pp. 334-346.
Carpéné et al.; "Expanding role for the apelin/APJ system in physiopathology" J. Physiol. Biochem., 63 (4), 359-374, 2007.
Charo et al.; "Endogenous regulation of cardiovascular function by apelin-APJ" Am J Physiol Heart Circ Physiol 297: H1904-H1913, 2009.
Cobellis et al.; "Modulation of apelin and APJ receptor in normal and preeclampsia-complicated placentas." Histol Histopathol. Jan. 2007, 22(1) pp. 1-8.

(Continued)

*Primary Examiner* — Kristin A Vajda
(74) *Attorney, Agent, or Firm* — Brinks Gilson & Lione

(57) ABSTRACT

This disclosure is directed to agonists of the apelin receptor (APJ) and uses of such agonists.

29 Claims, 1 Drawing Sheet

(56) References Cited

OTHER PUBLICATIONS

Giddings et al.; "Development of a functional HTS assay for the APJ receptor" International Journal of High Throughput Screening 2010:1 pp. 39-47.
Khan et al.; "Probe Report" Molecular Libraries, Jul. 2011, pp. 1-22.
Iturrioz et al.; "Identification and pharmacological properties of E339-3D6, the first nonpeptidic apelin receptor agonist" The FASEB Journal, May 2010, vol. 24, pp. 1506-1517.
International Search Report and Written Opinion dated Jan. 27, 2017 for International Application No. PCT/US2016/065808.
Kourtis et al.; "Apelin levels in normal pregnancy" Clinical Endocrinology (2011) 75, pp. 367-371.
Lathen et al.; "ERG-APLNR Axis Controls Pulmonary Venule Endothelial Proliferation in Pulmonary Veno-Occlusive Disease" Circulation 2014;130: pp. 1179-1191.
Maloney et al.; "Discovery of 4-oxo-6-((pyrimidin-2-ylthio)methyl)-4H-pyran-3-yl 4-nitrobenzoate (ML221) as a functional antagonist of the apelin (APJ) receptor" Bioorganic & Medicinal Chemistry Letters 22 (2012) pp. 6656-6660.
Narayanan et al.; "141—Discovery of small molecule functional agonist leads of APJ receptor" MEDI: Division of Medical Chemistry, 2015.
Sheikh et al.: "In vivo genetic profiling and cellular localization of apelin reveals a hypoxia-sensitive, endothelial-centered pathway activated in ischemic heart failure" Am J Physiol Heart Circ Physiol 294: H88-H98, 2008.
Tatemoto et al.; "Isolation and Characterization of a Novel Endogenous Peptide Ligand for the Human APJ Receptor" Biochemical and Biophysical Research Communications 251, pp. 471-476 (1998).
Tatemoto et al.; "The novel peptide apelin lowers blood pressure via a nitric oxide-dependent mechanism" Regulatory Peptides 99 Ž2001. pp. 87-92.
Tiemann et al., "Increasing myocardial contraction and blood pressure in C57BL/6 mice during early postnatal development" Am J Physiol Heart Circ Physiol 284:H464-H474, 2003.
XP-002768460 Database Registry, Chemical Abstracts Service. Nov. 22, 2009.
XP-002768454 Database Registry, Chemical Abstracts Service. Oct. 22, 2009.
XP-002768455 Database Registry, Chemical Abstracts Service. Sep. 16, 2009.
XP-002768456 Database Registry, Chemical Abstracts Service. Oct. 23, 2009.
XP-002768457 Database Registry, Chemical Abstracts Service. Oct. 25, 2009.
XP-002768458 Database Registry, Chemical Abstracts Service. Aug. 2, 2009.
XP-002768459 Database Registry, Chemical Abstracts Service. Nov. 20, 2009.
Office Action dated Jul. 3, 2018 for Chinese Application No. 201580030455.
Thomas et al., "1-({[1-(4-Fluorophenyl)-5-(2-methoxyphenyl)-1H-pyrazol-3-yl]carbonyl}amino)cyclohexane Carboxylic Acid as a Selective Nonpeptide Neurotensin Receptor Type 2 Compound," J. Med. Chem., 2014, vol. 57, pp. 5318-5332.
Baxendale et al., "The Synthesis of Neurotensin Antagonist SR 48692 for Prostate Cancer Research," Bioorg. Med. Chem., 2013, vol. 21, pp. 4378-4387.
Office Action dated Mar. 14, 2019 for Chinese Application No. 201580030455.
Office Action dated Mar. 26, 2019 for Japanese Application No. 2016-567569.

\* cited by examiner

Scheme 1
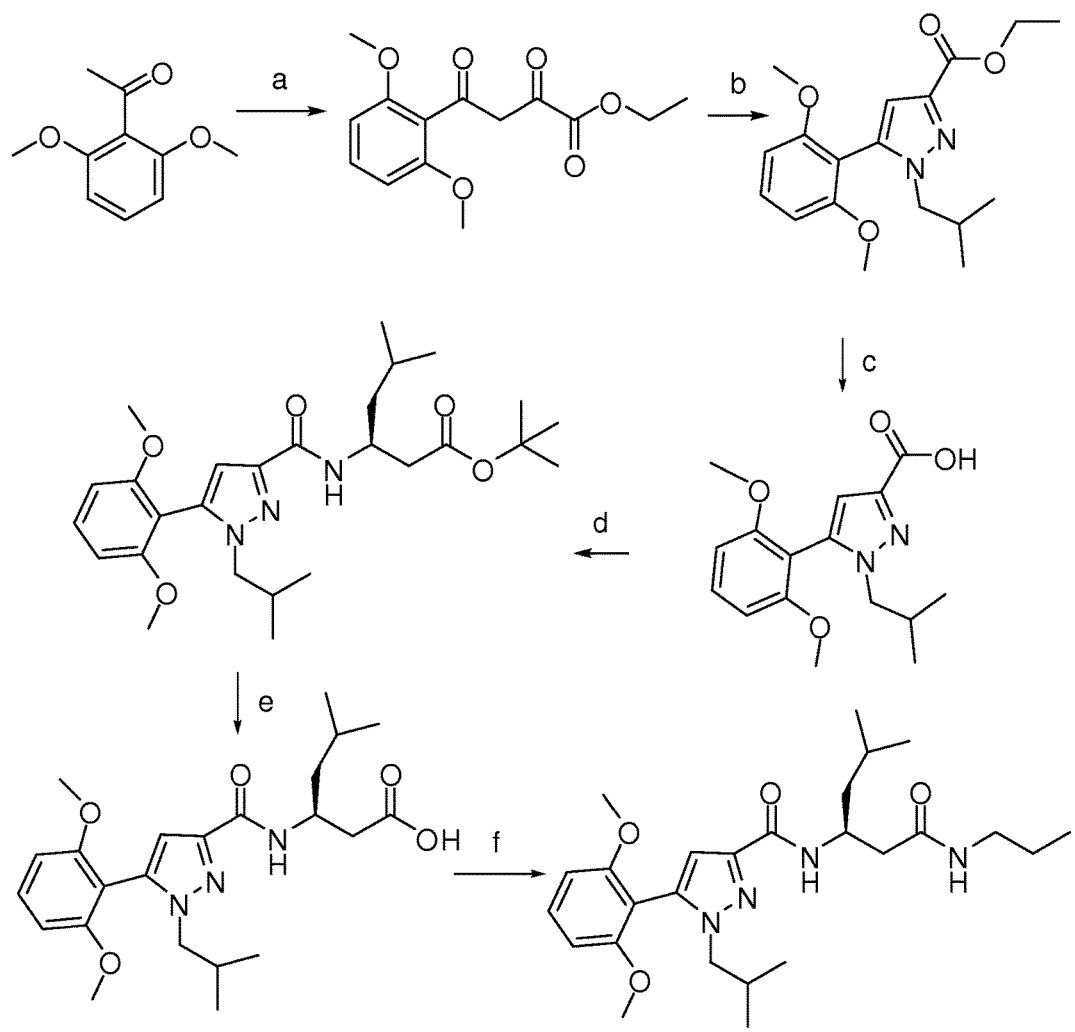

APELIN RECEPTOR (APJ) AGONISTS AND USES THEREOF

CROSS REFERENCE TO RELATED APPLICATIONS

This application claims the benefit of U.S. 62/008,688 filed Jun. 6, 2014, Runyon et al., entitled "Apelin Receptor (APJ) Agonists and Uses Thereof" which is hereby incorporated by reference in its entirety.

1. FIELD

This disclosure relates generally to the discovery of agonists of the apelin receptor (APJ) and uses of such agonists.

2. BACKGROUND

2.1. Introduction: Apelin and the Apelin Receptor (APJ)

The apelin receptor (APJ) was cloned in 1993 as an orphan G-protein coupled receptor (GPCR). The human APJ gene is located on the long arm of chromosome 11 and encodes a 377 amino acid G protein-coupled receptor. The gene for APJ was designated angiotensin-receptor like 1 (AGTRL1) due to sequence similarities between the two receptors. Carpene et al., J Physiol Biochem. 2007; 63(4): 359-373. However, none of the known peptidergic ligands for the angiotensin receptors, including angiotensin, activate APJ. APJ remained an orphan GPCR until 1998 when the peptide apelin was identified as its endogenous ligand. Lee et al., J Neurochem. 2000; 74(1):34-41; Habata et al., Biochim Biophys Acta. 1999; 1452(1):25-35.

Over the years, apelin and APJ have emerged as an important regulator of various physiological processes. Both apelin and APJ are expressed in the central nervous system (CNS) and peripherally in a number of tissues. Expression of APJ has been noted within the vasculature of some organs and is a potent regulator of related processes including angiogenesis and vasoconstriction. Cobellis et al. report increased of expression levels of both apelin and APJ receptor in preeclampsia-complicated pregnancies. Cobellis et al., Histol Histopathol. 2007; 22(1):1-8. APJ is also expressed in nonvascular cell types in heart, liver, and CNS where its primary role is currently under investigation. Medhurst et al., J Neurochem. 2003; 84(5):1162-1172. Apelin and APJ are often co-localized within the same organ suggesting an autocrine regulation of the receptor by its ligand. However, apelin has since been detected in blood suggesting that concomitant paracrine regulation of the receptor is also possible. The apelin—APJ system has been implicated as a regulator of various physiological functions and is believed to play an important role in thermoregulation, immunity, glucose metabolism, angiogenesis, fluid homeostasis, cardiac function, hepatic function and renal function. Ladeiras-Lopes et al., Arq Bras Cardiol. 2008; 90(5):343-349. APJ also acts as a co-receptor during HIV infection. O'Donnell et al., J Neurochem. 2007; 102(6): 1905-1917; Zou et al., FEBS Lett. 2000; 473(1):15-18.

Expression of apelin and APJ are either up- or down-regulated in various pathophysiological conditions. In particular, the APJ appears to be an emerging target for the treatment of cardiovascular failure, liver fibrosis, cancer, angiopathies, pancreatitis, and as a prophylactic against HIV infection. In 2011 Andersen et al. reviewed apelin and APJ as an opportunity for therapeutic uses for pulmonary hypertension and pulmonary arterial hypertension (PAH). Andersen et al. Pulm. Circ. 2011; 1(3) 334-346.

Unfortunately, small molecule ligands of the APJ having suitable pharmacological properties are lacking. Few non-peptide ligand systems has been reported to date. Iturrioz et al. report compounds that contain polycyclic fluorophores, such as lissamine, which make them ill-suited for pharmaceutical uses. Iturrioz et al., FASEB J. 2010; 24:1506-1517; EP 1903052 (Llorens-Cortes et al.). US Publ. Pat. Appn. 2014/0094450 (Hachtel et al.) discloses benzoimidazole-carboxylic acid amide derivatives as APJ receptor modulators.

Accordingly, there is a need for small molecule agonists of APJ.

3. SUMMARY OF THE DISCLOSURE

In particular non-limiting embodiments, the present disclosure provides in embodiment 1 a compound represented by the Formula I:

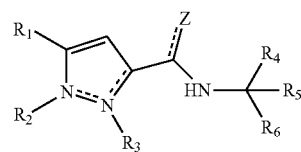

or a pharmaceutically acceptable salt, a prodrug, or a salt of a prodrug,
wherein
$R_1$ is represented by the formula:

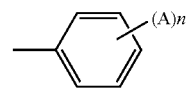

each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, —$CF_3$, —$(CH_2)_xNR_7R_8$, —CN, —$CONR_7R_8$, —$COR_7$, —$CO_2(CH_2)_xNR_7R_8$, —$CO_2R_7$, halogen, hydroxyl, —$N_3$, —$NHCOR_7$, —$NHSO_2C_{1-8}$ alkyl, —$NHCO_2C_{1-8}$ alkyl, —$NO_2$, —$NR_7R_8$, —$O(CH_2)_xNR_7R_8$, —$O(CH_2)_xCO_2R_7$, —$OCOC_{1-8}$ alkyl, —$OCO(CH_2)_xNR_7R_8$, —$SO_{(1-3)}R_7$, or —$SR_7$;

$R_7$ and $R_8$ are independently aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl guanidinyl, $C_{1-8}$ alkyl heteroaryl, $C_{1-8}$ alkyl imidazolyl, $C_{1-8}$ alkyl indolyl, $C_{1-8}$ alkyl thioether, $C_{1-8}$ alkyl thiol, $C_{2-8}$ alkenyl, $C_{3-8}$ alkynyl, $C_{3-8}$ cycloalkyl, —$(CH_2)_xCONHR_9$, —$(CH_2)_xCOR_9$, —$(CH_2)_xCO_2R_9$, or H; or $R_7$ and $R_8$ together make a 4-8 member ring which may be substituted with one or more heteroatoms;

n is 0, 1, 2, 3, 4 or 5;
each x is independently 0-8;
$R_2$ is present or absent, and if present, is aryl, $C_{1-8}$ alkyl, $C_{1-8}$ alkyl(aryl), $C_{1-8}$ alkyl ($C_{3-8}$ cycloalkyl), $C_{3-8}$ cycloalkyl;
$R_3$ is present or absent, is absent if $R_2$ is present, and if present is aryl, $C_{1-8}$ alkyl, $C_{1-8}$ alkyl(aryl), $C_{1-8}$ alkyl ($C_{3-8}$ cycloalkyl), $C_{3-8}$ cycloalkyl;

$R_4$, $R_5$, and $R_6$ are independently adamantanyl, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{1-8}$ alkyl imidazolyl, $C_{1-8}$ alkyl indolyl, $C_{1-8}$ alkyl thioether, $C_{1-8}$ alkyl thiol, $C_{2-8}$ alkenyl, $C_{3-8}$ alkynyl, $C_{3-8}$ cycloalkyl, $C_{3-8}$ cycloalkyl-$CO_2R_7$, —$(CH_2)_xNR_7R_8$, —$(CH_2)_xOR_7$, —$(CH_2)_xNHCOR_7$, —$(CH_2)_xNHCO_2R_7$, —$(CH_2)_xCONR_7R_8$, —$(CH_2)_xCONR_7(CH_2)_yCO_2R_9$, —$(CH_2)_xCONR_7(CH_2)_yCONR_7R_8$, —$(CH_2)_xCONR_7(CH_2)_yR_9$, —$(CH_2)_xCOR_7$, —$(CH_2)_xCO_2R_7$, —$CHR_7COR_9$, —$CHR_7CONHCHR_8COR_9$, —$CONR_7R_8$, —$CONR_7(CH_2)_xCO_2R_8$, —$CONR_7CHR_8CO_2R_9$, —$CO_2R_9$, or H; or $R_4$ and $R_5$ together make a 4-8 member ring which may be substituted with one or more heteroatoms or selected from the groups comprising $R_6$;

$R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl;

each y is independently 1-8;

and Z is $H_2$ or =O.

4. BRIEF DESCRIPTION OF THE FIGURES

FIG. 1 shows a general synthetic scheme for the synthesis of the compounds of the present disclosure. Reagents and conditions for scheme 1 are as follows: (a) Diethyl oxalate, NaOEt, EtOH, reflux, 3.5 h; (b) isobutylhydrazine trifluoroacetate, glacial acetic acid, conc. HCl, reflux, 3.5 h; (c) LiOH, MeOH/THF/$H_2O$, rt, 18 h; (d) (S)-tert-butyl 3-amino-5-methylhexanoate, BOP, $Et_3N$, THF, rt, 1.5 h; (e) TFA, DCM, rt, 1.5 h; (f) 1-Propylamine, BOP, $Et_3N$, THF, rt, 2 h.

5. DETAILED DESCRIPTION OF THE DISCLOSURE

In non-limiting embodiment 1, this disclosure provides a compound represented by the Formula I:

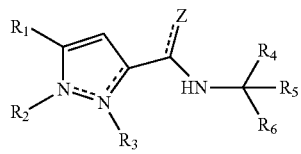

or a pharmaceutically acceptable salt, a prodrug, or a salt of a prodrug,
wherein
$R_1$ is represented by the formula:

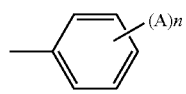

each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, —$CF_3$, —$(CH_2)_xNR_7R_8$, —CN, —$CONR_7R_8$, —$COR_7$, —$CO_2(CH_2)_xNR_7R_8$, —$CO_2R_7$, halogen, hydroxyl, —$N_3$, —$NHCOR_7$, —$NHSO_2C_{1-8}$ alkyl, —$NHCO_2C_{1-8}$ alkyl, —$NO_2$, —$NR_7R_8$, —$O(CH_2)_xNR_7R_8$, —$O(CH_2)_xCO_2R_7$, —$OCOC_{1-8}$ alkyl, —$OCO(CH_2)_xNR_7R_8$, —$SO_{(1-3)}R_7$, or —$SR_7$;

$R_7$ and $R_8$ are independently aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl guanidinyl, $C_{1-8}$ alkyl heteroaryl, $C_{1-8}$ alkyl imidazolyl, $C_{1-8}$ alkyl indolyl, $C_{1-8}$ alkyl thioether, $C_{1-8}$ alkyl thiol, $C_{2-8}$ alkenyl, $C_{3-8}$ alkynyl, $C_{3-8}$ cycloalkyl, —$(CH_2)_xCONHR_9$, —$(CH_2)_xCOR_9$, —$(CH_2)_xCO_2R_9$, or H; or $R_7$ and $R_8$ together make a 4-8 member ring which may be substituted with one or more heteroatoms;

n is 0, 1, 2, 3, 4 or 5;

each x is independently 0-8;

$R_2$ is present or absent, and if present, is aryl, $C_{1-8}$ alkyl, $C_{1-8}$ alkyl(aryl), $C_{1-8}$ alkyl ($C_{3-8}$ cycloalkyl), $C_{3-8}$ cycloalkyl;

$R_3$ is present or absent, is absent if $R_2$ is present, and if present is aryl, $C_{1-8}$ alkyl, $C_{1-8}$ alkyl(aryl), $C_{1-8}$ alkyl ($C_{3-8}$ cycloalkyl), $C_{3-8}$ cycloalkyl;

$R_4$, $R_5$, and $R_6$ are independently adamantanyl, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{1-8}$ alkyl imidazolyl, $C_{1-8}$ alkyl indolyl, $C_{1-8}$ alkyl thioether, $C_{1-8}$ alkyl thiol, $C_{2-8}$ alkenyl, $C_{3-8}$ alkynyl, $C_{3-8}$ cycloalkyl, $C_{3-8}$ cycloalkyl-$CO_2R_7$, —$(CH_2)_xNR_7R_8$, —$(CH_2)_xOR_7$, —$(CH_2)_xNHCOR_7$, —$(CH_2)_xNHCO_2R_7$, —$(CH_2)_xCONR_7R_8$, —$(CH_2)_xCONR_7(CH_2)_yCO_2R_9$, —$(CH_2)_xCONR_7(CH_2)_yCONR_7R_8$, —$(CH_2)_xCONR_7(CH_2)_yR_9$, —$(CH_2)_xCOR_7$, —$(CH_2)_xCO_2R_7$, —$CHR_7COR_9$, —$CHR_7CONHCHR_8COR_9$, —$CONR_7R_8$, —$CONR_7(CH_2)_xCO_2R_8$, —$CONR_7CHR_8CO_2R_9$, —$CO_2R_9$, or H; or $R_4$ and $R_5$ together make a 4-8 member ring which may be substituted with one or more heteroatoms or selected from the groups comprising $R_6$;

$R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl; each y is independently 1-8;

and Z is $H_2$ or =O.

In another non-limiting embodiment, n is 4; each A is independently $C_{1-4}$ alkoxy, $C_{1-4}$ alkoxy aryl, or halogen; $R_2$ is aryl, $C_{1-8}$ alkyl or $C_{3-8}$ cycloalkyl; $R_4$ is $C_{1-8}$ alkyl, $C_{1-8}$ alkyl(aryl), $C_{1-8}$ alkyl ($C_{3-8}$ cycloalkyl) or —$CO_2R_9$; $R_5$ is —$(CH_2)_xCNHCOR_7$, —$(CH_2)_xCNHCO_2R_7$, —$(CH_2)_xCONR_7R_8$, —$(CH_2)_xCONR_7(CH_2)_yCO_2R_9$, —$(CH_2)_xCONR_7(CH_2)_yCONR_7R_8$, —$(CH_2)_xCONR_7(CH_2)_yR_9$, —$(CH_2)_xCOR_7$, —$(CH_2)_xCO_2R_7$, —$CHR_7COR_9$, —$CHR_7CONHCHR_8COR_9$, —$CONR_7R_8$, —$CONR_7(CH_2)_xCO_2R_8$, or —$CO_2R_9$; $R_6$ is H; $R_9$ is $C_{1-8}$ alkyl, H, or heteroaryl which is an oxazole; x is 1-4; y is 1-3; and Z is =O.

In another non-limiting embodiment, n is 4; each A is independently $C_1$ alkoxy, $C_1$ alkoxy aryl, or halogen; $R_2$ is aryl, $C_4$ alkyl or $C_6$ cycloalkyl; $R_4$ is $C_{1-4}$ alkyl, $C_{1-8}$ alkyl(aryl), $C_{1-8}$ alkyl ($C_{3-8}$ cycloalkyl) or —$CO_2R_9$; $R_5$ is —$(CH_2)_xCNHCOR_7$, —$(CH_2)_xCNHCO_2R_7$, —$(CH_2)_xCONR_7R_8$, —$(CH_2)_xCONR_7(CH_2)_yCO_2R_9$, —$(CH_2)_xCONR_7(CH_2)_yCONR_7R_8$, —$(CH_2)_xCONR_7(CH_2)_yR_9$, —$(CH_2)_xCOR_7$, —$(CH_2)_xCO_2R_7$, —$CHR_7COR_9$, —$CHR_7CONHCHR_8COR_9$, —$CONR_7R_8$, —$CONR_7(CH_2)_xCO_2R_8$, or —$CO_2R_9$; $R_6$ is H; $R_8$ is $C_{1-4}$ alkyl or H; $R_9$ is $C_{1-8}$ alkyl, H, or heteroaryl which is an oxazole; x is 1-4; y is 1-3; and Z is =O.

In another non-limiting embodiment, n is 4; each A is independently $C_1$ alkoxy, $C_1$ alkoxy aryl, or fluorine; $R_2$ is aryl, $C_{1-4}$ alkyl, $C_{1-8}$ alkyl(aryl), $C_{1-8}$ alkyl ($C_{3-8}$ cycloalkyl) or $C_6$ cycloalkyl; $R_4$ is $C_{1-4}$ alkyl, $C_{1-8}$ alkyl(aryl), $C_{1-8}$ alkyl ($C_{3-8}$ cycloalkyl) or —$CO_2R_9$; $R_5$ is —$(CH_2)_xCNHCOR_7$, —$(CH_2)_xCNHCO_2R_7$, —$(CH_2)_xCONR_7R_8$, —$(CH_2)_xCONR_7(CH_2)_yCO_2R_9$, —$(CH_2)_xCONR_7(CH_2)_y$ $CONR_7R_8$, —$(CH_2)_xCONR_7(CH_2)_yR_9$, —$(CH_2)_xCOR_7$, —$(CH_2)_xCO_2R_7$, —$CHR_7COR_9$, —$CHR_7CONHCHR_8$ $COR_9$, —$CONR_7R_8$, —$CONR_7(CH_2)_xCO_2R_8$, or —$CO_2R_9$; $R_6$ is H; $R_8$ is $C_{1-4}$ alkyl or H; $R_9$ is $C_{1-8}$ alkyl, H, or heteroaryl which is an oxazole; x is 1-4; and y is 1-3.

In another non-limiting embodiment, n is 4; each A is independently $C_1$ alkoxy, $C_1$ alkoxy aryl, or fluorine; $R_2$ is aryl, $C_4$ alkyl, or $C_6$ cycloalkyl; $R_4$ is $C_{1-4}$ alkyl, $C_{1-4}$ alkyl(aryl), $C_{1-4}$ alkyl ($C_{5-8}$ cycloalkyl) or —$CO_2R_9$; $R_5$ is —$(CH_2)_xCNHCOR_7$, —$(CH_2)_xCNHCO_2R_7$, —$(CH_2)_x$ $CONR_7R_8$, —$(CH_2)_xCONR_7(CH_2)_yCO_2R_9$, —$(CH_2)_x$ $CONR_7(CH_2)_yCONR_7R_8$, —$(CH_2)_xCONR_7(CH_2)_yR_9$, —$(CH_2)_xCOR_7$, —$(CH_2)_xCO_2R_7$, —$CHR_7COR_9$, —$CHR_7CONHCHR_8COR_9$, —$CONR_7R_8$, —$CONR_7$ $(CH_2)_xCO_2R_8$, or —$CO_2R_9$; $R_6$ is H; $R_8$ is H; $R_9$ is $C_{1-8}$ alkyl, H, or heteroaryl which is an oxazole; x is 1-4; and y is 1-3.

In another non-limiting embodiment, n is 2; each A is independently $C_{1-4}$ alkoxy, $C_{1-4}$ alkoxy aryl; $R_2$ is aryl, $C_{1-8}$ alkyl or $C_{3-8}$ cycloalkyl; $R_4$ is $C_{1-8}$ alkyl, $C_{1-8}$ alkyl(aryl), $C_{1-8}$ alkyl ($C_{3-8}$ cycloalkyl) or —$CO_2R_9$; $R_5$ is —$(CH_2)_x$ $CNHCOR_7$, —$(CH_2)_xCNHCO_2R_7$, —$(CH_2)_xCONR_7R_8$, —$(CH_2)_xCONR_7(CH_2)_yCO_2R_9$, —$(CH_2)_xCONR_7(CH_2)_y$ $CONR_7R_8$, —$(CH_2)_xCONR_7(CH_2)_yR_9$, —$(CH_2)_xCOR_7$, —$(CH_2)_xCO_2R_7$, —$CHR_7COR_9$, —$CHR_7CONHCHR_8$ $COR_9$, —$CONR_7R_8$, —$CONR_7(CH_2)_xCO_2R_8$, or —$CO_2R_9$; $R_6$ is H; $R_8$ is $C_{1-4}$ alkyl or H; $R_9$ is $C_{1-8}$ alkyl, H, or heteroaryl which is an oxazole; x is 1-4; y is 1-3; and Z is =O.

In another non-limiting embodiment, n is 2; each A is independently $C_1$ alkoxy, $C_1$ alkoxy aryl; $R_2$ is aryl, $C_4$ alkyl or $C_6$ cycloalkyl; $R_4$ is $C_{1-8}$ alkyl, $C_{1-8}$ alkyl(aryl), $C_{1-8}$ alkyl ($C_{3-8}$ cycloalkyl) or —$CO_2R_9$; $R_5$ is —$(CH_2)_xCNHCOR_7$, —$(CH_2)_xCNHCO_2R_7$, —$(CH_2)_xCONR_7R_8$, —$(CH_2)_x$ $CONR_7(CH_2)_yCO_2R_9$, —$(CH_2)_xCONR_7(CH_2)_yCONR_7R_8$, —$(CH_2)_xCONR_7(CH_2)_yR_9$, —$(CH_2)_xCOR_7$, —$(CH_2)_x$ $CO_2R_7$, —$CHR_7COR_9$, —$CHR_7CONHCHR_8COR_9$, —$CONR_7R_8$, —$CONR_7(CH_2)_xCO_2R_8$, or —$CO_2R_9$; $R_6$ is H; $R_8$ is $C_{1-4}$ alkyl or H; $R_9$ is $C_{1-8}$ alkyl, H, or heteroaryl which is an oxazole; x is 1-4; y is 1-3; and Z is =O.

$R_4$, $R_5$, or $R_6$ are $C_{1-8}$ alkyl heteroaryl and the $C_{1-8}$ alkyl heteroaryl is a $C_{1-8}$ alkyl tetrazole, such as a $C_1$ alkyl tetrazole or a $C_2$ alkyl tetrazole.

In other non-limiting embodiments, n is 2; each A is $C_1$ alkoxy; $R_2$ is $C_4$ alkyl; $R_3$ is absent; $R_4$ is $C_2$ alkyl(aryl); $R_5$ is —$CONR_7R_8$; $R_6$ is H; $R_7$ is methyl; $R_8$ is $C_{1-4}$ alkoxy; and Z is =O; n is 2; alternatively each A is $C_1$ alkoxy; $R_2$ is $C_4$ alkyl; $R_3$ is absent; $R_4$ is $C_2$ alkyl(phenyl); $R_5$ is —$CONR_7R_8$; $R_6$ is H; $R_7$ is methyl; $R_8$ is $C_3$ alkoxy; and Z is =O.

In other non-limiting embodiments, n is 2; each A is $C_1$ alkoxy; $R_2$ is $C_5$ cycloalkyl; $R_3$ is absent; $R_4$ is $C_{1-4}$ alkyl $C_6$ heterocycloalkyl; $R_5$ is —$CH_2CONR_7R_8$; $R_6$ is H; $R_7$ is H; $R_8$ is $C_{4-6}$ cycloalkyl; and Z is =O; alternatively n is 2; $R_2$ is $C_5$ cycloalkyl; $R_3$ is absent; $R_4$ is $C_{12}$ alkyl $C_6$ heterocycloalkyl; $R_5$ is —$CH_2CONR_7R_8$; $R_6$ is H; $R_7$ is H; $R_8$ is $C_4$ cycloalkyl; and Z is =O.

In other non-limiting embodiments, n is 2; each A is $C_1$ alkoxy; $R_2$ is $C_4$ alkyl; $R_3$ is absent; $R_4$ is $C_2$ alkyl(aryl); $R_5$ is —$CONR_7R_8$; $R_6$ is H; $R_7$ is methyl; $R_8$ is $C_{1-4}$ hydroxyalkyl; and Z is =O; n is 2; alternatively each A is $C_1$ alkoxy; $R_2$ is $C_4$ alkyl; $R_3$ is absent; $R_4$ is $C_2$ alkyl(phenyl); $R_5$ is —$CONR_7R_8$; $R_6$ is H; $R_7$ is methyl; $R_8$ is $C_4$ hydroxyalkyl; and Z is =O.

In other non-limiting embodiments, n is 2; each A is $C_1$ alkoxy; $R_2$ is $C_4$ alkyl; $R_3$ is absent; $R_4$ is $C_2$ alkyl(aryl); $R_5$ is —$CONR_7R_8$; $R_6$ is H; $R_7$ is H; $R_8$ is —$(CH_2)_{1-4}CO_2R_9$; $R_9$ is $C_{1-4}$ alkyl; and Z is =O; n is 2; alternatively each A is $C_1$ alkoxy; $R_2$ is $C_4$ alkyl; $R_3$ is absent; $R_4$ is $C_2$ alkyl (phenyl); $R_5$ is —$CONR_7R_8$; $R_6$ is H; $R_7$ is methyl; $R_8$ is —$(CH_2)_{1-2}CO_2R_9$; $R_9$ is $C_{1-2}$ alkyl; and Z is =O.

In other non-limiting embodiments, n is 2; one A is $C_1$ alkoxy and one A is $C_1$ alkyl aryl; $R_2$ is $C_4$ alkyl; $R_3$ is absent; $R_4$ is $C_2$ alkyl(aryl); $R_5$ is —$CONR_7R_8$; $R_6$ is H; $R_7$ is methyl; $R_8$ is $C_{1-4}$ alkoxy; and Z is =O; n is 2; alternatively one A is $C_1$ alkoxy and one A is $C_1$ alkyl aryl; $R_2$ is $C_4$ alkyl; $R_3$ is absent; $R_4$ is $C_2$ alkyl(phenyl); $R_5$ is —$CONR_7R_8$; $R_6$ is H; $R_7$ is methyl; $R_8$ is $C_3$ alkoxy; and Z is =O.

In other non-limiting embodiments, n is 2; one A is $C_1$ alkoxy and one A is $C_1$ alkyl aryl; $R_2$ is $C_5$ cycloalkyl; $R_3$ is absent; $R_4$ is $C_{1-4}$ alkyl $C_6$ heterocycloalkyl; $R_5$ is —$CH_2CONR_7R_8$; $R_6$ is H; $R_7$ is H; $R_8$ is $C_{4-6}$ cycloalkyl; and Z is =O; alternatively n is 2; one A is $C_1$ alkoxy and one A is $C_1$ alkyl aryl; $R_2$ is $C_5$ cycloalkyl; $R_3$ is absent; $R_4$ is $C_{12}$ alkyl $C_6$ heterocycloalkyl; $R_5$ is —$CH_2CONR_7R_8$; $R_6$ is H; $R_7$ is H; $R_8$ is $C_4$ cycloalkyl; and Z is =O.

In other non-limiting embodiments, n is 2; one A is $C_1$ alkoxy and one A is $C_1$ alkyl aryl; $R_2$ is $C_4$ alkyl; $R_3$ is absent; $R_4$ is $C_2$ alkyl(aryl); $R_5$ is —$CONR_7R_8$; $R_6$ is H; $R_7$ is methyl; $R_8$ is $C_{1-4}$ hydroxyalkyl; and Z is =O; n is 2; alternatively one A is $C_1$ alkoxy and one A is $C_1$ alkyl aryl; $R_2$ is $C_4$ alkyl; $R_3$ is absent; $R_4$ is $C_2$ alkyl(phenyl); $R_5$ is —$CONR_7R_8$; $R_6$ is H; $R_7$ is methyl; $R_8$ is $C_4$ hydroxyalkyl; and Z is =O.

In other non-limiting embodiments, n is 2; one A is $C_1$ alkoxy and one A is $C_1$ alkyl aryl; $R_2$ is $C_4$ alkyl; $R_3$ is absent; $R_4$ is $C_2$ alkyl(aryl); $R_5$ is —$CONR_7R_8$; $R_6$ is H; $R_7$ is H; $R_8$ is —$(CH_2)_{1-4}CO_2R_9$; $R_9$ is $C_{1-4}$ alkyl; and Z is =O; n is 2; alternatively one A is $C_1$ alkoxy and one A is $C_1$ alkyl aryl; $R_2$ is $C_4$ alkyl; $R_3$ is absent; $R_4$ is $C_2$ alkyl(phenyl); $R_5$ is —$CONR_7R_8$; $R_6$ is H; $R_7$ is methyl; $R_8$ is —$(CH_2)_{1-2}$ $CO_2R_9$; $R_9$ is $C_{1-2}$ alkyl; and Z is =O.

In other non-limiting embodiments, n is 2; one A is $C_1$ alkoxy and one A is $C_1$ alkyl phenyl; $R_2$ is $C_4$ alkyl; $R_3$ is absent; $R_4$ is $C_2$ alkyl(aryl); $R_5$ is —$CONR_7R_8$; $R_6$ is H; $R_7$ is methyl; $R_8$ is $C_{1-4}$ alkoxy; and Z is =O; n is 2; alternatively one A is $C_1$ alkoxy and one A is $C_1$ alkyl phenyl; $R_2$ is $C_4$ alkyl; $R_3$ is absent; $R_4$ is $C_2$ alkyl(phenyl); $R_5$ is —$CONR_7R_8$; $R_6$ is H; $R_7$ is methyl; $R_8$ is $C_3$ alkoxy; and Z is =O.

In other non-limiting embodiments, n is 2; one A is $C_1$ alkoxy and one A is $C_1$ alkyl phenyl; $R_2$ is $C_5$ cycloalkyl; $R_3$ is absent; $R_4$ is $C_{1-4}$ alkyl $C_6$ heterocycloalkyl; $R_5$ is —$CH_2CONR_7R_8$; $R_6$ is H; $R_7$ is H; $R_8$ is $C_{4-6}$ cycloalkyl; and Z is =O; alternatively n is 2; one A is $C_1$ alkoxy and one A is $C_1$ alkyl phenyl; $R_2$ is $C_5$ cycloalkyl; $R_3$ is absent; $R_4$ is $C_{12}$ alkyl $C_6$ heterocycloalkyl; $R_5$ is —$CH_2CONR_7R_8$; $R_6$ is H; $R_7$ is H; $R_8$ is $C_4$ cycloalkyl; and Z is =O.

In other non-limiting embodiments, n is 2; one A is $C_1$ alkoxy and one A is $C_1$ alkyl phenyl; $R_2$ is $C_4$ alkyl; $R_3$ is absent; $R_4$ is $C_2$ alkyl(aryl); $R_5$ is —$CONR_7R_8$; $R_6$ is H; $R_7$ is methyl; $R_8$ is $C_{1-4}$ hydroxyalkyl; and Z is =O; n is 2; alternatively one A is $C_1$ alkoxy and one A is $C_1$ alkyl phenyl; $R_2$ is $C_4$ alkyl; $R_3$ is absent; $R_4$ is $C_2$ alkyl(phenyl); $R_5$ is —$CONR_7R_8$; $R_6$ is H; $R_7$ is methyl; $R_8$ is $C_4$ hydroxyalkyl; and Z is =O.

In other non-limiting embodiments, n is 2; one A is $C_1$ alkoxy and one A is $C_1$ alkyl phenyl; $R_2$ is $C_4$ alkyl; $R_3$ is absent; $R_4$ is $C_2$ alkyl(aryl); $R_5$ is —$CONR_7R_8$; $R_6$ is H; $R_7$ is H; $R_8$ is —$(CH_2)_{1-4}CO_2R_9$; $R_9$ is $C_{1-4}$ alkyl; and Z is =O; n is 2; alternatively one A is $C_1$ alkoxy and one A is $C_1$ alkyl phenyl; $R_2$ is $C_4$ alkyl; $R_3$ is absent; $R_4$ is $C_2$ alkyl(phenyl);

$R_5$ is —$CONR_7R_8$; $R_6$ is H; $R_7$ is methyl; $R_8$ is —$(CH_2)_{1-2}CO_2R_9$; $R_9$ is $C_{1-2}$ alkyl; and Z is =O.
In additional non-limiting embodiments, the compound may have one of the following structures.
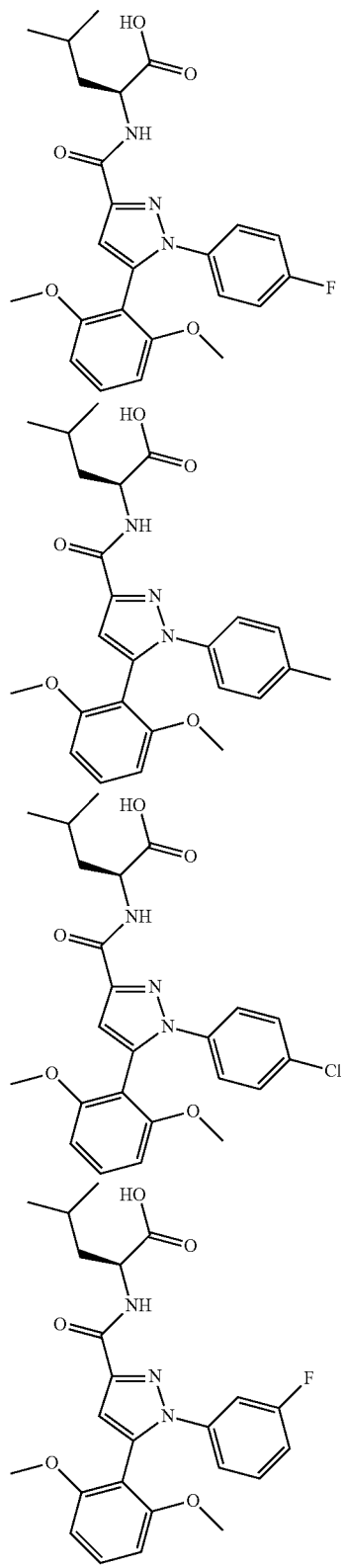
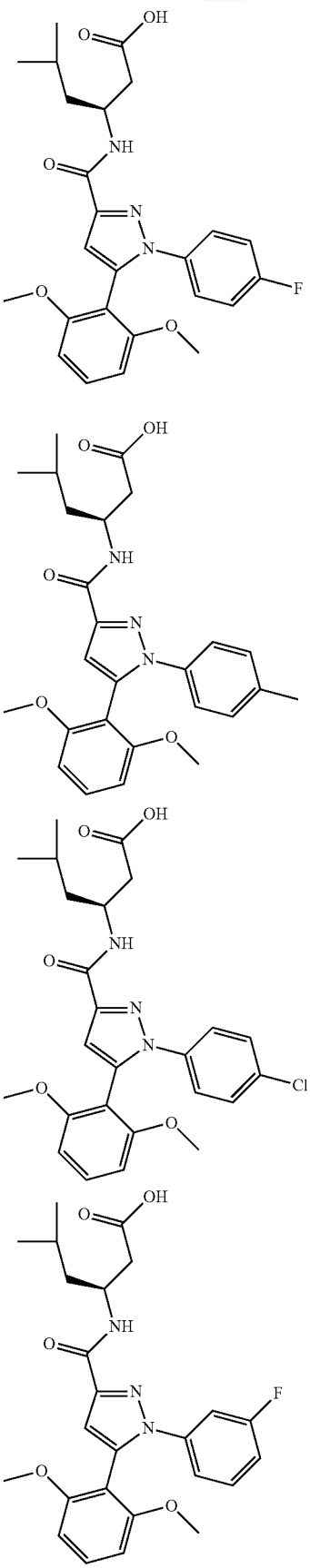
-continued

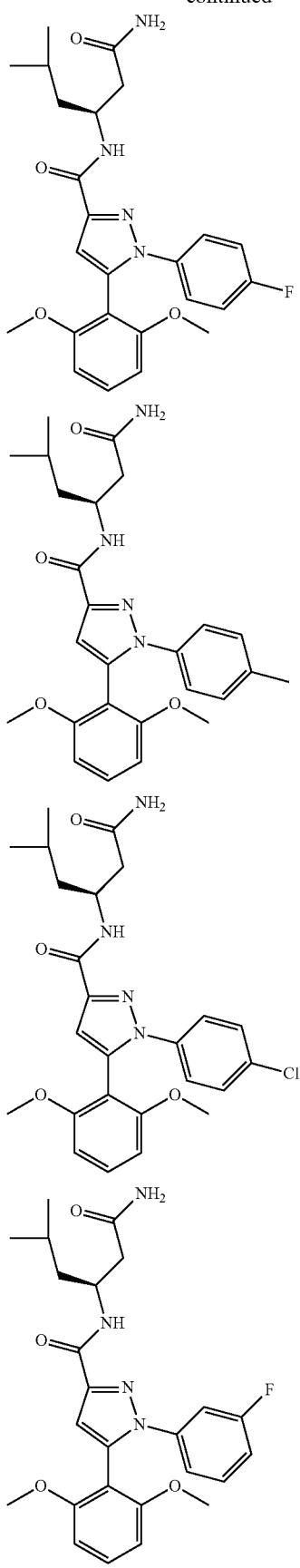
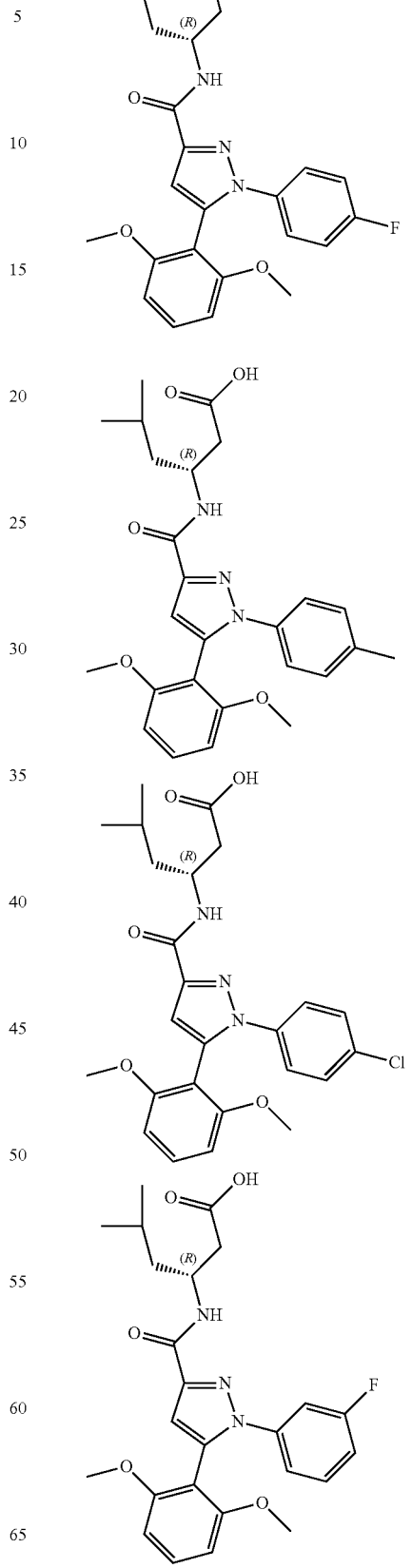

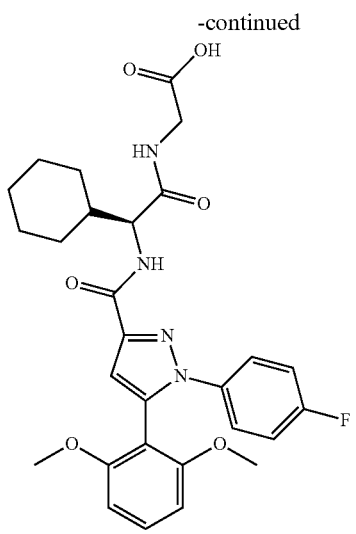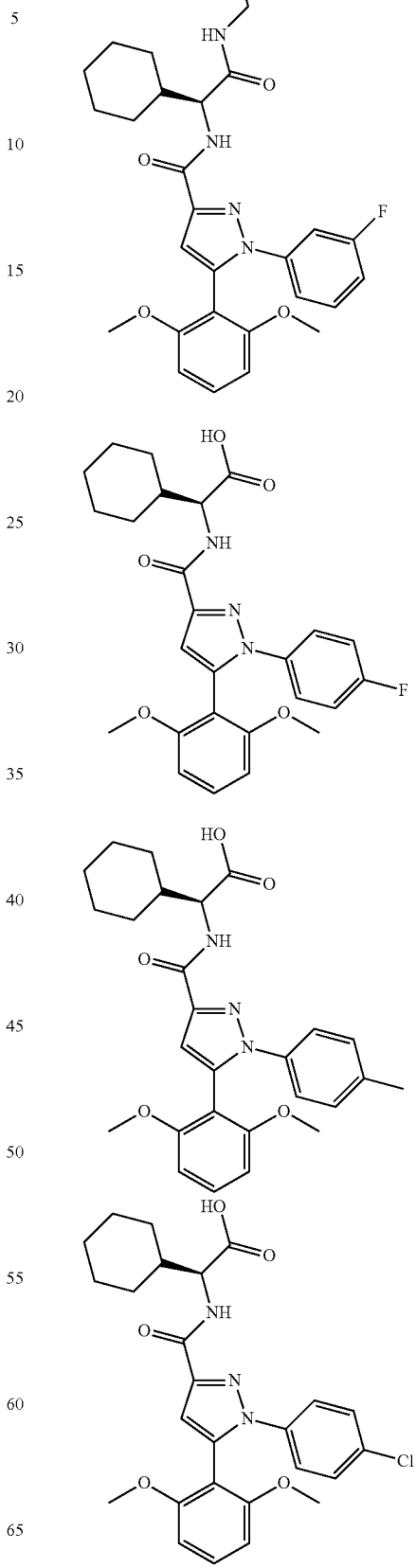

-continued
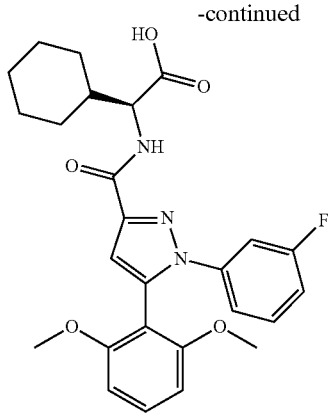
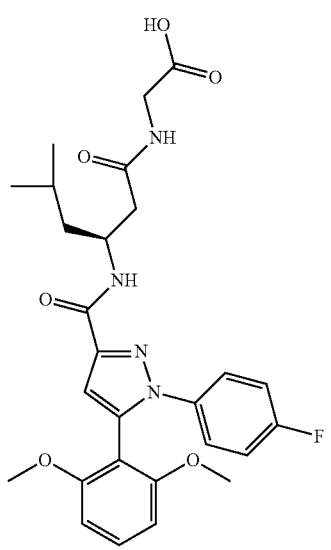
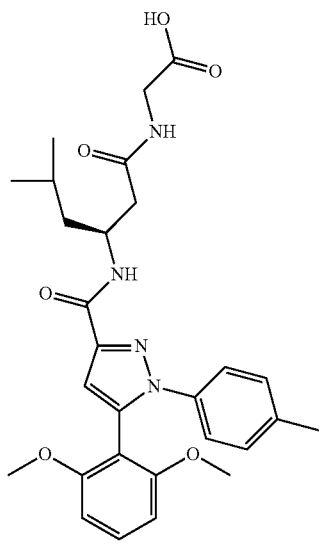
-continued
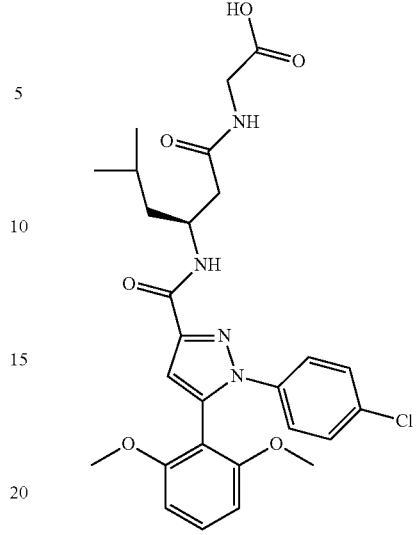
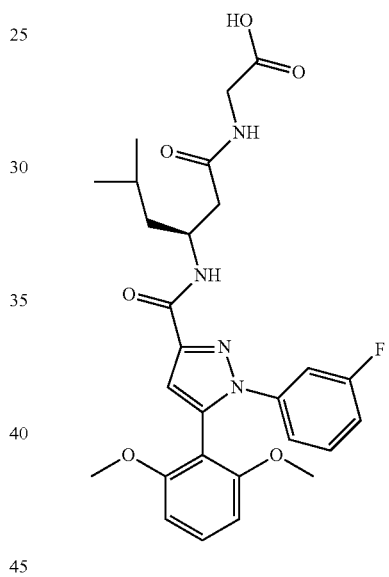
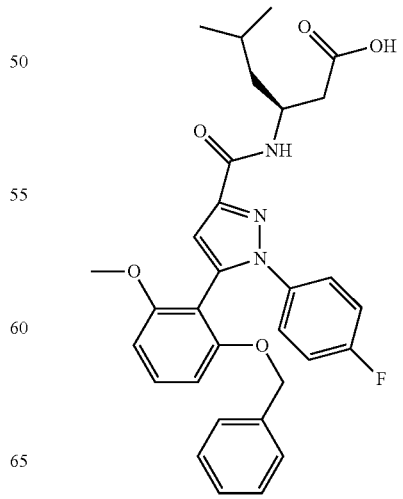

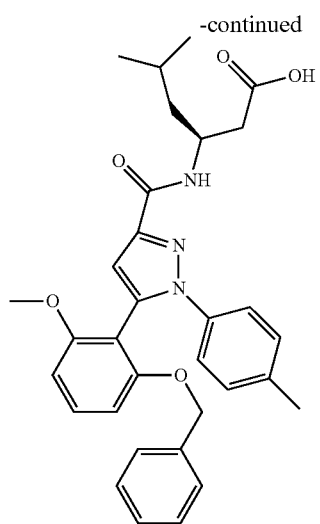
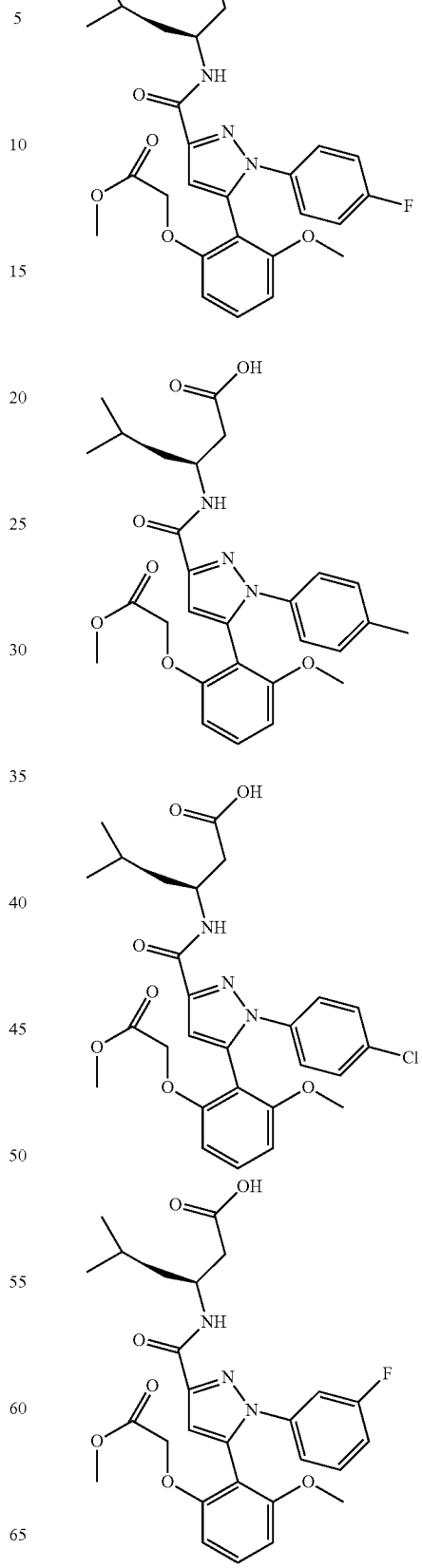

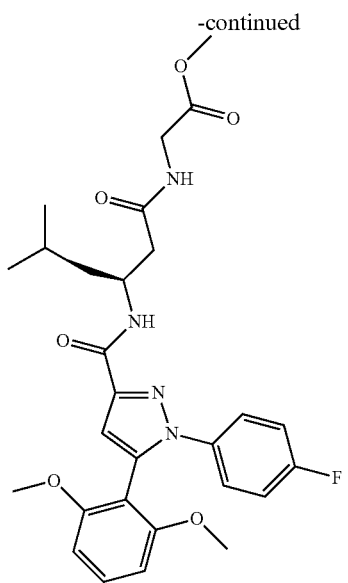
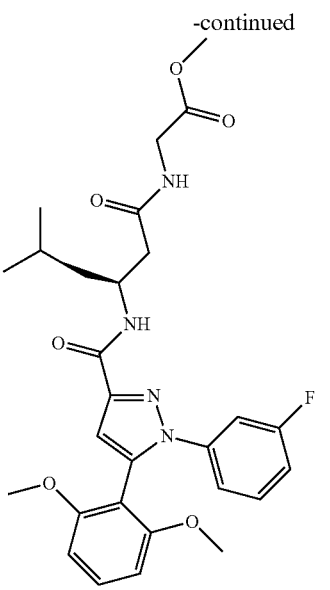
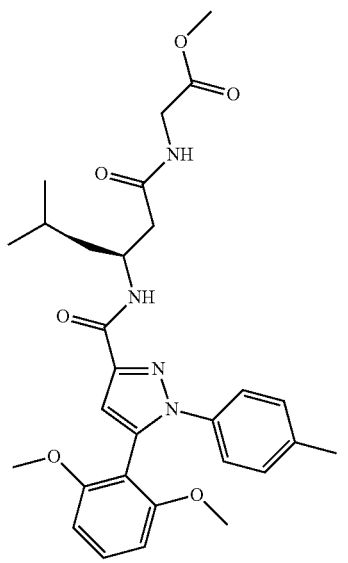
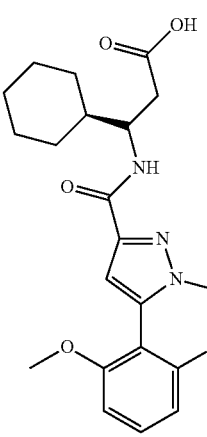
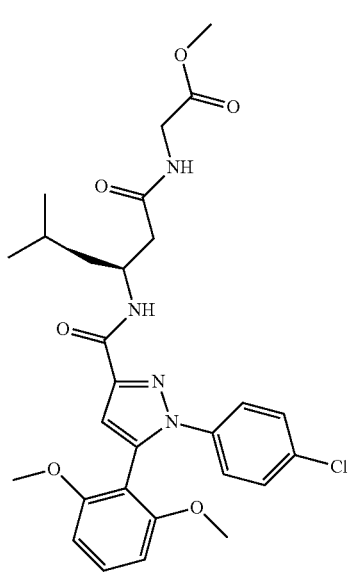
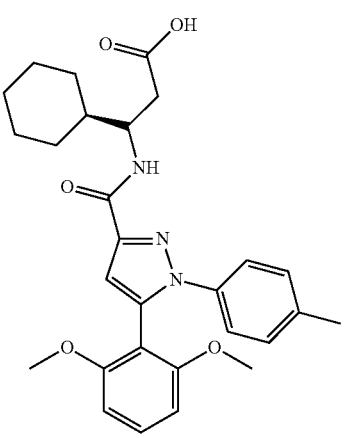

-continued
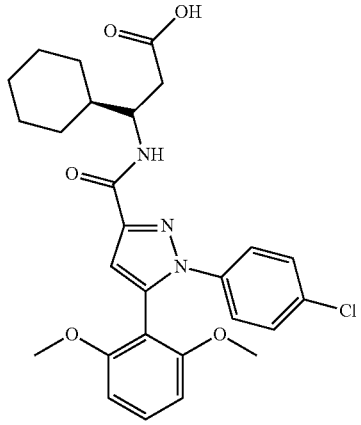
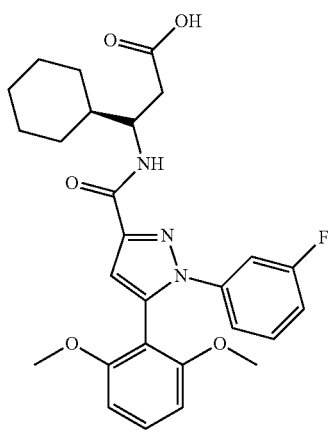
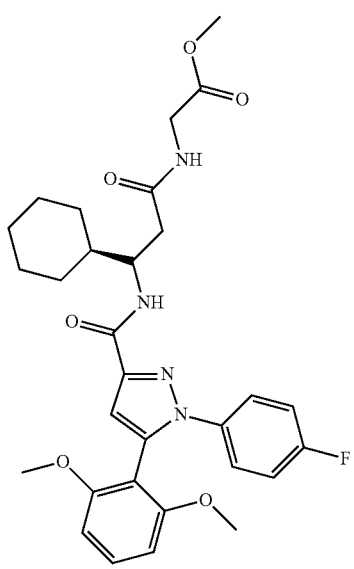
-continued
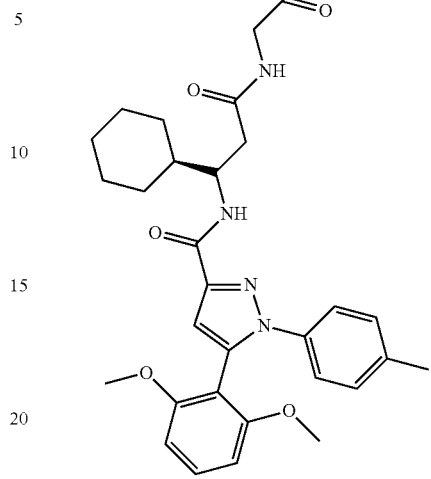
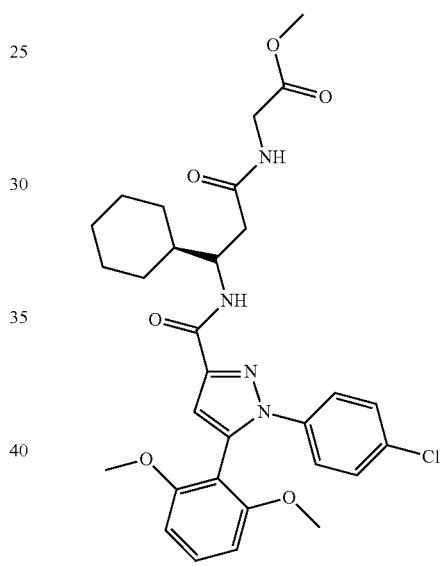
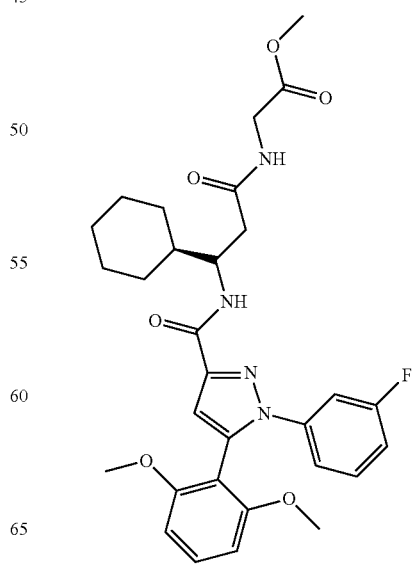

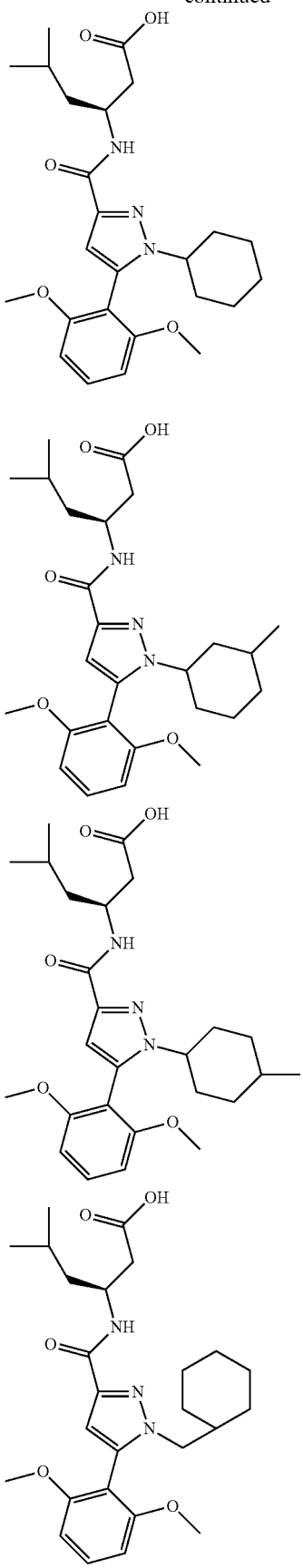
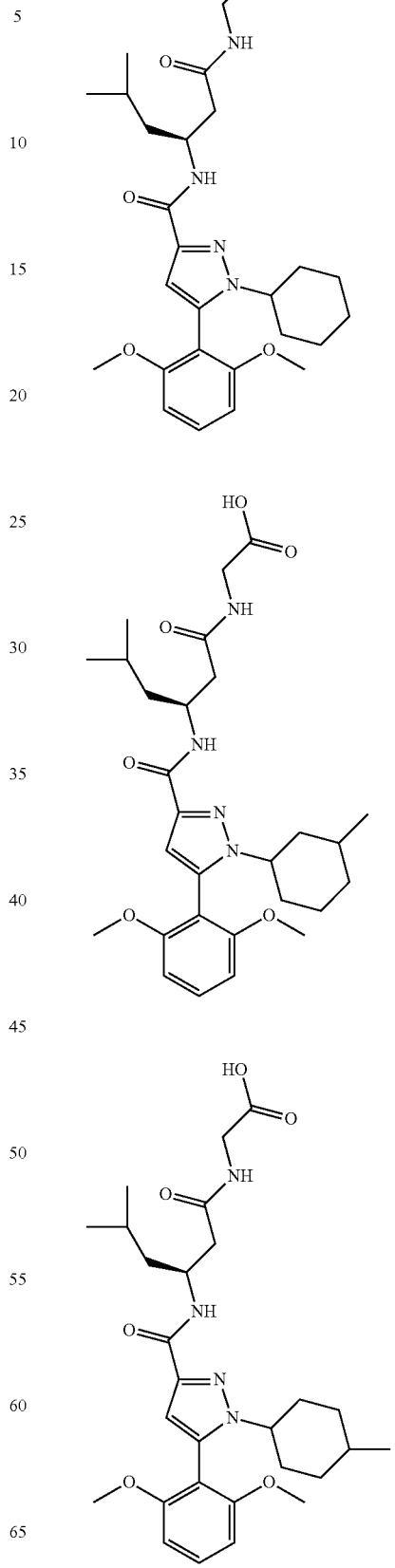

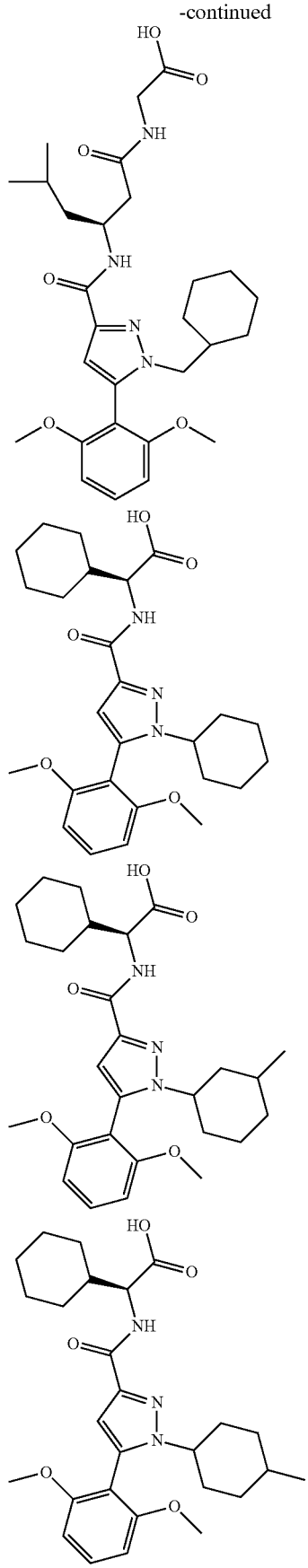
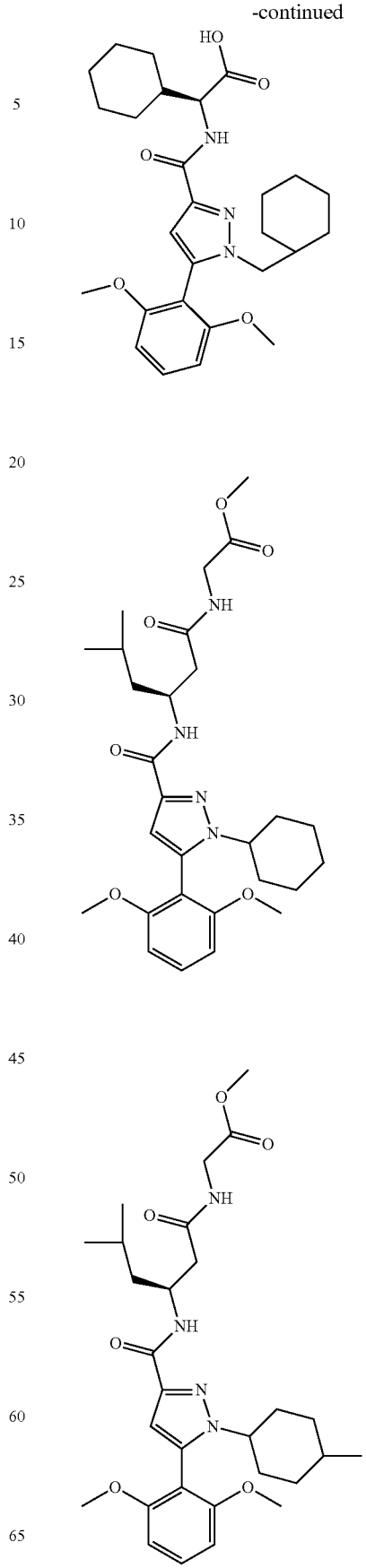

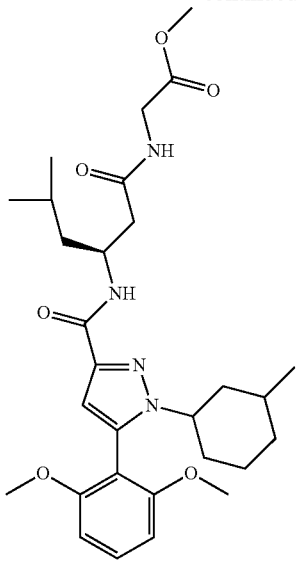
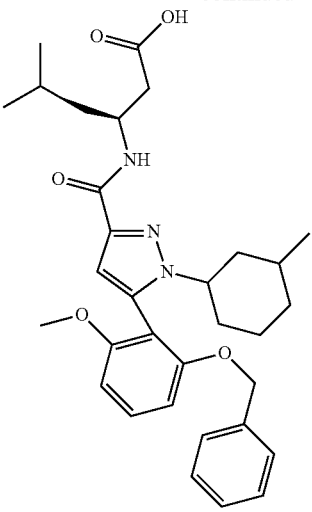
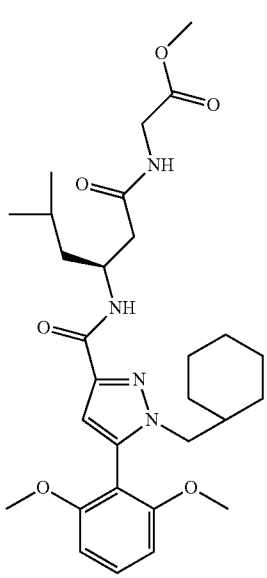
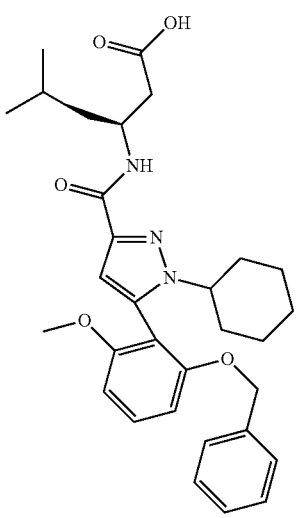
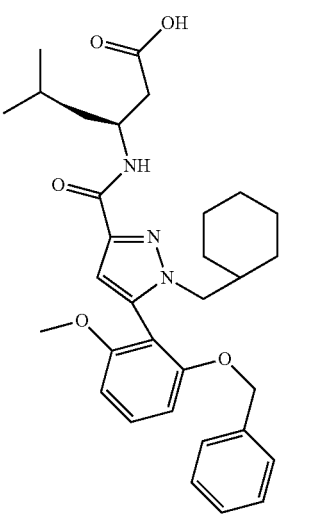

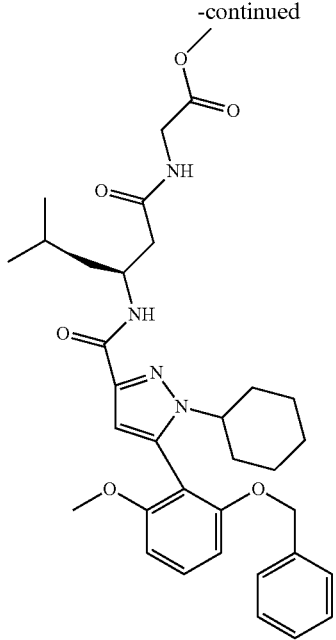
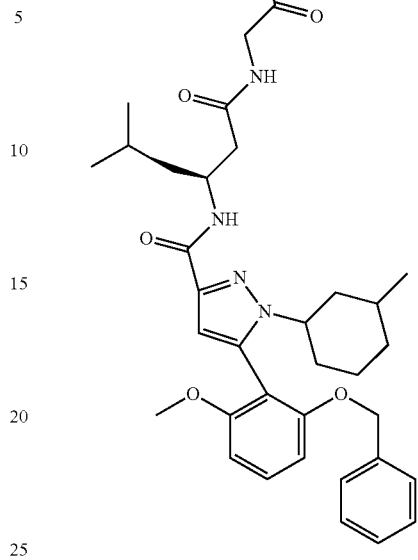
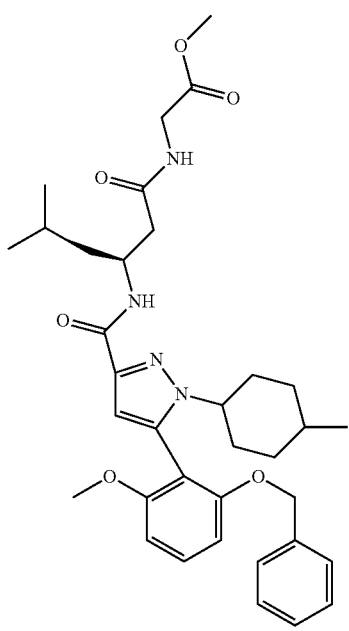
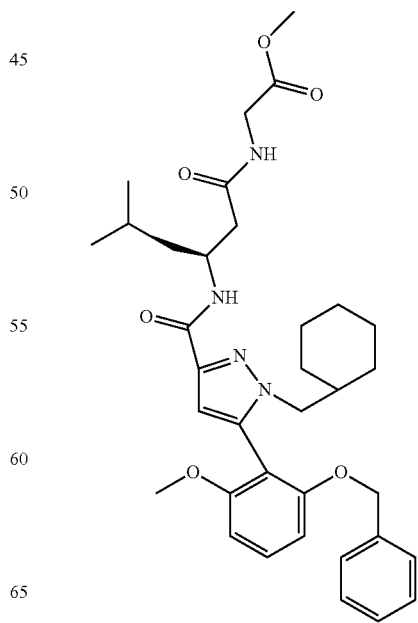

29
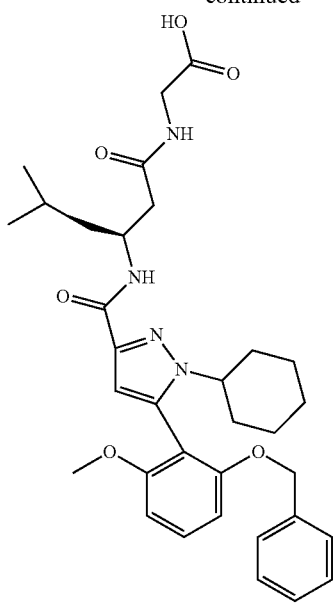
30
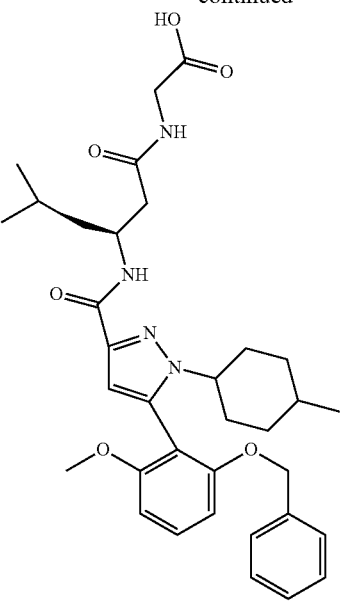
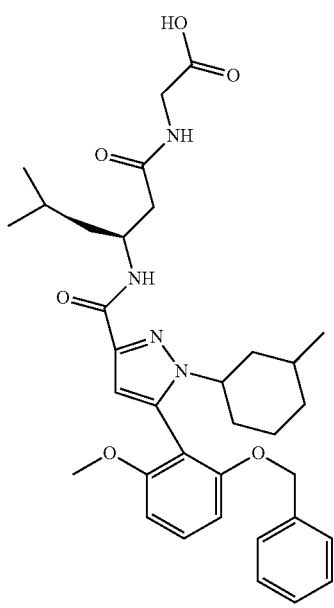
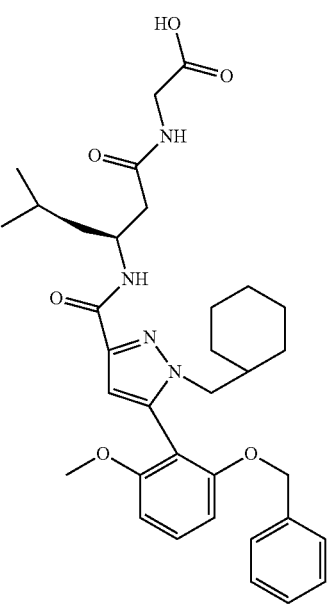

31
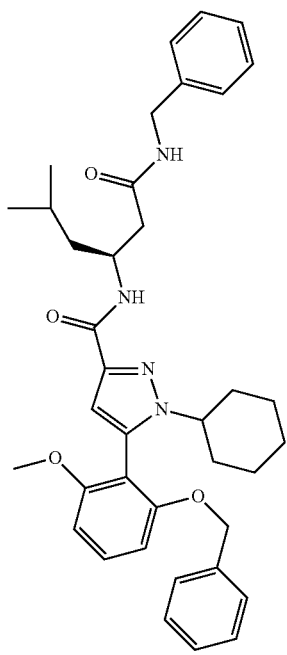
32
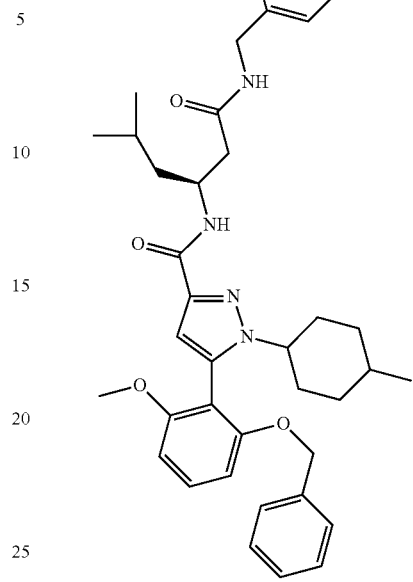
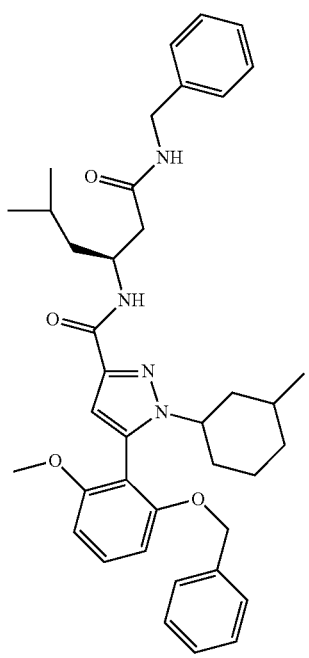
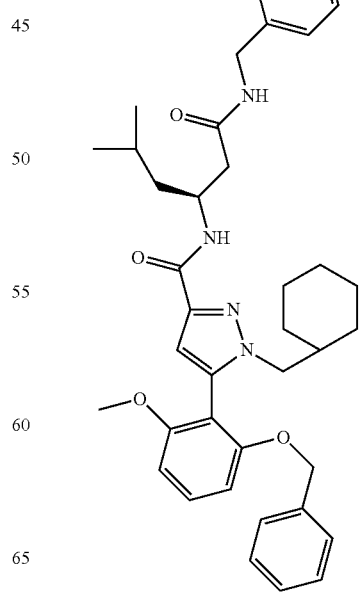

33
-continued
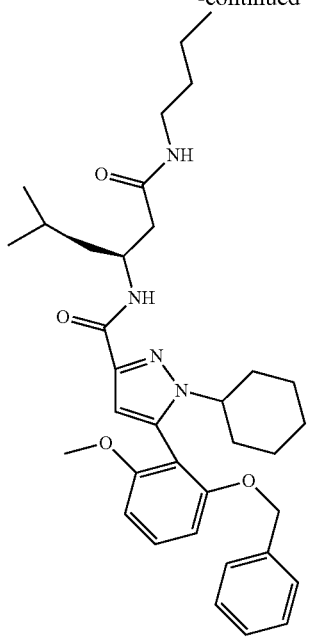
34
-continued
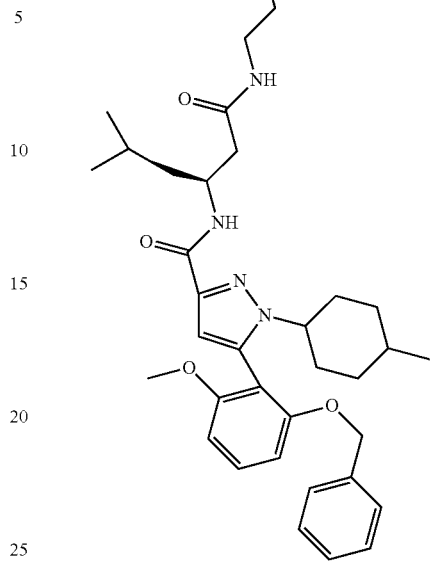
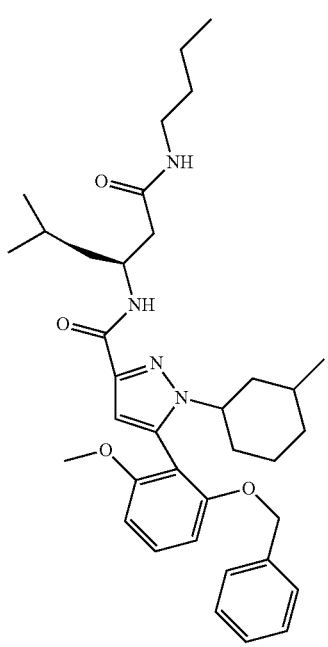
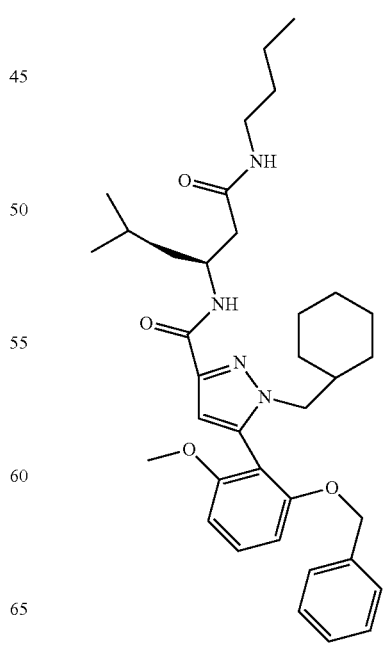

35
-continued
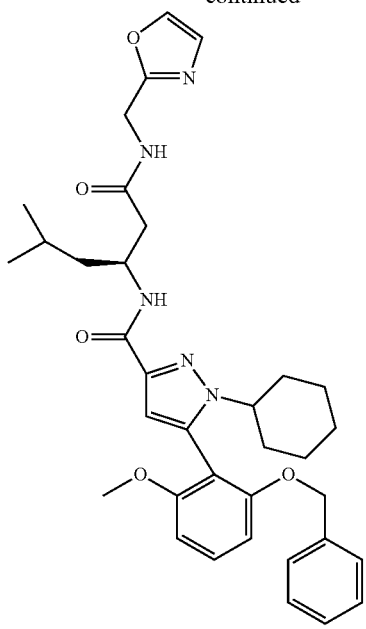
36
-continued
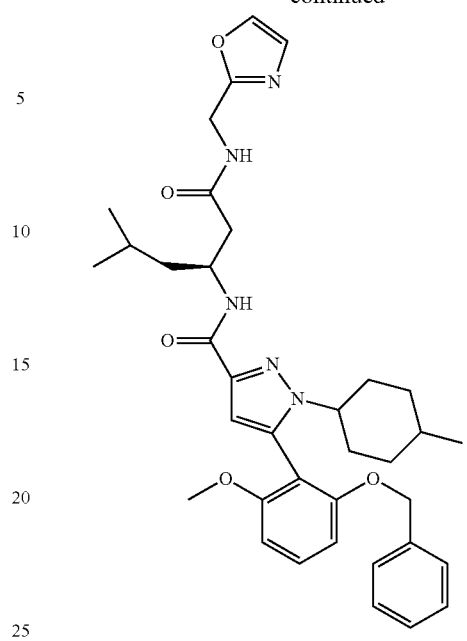
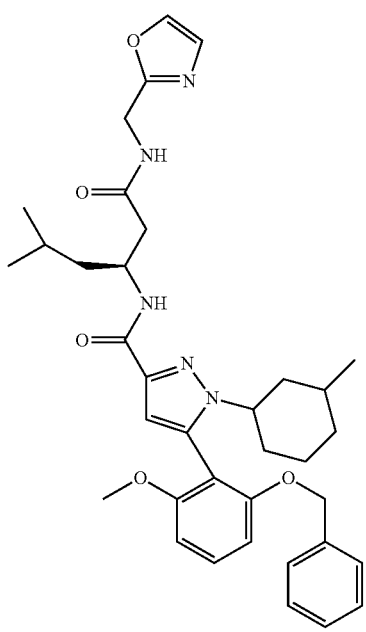
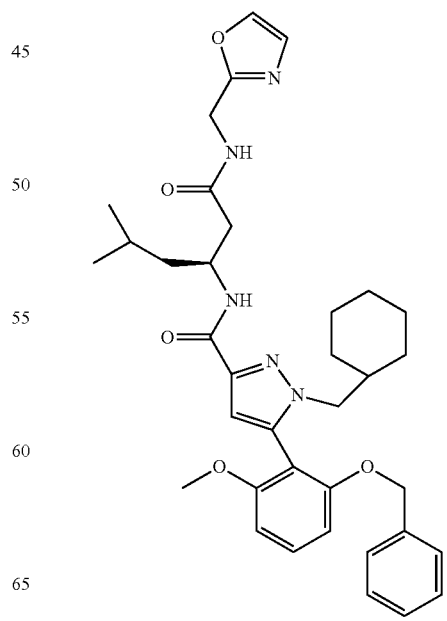

37
-continued
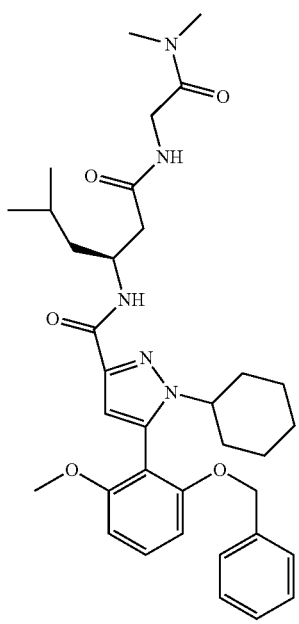
38
-continued
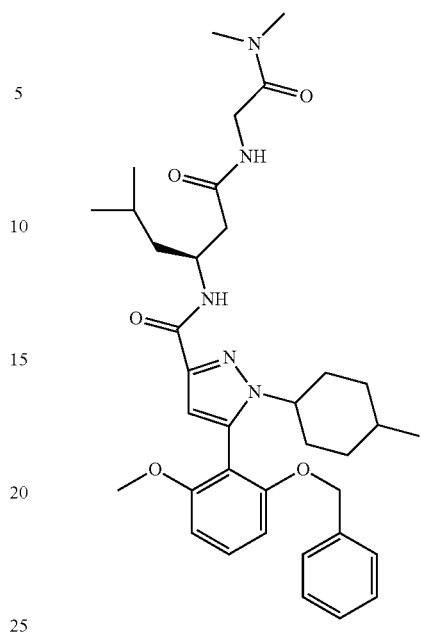
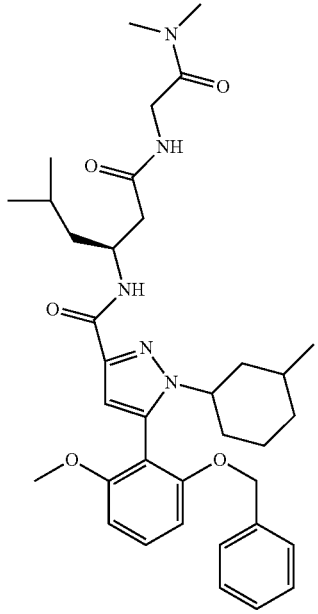
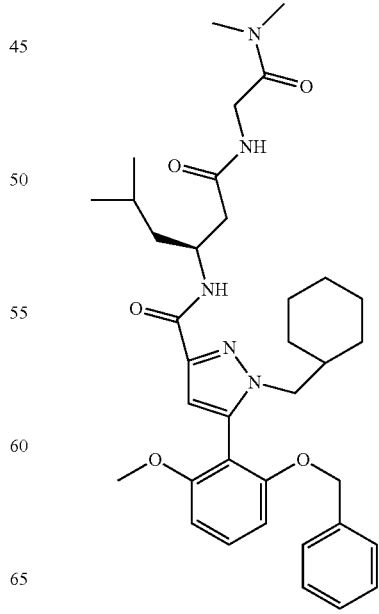

39
-continued
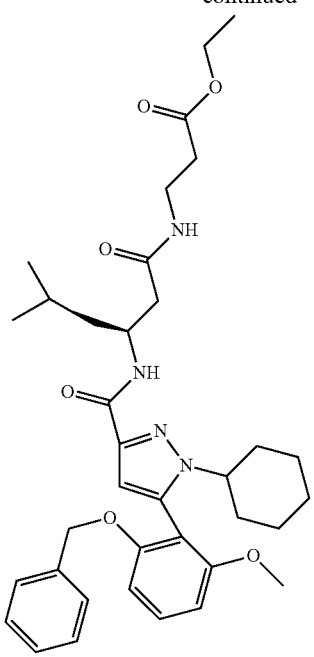
40
-continued
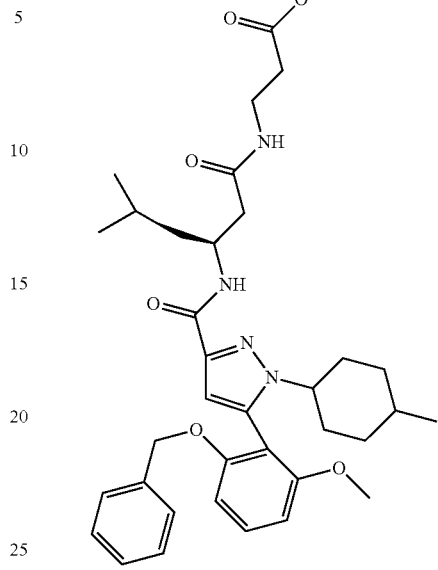
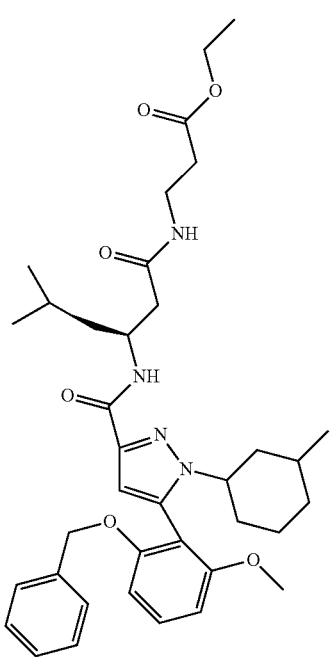
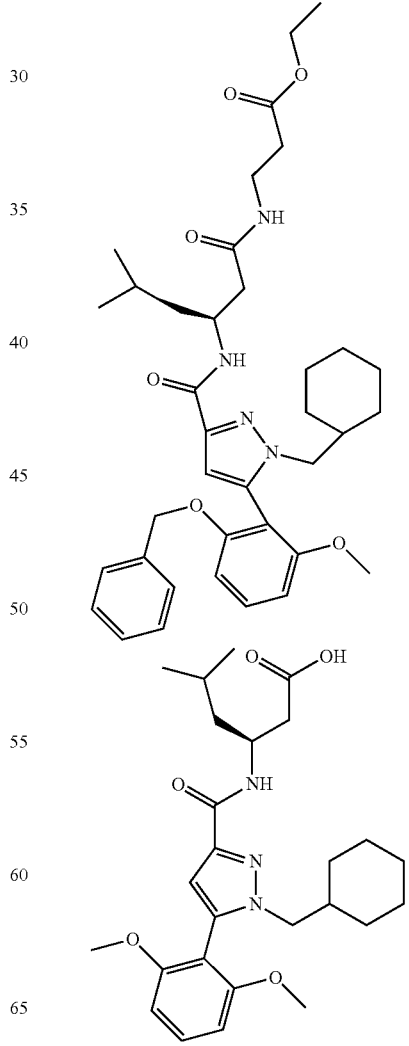

41
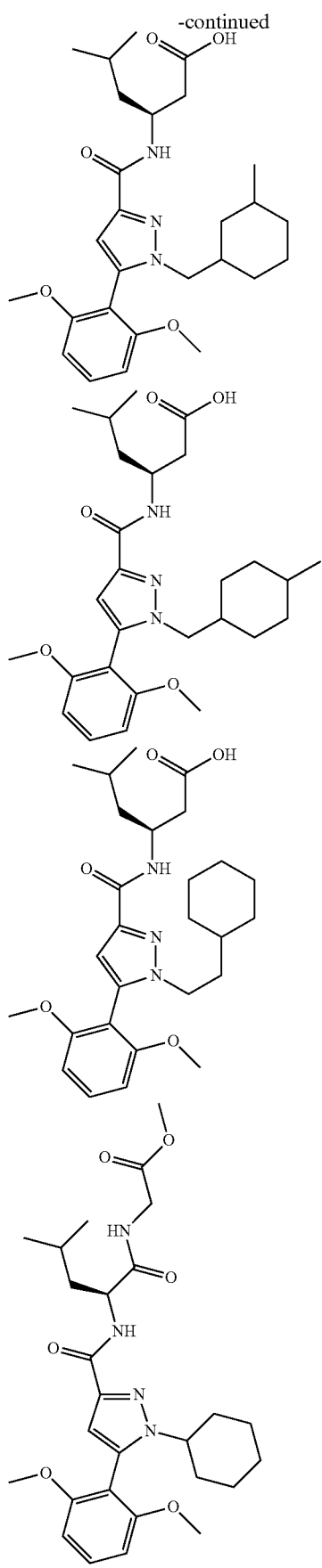
42
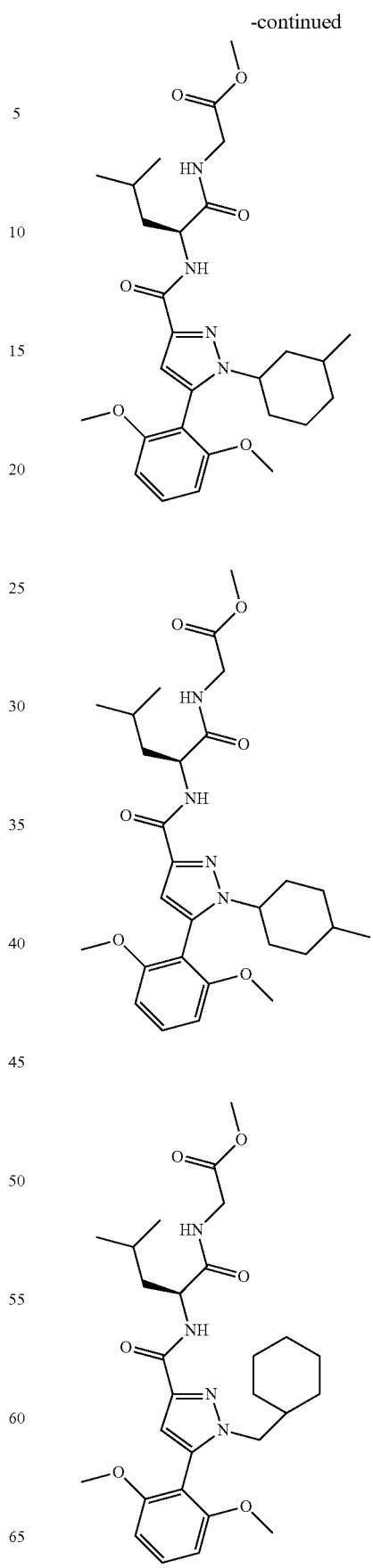

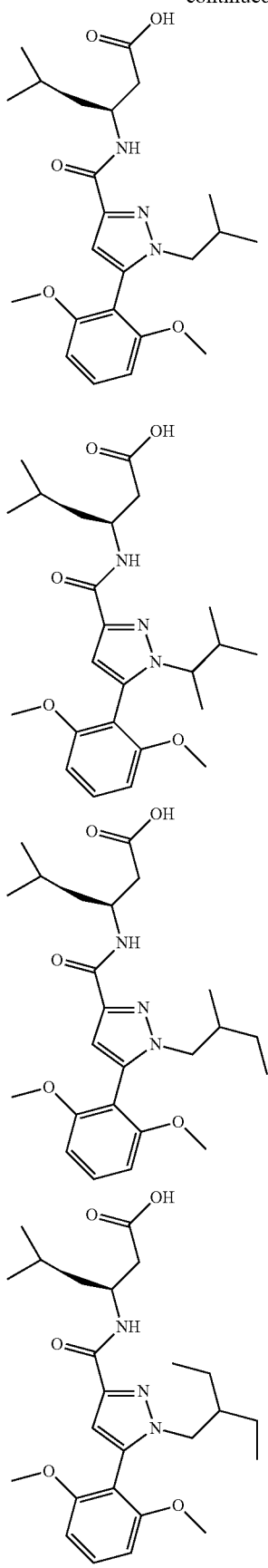
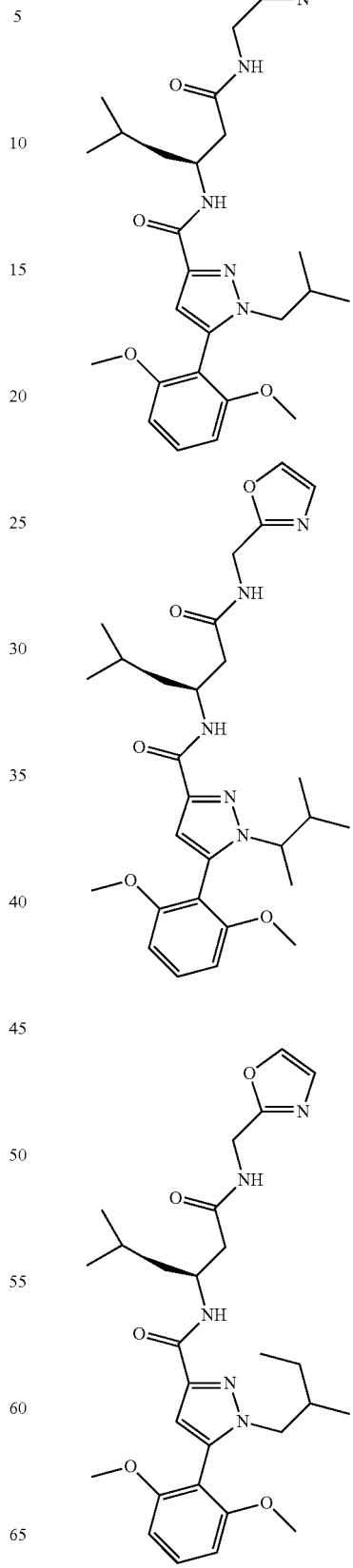

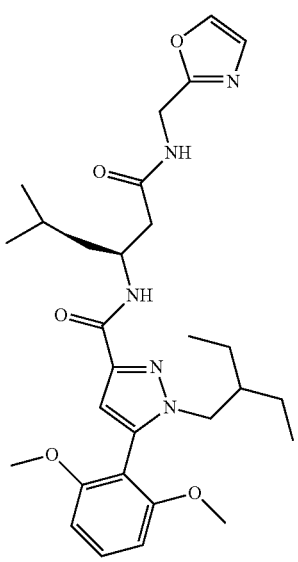
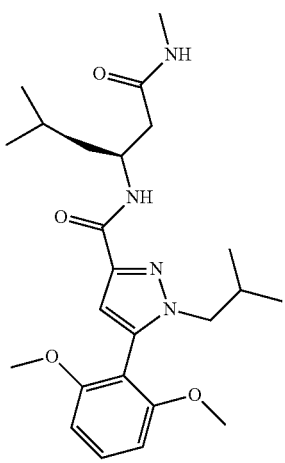
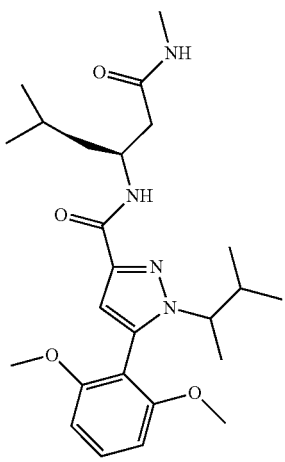
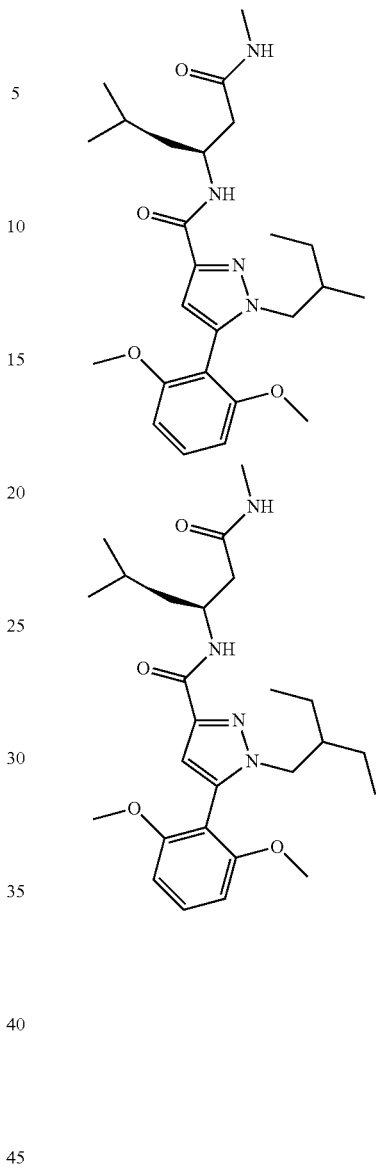
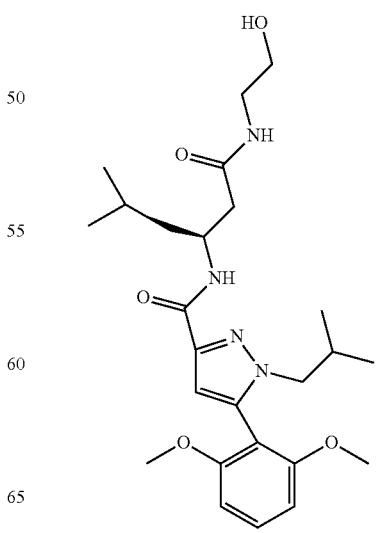

-continued
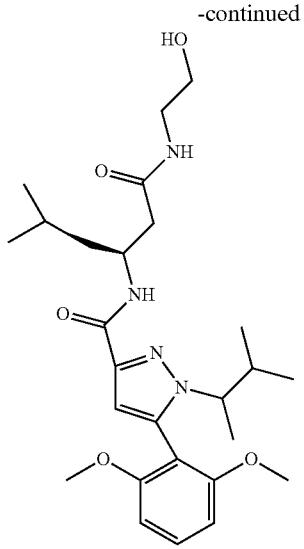
-continued
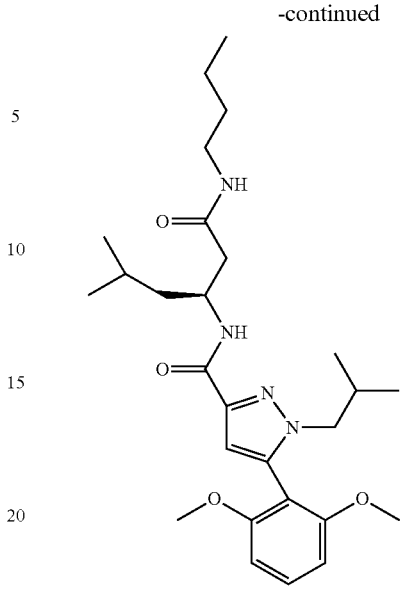

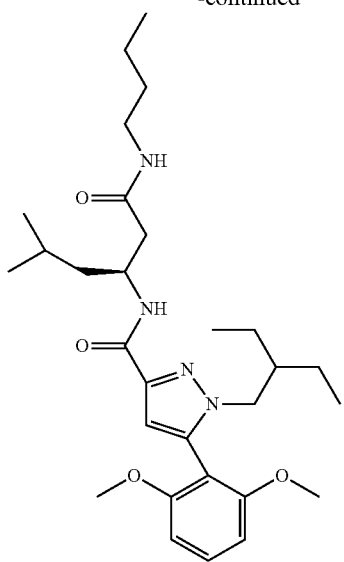
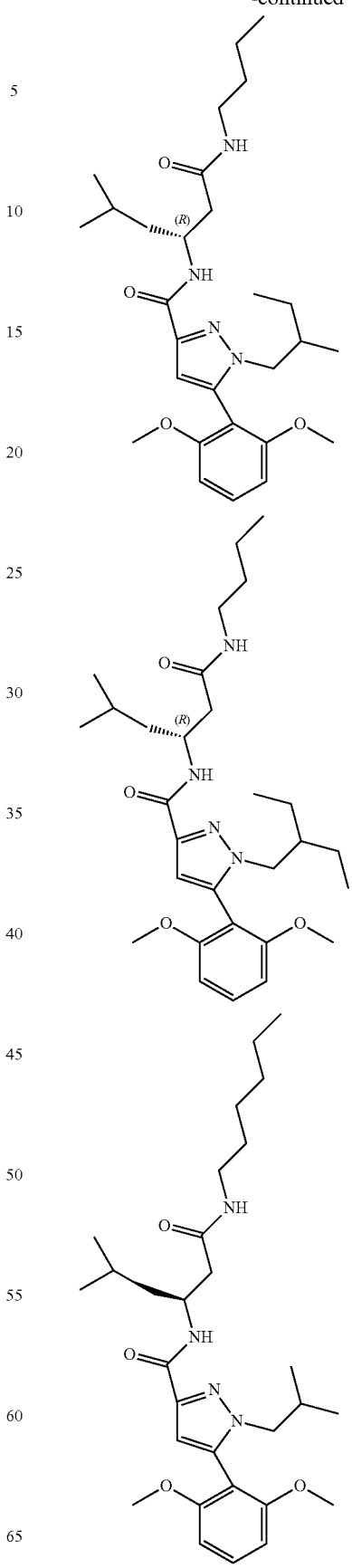

51
-continued
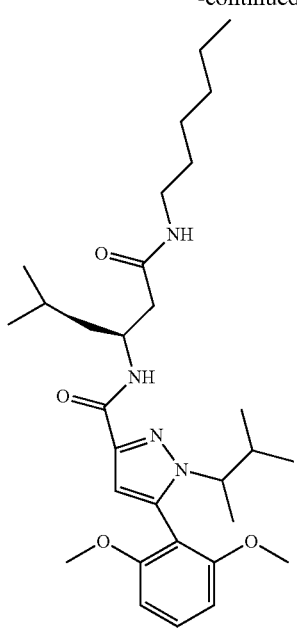
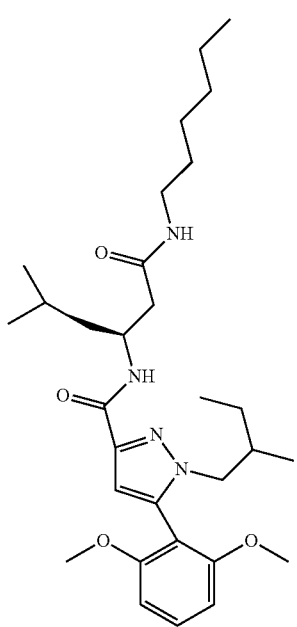
52
-continued
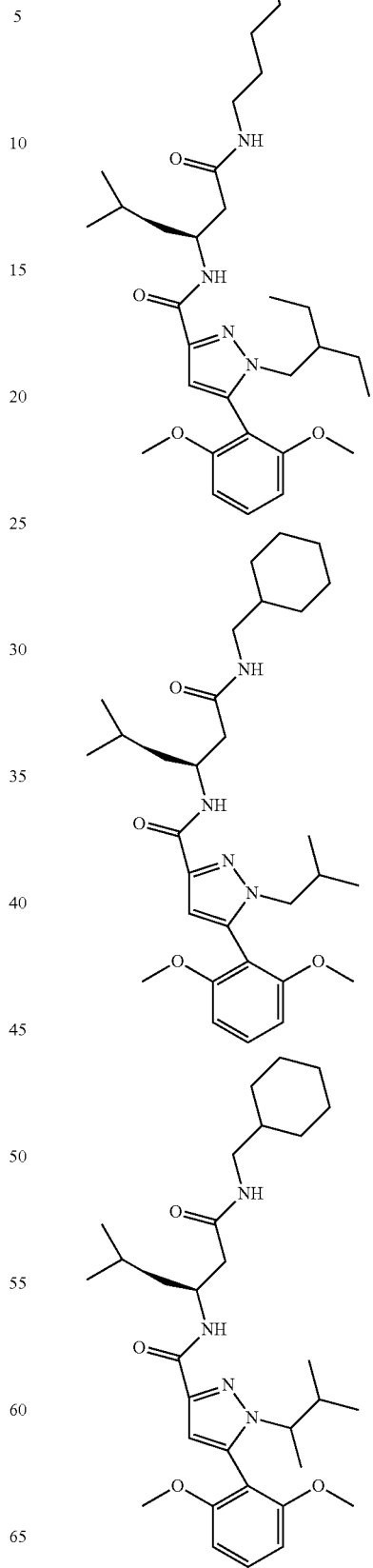

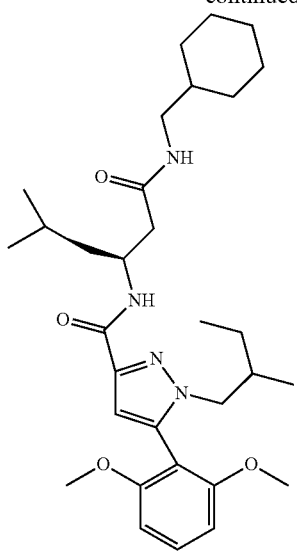
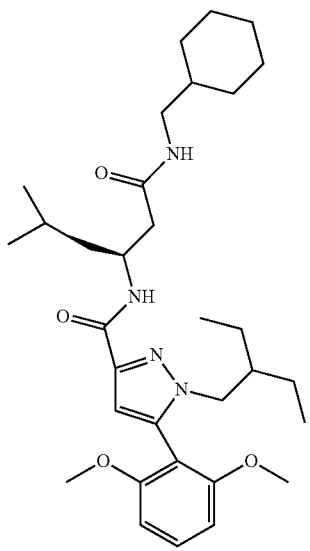
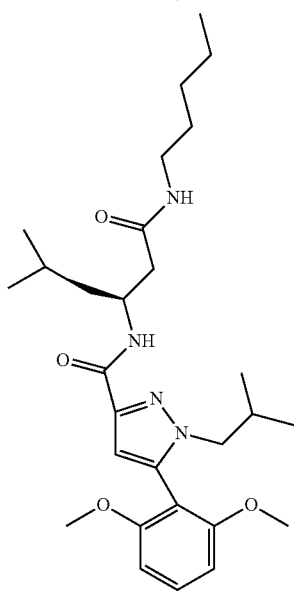
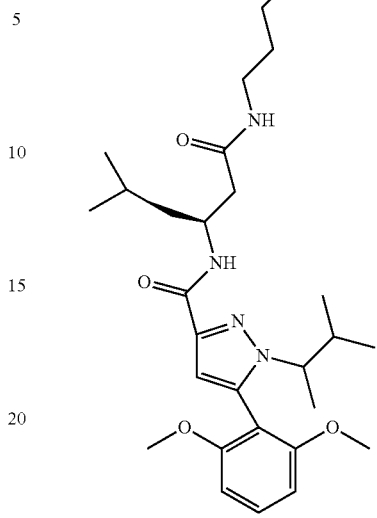
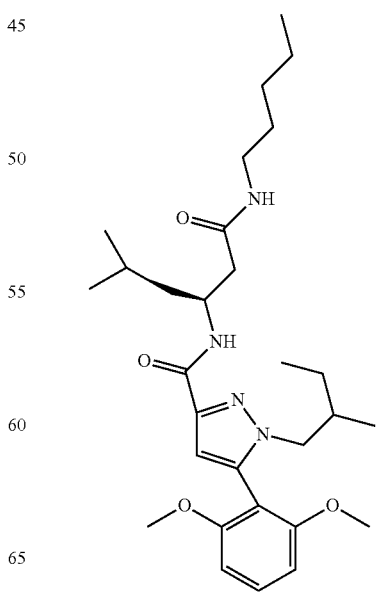

55
-continued
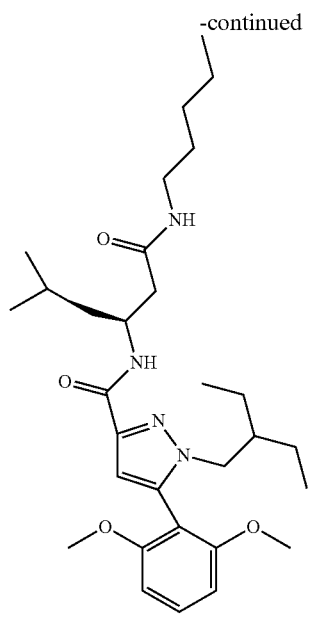
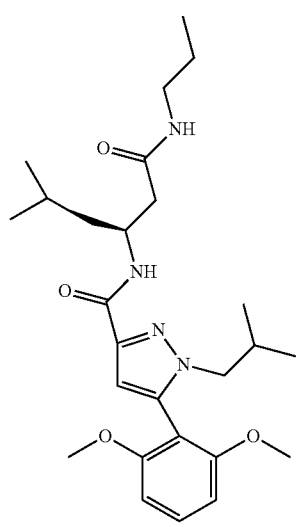
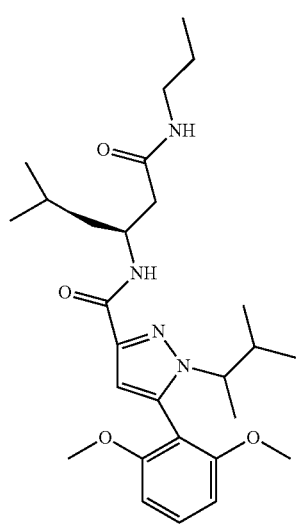
56
-continued
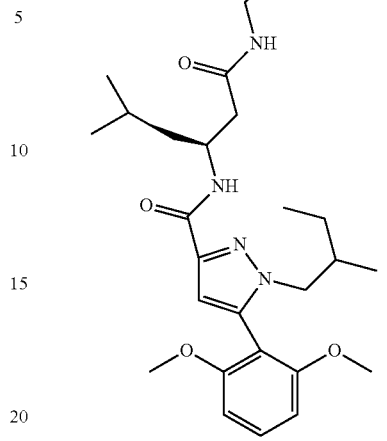
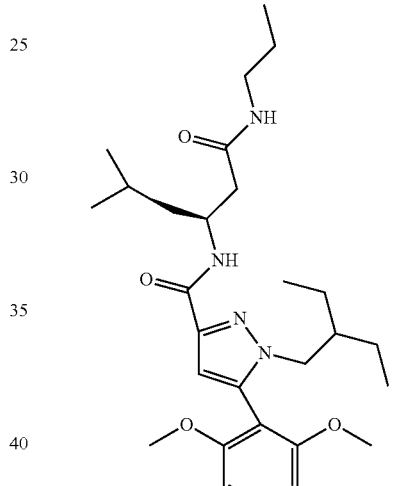
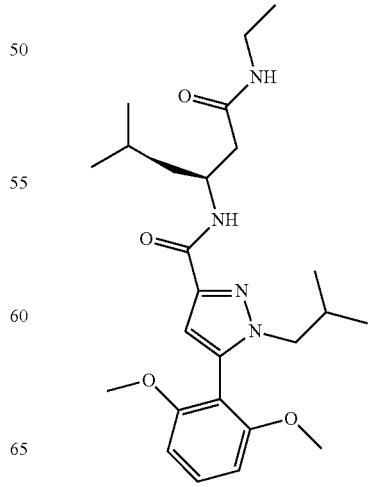

-continued
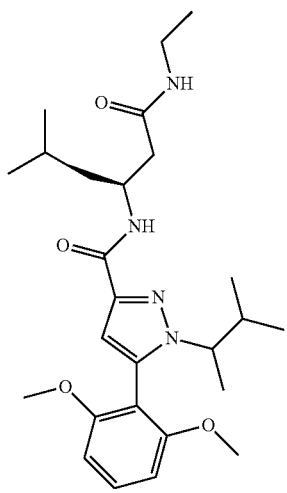
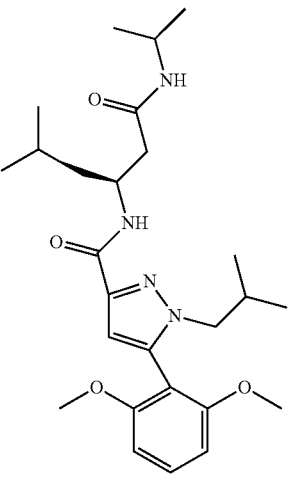
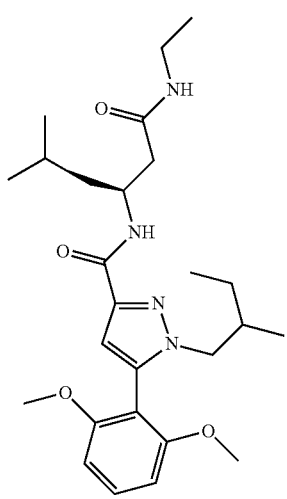
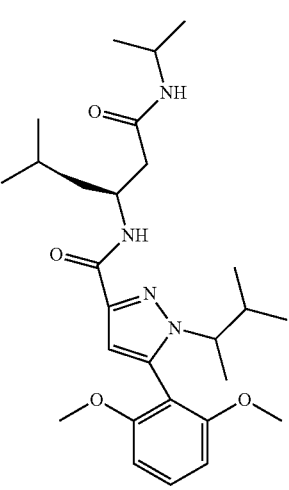
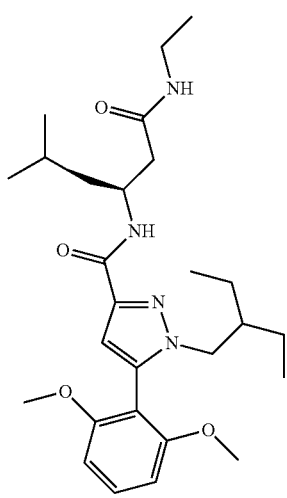
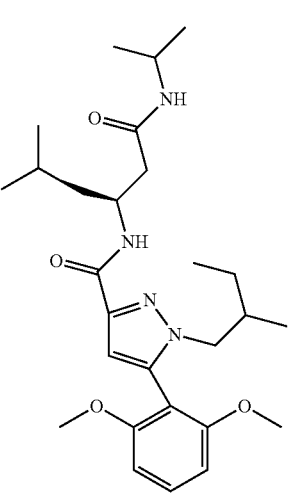

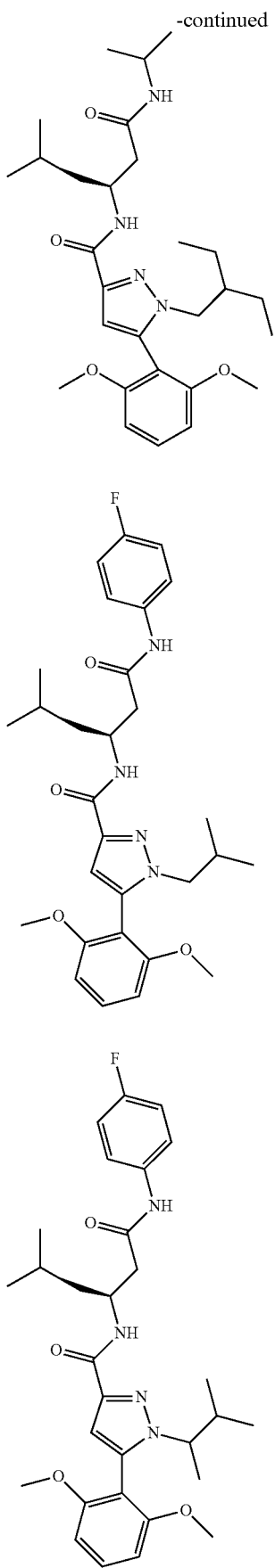
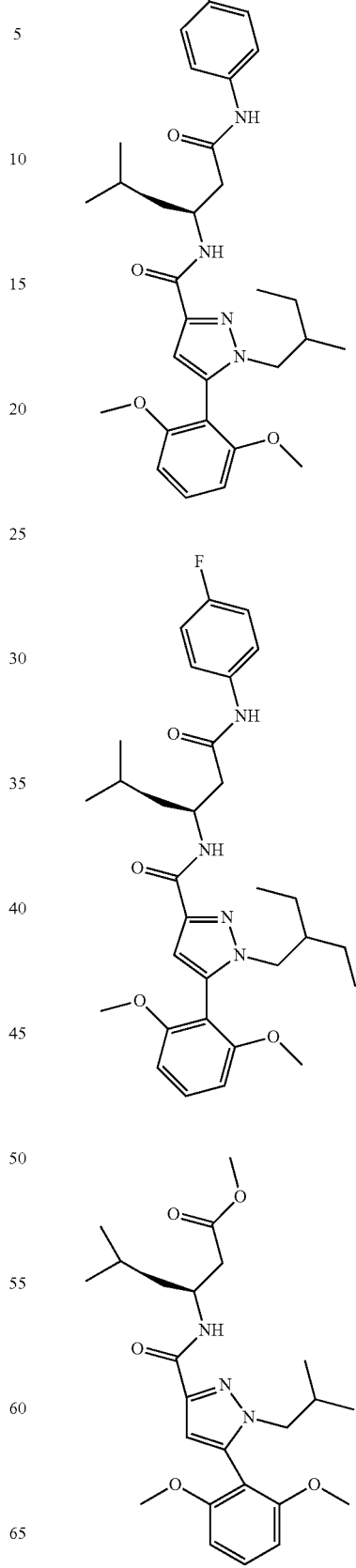

61
-continued
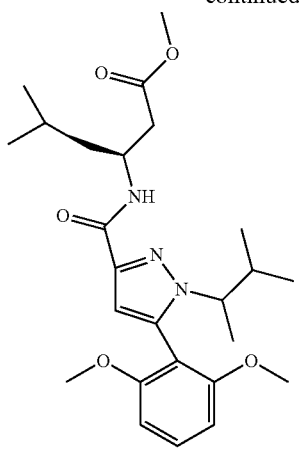
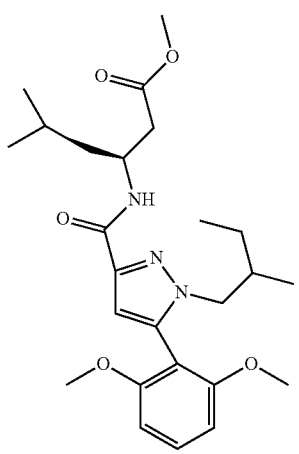
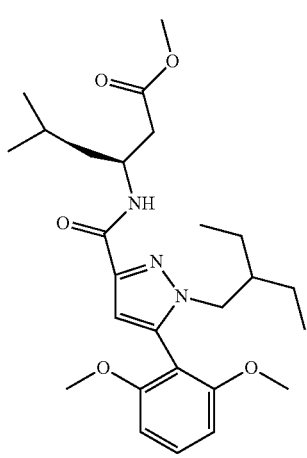
62
-continued
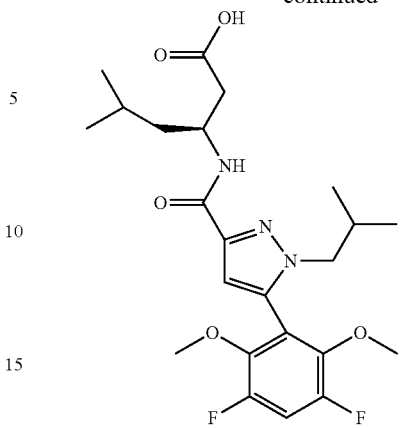
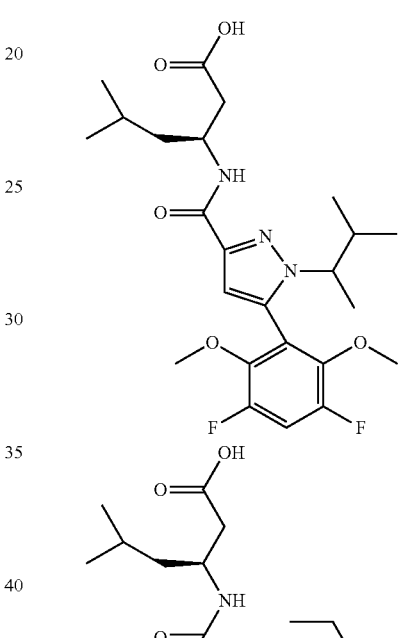
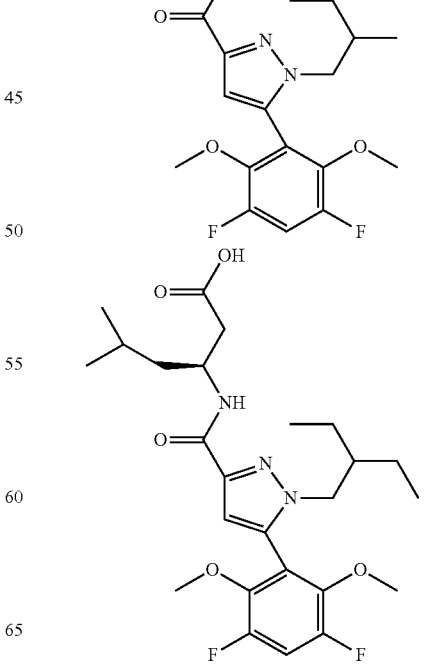

63
-continued
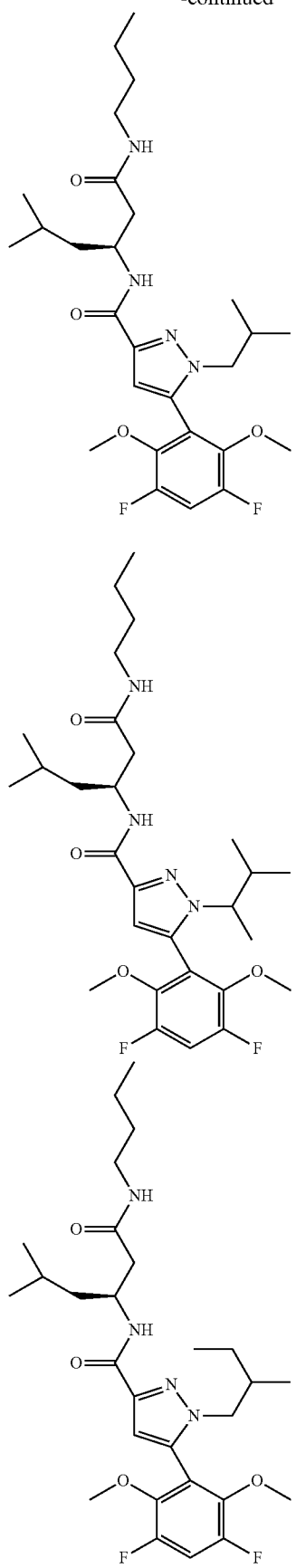
64
-continued
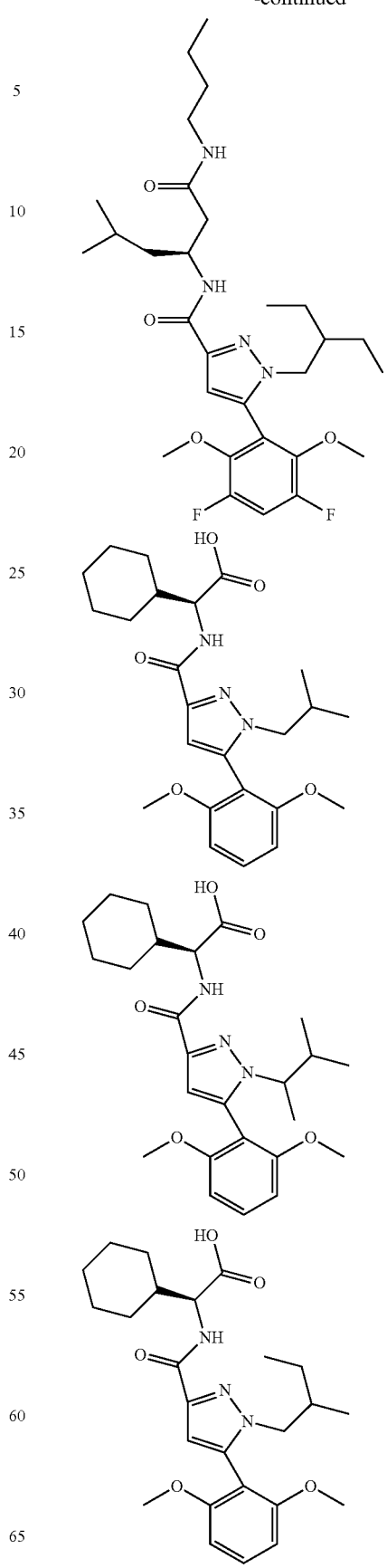

65
-continued
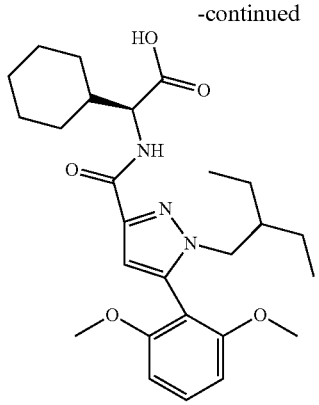
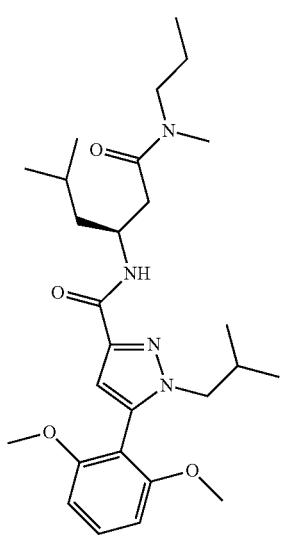
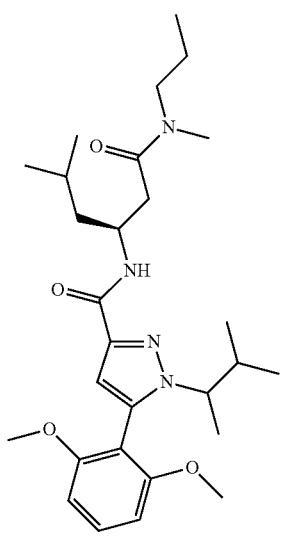
66
-continued
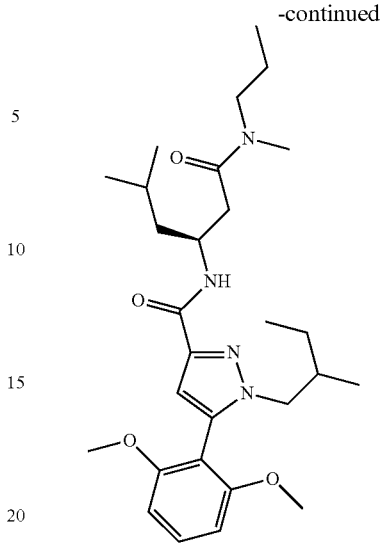
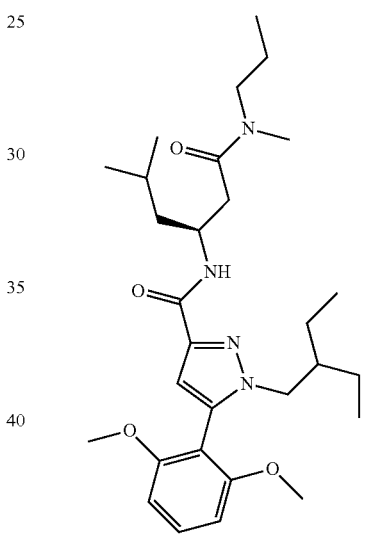
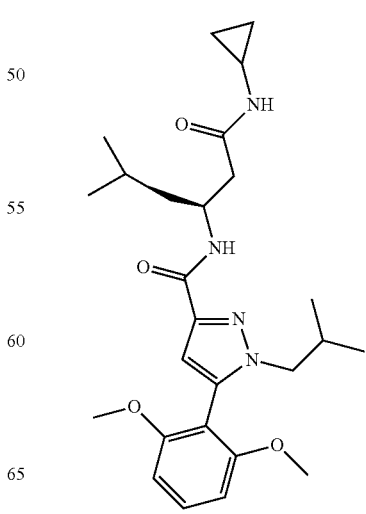

67
-continued
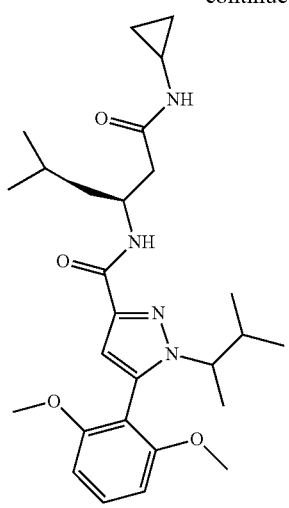
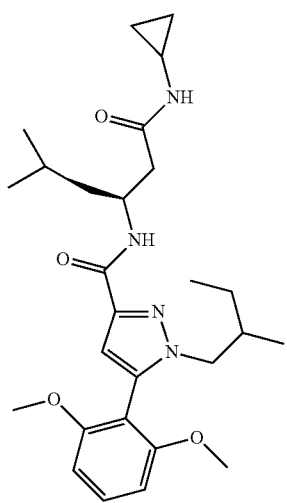
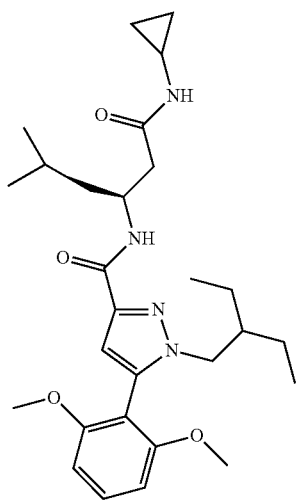
68
-continued
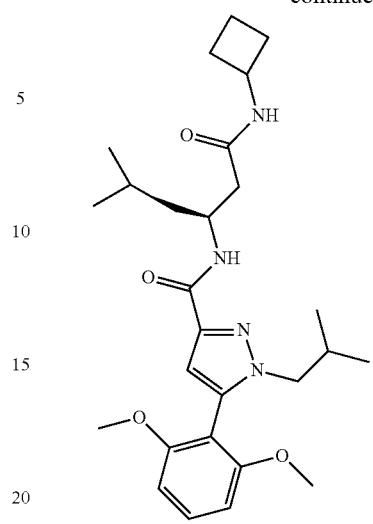
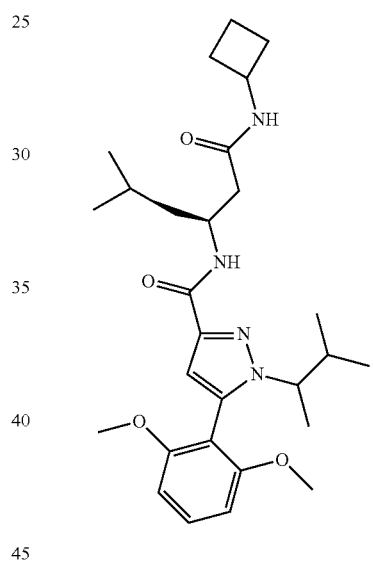
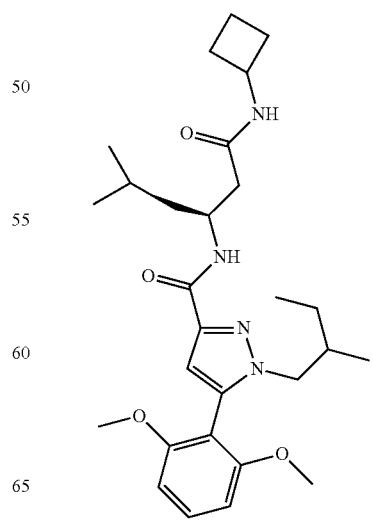

69
-continued
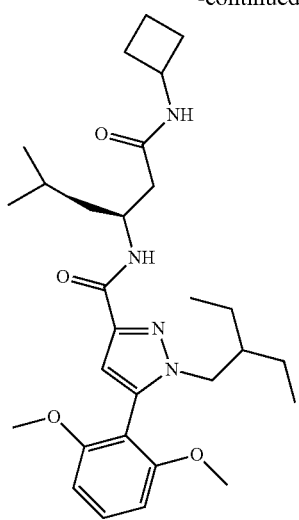
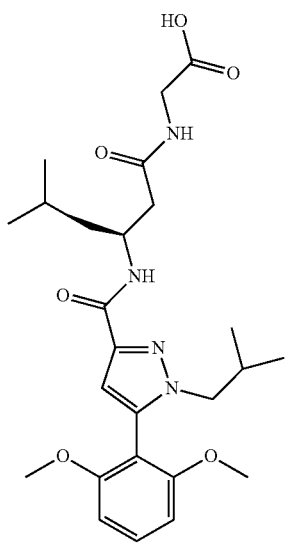
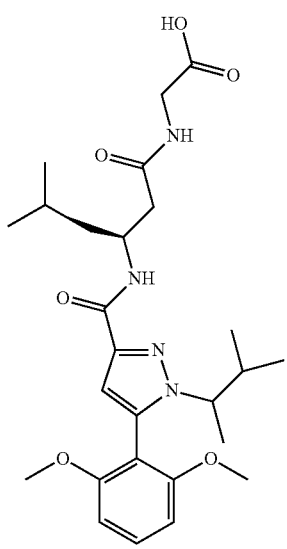
70
-continued
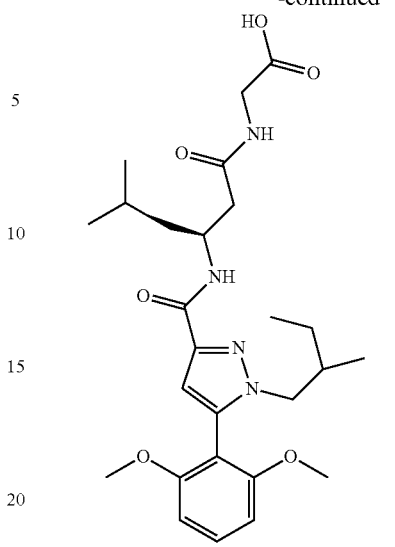
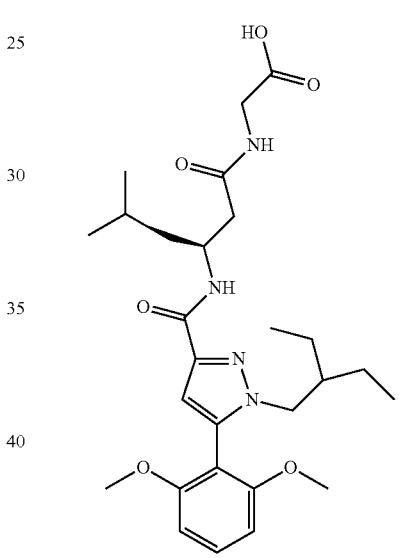
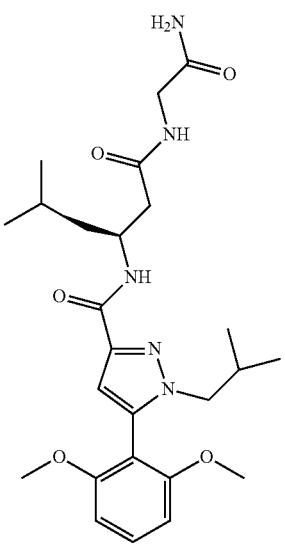

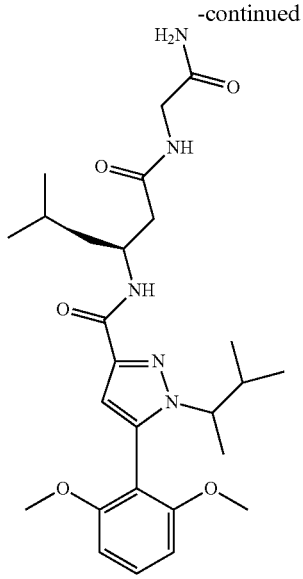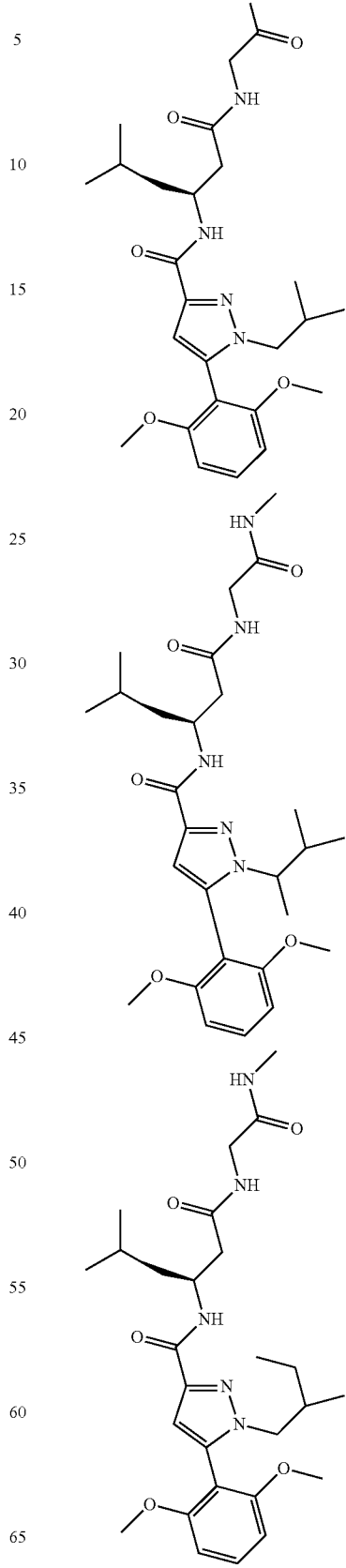

73
-continued
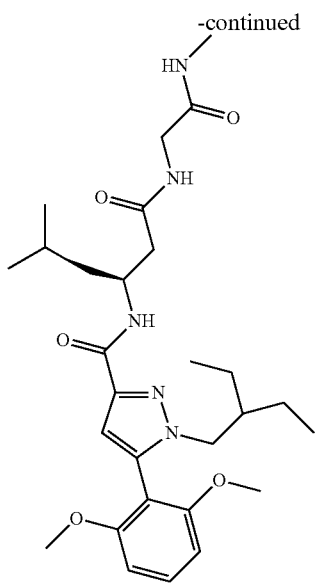
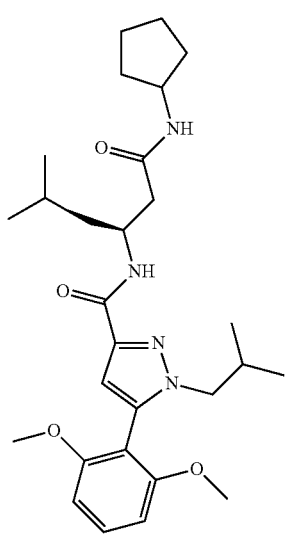
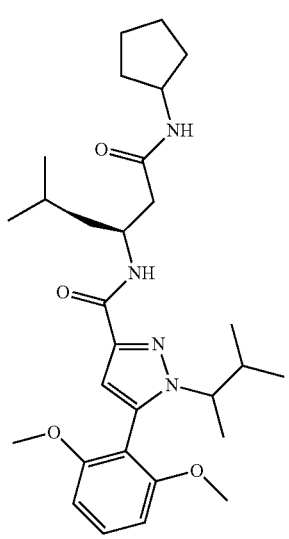
74
-continued
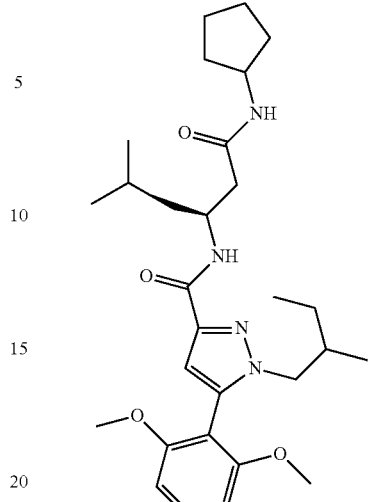
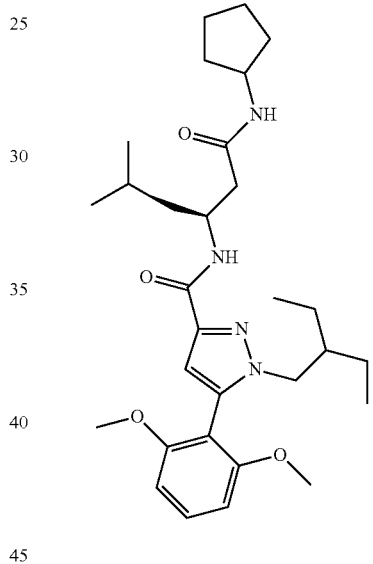
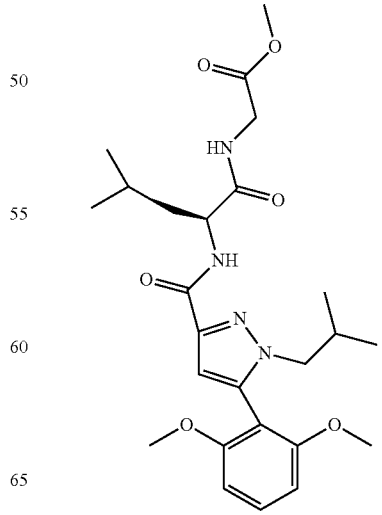

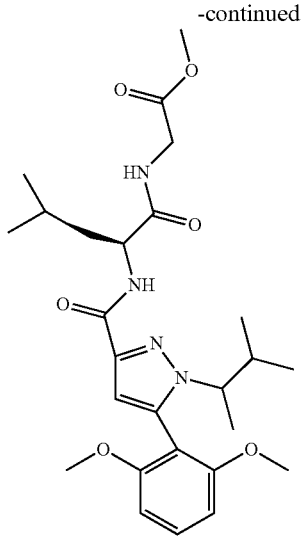
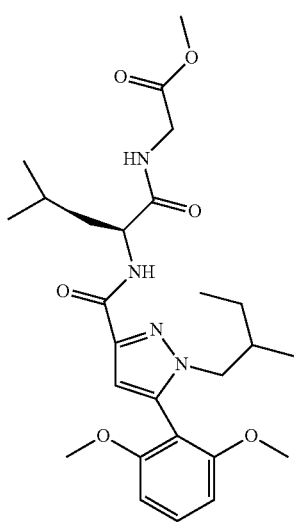
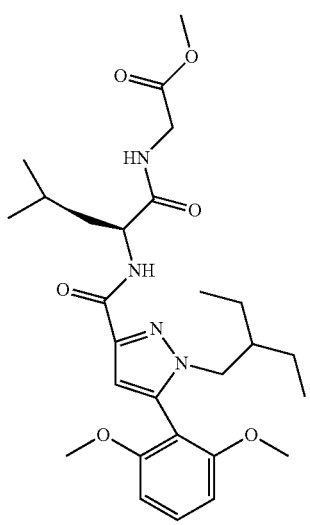
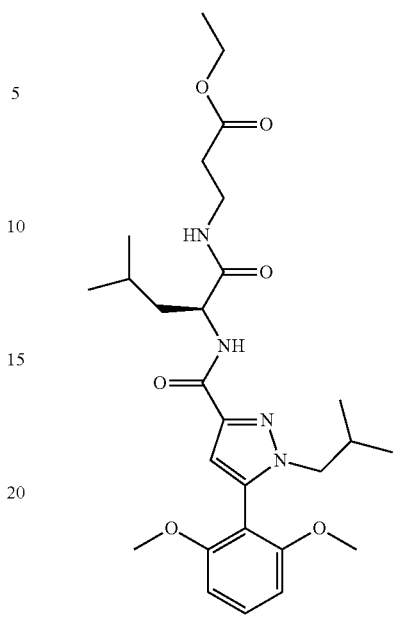

77
-continued
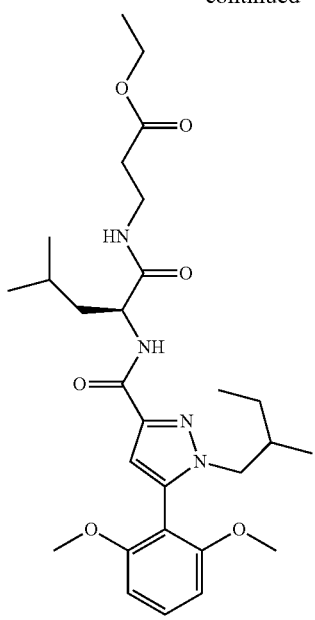
78
-continued
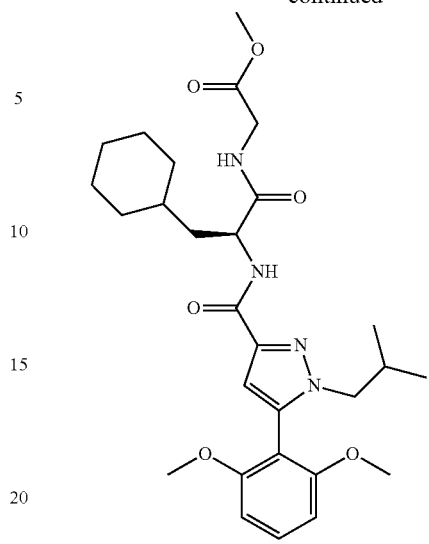
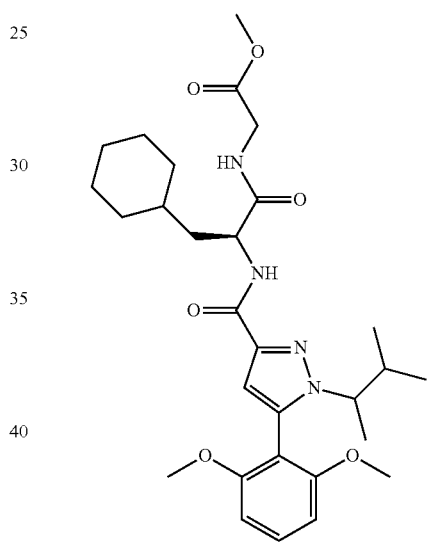
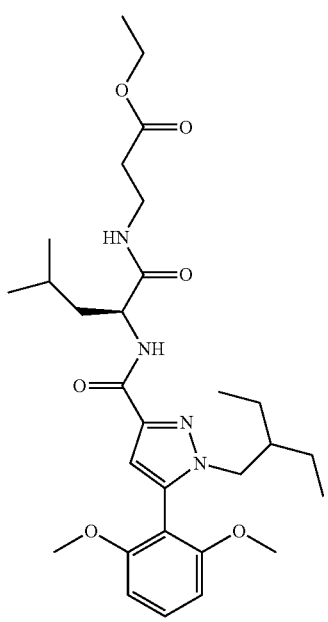
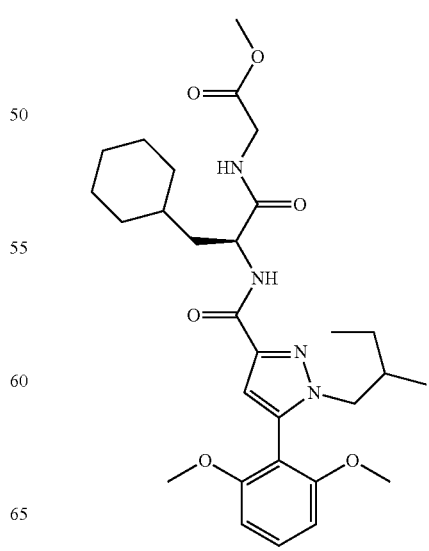

79
-continued
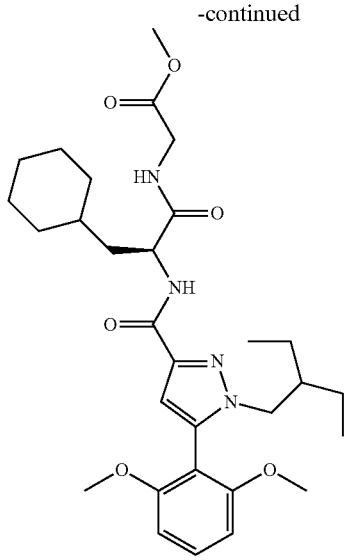
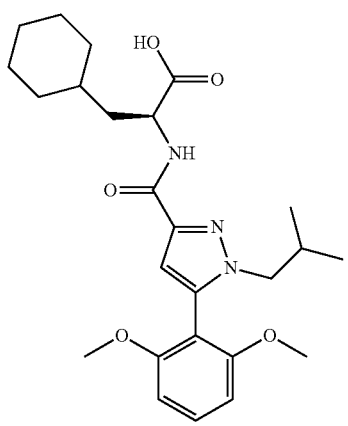
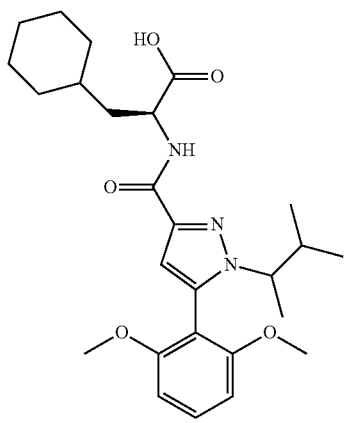
80
-continued
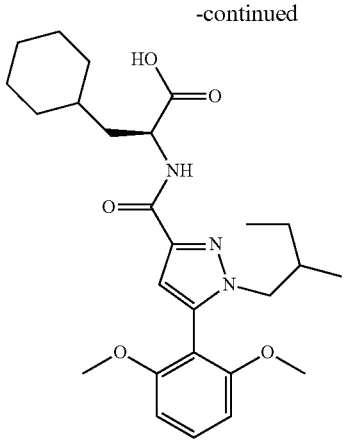
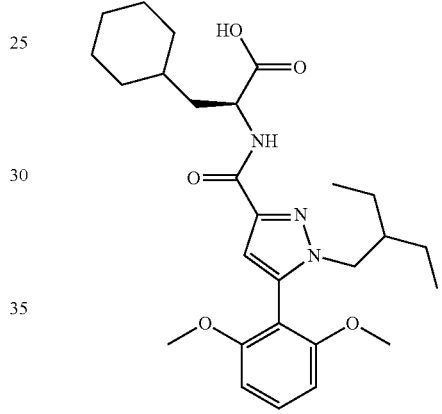
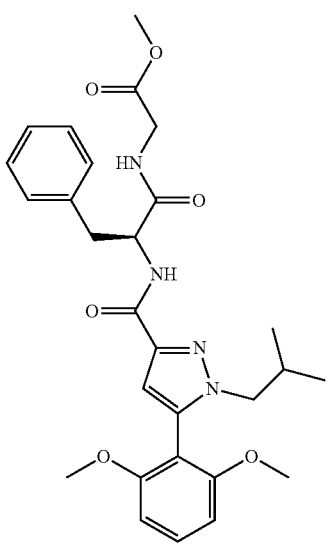

81
-continued
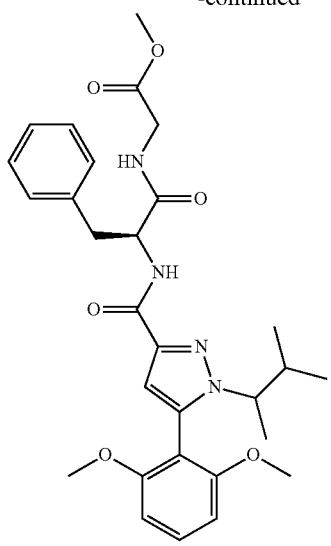
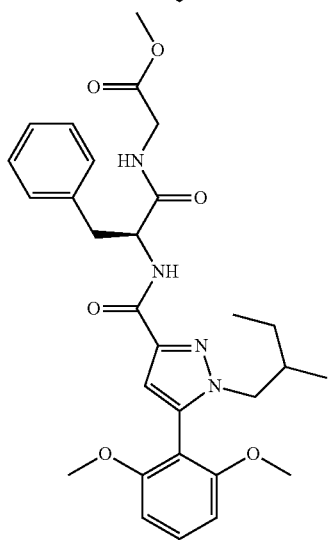
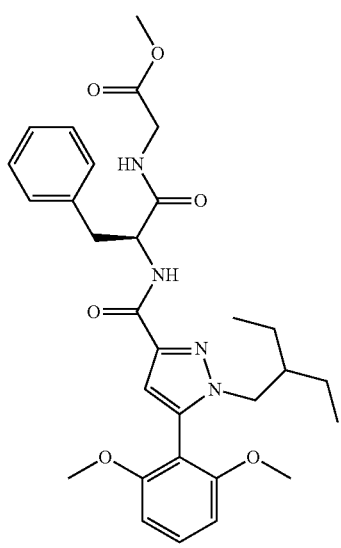
82
-continued
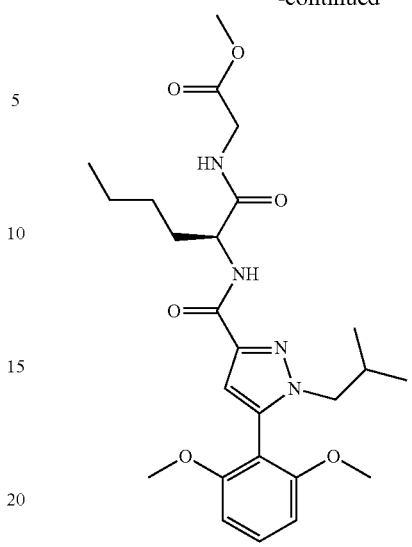
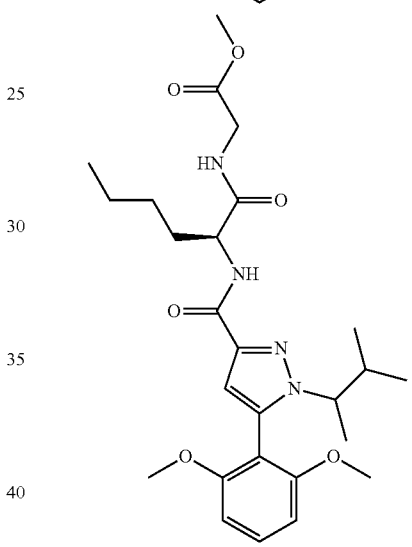
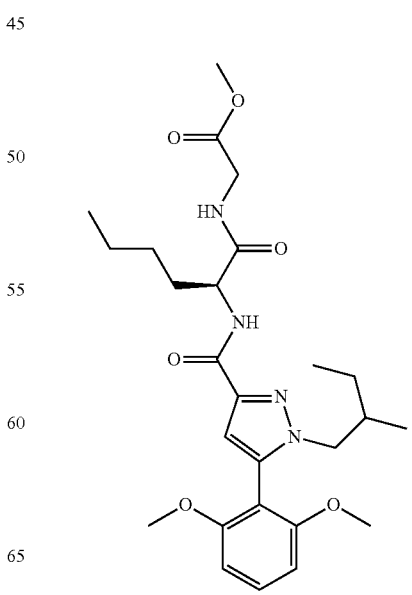

83
-continued
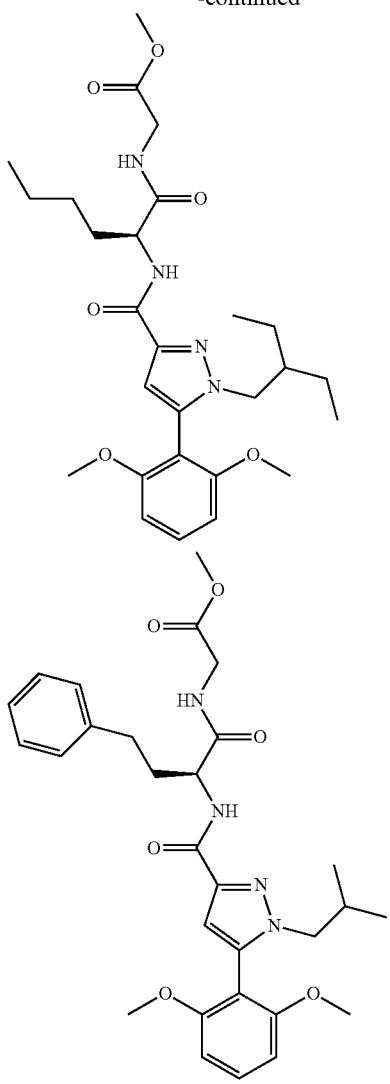
84
-continued
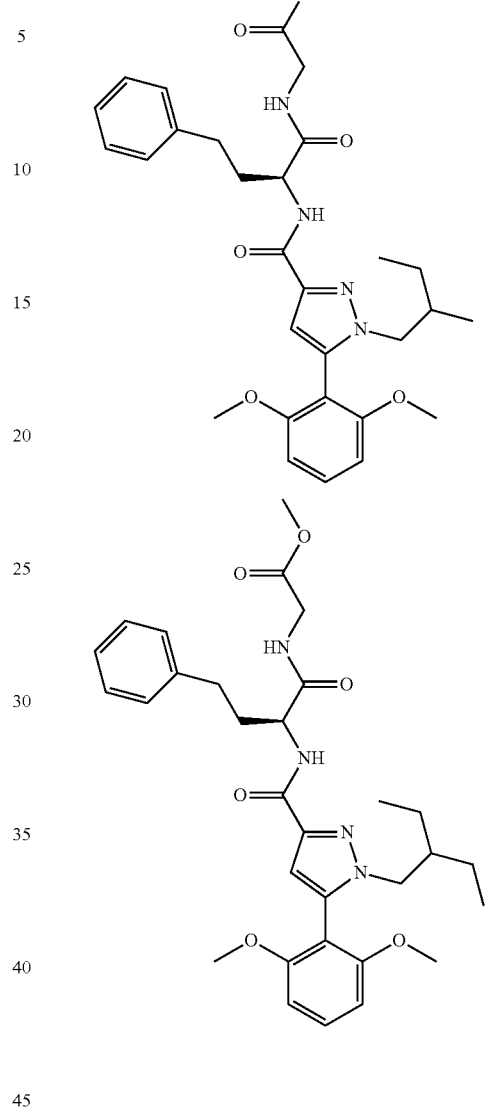
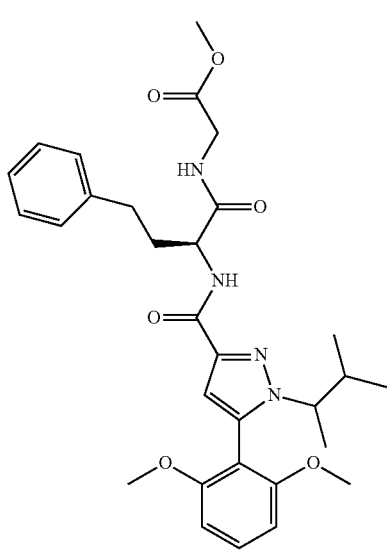
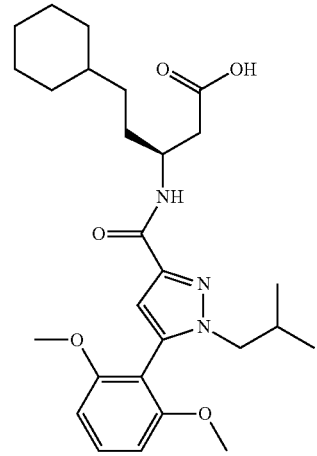

85
-continued
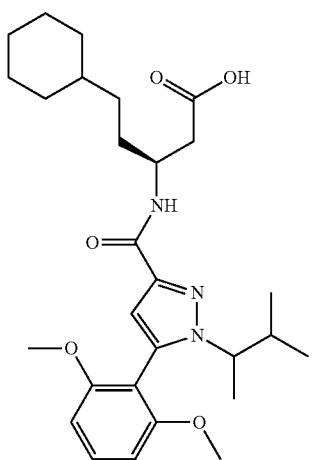
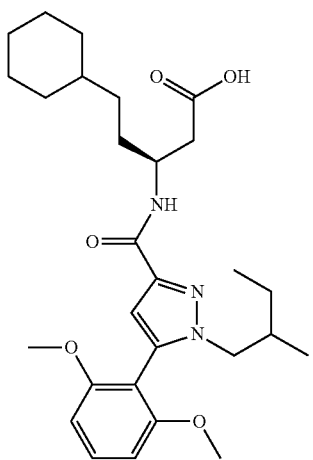
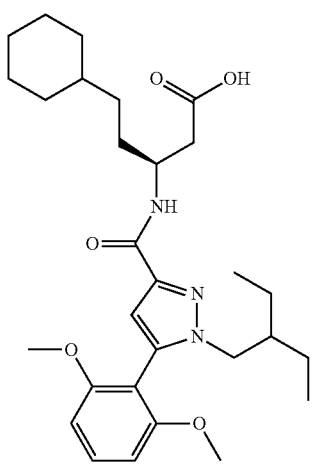
86
-continued
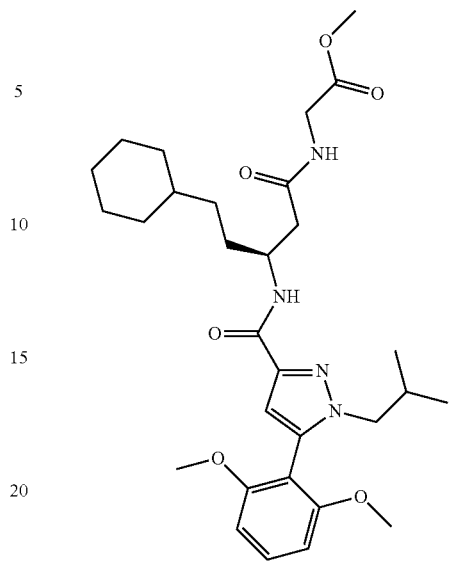
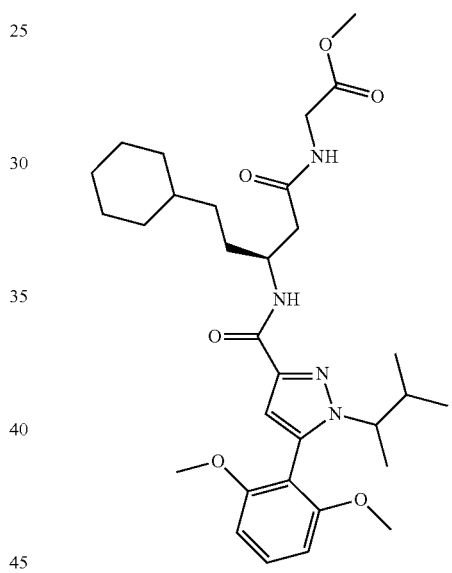
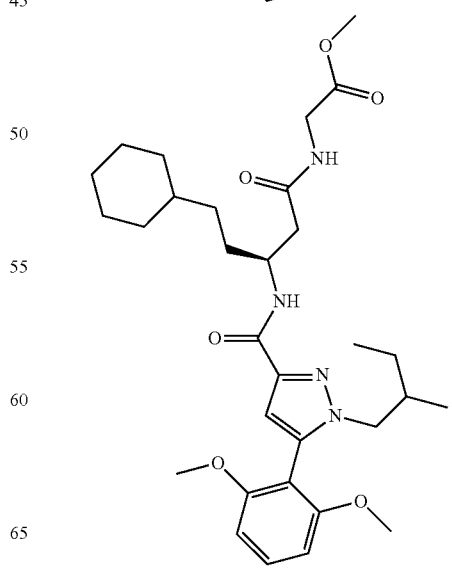

87
-continued
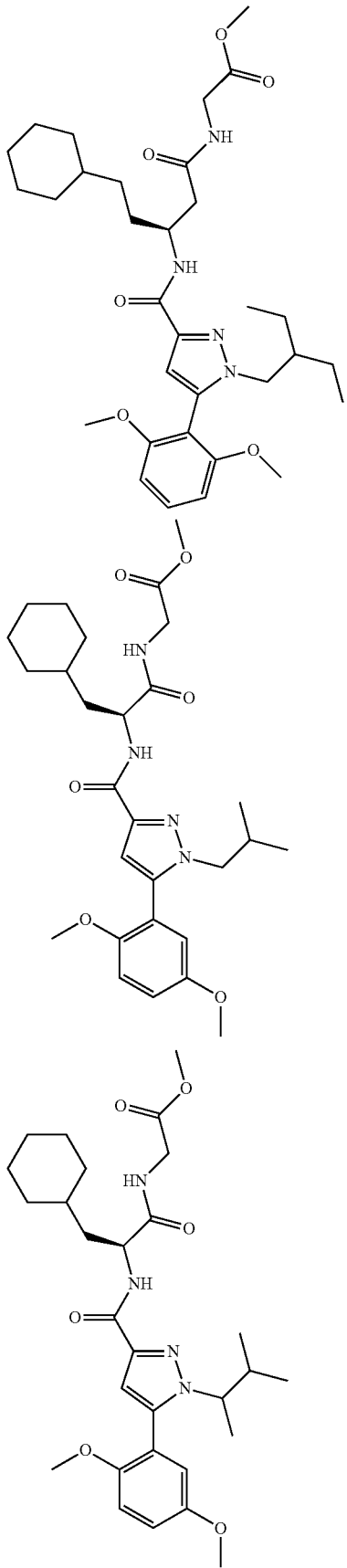
88
-continued
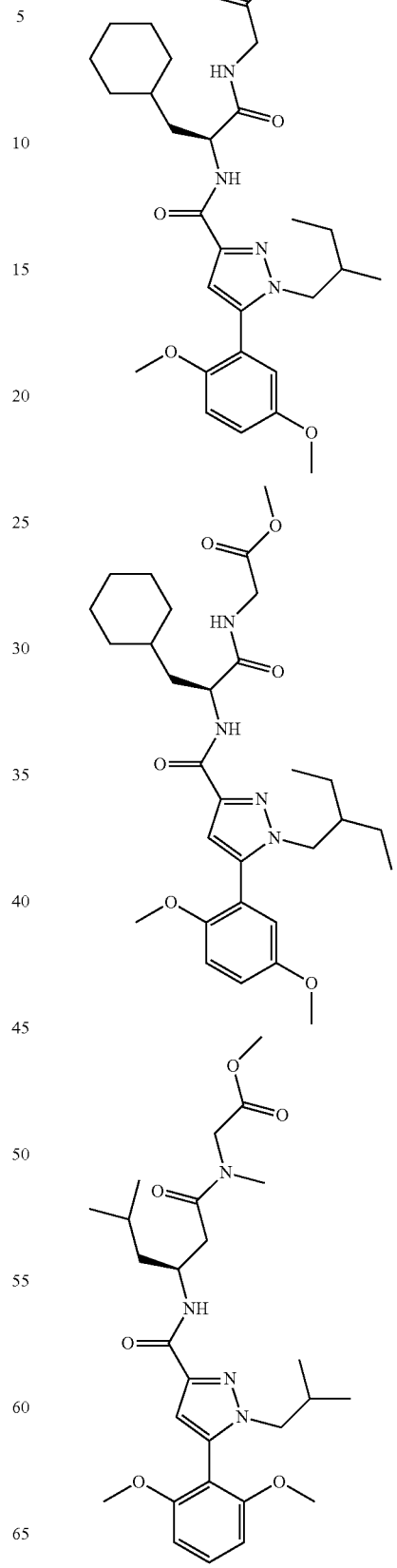

89
-continued
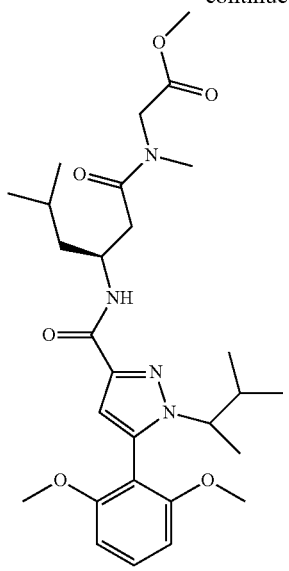
90
-continued
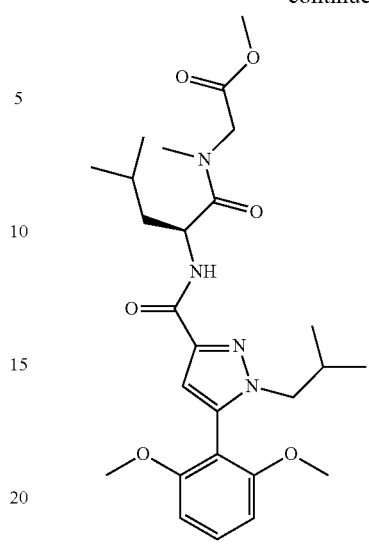
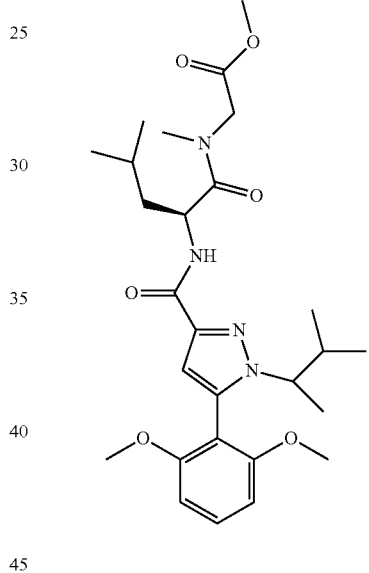
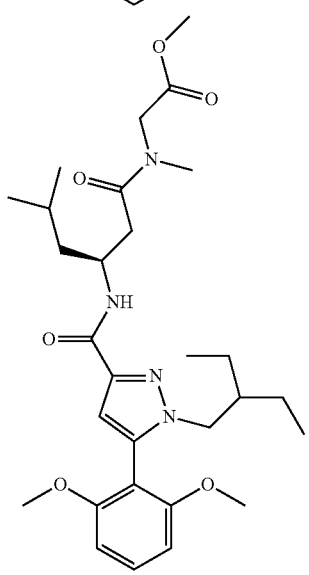
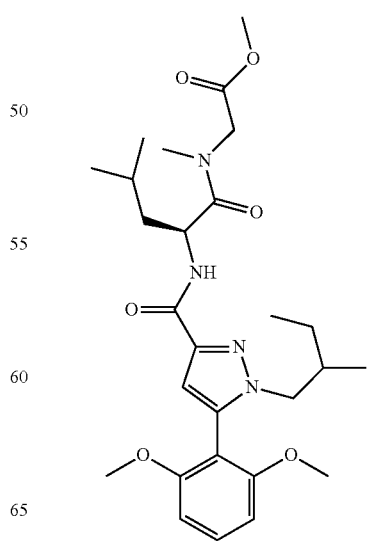

91
-continued
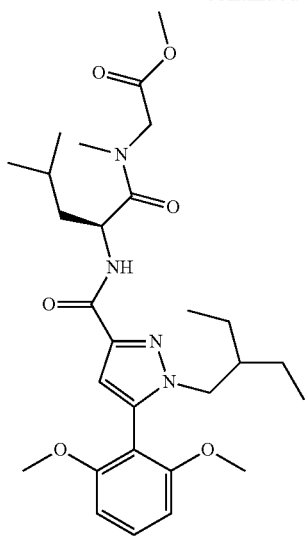
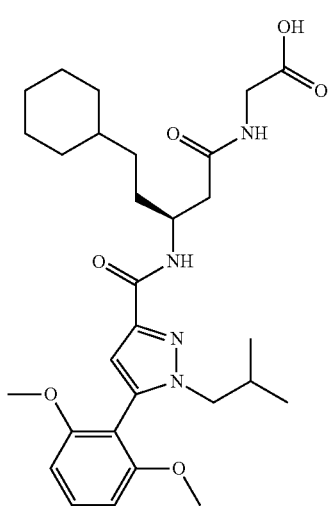
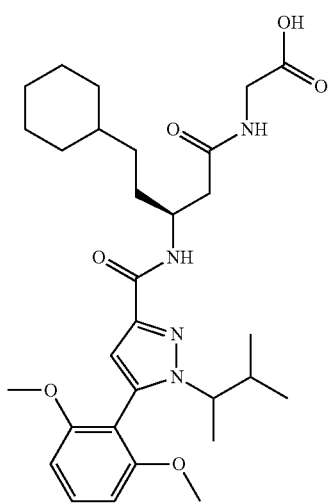
92
-continued
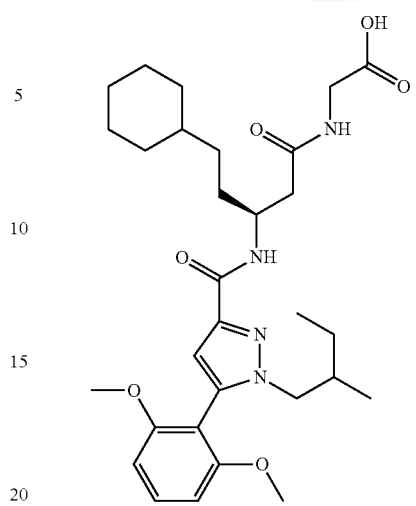
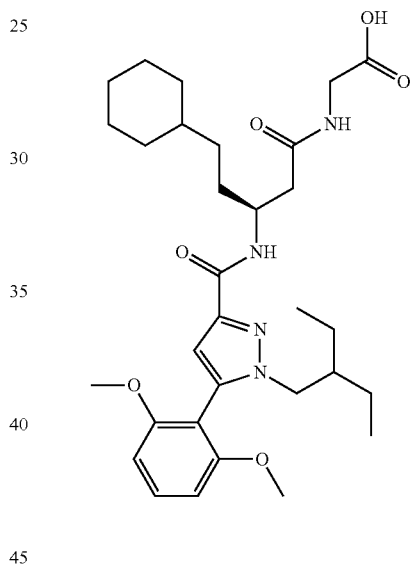
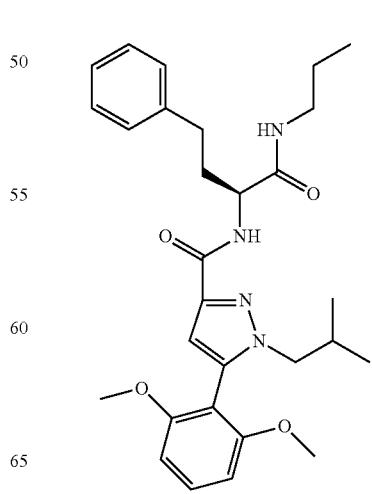

93
-continued
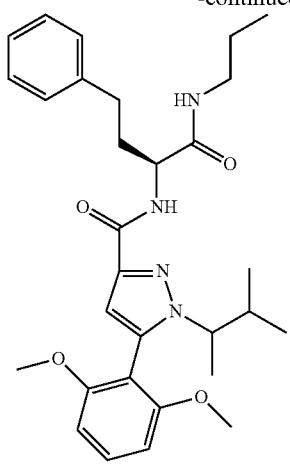
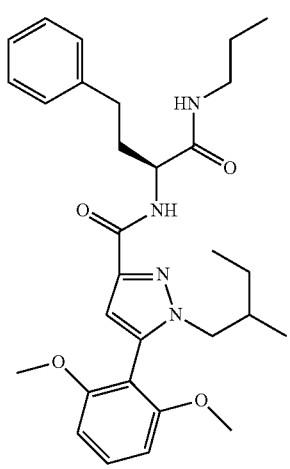
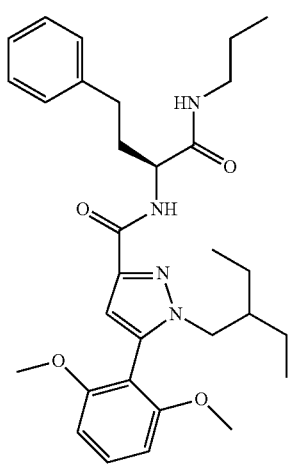
94
-continued
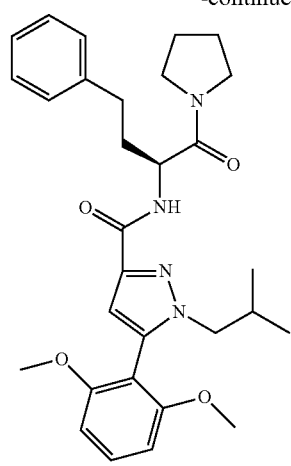
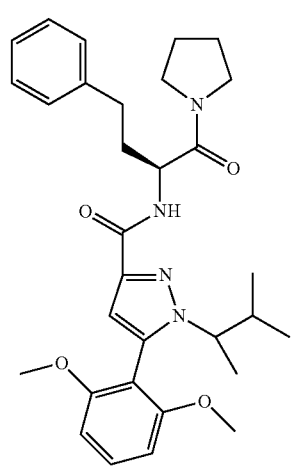
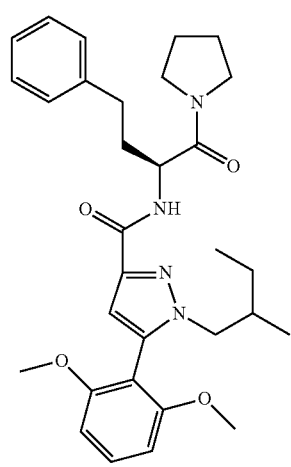

95
-continued
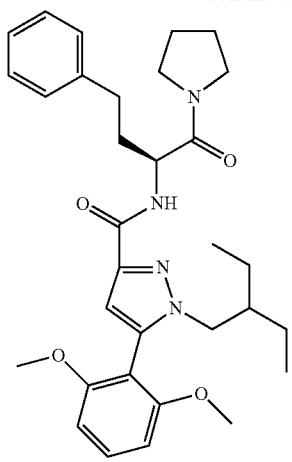
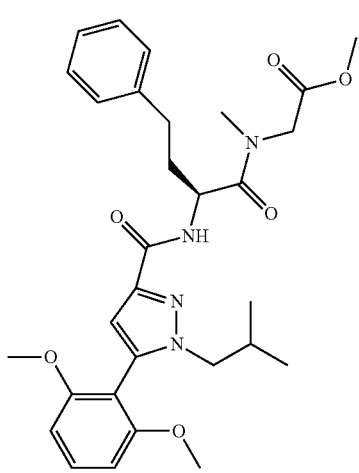
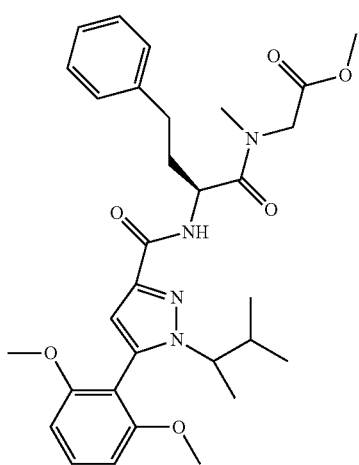
96
-continued
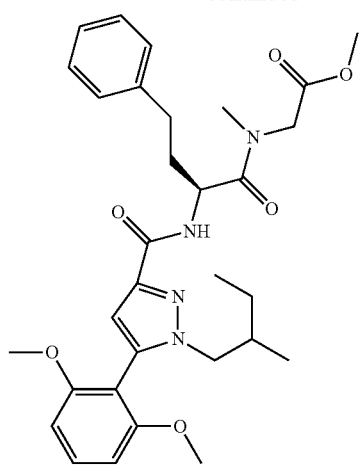
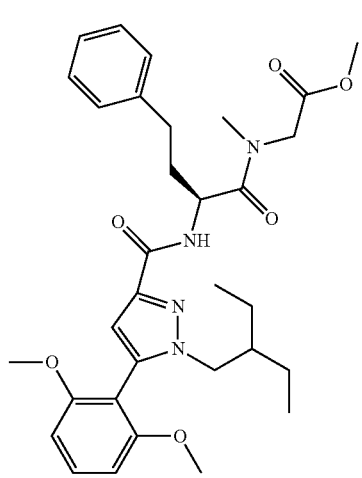
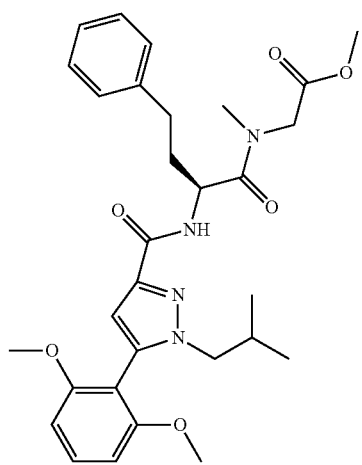

97
-continued
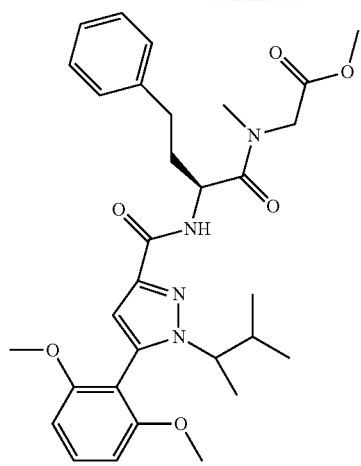
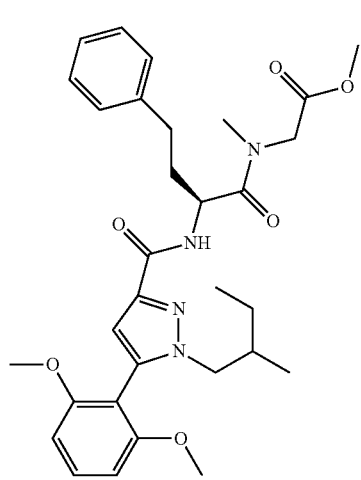
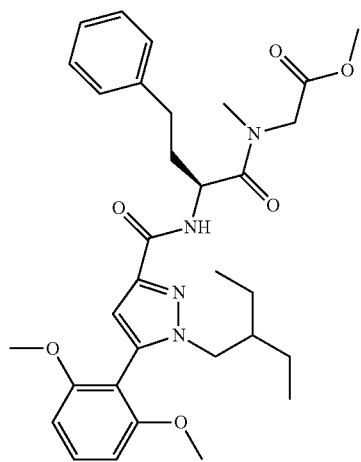
98
-continued
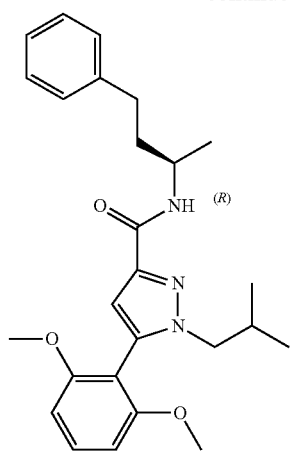
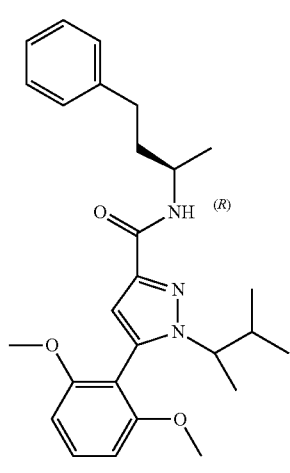
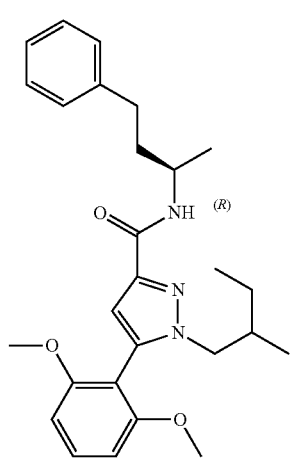

99
-continued
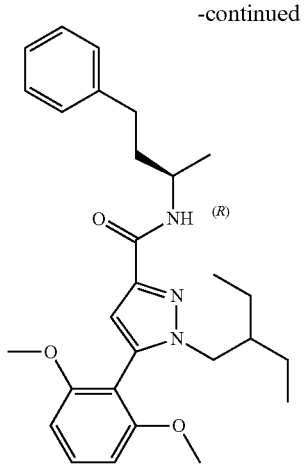
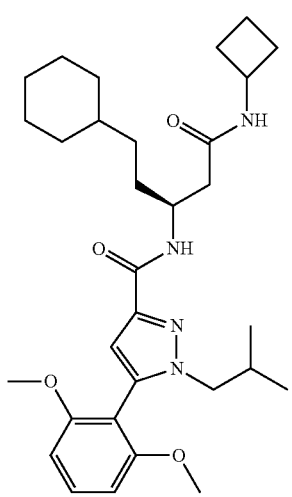
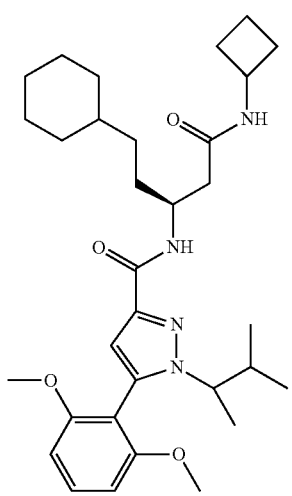
100
-continued
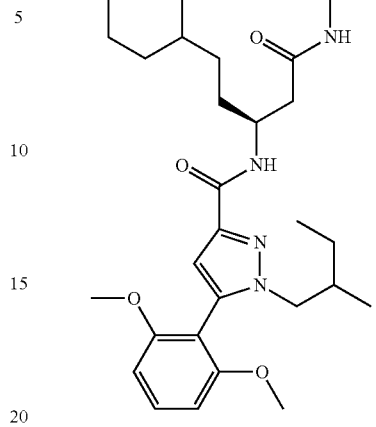
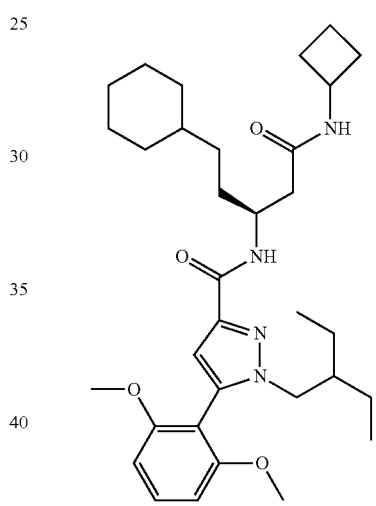
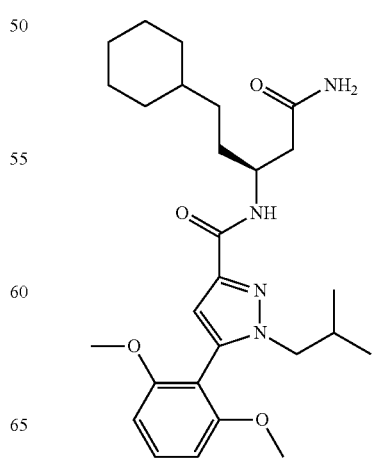

101
-continued
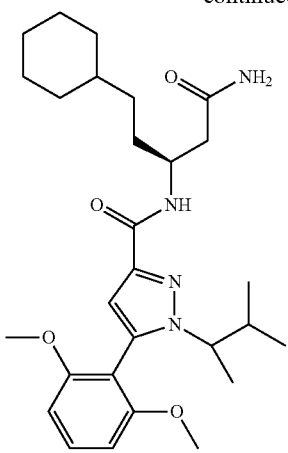
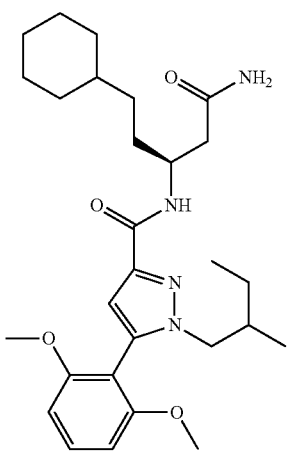
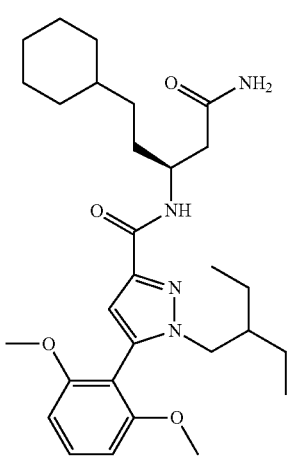
102
-continued
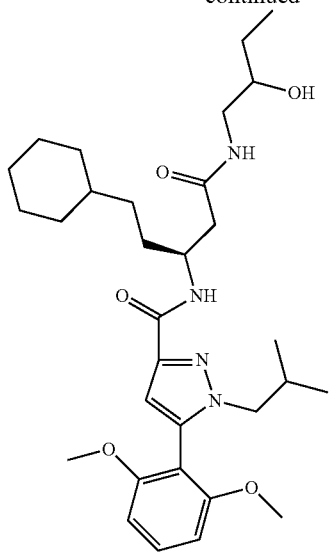
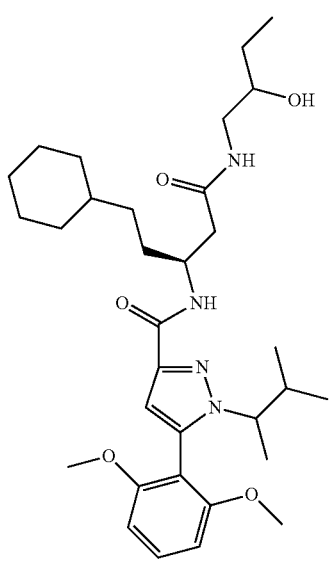
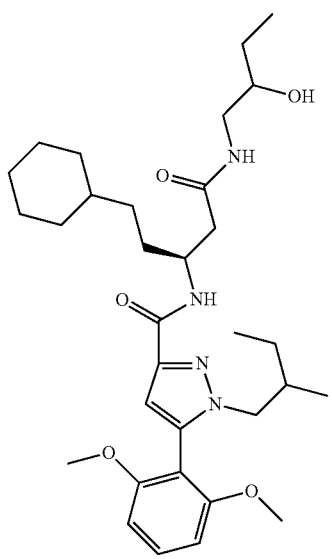

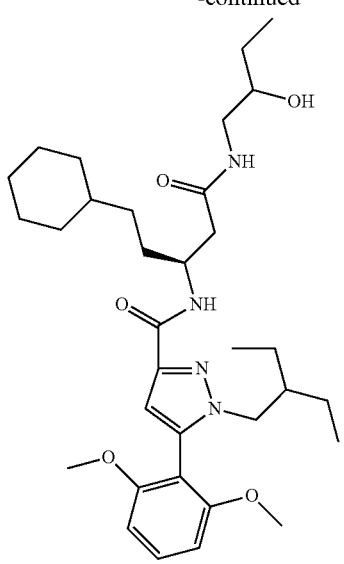
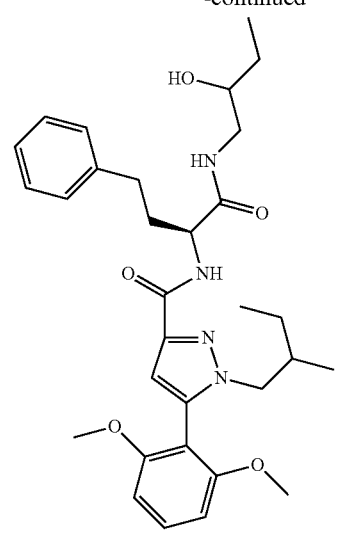
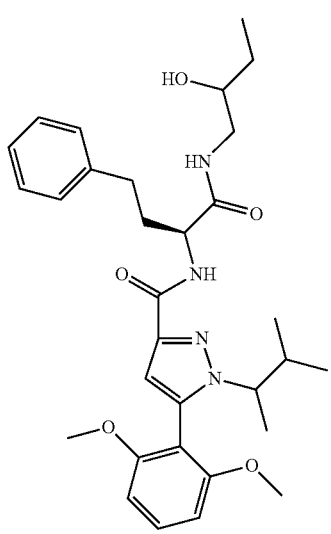
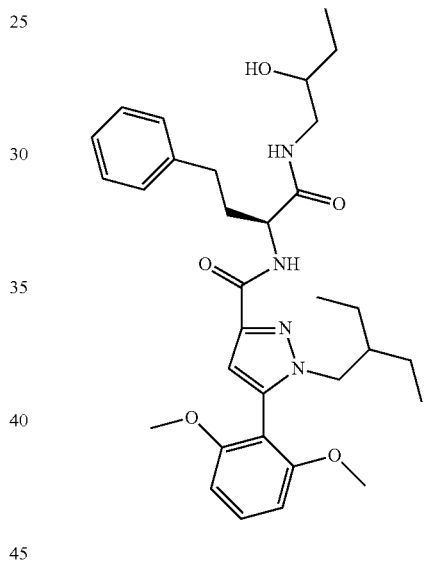
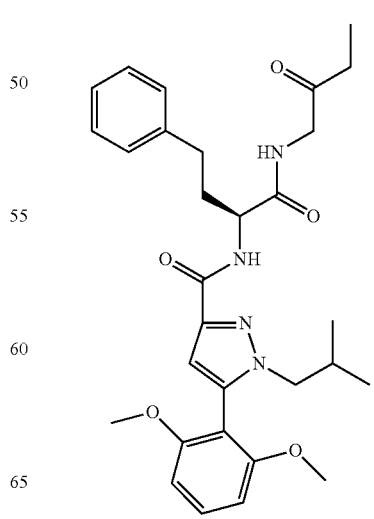

105
-continued
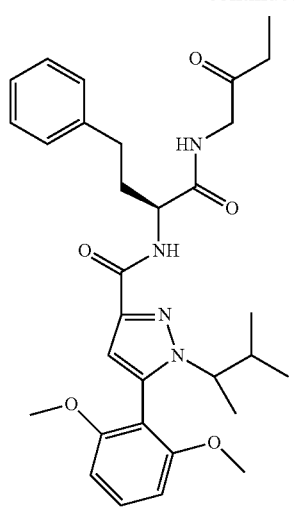
106
-continued
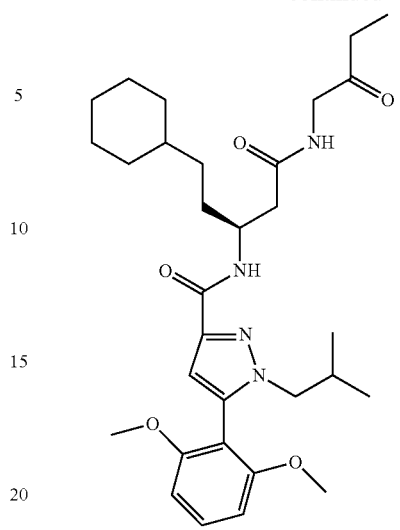
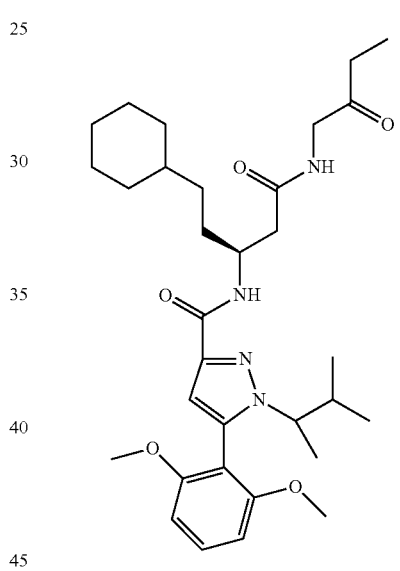
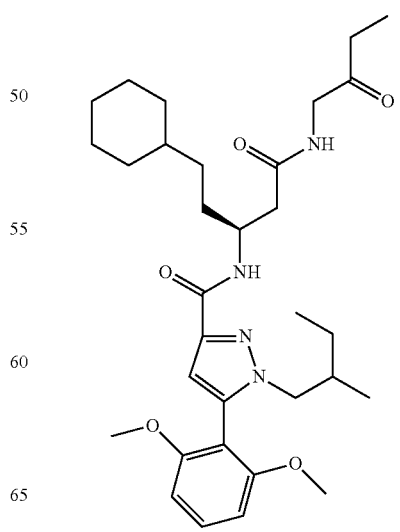

107
-continued
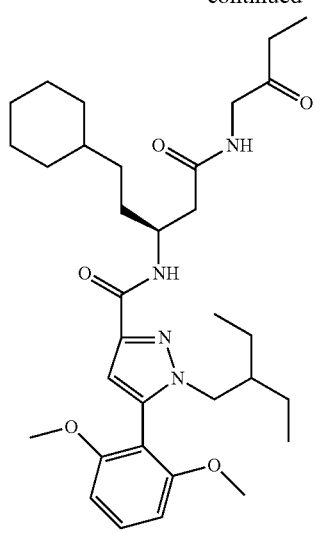
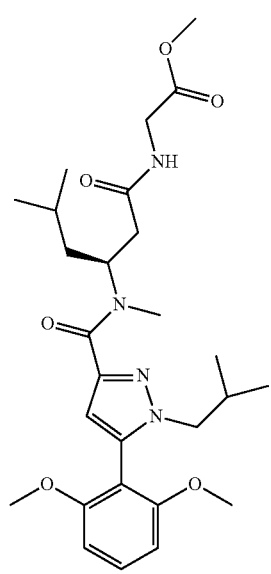
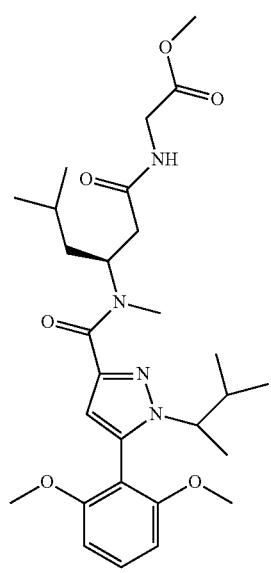
108
-continued
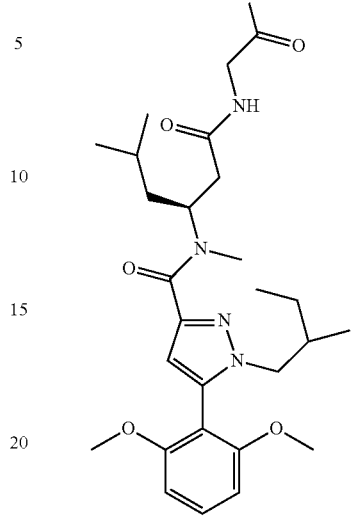
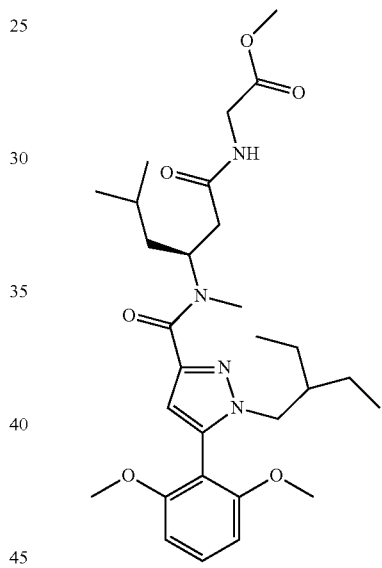
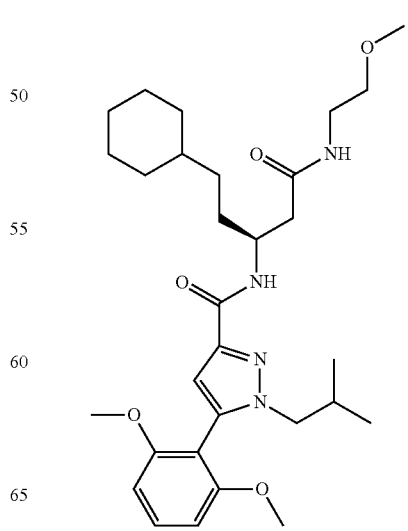

109
-continued
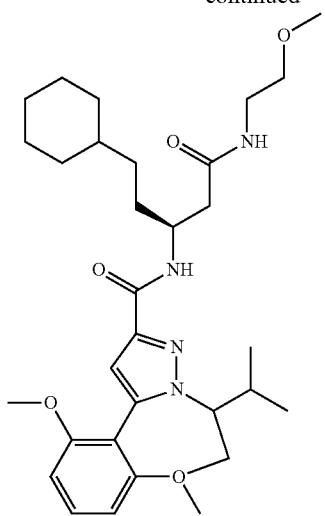
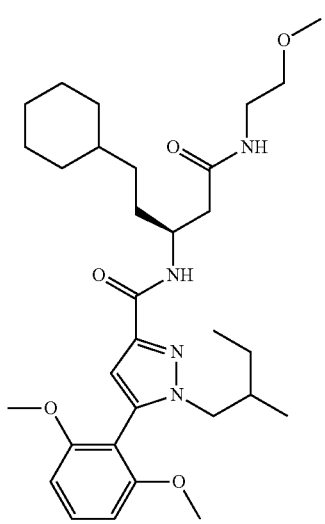
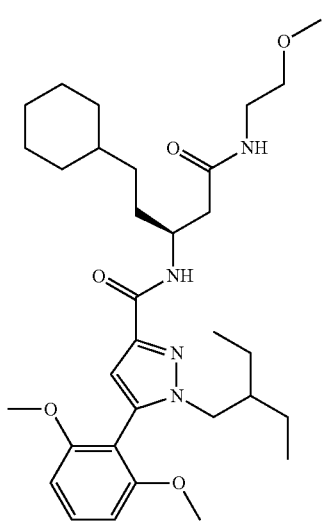
110
-continued
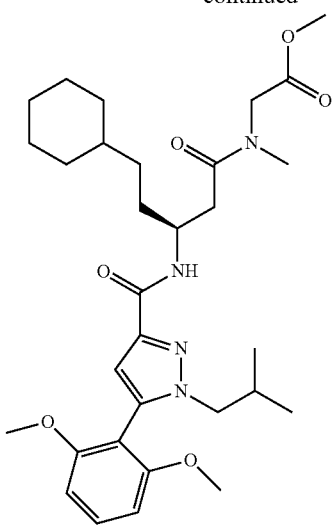
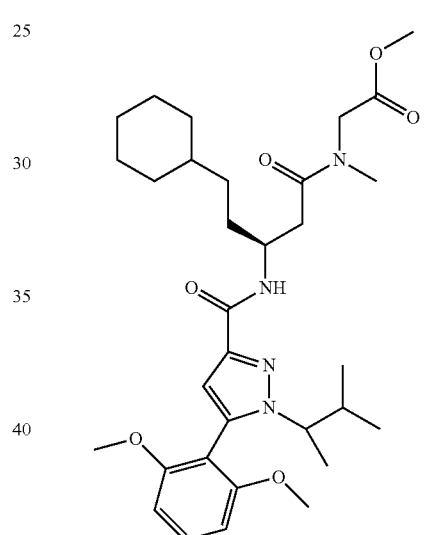
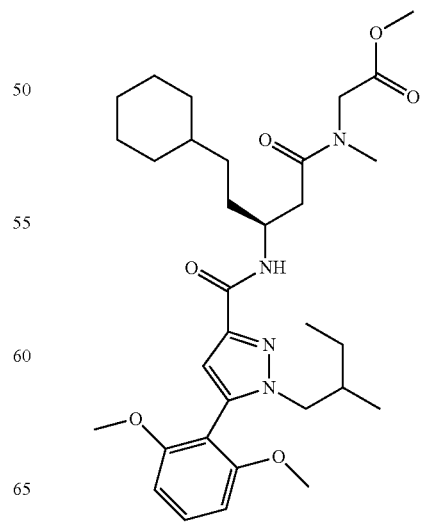

111
-continued
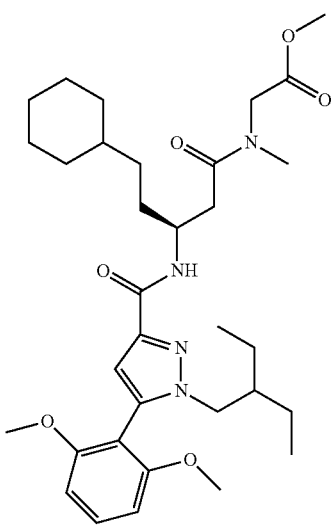
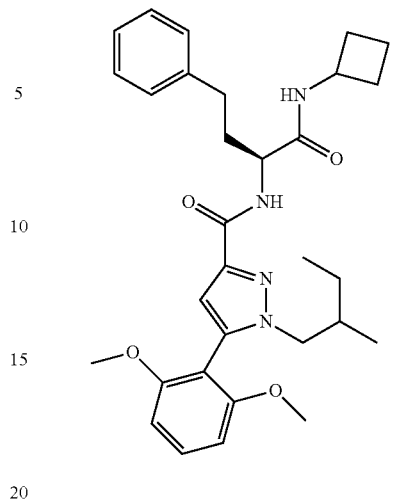
112
-continued
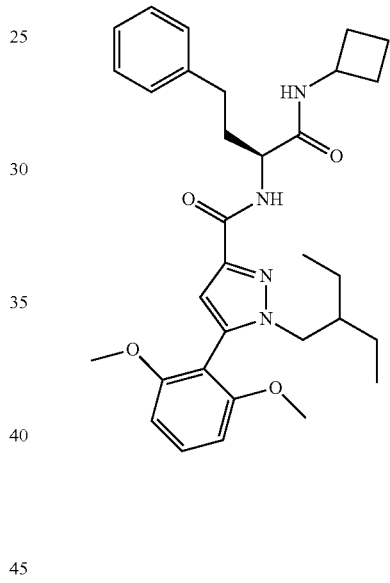
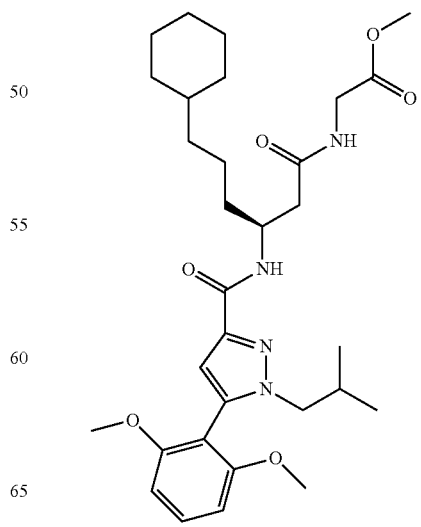

113
-continued
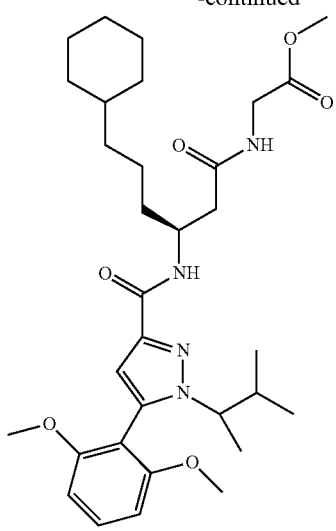
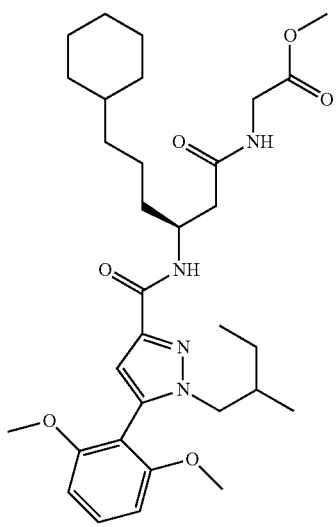
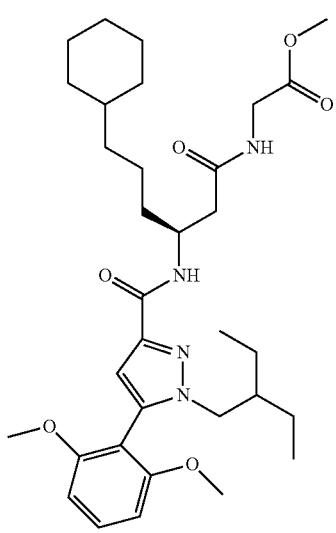
114
-continued
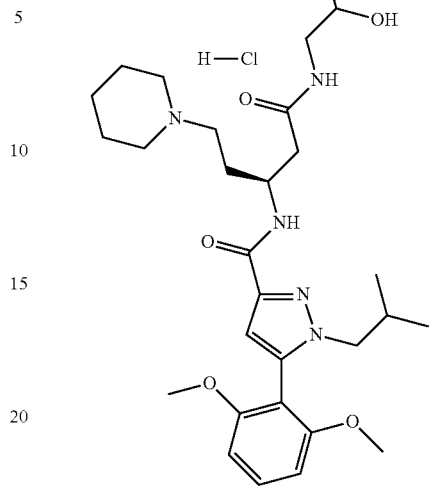
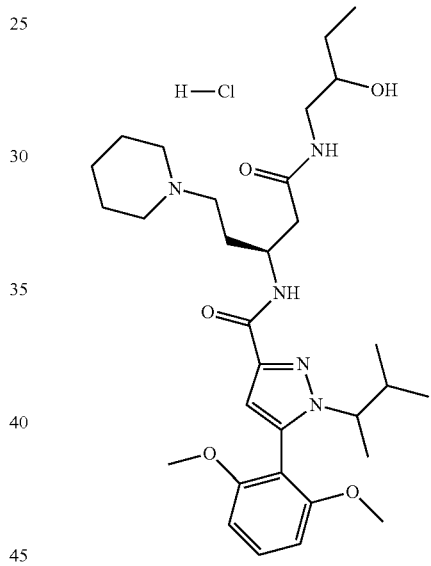
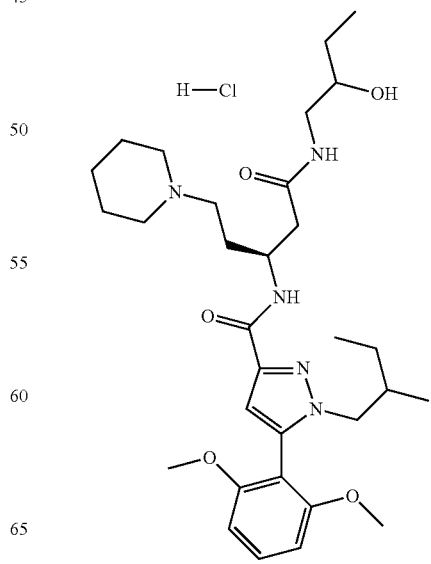

115
-continued
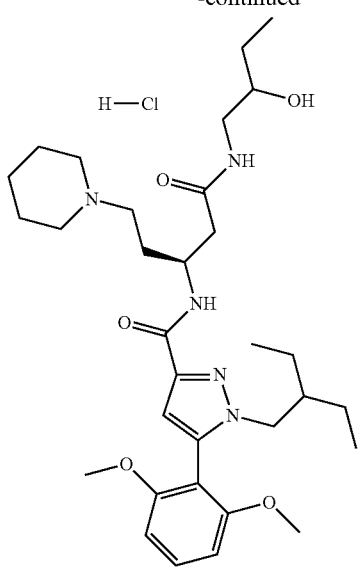
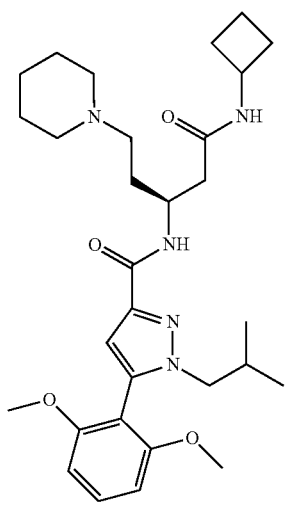
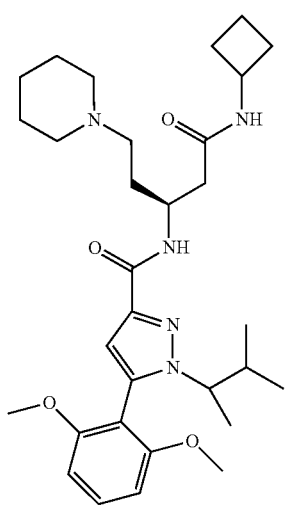
116
-continued
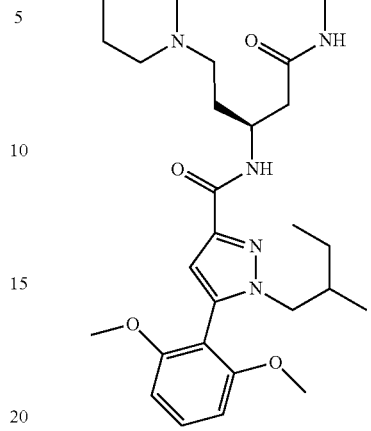
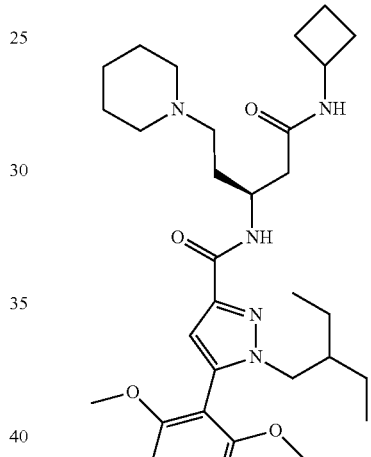
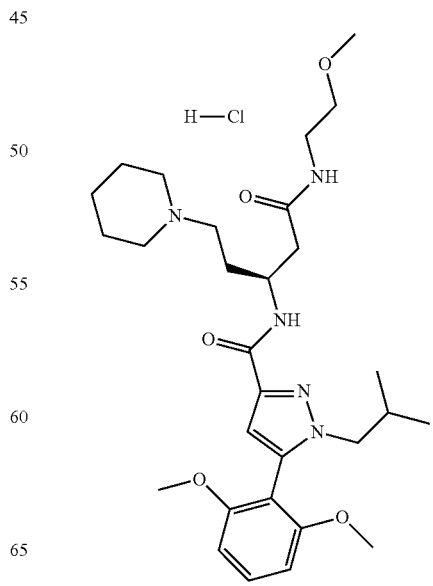

117
-continued
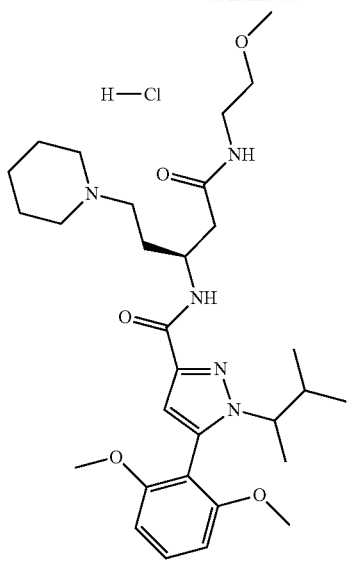
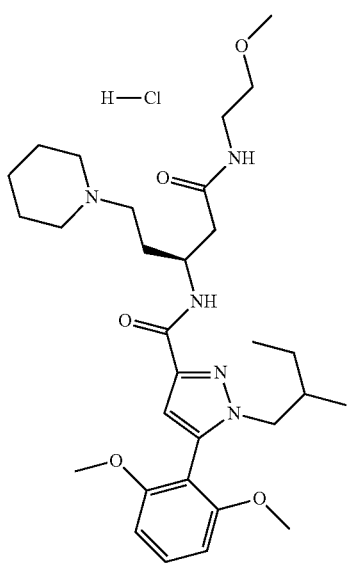
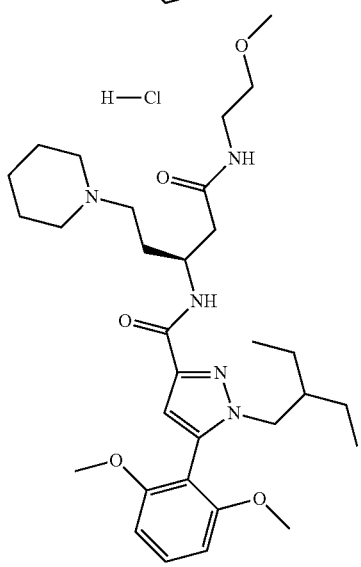
118
-continued
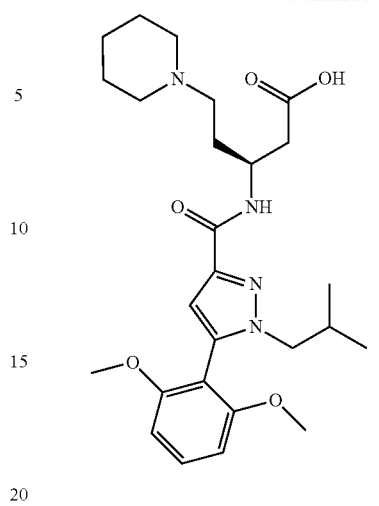
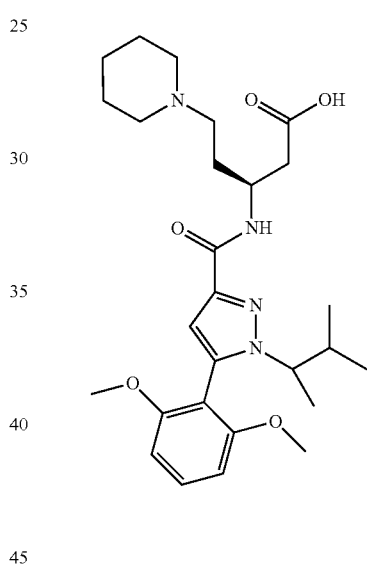
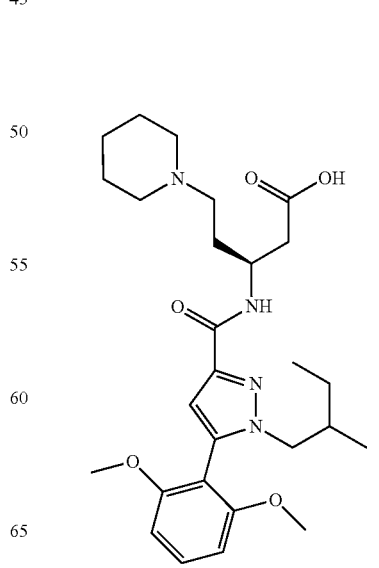

119
-continued
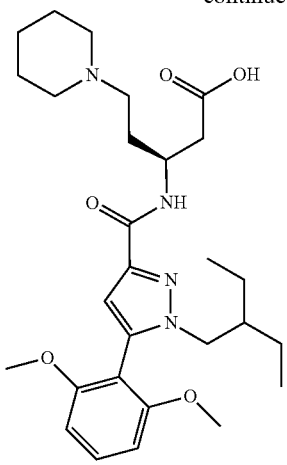
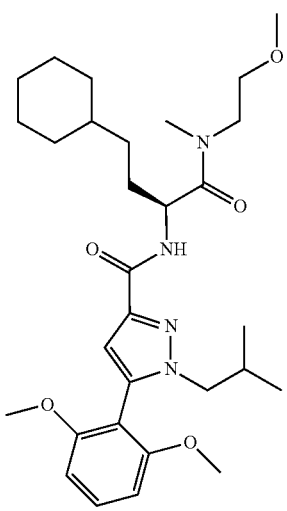
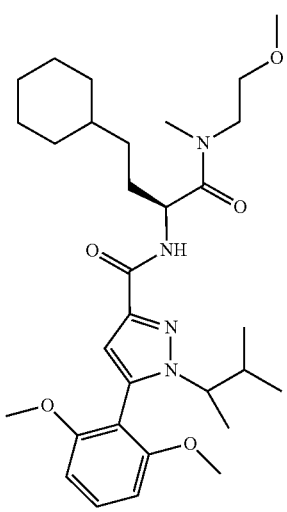
120
-continued
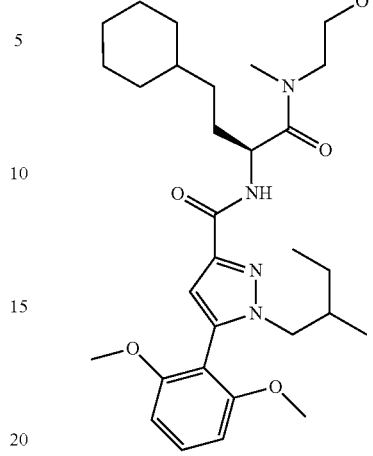
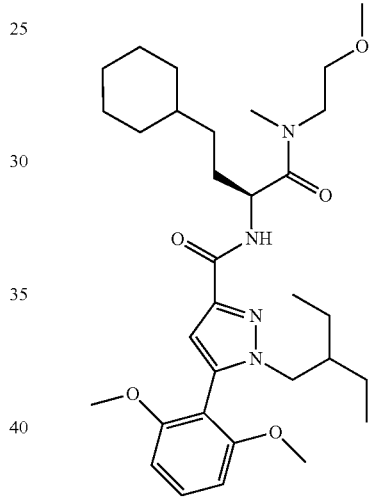
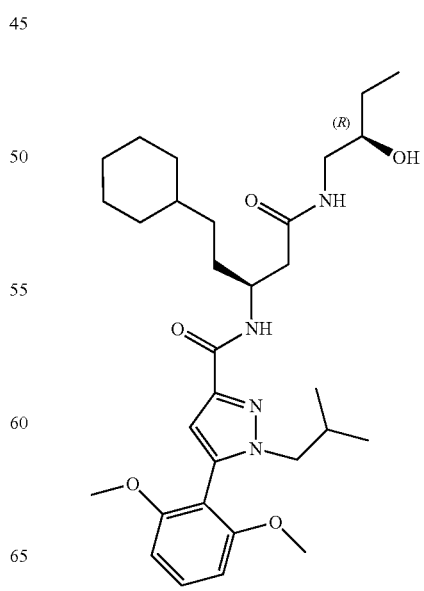

121
-continued
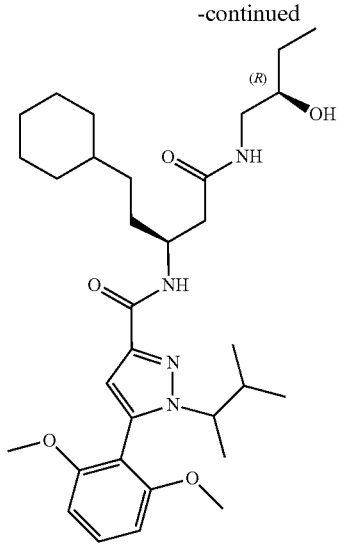
122
-continued
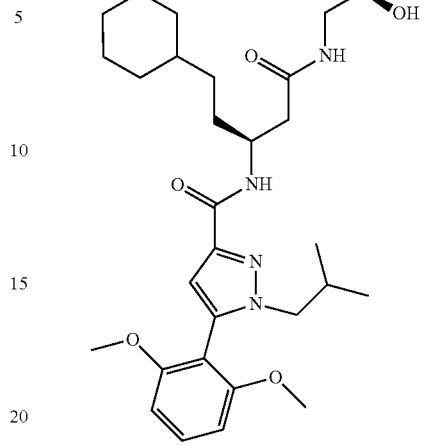
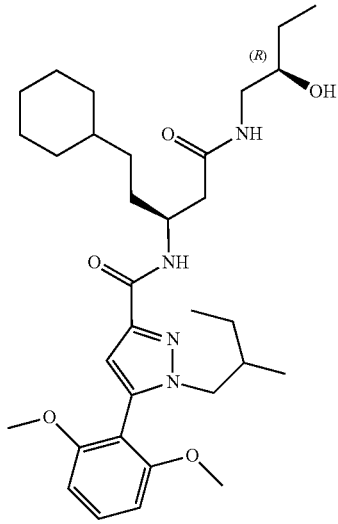
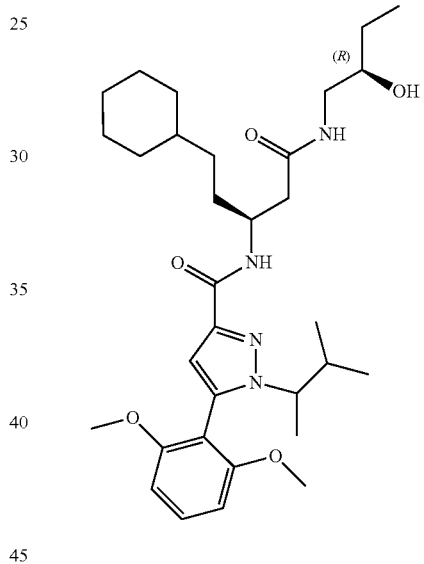
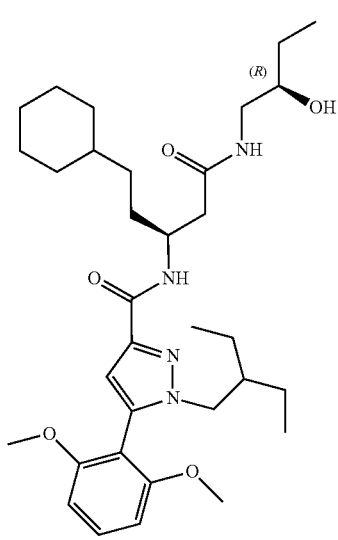
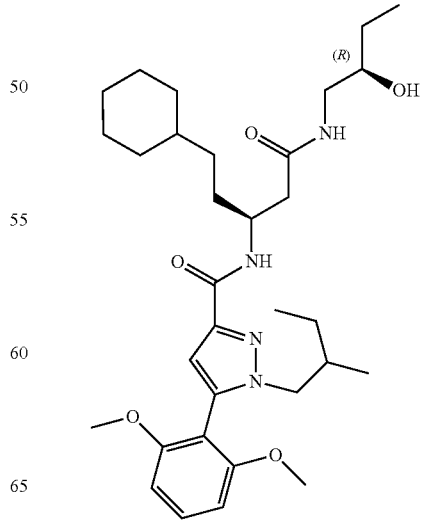

123
-continued
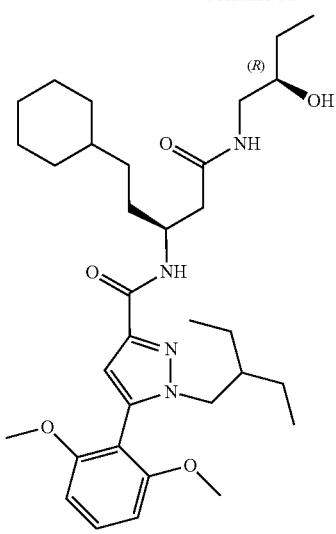
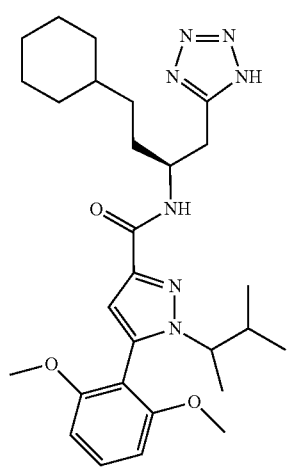
124
-continued
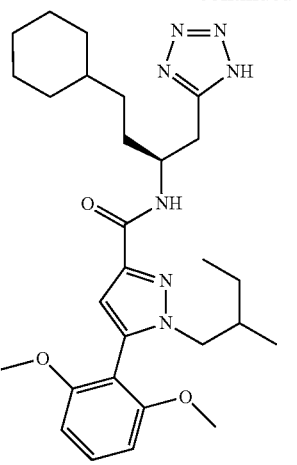
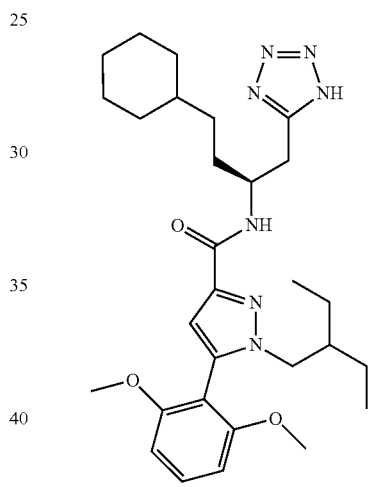
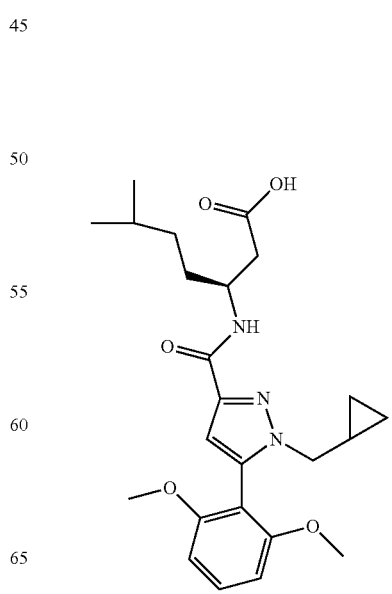

125
-continued
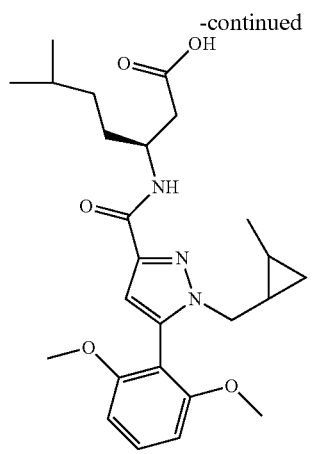
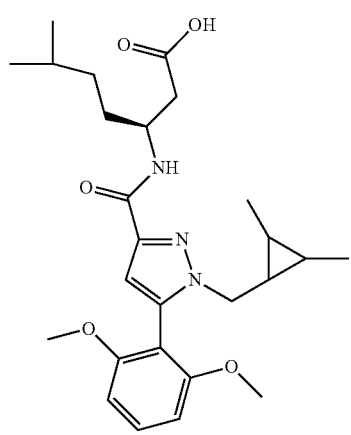
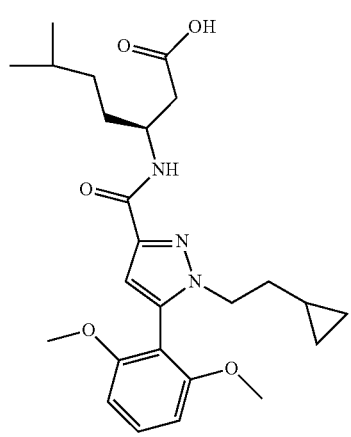
126
-continued
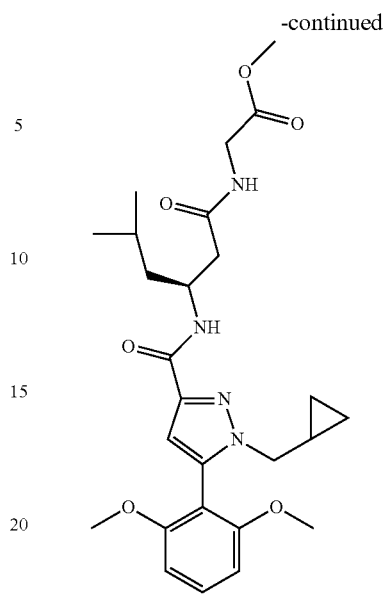
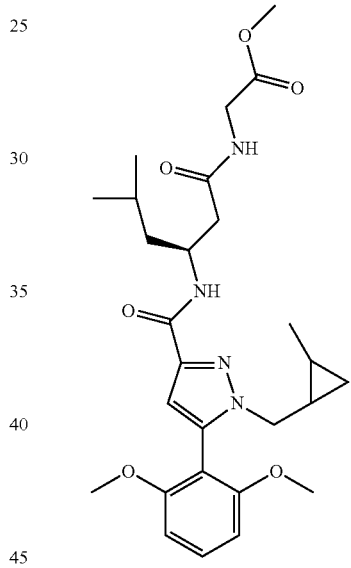
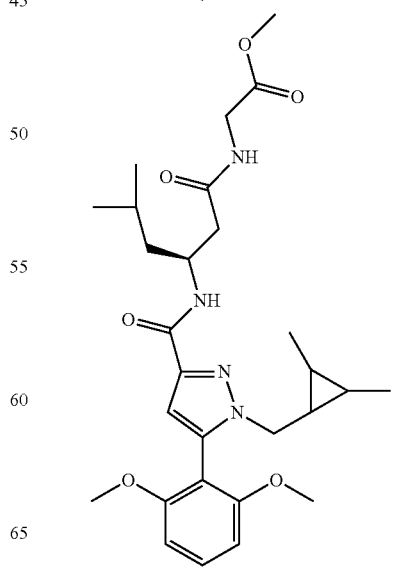

127
-continued
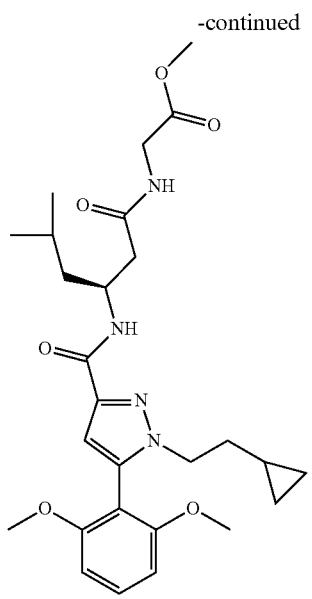
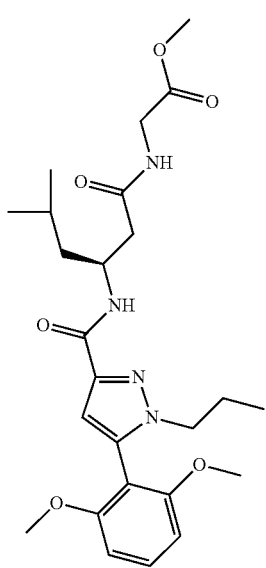
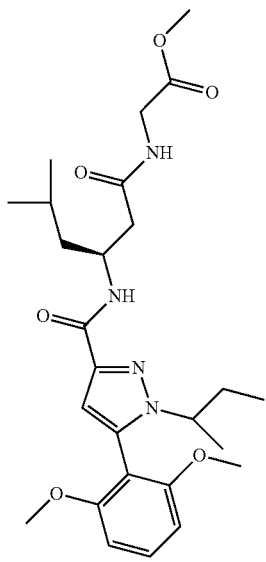
128
-continued
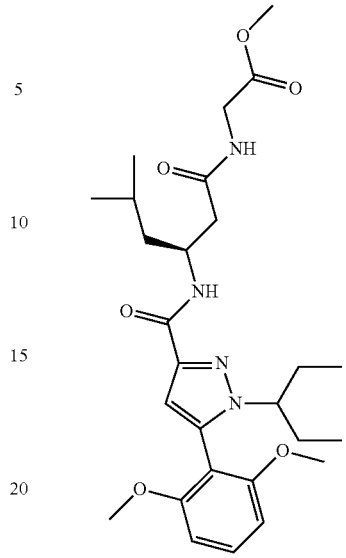
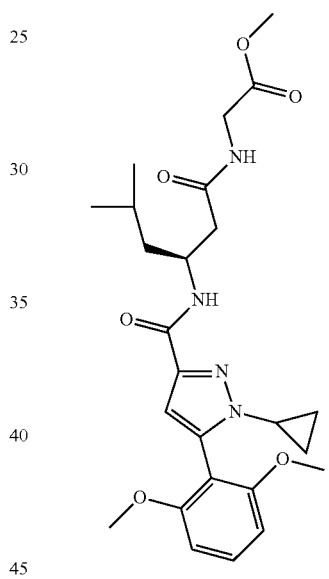
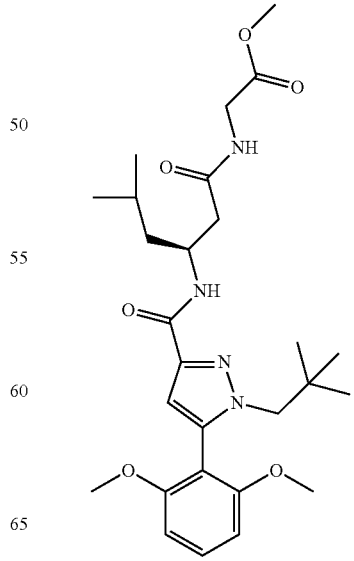

129
-continued
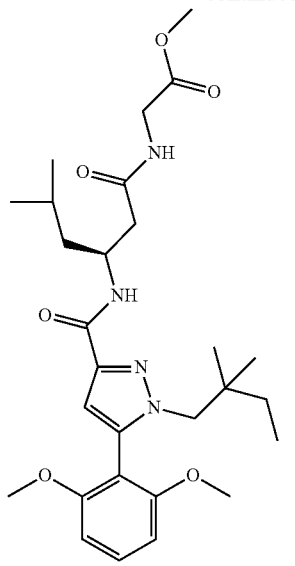
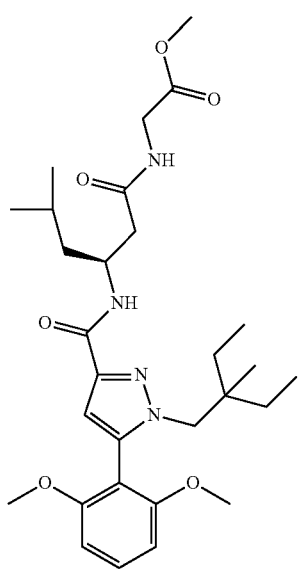
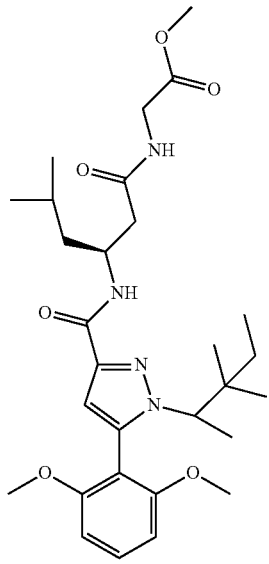
130
-continued
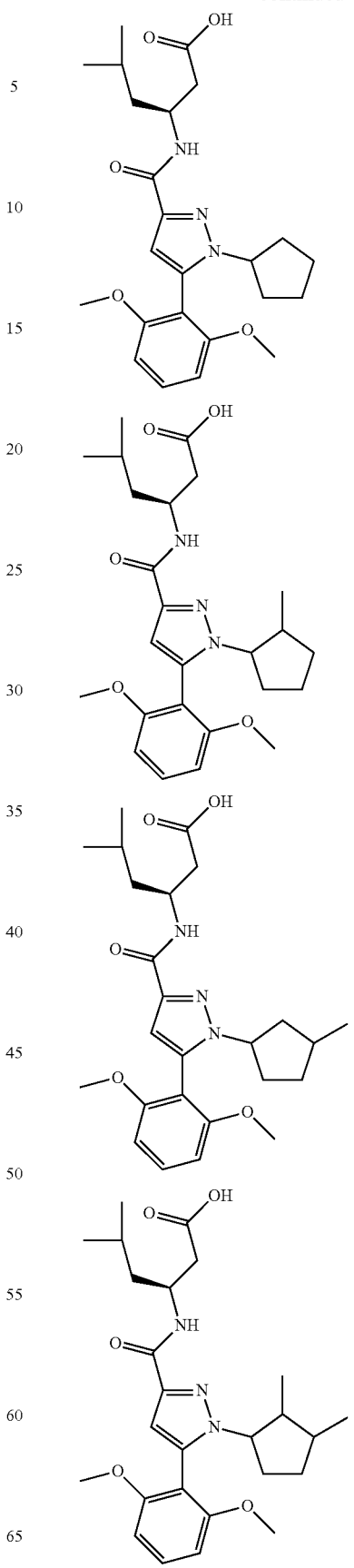

131
-continued
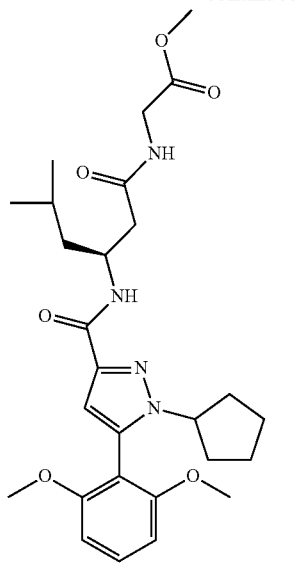
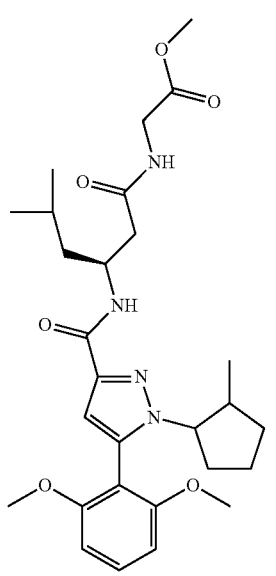
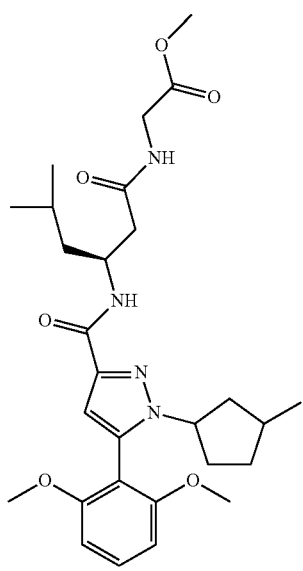
132
-continued
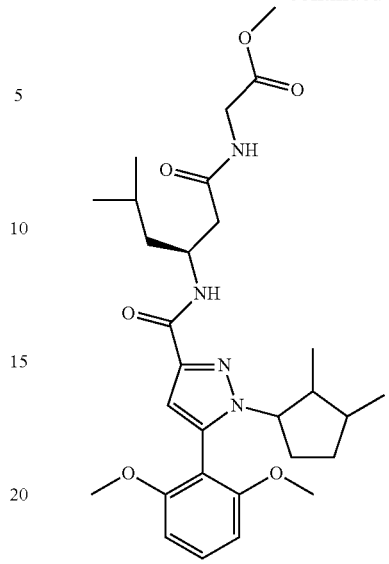
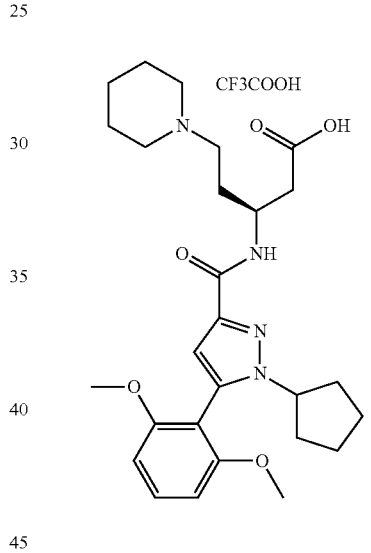
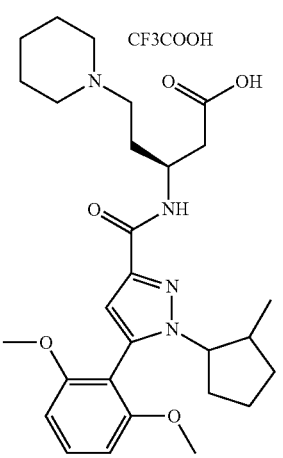

133
-continued
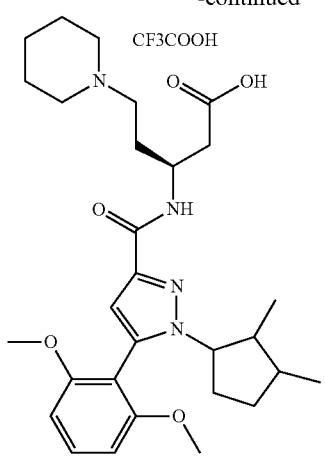
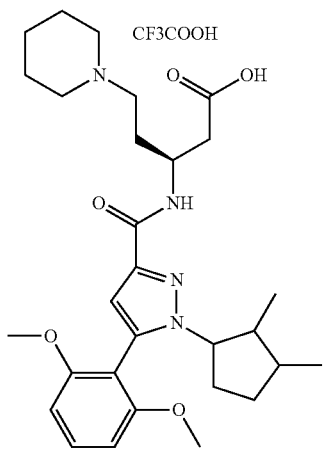
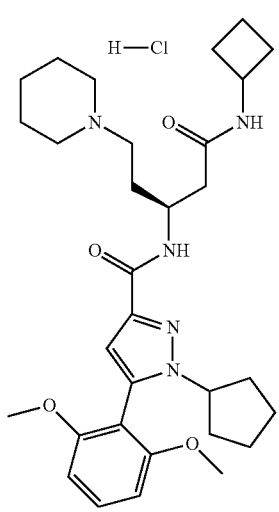
134
-continued
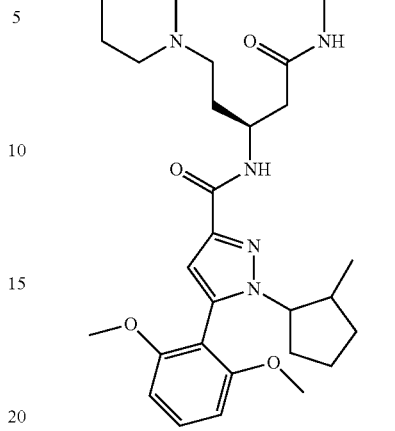
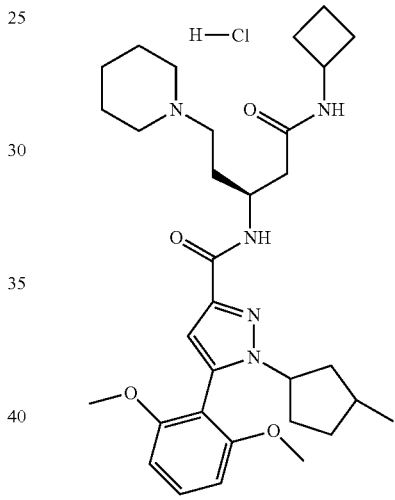
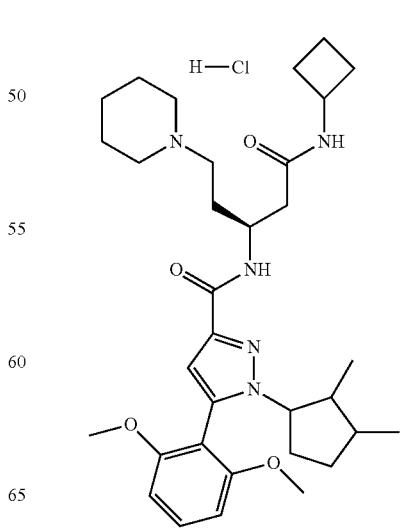

-continued

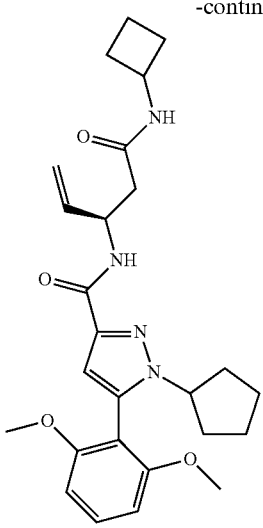

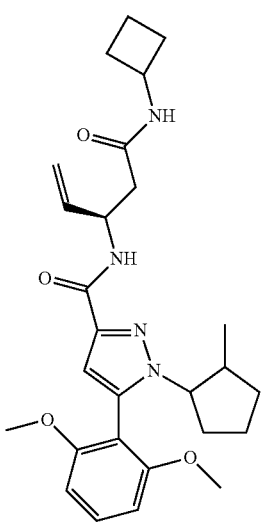

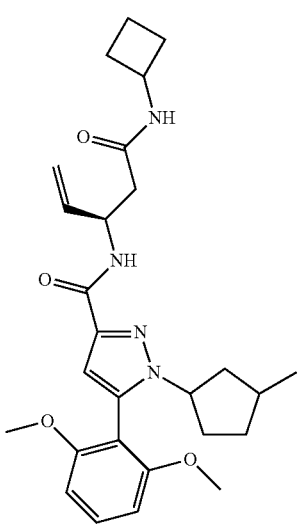

-continued

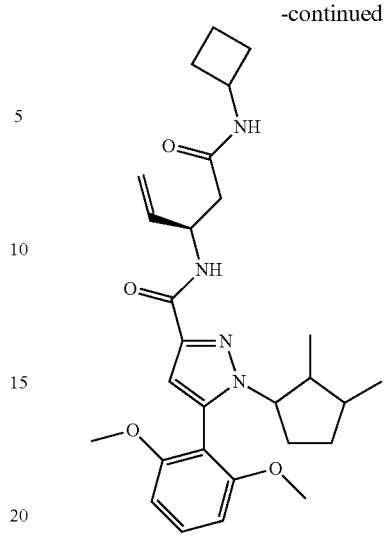

In another non-limiting embodiment, the disclosure provides a compound having the structure of any of compounds 34, 56, 65, 67, 70, 71, 77, 79, 81, 82, 86, 93, 95, 103, 118, 126, 127, 129, 130, 132, 133, 134, 136, 137, 138, 140, 141, 142, 143, 153, 154, 155, 156, 157, 161, 162, 163, 164, 167, 168, 169, 171, 172, 173, 174, 175, 176, 181, 182, 183, 184, 185, 186, 187, 188, 189, 191, 198, 204, 205, 212, 213, 214, 215, 217, 218, 219, 220, 225, 226, 228, 229, 231, 232, 233, 234, 235, 236, 238, 239, 240, 241, 242, 245, 247, 249, 251, 252, 253, 256, 257, 258, 259, 263 and 265 as set forth in Table 1.

As used herein the substituents $R_4$, $R_5$, $R_6$, $R_7$, or $R_8$ may independently may be single α, β, γ, δ amino acids, or their corresponding side chains, such as the twenty naturally occurring amino acids, e.g., alanine (Ala/A); arginine (Arg/R); asparagine (Asn/N); aspartic acid (Asp/D); cysteine (Cys/C); glutamic acid (Glu/E); glutamine (Gln/Q); glycine (Gly/G); histidine (His/H); isoleucine (Ile/I); leucine (Leu/L); lysine (Lys/K); methionine (Met/M); phenylalanine (Phe/F); proline (Pro/P); Serine (Ser/S); threonine (Thr/T); tryptophan (Trp/W); tyrosine (Tyr/Y); and valine (Val/V). The individual amino acids may be of either the R or the S chirality. Alternatively, $R_4$, $R_5$, $R_6$, $R_7$, or $R_8$ independently may be two or three amino acids linked by a peptide bond. $R_4$, $R_5$, $R_6$, $R_7$, or $R_8$ independently may be dipeptides or tripeptides (Hobbs et al., Proc Nat Acad Sci USA. 1993, 90, 6909-6913); U.S. Pat. No. 6,075,121 (Bartlett et al.) peptoids; or vinylogous polypeptides (Hagihara et al., J Amer Chem Soc. 1992, 114, 6568), the contents of which are hereby incorporated by reference in their entireties. $R_4$, $R_5$, $R_6$, $R_7$, or $R_8$ independently may be part of the extended unnatural amino acids, e.g., Xie and Schultz, Nat Rev Mol Cell Biol. 2006, 7(10):775-82 or Wang et al., Chem Biol. 2009, 16(3):323-36, the contents of which are hereby incorporated by reference in their entireties.

A pharmaceutical composition comprising at least one pharmaceutically acceptable excipient and a therapeutically effective amount of the compound of embodiment 1. In the pharmaceutical composition of the compound may be present in amount effective for the treatment of asthma, atherosclerosis, cancer, cardiomyopathy, diabetes, dyslipidemia, hypertension, inflammation, liver disease, metabolic disorder, neurodegenerative disease, obesity, preeclampsia, or renal disease. More specifically, the hypertension may be pulmonary arterial hypertension. The liver disease may be alcoholic liver disease, toxicant-induced liver disease or viral-induced liver disease and the renal dysfunction may be polycystic kidney disease. Alternatively, the compound may be present in amount effective for the prevention of HIV neurodegeneration.

5.1. Definitions

"Alkenyl" refers to an unsaturated branched, straight-chain or cyclic alkyl group having at least one carbon-carbon double bond derived by the removal of one hydrogen atom from a single carbon atom of a parent alkene. The group may be in either the Z- and E-forms (or cis or trans conformation) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. The alkenyl group may be substituted or unsubstituted. In certain embodiments, an alkenyl group has from 2 to 20 carbon atoms and in other embodiments from 2 to 8 carbon atoms.

"Alkoxy" refers to a radical —OR where R represents an alkyl, alkyl, cycloalkyl, aryl, or heteroaryl group as defined herein. Representative examples include, but are not limited to, methoxy, ethoxy, propoxy, butoxy, cyclohexyloxy, and the like.

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. The alkyl group may be substituted or unsubstituted; for example with a halogen. In certain embodiments, an alkyl group comprises from 1 to 20 carbon atoms. Alternatively, an alkyl group may comprise from 1 to 8 carbon atoms.

"Alkyl(aryl)" refers to an acyclic alkyl group in which one of the hydrogen atoms bonded to a carbon atom, typically a terminal or sp$^3$ carbon atom, is replaced with an aryl group. Typical alkyl(aryl) groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. In certain embodiments, an alkyl(aryl) group can be $(C_{6-20})$ alkyl(aryl) e.g., the alkyl group may be $(C_{1-10})$ and the aryl moiety may be $(C_{5-10})$.

"Alkynyl" refers to an unsaturated branched or straight-chain having at least one carbon-carbon triple bond derived by the removal of one hydrogen atom from a single carbon atom of a parent alkyne. Typical alkynyl groups include, but are not limited to, ethynyl, propynyl, butenyl, 2-pentynyl, 3-pentynyl, 2-hexynyl, 3-hexynyl and the like. The alkynyl group may be substituted or unsubstituted. In certain embodiments, an alkynyl group has from 3 to 20 carbon atoms and in other embodiments from 3 to 8 carbon atoms.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene or cyclopentadiene; bicyclic ring systems wherein at least one ring is carbocyclic and aromatic, for example, naphthalene, indane; or two aromatic ring systems, for example benzyl phenyl, biphenyl, diphenylethane, diphenylmethane. The aryl group may be substituted or unsubstituted, for example with a halogen.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. The cycloalkyl group may be substituted or unsubstituted. In certain embodiments, the cycloalkyl group can be $C_{3-10}$ cycloalkyl, such as, for example, $C_6$ cycloalkyl.

"Disease" refers to any disease, disorder, condition, symptom, or indication.

"Halogen" refers to a fluoro, chloro, bromo, or iodo group.

"Heteroaryl" refers to a monovalent heteroaromatic group derived by the removal of one hydrogen atom from a single atom of a parent heteroaromatic ring system. Heteroaryl encompasses: 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. The heteroaryl group may be substituted or unsubstituted.

For example, heteroaryl includes a 5- to 7-membered heteroaromatic ring fused to a 5- to 7-membered cycloalkyl ring and a 5- to 7-membered heteroaromatic ring fused to a 5- to 7-membered heterocycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, piperidine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereoisomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, $CO_2H$, halogen, hydroxyl, $-N_3$, $-NH_2$, $-SO_{(1-3)}H$, or $-SH$.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

5.2. Pharmaceutical Compositions

The disclosure also provides pharmaceutical compositions comprising an effective amount of a compound Formula I (e.g., any of the formulae and/or structures disclosed herein), or a pharmaceutically acceptable salt of said compound; and a pharmaceutically acceptable carrier.

Pharmaceutically acceptable carriers, adjuvants and vehicles that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. If required, the solubility and bioavailability of the compounds of the present disclosure in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this disclosure optionally formulated with a poloxamer, such as LUTROL™ and PLURONIC™ (BASF Corporation), or block copolymers of ethylene oxide and propylene oxide. See U.S. Pat. No. 7,014,866 (Infeld et al.); and US Pat. Pubs. 20060094744 (Maryanoff et al.) and 20060079502 (Lang).

The pharmaceutical compositions of the disclosure include those suitable for oral, rectal, nasal, topical (including buccal and sublingual), pulmonary, vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product. In certain embodiments, the compound is administered orally. Compositions of the present disclosure suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this disclosure may be administered in the form of suppositories for rectal administration. These compositions can be prepared by mixing a compound of this disclosure with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g., U.S. Pat. No. 6,803,031 (Rabinowitz & Zaffaroni).

Topical administration of the pharmaceutical compositions of this disclosure is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene or polyoxypropylene compounds, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this disclosure may also be topically applied to the lower intestinal tract by rectal suppository formulation or in a suitable enema formulation. Topically-transdermal patches and iontophoretic administration are also included in this disclosure.

Application of the therapeutics may be local, so as to be administered at the site of interest. Various techniques can be used for providing the compositions at the site of interest, such as injection, use of catheters, trocars, projectiles, pluronic gels, stents, sustained drug release polymers or other devices which provide for internal access. Thus, according to yet another embodiment, the compounds of this disclosure may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. No. 6,099,562 (Ding & Helmus); U.S. Pat. No. 5,886,026 (Hunter et al.); and U.S. Pat. No. 5,304,121 (Sahatjian). The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the disclosure provides a method of coating an implantable medical device comprising the step of contacting said device with the coating composition described above. It will be obvious to those skilled in the art that the coating of the device will occur prior to implantation into a mammal.

According to another embodiment, the disclosure provides a method of impregnating an implantable drug release device comprising the step of contacting said drug release device with a compound or composition of this disclosure Implantable drug release devices include, but are not limited to, biodegradable polymer capsules or bullets, non-degradable, diffusible polymer capsules and biodegradable polymer wafers.

According to another embodiment, the disclosure provides an implantable medical device coated with a compound or a composition comprising a compound of this disclosure, such that said compound is therapeutically active.

According to another embodiment, the disclosure provides an implantable drug release device impregnated with or containing a compound or a composition comprising a compound of this disclosure, such that said compound is released from said device and is therapeutically active. Where an organ or tissue is accessible because of removal from the subject, such organ or tissue may be bathed in a medium containing a composition of this disclosure, a composition of this disclosure may be painted onto the organ, or a composition of this disclosure may be applied in any other convenient way.

In one embodiment, this disclosure provides a composition comprising a compound of Formula I, or more specific compounds disclosed herein, to treat or prevent asthma, atherosclerosis, cancer, cardiomyopathy, diabetes, dyslipidemia, HIV neurodegeneration, hypertension, inflammation, liver disease, metabolic disorder, neurodegenerative disease, obesity, or preeclampsia. In another embodiment, the disclosure provides a composition comprising a compound of Formula I, or more specific compounds disclosed herein, to treat or prevent cancer, cell proliferation, diabetes, fluid homeostasis, heart diseases (e.g., hypertension and heart failure, such as congestive heart failure), HIV infection, immune function, obesity, stem cell trafficking, metastatic cancer or a vein-related disorder such as an angioma, a venous insufficiency, a stasis, or a thrombosis.

In another embodiment, a composition of this disclosure further comprises a second therapeutic agent. In one embodiment, the second therapeutic agent is one or more additional compounds of the disclosure. In another embodiment, the second therapeutic agent may be selected from any compound or therapeutic agent known to have or that demonstrates advantageous properties when administered with a compound having the same mechanism of action as the APJ receptor compound of Formula I.

In a particular embodiment, the second therapeutic is an agent useful in the treatment or prevention of a disease or condition selected from asthma, atherosclerosis, cancer, cardiomyopathy, diabetes, dyslipidemia, HIV neurodegeneration, hypertension, inflammation, liver disease, metabolic disorder, neurodegenerative disease, obesity, or preeclampsia. In another embodiment, the second therapeutic is an agent useful in the treatment or prevention of a disease or condition selected from cancer, cell proliferation, diabetes, fluid homeostasis, heart diseases (e.g., hypertension and heart failure, such as congestive heart failure), HIV infection, immune function, obesity, stem cell trafficking, or metastatic cancer.

For example, when the disease or condition is congestive heart failure, the second therapeutic agent can be selected from: ACE inhibitors, beta blockers, vasodilator, calcium channel blockers, loop diuretics, aldosterone antagonists, and angiotensin receptor blockers.

When the disease or condition being treated is hypertension, the second therapeutic agent can be selected from: α-blockers, β-blockers, calcium channel blockers, diuretics, natriuretics, saluretics, centrally acting antihypertensives, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonists.

α-Blockers include doxazosin, prazosin, tamsulosin, and terazosin.

β-Blockers for combination therapy are selected from acebutolol, acetutolol, atenolol, bisoprol, bupranolol, carteolol, carvedilol, celiprolol, esmolol, mepindolol, metoprolol, nadolol, oxprenolol, penbutolol, pindolol, propanolol, taliprolol, and their pharmaceutically acceptable salts.

Calcium channel blockers include dihydropyridines (DHPs) and non-DHPs. The preferred DHPs are selected from the group consisting of amlodipine, felodipine, isradipine, lacidipine, nicardipine, nifedipine, nigulpidine, niludipine, nimodiphine, nisoldipine, nitrendipine, nivaldipine, ryosidine, and their pharmaceutically acceptable salts. Non-DHPs are selected from anipamil, diltiazem, fendiline, flunarizine, gallopamil, mibefradil, prenylamine, tiapamil, and verampimil and their pharmaceutically acceptable salts.

A diuretic is, for example, a thiazide derivative selected from amiloride, chlorothalidon, chlorothiazide, hydrochlorothiazide, and methylchlorothiazide.

Centrally acting antihypertensives include clonidine, guanabenz, guanfacine and methyldopa.

ACE inhibitors include alacepril, benazepril, benazaprilat, captopril, ceronapril, cilazapril, delapril, enalapril, enalaprilat, fosinopril, lisinopril, moexipiril, moveltopril, perindopril, quinapril, quinaprilat, ramipril, ramiprilat, spirapril, temocapril, trandolapril, and zofenopril. Preferred ACE inhibitors are benazepril, enalpril, lisinopril, and ramipril.

Dual ACE/NEP inhibitors are, for example, omapatrilat, fasidotril, and fasidotrilat.

Preferred ARBs include candesartan, eprosartan, irbesartan, losartan, olmesartan, tasosartan, telmisartan, and valsartan.

Preferred aldosterone synthase inhibitors are anastrozole, fadrozole, and exemestane.

Preferred aldosterone-receptor antagonists are spironolactone and eplerenone.

A preferred endothelin antagonist is, for example, bosentan, enrasentan, atrasentan, darusentan, sitaxentan, and tezosentan and their pharmaceutically acceptable salts.

In one embodiment, the disclosure provides separate dosage forms of a compound of this disclosure and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the disclosure, the compound of the present disclosure is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy. Preferably, the compound is present in the composition in an amount of from 0.1 to 50 wt. %, more preferably from 1 to 30 wt. %, most preferably from 5 to 20 wt. %.

The interrelationship of dosages for animals and humans (based on milligrams per meter squared of body surface) is described in Freireich et al., (1966) Cancer Chemother. Rep 50: 219. Body surface area may be approximately determined from height and weight of the subject. See, e.g., Scientific Tables, Geigy Pharmaceuticals, Ardsley, N.Y., 1970,537.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

The compounds for use in the method of the disclosure can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily treatment dose or one of multiple daily treatment doses (e.g., about 1 to 4 or more times per day). When multiple daily treatment doses are used, the unit dosage form can be the same or different for each dose.

5.3. Methods of Treatment

The disclosure also includes methods of treating diseases, disorders or pathological conditions which benefit from modulation of the APJ receptor comprising administering an effective amount of an APJ receptor compound of the disclosure to a subject in need thereof. Diseases and conditions which can benefit from modulation (inhibition or activation) of the APJ receptor include, but are not limited to, asthma, atherosclerosis, cancer, cardiomyopathy, diabetes, dyslipidemia, hypertension, inflammation, liver disease, metabolic disorder, neurodegenerative disease, obesity, preeclampsia, or renal disease. More specifically, the hypertension may be pulmonary arterial hypertension. The liver disease may be alcoholic liver disease, toxicant-induced liver disease or viral-induced liver disease and the renal dysfunction may be polycystic kidney disease. The apelin receptor system is involved in vein-related disorders. See, e.g., Lathen et al., "ERG-APLNR Axis Controls Pulmonary Venule Endothelial Proliferation in Pulmonary Veno-Occlusive Disease" 2014 Circulation 130: 1179-1191. Apelin receptor system has also been implicated in heart failure. See, e.g., Sheikh et al., "In vivo genetic profiling and cellular localization of apelin reveals a hypoxia-sensitive, endothelial-centered pathway activated in ischemic heart failure" 2007 Am J Physiol Heart Circ Physiol 294: H88-H98. The contents of both Lathen et al. and Sheikh et al. are hereby incorporated by reference in their entireties into the present disclosure.

In one non-limiting embodiment, the disclosure provides a method of treating an apelin receptor (APJ) related disorder in a subject which comprises administering to the subject the compound of mbodiment 1. The apelin receptor (APJ) related disorder may be asthma, atherosclerosis, cancer, cardiomyopathy, diabetes, dyslipidemia, hypertension, inflammation, liver disease, metabolic disorder, neurodegenerative disease, obesity, or preeclampsia. The disclosure provides methods further comprising treating the subject with an α-blocker, an angiotensin converting enzyme (ACE) inhibitor, an angiotensin-receptor blocker (ARB), a β-blocker, a calcium channel blocker, or a diuretic. Alternatively, the disclosure provides a method to treat or prevent a vein-related disorder such as an angioma, a venous insufficiency, a stasis or a thrombosis.

In addition, the disclosure provides a method of preventing HIV neurodegeneration in a subject which comprises administering to the subject the compound of embodiment 1.

In one embodiment, an effective amount of a compound of this disclosure can range from about 0.005 mg to about 5000 mg per treatment. In more specific embodiments, the range is from about 0.05 mg to about 1000 mg, or from about 0.5 mg to about 500 mg, or from about 5 mg to about 50 mg. Treatment can be administered one or more times per day (for example, once per day, twice per day, three times per day, four times per day, five times per day, etc.). When multiple treatments are used, the amount can be the same or different. It is understood that a treatment can be administered every day, every other day, every 2 days, every 3 days, every 4 days, every 5 days, etc. For example, with every other day administration, a treatment dose can be initiated on Monday with a first subsequent treatment administered on Wednesday, a second subsequent treatment administered on Friday, etc. Treatment is typically administered from one to two times daily. Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

Alternatively, the effective amount of a compound of the disclosure is from about 0.01 mg/kg/day to about 1000 mg/kg/day, from about 0.1 mg/kg/day to about 100 mg/kg/day, from about 0.5 mg/kg/day to about 50 mg/kg/day, or from about 1 mg/kg/day to 10 mg/kg/day.

In another embodiment, any of the above methods of treatment comprises the further step of co-administering to said subject one or more second therapeutic agents. The choice of second therapeutic agent may be made from any second therapeutic agent known to be useful for co-administration with a compound that modulates the APJ receptor. The choice of second therapeutic agent is also dependent upon the particular disease or condition to be treated. Examples of second therapeutic agents that may be employed in the methods of this disclosure are those set forth above for use in combination compositions comprising a compound of this disclosure and a second therapeutic agent.

The term "co-administered" as used herein means that the second therapeutic agent may be administered together with a compound of this disclosure as part of a single dosage form (such as a composition of this disclosure comprising a compound of the disclosure and a second therapeutic agent as described above) or as separate, multiple dosage forms. Alternatively, the additional agent may be administered prior to, consecutively with, or following the administration of a compound of this disclosure. In such combination therapy treatment, both the compounds of this disclosure and the second therapeutic agent(s) are administered by conventional methods. The administration of a composition of this disclosure, comprising both a compound of the disclosure and a second therapeutic agent, to a subject does not preclude the separate administration of that same therapeutic agent, any other second therapeutic agent or any compound of this disclosure to said subject at another time during a course of treatment.

In one embodiment of the disclosure, where a second therapeutic agent is administered to a subject, the effective amount of the compound of this disclosure is less than its effective amount would be where the second therapeutic agent is not administered. In another embodiment, the effective amount of the second therapeutic agent is less than its effective amount would be where the compound of this disclosure is not administered. In this way, undesired side effects associated with high doses of either agent may be minimized. Other potential advantages (including without limitation improved dosing regimens and/or reduced drug cost) will be apparent to those of skill in the art.

5.4. Kits

The present disclosure also provides kits for use to treat the target disease, disorder or condition. These kits comprise (a) a pharmaceutical composition comprising a compound of Formula I, or a salt thereof, wherein said pharmaceutical composition is in a container; and (b) instructions describing a method of using the pharmaceutical composition to treat the target disease, disorder or condition.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this disclosure may also comprise a device to administer or to measure out a unit dose of the pharmaceutical composition. Such a device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiments, the kits of this disclosure may comprise in a separate vessel of container a pharmaceutical composition comprising a second therapeutic agent, such as one of those listed above for use for co-administration with a compound of this disclosure.

Unless defined otherwise, all technical and scientific terms used herein have the same meaning as commonly understood by one of ordinary skill in the art to which this disclosure belongs. The article "a" and "an" are used herein to refer to one or more than one (i.e., to at least one) of the grammatical object(s) of the article. By way of example, "an element" means one or more elements.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

The following Examples further illustrate the disclosure and are not intended to limit the scope of the disclosure. In particular, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

6. EXAMPLES 6.1. Method and Preparation of a Representative Compound

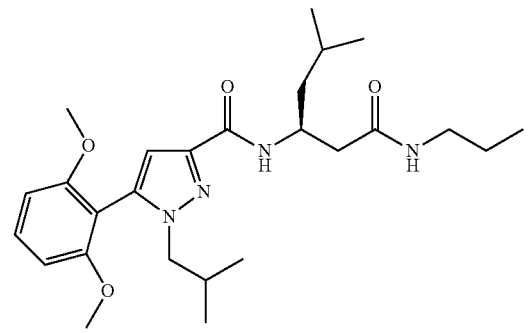 [SMILES: CCCNC(=O)C[C@H](CC(C)C)NC(=O)c1cc(-c2c(OC)cccc2OC)n(CC(C)C)n1]

157: (S)-5-(2,6-dimethoxyphenyl)-1-isobutyl-N-(5-methyl-1-oxo-1-(propylamino)hexan-3-yl)-1H-pyrazole-3-carboxamide (Also see FIG. 1/Scheme 1).

Experimental Details:

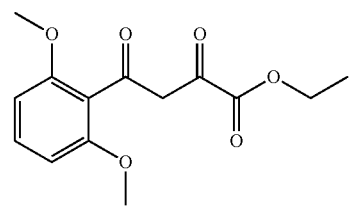 [SMILES: CCOC(=O)C(=O)CC(=O)c1c(OC)cccc1OC]

Step 1: Preparation of ethyl 4-(2,6-dimethoxyphenyl)-2,4-dioxobutanoate: To a solution of sodium ethoxide (21% in EtOH) (5.4 mL, 14.37 mmol) was added dropwise a mixture of diethyl oxalate (1.85 mL, 13.690 mmol) and 2,6-dimethoxy acetophenone (2.45 g, 13.690 mmol) in anhydrous ethanol (15 mL). The resultant mixture was stirred at room temperature for 30 minutes, upon which yellow suspension formed. The reaction mixture was heated to reflux for 4 h. The reaction was cooled to room temperature. Ethanol was evaporated in vacuo. The resultant residue was triturated with diethyl ether (30 mL) and filtered to obtain sodium salt of ethyl 4-(2,6-dimethoxyphenyl)-2,4-dioxobutanoate as yellow solid (4.0 g, 97%). MS m/z: Calcd. for $C_{14}H_{16}O_6$ 280.09 $[M]^+$, found 279.3 $[M-H]^+$.

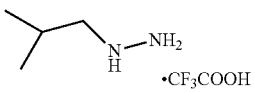

Step 2: Preparation of isobutylhydrazine trifluoroacetate: Preparation of tert-butyl 2-isobutylhydrazinecarboxylate: Isobutyraldehyde (1.0 g, 13.867 mmol) and tert-butyl carbazate (1.8 g, 13.867 mmol) in methanol (20 mL) was stirred at room temperature for 1 h. The solvent was evaporated and the resulting solid was dried in vacuo to give white solid of (E)-tert-butyl 2-(2-methylpropylidene)hydrazine carboxylate in quantitative yield. Sodium cyanoborohydride (1.2 g, 20.134 mmol) was added portionwise to a mixture of the (E)-tert-butyl 2-(2-methylpropylidene)hydrazine carboxylate (2.5 g, 13.423 mmol) in 75% of aqueous acetic acid (25 mL) at room temperature. The resultant solution was stirred for 3 h at room temperature. The reaction mixture was neutralized with 1N NaOH, extracted with $CH_2Cl_2$ (3×25 mL), washed with saturated $NaHCO_3$, dried with $Na_2SO_4$, filtered, and evaporated to give title compound as oil (2.4 g, 95%). $^1H$ NMR ($CDCl_3$, 300 MHz) δ 0.93 (d, J=6.78 Hz, 6H), 1.46 (s, 9 H), 1.64-1.82 (m, 1 H), 2.43 (br. s., 1 H), 2.67 (d, J=6.78 Hz, 2 H). MS m/z: Calcd. for $C_9H_{20}N_2O_2$ 188.15 $[M]^+$, found 189.3 $[M+H]^+$.

Preparation of isobutylhydrazine trifluoroacetate: Trifluoroacetic acid (12 mL) was added dropwise to a solution of the tert-butyl 2-isobutylhydrazinecarboxylate (2.4 g, 12.747 mmol) in $CH_2Cl_2$ (12 mL). The reaction mixture was stirred at room temperature for 1.5 h. The solvent was evaporated to give the trifluoroacetate salt of the title compound as colorless oil in quantitative yield. $^1H$ NMR ($CDCl_3$, 300 MHz) δ 1.04 (dd, J=9.04, 6.78 Hz, 6 H), 2.04-2.25 (m, 1 H), 3.02 (dd, J=6.97, 3.96 Hz, 2 H). MS m/z: Calcd. for $C_4H_{12}N_2$ 88.10 $[M]^+$, found 89.4 $[M+H]^+$.

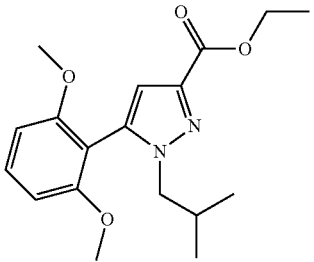 [SMILES: CCOC(=O)c1cc(-c2c(OC)cccc2OC)n(CC(C)C)n1]

Step 3: Preparation of ethyl 5-(2,6-dimethoxyphenyl)-1-isobutyl-1H-pyrazole-3-carboxylate: Sodium salt of ethyl 4-(2,6-dimethoxyphenyl)-2,4-dioxobutanoate (1.2 g, 3.965 mmol) and isobutylhydrazine trifluoroacetate (0.962 g, 4.758 mmol) was mixed with glacial acetic acid (25 mL) and conc. HCl (0.6 mL). The reaction mixture was heated to reflux for 3.5 h. After cooling, reaction mixture was poured into water (25 mL). The aqueous layer was extracted with $CH_2Cl_2$ (3×30 mL) and the combined $CH_2Cl_2$ layer was washed with saturated aqueous $NaHCO_3$. The organic layer was then washed with saturated brine, dried over $Na_2SO_4$, followed by filtration. The solvent was evaporated in vacuo. The residue was purified by silica gel flash chromatography (EtOAc:Hex) to give the title compound as oil (0.535 g, 40%). $^1H$ NMR ($CDCl_3$, 300 MHz) δ 0.72 (d, J=6.78 Hz, 6 H), 1.39 (t, J=7.15 Hz, 3 H), 2.10-2.24 (m, 1 H), 3.72 (d, J=6.0 Hz, 2 H), 3.74 (s, 6 H), 4.41 (q, J=7.16 Hz, 2 H), 6.62 (d, J=8.67 Hz, 2 H), 6.73 (s, 1 H), 7.38 (t, J=8.48 Hz, 1 H). MS m/z: Calcd. for $C_{18}H_{24}N_2O_4$ 332.17 $[M]^+$, found 333.4 $[M+H]^+$.

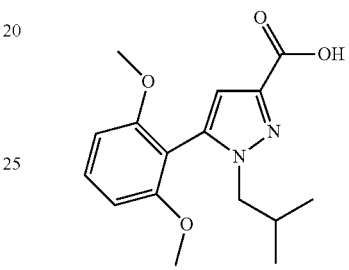

Step 4: Preparation of 5-(2,6-Dimethoxyphenyl)-1-isobutyl-1H-pyrazole-3-carboxylic acid: Lithium hydroxide monohydrate (189 mg, 4.513 mmol) in 1 mL of water was added to a solution of ethyl 5-(2,6-dimethoxyphenyl)-1-isobutyl-1H-pyrazole-3-carboxylate (500 mg, 1.504 mmol) in MeOH (11 mL) and THF (2 mL). The mixture was stirred at room temperature for 18 h. The reaction mixture was concentrated to about half the volume and then extracted with ether (2×15 mL). The aqueous layer was acidified with 1 N HCl and extracted with $CH_2Cl_2$ (3×25 mL). The combined organic layers were washed with water, brine and then dried with $Na_2SO_4$. The solvent was evaporated in vacuo to give the title compound as white solid (440 mg, 96%).

$^1H$ NMR ($CDCl_3$, 300 MHz) δ 0.74 (d, J=6.40 Hz, 6 H), 2.10-2.24 (m, 1 H), 3.72 (d, J=7.54 Hz, 2 H), 3.75 (s, 6 H), 6.63 (d, J=9.0 Hz, 2 H), 6.79 (s, 1 H), 7.40 (t, J=8.48 Hz, 1 H). MS m/z: Calcd. for $C_{16}H_{20}N_2O_4$ 304.14 $[M]^+$, found 303.3 $[M-H]^+$.

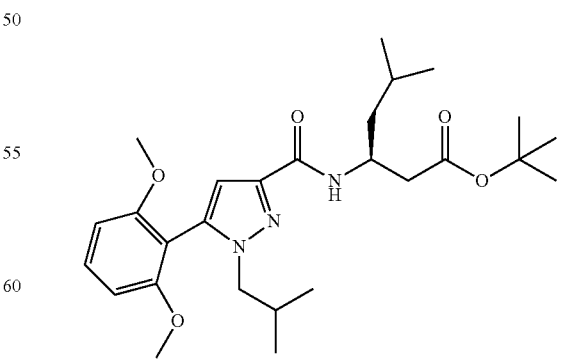

Step 5: Preparation of (S)-tert-butyl 3-(5-(2,6-dimethoxyphenyl)-1-isobutyl-1H-pyrazole-3-carboxamido)-5-methylhexanoate: 5-(2,6-Dimethoxyphenyl)-1-isobutyl-1H-pyrazole-3-carboxylic acid (50 mg, 0.164 mmol) was dissolved in THF (1.5 mL). To the solution was added benzotriazol-1-yl-oxy-tris(dimethylamino)phosphonium hexafluorophosphate (BOP) (72 mg, 0.164 mmol) and triethylamine (0.050 mL, 0.493 mmol). The resulting mixture was stirred at room temperature for 15 minutes. (S)-Tert-butyl 3-amino-5-methylhexanoate (36 mg, 0.180 mmol) in 0.3 mL of THF was added dropwise, and stirred at room temperature for 1.5 h. THF was evaporated in vacuo, water was added to the residue and the aqueous layer was extracted with $CH_2Cl_2$ (3×15 mL). The combined organic layers were washed with water, brine and then dried with $Na_2SO_4$, followed by filtration. The solvent was evaporated in vacuo. The residue was purified by silica gel flash chromatography (EtOAc:Hex) to give the title compound as oil (61 mg, 76%). $^1H$ NMR ($CDCl_3$, 300 MHz) δ 0.74 (d, J=6.40 Hz, 3H), 0.73 (d, J=6.78 Hz, 3 H), 0.97 (d, J=7.91 Hz, 6 H), 1.35-1.44 (m, 1 H), 1.47 (s, 9 H), 1.56-1.80 (m, 2 H), 2.07-2.19 (m, 1 H), 2.54 (d, J=5.65 Hz, 2 H), 3.63 (d, J=6.15 Hz, 2 H), 3.72(s, 3 H), 3.73 (s, 3 H), 4.45-4.57 (m, 1 H), 6.61 (d, J=8.29 Hz, 2 H), 6.69 (s, 1 H), 7.19 (d, J=9.42 Hz, 1 H),7.37 (t, J=8.29 Hz, 1 H). MS m/z: Calcd. for $C_{27}H_{41}N_3O_5$ 487.30 $[M]^+$, found 488.7 $[M+H]^+$.

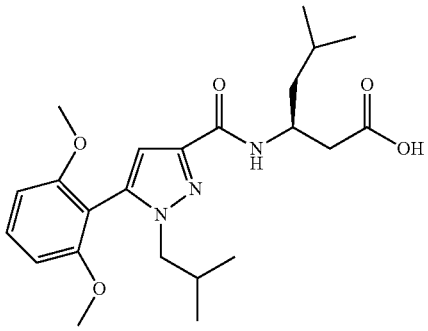 [SMILES: COc1cccc(OC)c1-c1cc(C(=O)N[C@H](CC(=O)O)CC(C)C)nn1CC(C)C]

Step 6: Preparation of (S)-3-(5-(2,6-Dimethoxyphenyl)-1-isobutyl-1H-pyrazole-3-carboxamido)-5-methylhexanoic acid: Trifluoroacetic acid (0.4 mL) was added dropwise to a solution of (S)-tert-butyl 3-(5-(2,6-dimethoxyphenyl)-1-isobutyl-1H-pyrazole-3-carboxamido)-5-methylhexanoate (40 mg, 0.820 mmol) in $CH_2Cl_2$ (1 mL). The reaction mixture was stirred at room temperature for 1 h. The solvent was evaporated in vacuo. To the residue was added ether/hexane (1:2) triturated and filtered to give the title compound as white solid (36 mg, 86%). $^1H$ NMR ($CDCl_3$, 300 MHz) δ 0.74 (d, J=6.78 Hz, 6 H), 0.97 (d, J=6.22 Hz, 6 H), 1.42-1.57 (m, 1 H), 1.64-1.84 (m, 2 H), 2.02-2.18 (m, 1 H), 2.71 (d, J=5.27 Hz, 2 H), 3.65 (d, J=7.54 Hz, 2 H), 3.74 (s, 6 H), 4.41-4.53 (m, 1 H), 6.62 (d, J=8.29 Hz, 2 H), 6.71 (s, 1 H), 7.29-7.42 (m, 2 H). MS m/z: Calcd. for $C_{23}H_{33}N_3O_5$ 431.24 $[M]^+$, found 430.5 $[M-H]^+$.

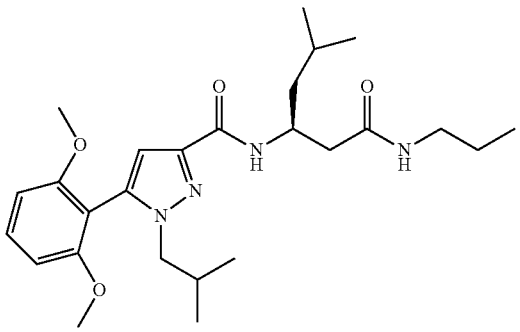 [SMILES: CCCNC(=O)C[C@H](CC(C)C)NC(=O)c1cc(-c2c(OC)cccc2OC)n(CC(C)C)n1]

Step 7: Preparation of (S)-5-(2,6-Dimethoxyphenyl)-1-isobutyl-N-(5-methyl-1-oxo-1-(propylamino)hexan-3-yl)-1H-pyrazole-3-carboxamide: (S)-3-(5-(2,6-Dimethoxyphenyl)-1-isobutyl-1H-pyrazole-3-carboxamido)-5-methylhexanoic acid (30 mg, 0.069 mmol) was dissolved in THF (1.5 mL). To the solution was added benzotriazol-1-yl-oxy-tris(dimethylamino)phosphonium hexafluorophosphate (BOP) (31 mg, 0.069 mmol) and triethylamine (0.029 mL, 0.208 mmol). The resulting mixture was stirred at room temperature for 15 minutes. 1-Propylamine (4.5 mg, 0.0759 mmol) in 0.2 mL of THF was added dropwise, and stirred at room temperature for 2 h. THF was evaporated in vacuo, water was added to the residue and the aqueous layer was extracted with $CH_2Cl_2$ (3×15 mL). The combined organic layers were washed with water, brine and then dried with $Na_2SO_4$, followed by filtration. The solvent was evaporated in vacuo. The residue was purified by silica gel flash chromatography (EtOAc:Hex) to give the title compound as white solid (25 mg, 76%). 76% yield; $^1H$ NMR ($CDCl_3$, 300 MHz) δ 0.73 (dd, J=6.78, 1.88 Hz, 6 H), 0.87 (t, J=7.35 Hz, 3 H), 0.95 (d, J=6.78 Hz, 6 H), 1.40-1.56 (m, 3 H), 1.61-1.82 (m, 2 H), 2.05-2.19 (m, 1 H), 2.54 (d, J=6.03 Hz, 2 H), 3.14-3.26 (m, 2 H), 3.63 (d, J=7.54 Hz, 2 H), 3.74 (s, 6 H), 4.34-4.46 (m, 1 H), 6.48-6.57 (m, 1 H), 6.62 (d, J=8.29 Hz, 2 H), 6.67 (s, 1 H), 7.08 (d, J=9.04 Hz, 1 H), 7.37 (t, J=8.48 Hz, 1 H). MS m/z: Calcd. for $C_{26}H_{40}N_4O_4$ 472.62 $[M]^+$, found 473.9 $[M+H]^+$.

Characterization of Selected Compounds

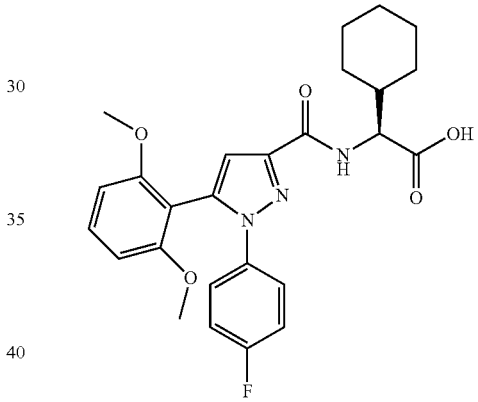

71: (S)-2-Cyclohexyl-2-(5-(2,6-dimethoxyphenyl)-1-(4-fluorophenyl)-1H-pyrazole-3-carboxamido)acetic acid: 94% yield; $^1H$ NMR (MeOH-$d_4$, 300 MHz) δ 1.11-1.41 (m, 5 H), 1.60-1.86 (m, 5 H), 1.89-2.04 (m, 1 H), 3.60 (br. s., 6 H), 4.57 (d, J=6.03 Hz, 1 H), 6.62 (d, J=8.29 Hz, 2 H), 6.80 (s, 1 H), 7.02-7.10 (m, 2 H), 7.25-7.38 (m, 4H). MS m/z: Calcd for $C_{26}H_{28}FN_3O_5$ 481.20 $[M]^+$, found 482.5 $[M+H]^+$.

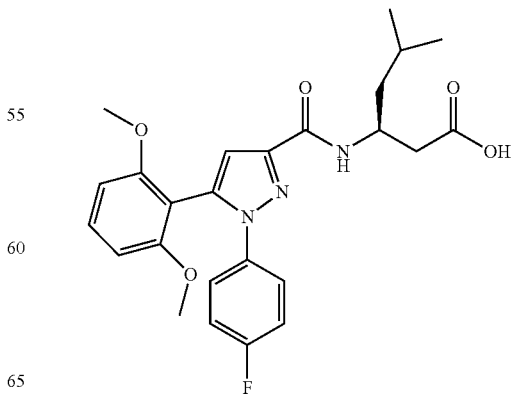

56: (S)-3-(5-(2,6-Dimethoxyphenyl)-1-(4-fluorophenyl)-1H-pyrazole-3-carboxamido)-5-methylhexanoic acid: 81% yield; $^1$H NMR (CDCl$_3$, 300 MHz) δ 0.96 (t, J=6.78 Hz, 6 H), 1.40-1.51 (m, 1 H), 1.62-1.82 (m, 2 H), 2.70 (d, J=5.27 Hz, 2 H), 3.52 (s, 3 H), 3.59 (m, 3 H), 4.47-4.60 (m, 1 H), 6.50 (d, J=8.67 Hz, 2 H), 6.93-7.02 (m, 2 H), 7.22-7.35 (m, 5 H). MS m/z: Calcd. for C$_{25}$H$_{28}$FN$_3$O$_5$ 469.20 [M]$^+$, found 470.6 [M+H]$^+$.

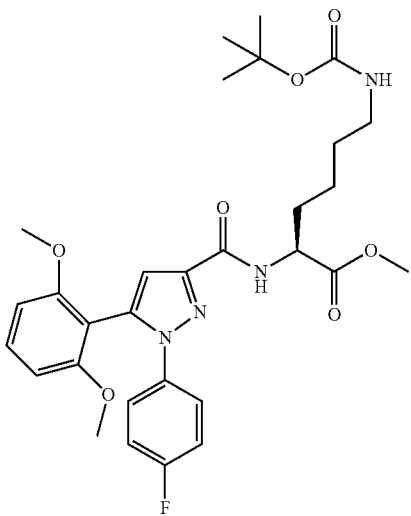 [SMILES: COC(=O)[C@H](CCCCNC(=O)OC(C)(C)C)NC(=O)c1cc(-c2c(OC)cccc2OC)n(-c2ccc(F)cc2)n1]

62: (S)-Methyl 6-((tert-butoxycarbonyl)amino)-2-(5-(2,6-dimethoxyphenyl)-1-(4-fluorophenyl)-1H-pyrazole-3-carboxamido)hexanoate: 57% yield; $^1$H NMR (CDCl$_3$, 300 MHz) δ 1.42 (s, 9H), 1.44-1.58 (m, 4 H), 1.70-1.87 (m, 1 H), 1.90-2.04 (m, 1 H), 3.03-3.19 (m, 2 H), 3.55 (s, 3 H), 3.61 (s, 3 H), 3.77 (s, 3 H), 4.57 (br. s., 1 H), 4.81-4.88 (m, 1 H), 6.51 (t, J=7.54 Hz, 2 H), 6.93-7.01 (m, 2 H), 7.23-7.33 (m, 4 H), 7.41 (d, J=8.29 Hz, 1 H). MS m/z: Calcd. for C$_{30}$H$_{37}$FN$_4$O$_7$ 584.26 [M]$^+$, found 585.8 [M+H]$^+$.

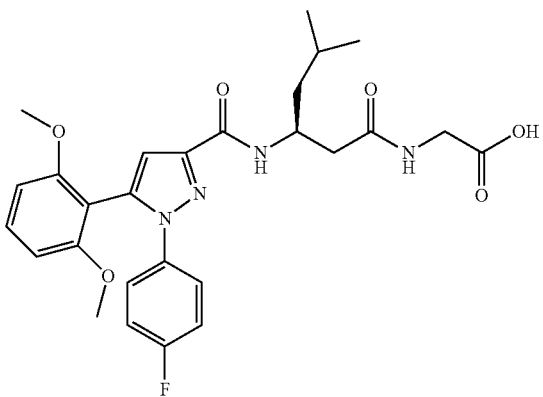 [SMILES: COc1cccc(OC)c1-c1cc(C(=O)N[C@H](CC(=O)NCC(=O)O)CC(C)C)nn1-c1ccc(F)cc1]

77: (S)-2-(3-(5-(2,6-Dimethoxyphenyl)-1-(4-fluorophenyl)-1H-pyrazole-3-carboxamido)-5-methylhexanamido)acetic acid: 64% yield; $^1$H NMR (CDCl$_3$, 300 MHz) δ 0.93 (d, J=6.40 Hz, 6 H), 1.13-1.35 (m, 1 H), 1.46-1.59 (m, 1 H), 1.62-1.81 (m, 1 H), 2.49 (dd, J=13.94, 7.54 Hz, 1 H), 2.84 (dd, J=14.32, 6.03 Hz, 1 H), 3.58 (s, 6 H), 4.01-4.19 (m, 2 H), 4.51 (br. s., 1 H), 6.50 (d, J=8.29 Hz, 2 H), 6.91 (s, 1 H), 6.97 (t, J=9.0 Hz, 2 H), 7.18-7.40 (m, 5 H). MS m/z: Calcd. for C$_{27}$H$_{31}$FN$_4$O$_6$ 526.22 [M]$^+$, found 525.6 [M-H]$^+$.

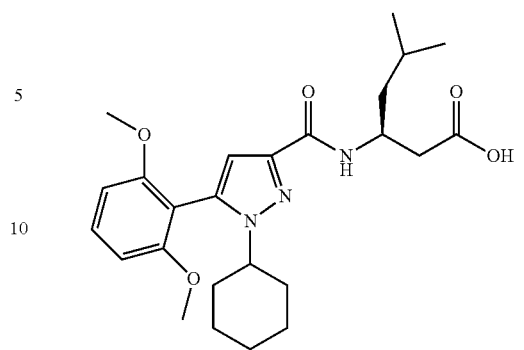

79: (S)-3-(1-Cyclohexyl-5-(2,6-dimethoxyphenyl)-1H-pyrazole-3-carboxamido)-5-methylhexanoic acid: 92% yield; $^1$H NMR (CDCl$_3$, 300 MHz) δ 0.97 (d, J=6.40 Hz, 6 H), 1.11-1.32 (m, 4 H), 1.43-1.57 (m, 1 H), 1.60-1.98 (m, 8 H), 2.65-2.79 (m, 2 H), 3.59-3.70 (m, 1 H), 3.74 (s, 6 H), 4.36-4.51 (m, 1 H), 6.62 (s, 1 H), 6.66 (d, J=7.54 Hz, 2 H), 7.22 (br. s, 1 H), 7.38 (t, J=8.29 Hz, 1 H). MS m/z: Calcd. for C$_{25}$H$_{35}$N$_3$O$_5$ 457.26 [M]$^+$, found 456.3 [M-H]$^+$.

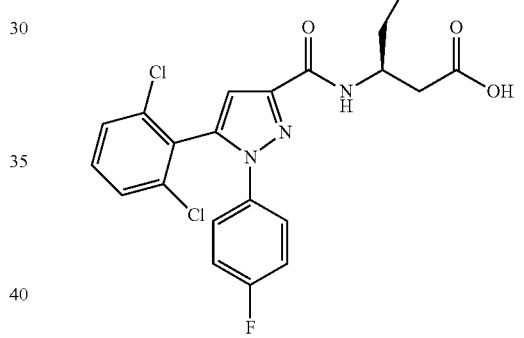

80: (S)-3-(5-(2,6-Dichlorophenyl)-1-(4-fluorophenyl)-1H-pyrazole-3-carboxamido)-5-methylhexanoic acid: 77% yield; $^1$H NMR (CDCl$_3$, 300 MHz) δ 0.97 (dd, J=8.10, 6.59 Hz, 6 H), 1.41-1.53 (m, 1 H), 1.63-1.82 (m, 2 H), 2.72 (d, J=5.65 Hz, 2 H), 4.51-4.62 (m, 1 H), 6.96-7.05 (m, 3 H), 7.24-7.37 (m, 6 H). MS m/z: Calcd. for C$_{23}$H$_{22}$Cl$_2$FN$_3$O$_3$ 477.10 [M]$^+$, found 476.5 [M-H]$^+$.

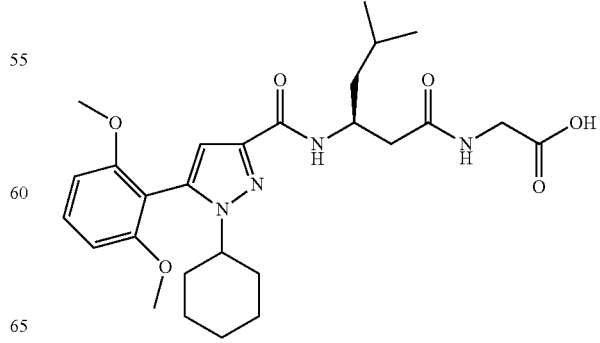

81: (S)-2-(3-(1-Cyclohexyl-5-(2,6-dimethoxyphenyl)-1H-pyrazole-3-carboxamido)-5-methylhexanamido)acetic acid: 80% yield; ¹H NMR (CDCl₃, 300 MHz) δ 0.95 (t, J=6.40 Hz, 6 H), 1.09-1.35 (m, 3 H), 1.49-1.76 (m, 5 H), 1.77-1.95 (m, 5 H), 2.48 (dd, J=14.13, 7.35 Hz, 1 H), 2.86 (dd, J=13.75, 6.22 Hz, 1 H), 3.61-3.70 (m, 1 H), 3.75 (s, 6 H), 3.99-4.19 (m, 2 H), 4.38-4.52 (m, 1 H), 6.63 (d, J=3.01 Hz, 2 H), 6.65 (s, 1 H), 7.13 (d, J=8.67 Hz, 1 H), 7.38 (t, J=8.29 Hz, 1 H), 7.51 (t, J=4.52 Hz, 1 H). MS m/z: Calcd. for $C_{27}H_{38}N_4O_6$ 514.28 [M]⁺, found 513.5 [M−H]⁺.

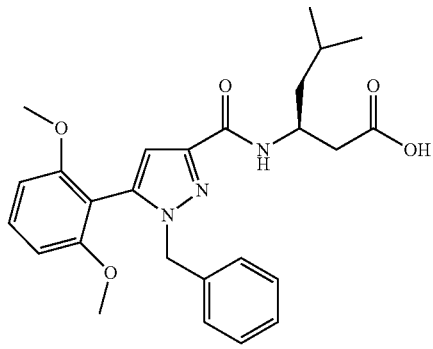

94: (S)-3-(1-Benzyl-5-(2,6-dimethoxyphenyl)-1H-pyrazole-3-carboxamido)-5-methylhexanoic acid: 93% yield; ¹H NMR (CDCl₃, 300 MHz) δ 0.96 (dd, J=6.40, 3.01 Hz, 6 H), 1.39-1.58 (m, 1 H), 1.62-1.80 (m, 2 H), 2.63-2.76 (m, 2 H), 3.59 (s, 3 H), 3.61 (s, 3 H), 4.39-4.51 (m, 1 H), 5.09 (s, 2 H), 6.53 (d, J=8.29 Hz, 2 H), 6.78 (s, 1 H), 6.91-6.99 (m, 2 H), 7.16-7.24 (m, 3 H), 7.33 (t, J=8.48 Hz, 2 H). MS m/z: Calcd. for $C_{26}H_{31}N_3O_5$ 465.23 [M]⁺, found 464.6 [M−H]⁺.

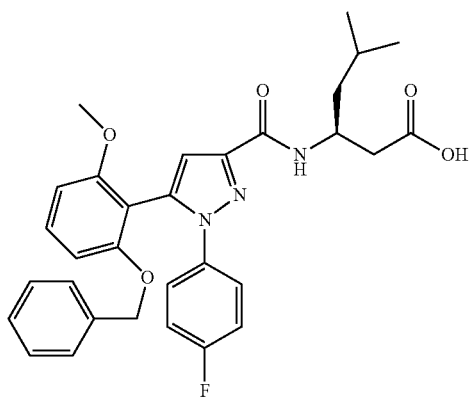 [SMILES: COc1cccc(OCc2ccccc2)c1-c1cc(C(=O)N[C@H](CC(=O)O)CC(C)C)nn1-c1ccc(F)cc1]

82: (3S)-3-(5-(2-(Benzyloxy)-6-methoxyphenyl)-1-(4-fluorophenyl)-1H-pyrazole-3-carboxamido)-5-methylhexanoic acid: 85% yield; ¹H NMR (CDCl₃, 300 MHz) δ 0.97 (t, J=6.40 Hz, 6 H), 1.39-1.55 (m, 1 H), 1.61-1.82 (m, 2 H), 2.71 (d, J=2.64 Hz, 2 H), 3.61 (d, J=6.78 Hz, 3 H), 4.46-4.62 (m, 1 H), 4.86 (dd, J=12.62, 8.10 Hz, 1 H), 4.98 (dd, J=12.62, 6.22 Hz, 1 H), 6.50 (d, J=8.29 Hz, 2 H), 6.92 (t, J=9.0, 1 H), 6.98 (s, 1 H), 7.07 (br. s., 1 H), 7.03-7.11 (m, 2 H), 7.15-7.34 (m, 7 H). MS m/z: Calcd. for $C_{31}H_{32}FN_3O_5$ 545.23 [M]⁺, found 544.7 [M−H]⁺.

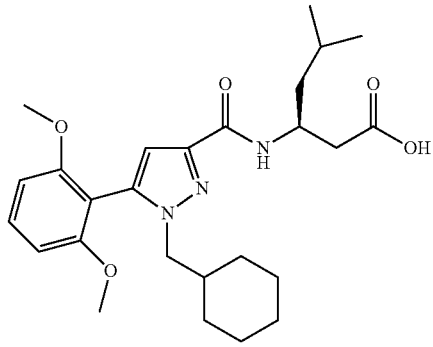

95: (S)-3-(1-(Cyclohexylmethyl)-5-(2,6-dimethoxyphenyl)-1H-pyrazole-3-carboxamido)-5-methylhexanoic acid: 82% yield; ¹H NMR (CDCl₃, 300 MHz) δ 0.64-0.80 (m, 2 H), 0.97 (d, J=6.40 Hz, 6 H), 1.02-1.18 (m, 3 H), 1.42-1.64 (m, 7 H), 1.65-1.83 (m, 3 H), 2.65-2.78 (m, 2 H), 3.68 (d, J=7.16 Hz, 2 H), 3.73 (s, 3 H), 3.74 (s, 3 H), 4.39-4.53 (m, 1 H), 6.61-6.65 (m, 1 H), 6.62 (t, J=8.48 Hz, 2 H), 6.70 (s, 1 H), 7.38 (t, J=9.0 Hz, 1 H). MS m/z: Calcd. for $C_{26}H_{37}N_3O_5$ 471.27 [M]⁺, found 470.6 [M−H]⁺.

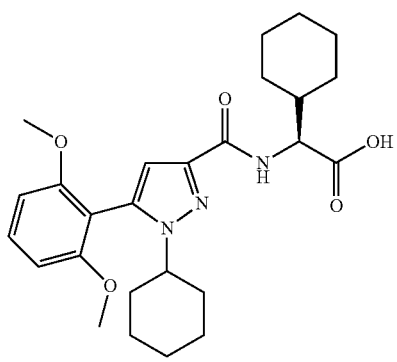 [SMILES: COc1cccc(OC)c1-c1cc(C(=O)N[C@H](C(=O)O)C2CCCCC2)nn1C1CCCCC1]

93: (S)-2-Cyclohexyl-2-(1-cyclohexyl-5-(2,6-dimethoxyphenyl)-1H-pyrazole-3-carboxamido)acetic acid: 87% yield; ¹H NMR (CDCl₃, 300 MHz) δ 1.08-1.39 (m, 8 H), 1.59-1.73 (m, 2 H), 1.74-1.98 (m, 10 H), 2.01-2.16 (m, 1 H), 3.62-3.70 (m, 1 H), 3.73 (s, 3 H), 3.75 (s, 3 H), 4.50- 4.59 (m, 1 H), 6.63 (d, J=8.29 Hz, 2 H), 6.68 (s, 1 H), 7.38 (t, J=8.48 Hz, 1 H), 7.46 (d, J=7.91 Hz, 1 H). MS m/z: Calcd. for $C_{26}H_{35}N_3O_5$ 469.26 [M]⁺, found 468.5 [M−H]⁺.

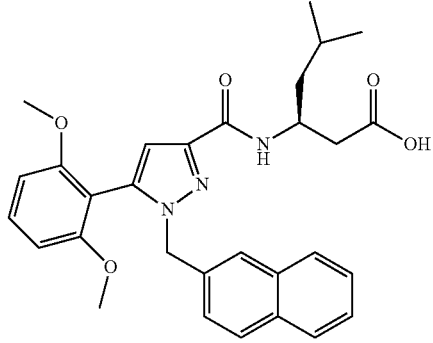 [SMILES: COc1cccc(OC)c1-c1cc(C(=O)N[C@H](CC(=O)O)CC(C)C)nn1Cc1ccc2ccccc2c1]

96: (S)-3-(5-(2,6-Dimethoxyphenyl)-1-(naphthalen-2-yl-methyl)-1H-pyrazole-3-carboxamido)-5-methylhexanoic acid: 93% yield; ¹H NMR (CDCl₃, 300 MHz) δ 0.96 (d, J=4.90 Hz, 3 H), 0.94 (d, J=4.90 Hz, 3 H), 1.37-1.50 (m, 1 H), 1.62-1.80 (m, 2 H), 2.62-2.75 (m, 2 H), 3.51 (s, 3 H), 3.52 (s, 3 H), 4.39-4.53 (m, 1 H), 5.25 (s, 2 H), 6.50 (d, J=6.10 Hz, 1 H), 6.80 (s, 1 H), 7.15 (dd, J=8.48, 1.70 Hz, 1 H), 7.25-7.37 (m, 4 H), 7.39-7.45 (m, 2 H), 7.63-7.75 (m, 3 H). MS m/z: Calcd. for $C_{30}H_{33}N_3O_5$ 515.24 [M]⁺, found 514.6 [M–H]⁺.

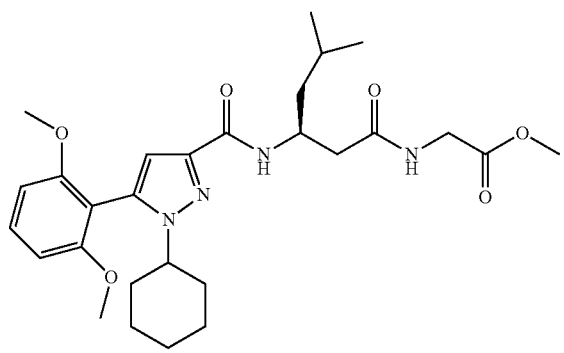 [SMILES: COC(=O)CNC(=O)C[C@H](CC(C)C)NC(=O)c1cc(-c2c(OC)cccc2OC)n(C2CCCCC2)n1]

103: (S)-Methyl 2-(3-(1-cyclohexyl-5-(2,6-dimethoxyphenyl)-1H-pyrazole-3-carboxamido)-5-methylhexanamido)acetate: 90% yield; ¹H NMR (CDCl₃, 300 MHz) δ 0.95 (d, J=6.40 Hz, 6 H), 1.09-1.35 (m, 4 H), 1.34-1.54 (m, 1 H), 1.56-1.69 (m, 2 H), 1.71-1.98 (m, 7 H), 2.61 (d, J=6.40 Hz, 2 H), 3.65 (s, 3 H), 3.74 (s, 6 H), 4.04 (d, J=5.27 Hz, 2 H), 4.43-4.55 (m, 1 H), 6.59-6.69 (m, 3 H), 7.08 (t, J=5.27 Hz, 1 H), 7.15 (d, J=9.04 Hz, 1 H), 7.38 (t, J=8.48 Hz, 1 H). MS m/z: Calcd. for $C_{28}H_{40}N_4O_6$ 528.64 [M]⁺, found 529.8 [M+H]⁺.

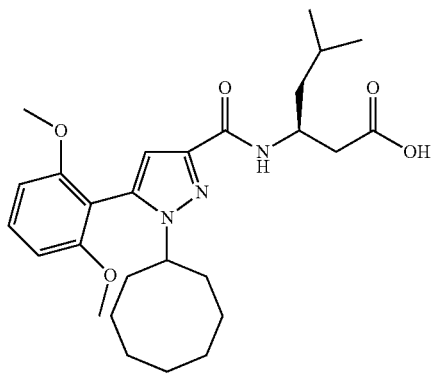 [SMILES: COc1cccc(OC)c1-c1cc(C(=O)N[C@H](CC(=O)O)CC(C)C)nn1C1CCCCCCC1]

125: (S)-3-(1-Cyclooctyl-5-(2,6-dimethoxyphenyl)-1H-pyrazole-3-carboxamido)-5-methylhexanoic acid: 94% yield; ¹H NMR (CDCl₃, 300 MHz) δ 0.97 (d, J=6.40 Hz, 6 H), 1.23-1.45 (m, 6 H), 1.48-1.63 (m, 4 H), 1.66-1.86 (m, 5 H), 2.03-2.19 (m, 2 H), 2.72 (t, J=5.46 Hz, 2 H), 3.74 (s, 6 H), 3.94-4.05 (m, 1 H), 4.37-4.49 (m, 1 H), 6.63 (d, J=8.29 Hz, 2 H), 6.67 (s, 1 H), 7.23 (s, 1 H), 7.38 (t, J=8.48 Hz, 1 H). MS m/z: Calcd. for $C_{27}H_{39}N_3O_5$ 485.29 [M]⁺, found 484.5 [M–H]⁺.

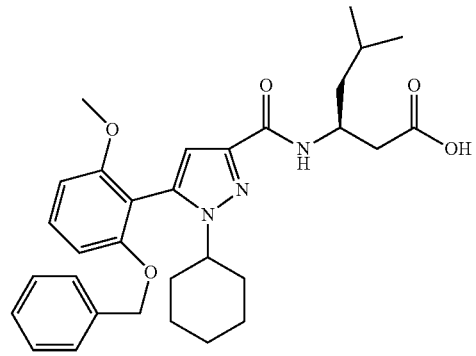 [SMILES: COc1cccc(OCc2ccccc2)c1-c1cc(C(=O)N[C@H](CC(=O)O)CC(C)C)nn1C1CCCCC1]

126: (3S)-3-(5-(2-(Benzyloxy)-6-methoxyphenyl)-1-cyclohexyl-1H-pyrazole-3-carboxamido)-5-methylhexanoic acid: 98% yield; ¹H NMR (CDCl₃, 300 MHz) δ 0.98 (dd, J=6.40, 1.51 Hz, 6 H), 1.10-1.31 (m, 4 H), 1.45-1.58 (m, 2 H), 1.58-1.70 (m, 2 H), 1.71-1.95 (m, 8 H), 2.70-2.76 (m, 2 H), 3.64-3.72 (m, 1 H), 4.36-4.49 (m, 1 H), 5.05 (s, 2 H), 6.63 (dd, J=8.48, 2.45 Hz, 2 H), 6.71 (s, 1 H), 7.16-7.35 (m, 7 H). MS m/z: Calcd. for $C_{31}H_{39}N_3O_5$ 533.29 [M]⁺, found 532.6 [M–H]⁺.

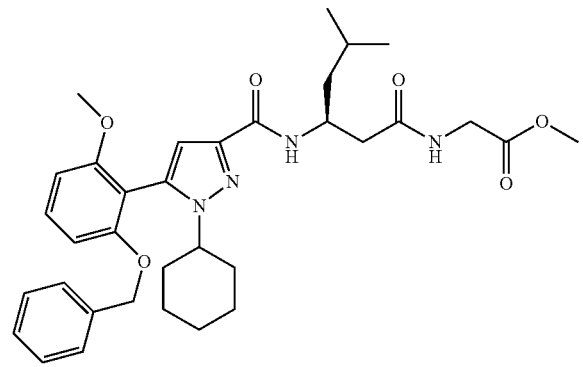 [SMILES: COC(=O)CNC(=O)C[C@H](CC(C)C)NC(=O)c1cc(-c2c(OC)cccc2OCc2ccccc2)n(C2CCCCC2)n1]

127: Methyl 2-((3S)-3-(5-(2-(benzyloxy)-6-methoxyphenyl)-1-cyclohexyl-1H-pyrazole-3-carboxamido)-5-methylhexanamido)acetate: 34% yield; ¹H NMR (CDCl₃, 300 MHz) δ 0.97 (dd, J=6.22, 2.07 Hz, 6 H), 1.09-1.31 (m, 4 H), 1.42-1.57 (m, 3 H), 1.68-1.94 (m, 6 H), 2.62 (d, J=6.03 Hz, 2 H), 3.65 (s, 3 H), 3.66-3.72 (m, 1 H), 3.74 (s, 3 H), 4.03 (t, J=5.27 Hz, 2 H), 4.42-4.55 (m, 1 H), 5.05 (s, 2 H), 6.63 (dd, J=8.29, 3.01 Hz, 2 H), 6.68 (s, 1 H), 7.07 (d, J=6.03 Hz, 1 H), 7.13-7.23 (m, 3 H), 7.25-7.39 (m, 4 H). MS m/z: Calcd. for $C_{34}H_{44}N_4O_6$ 604.74 [M]⁺, found 605.8 [M+H]⁺.

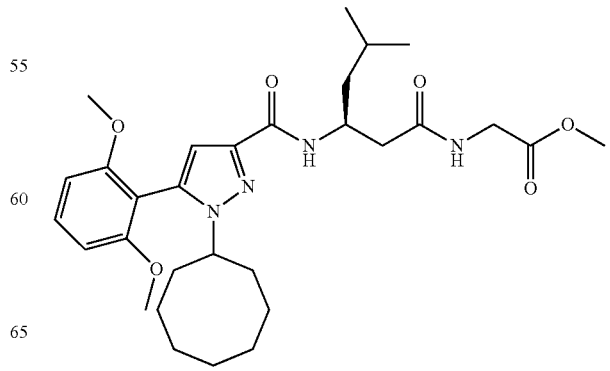

128: (S)-Methyl 2-(3-(1-cyclooctyl-5-(2,6-dimethoxyphenyl)-1H-pyrazole-3-carboxamido)-5-methylhexanamido)acetate: 87% yield; $^1$H NMR (CDCl$_3$, 300 MHz) δ 0.96 (d, J=6.78 Hz, 6 H), 1.22-1.46 (m, 6 H), 1.48-1.56 (m, 4 H), 1.65-1.84 (m, 5 H), 2.06-2.18 (m, 2 H), 2.58-2.64 (m, 2 H), 3.66 (s, 3 H), 3.73 (s, 3 H), 3.74 (s, 3 H), 3.93-4.02 (m, 1 H), 4.04 (d, J=5.65 Hz, 2 H), 4.42-4.51 (m, 1 H), 6.60-6.67 (m, 3 H), 7.06-7.16 (m, 2 H), 7.32-7.42 (m, 1 H). MS m/z: Calcd. for C$_{30}$H$_{44}$N$_4$O$_6$ 556.33 [M]$^+$, found 557.9 [M+H]$^+$.

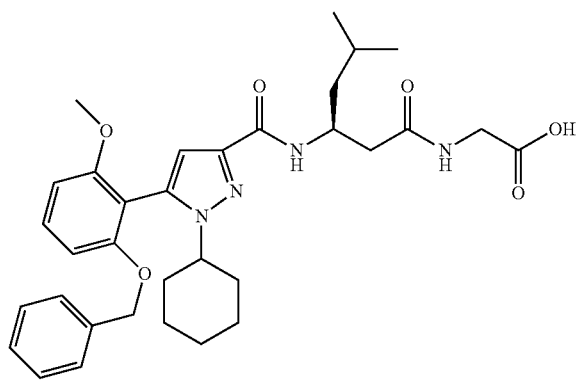 [SMILES: COc1cccc(OCc2ccccc2)c1-c1cc(C(=O)N[C@H](CC(=O)NCC(=O)O)CC(C)C)nn1C1CCCCC1]

129: 2-((3S)-3-(5-(2-(Benzyloxy)-6-methoxyphenyl)-1-cyclohexyl-1H-pyrazole-3-carboxamido)-5-methylhexanamido)acetic acid: 82% yield; $^1$H NMR (CDCl$_3$, 300 MHz) δ 0.90-1.04 (m, 6 H), 1.09-1.38 (m, 4 H), 1.52-1.91 (m, 9 H), 2.50 (ddd, J=14.32, 6.97, 2.83 Hz, 1 H), 2.78-2.88 (m, 1 H), 2.89 (s, 1 H), 3.74 (d, J=1.51 Hz, 4 H), 3.98-4.24 (m, 2 H), 4.46 (br. s., 1 H), 5.05 (s, 2 H), 6.41-6.71 (m, 3 H), 7.05-7.38 (m, 7 H), 7.47 (d, J=3.01 Hz, 1 H). MS m/z: Calcd. for C$_{33}$H$_{42}$N$_4$O$_6$ 590.31 [M]$^+$, found 589.7 [M–H]$^+$.

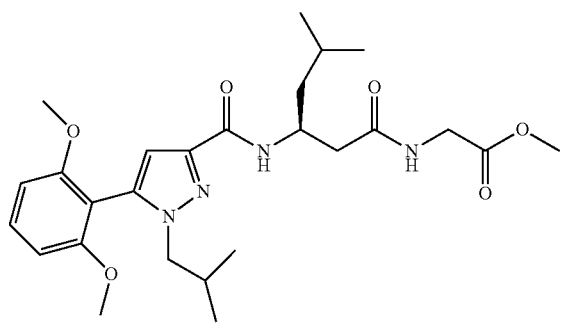 [SMILES: COC(=O)CNC(=O)C[C@H](CC(C)C)NC(=O)c1cc(-c2c(OC)cccc2OC)n(CC(C)C)n1]

130: (S)-Methyl 2-(3-(5-(2,6-dimethoxyphenyl)-1-isobutyl-1H-pyrazole-3-carboxamido)-5-methylhexanamido)acetate: 69% yield; $^1$H NMR (CDCl$_3$, 300 MHz) δ 0.74 (dd, J=6.78, 1.88 Hz, 6 H), 0.95 (dd, J=6.40, 1.51 Hz, 6 H), 1.37-1.51 (m, 1 H), 1.61-1.83 (m, 2 H), 2.05-2.16 (m, 1 H), 2.61 (d, J=5.65 Hz, 2 H), 3.63 (d, J=7.16 Hz, 2 H), 3.68 (s, 3 H), 3.73 (s, 3 H), 3.74 (s, 3 H), 4.04 (d, J=5.65 Hz, 2 H), 4.42-4.54 (m, 1 H), 6.62 (d, J=8.67 Hz, 2 H), 6.68 (s, 1 H), 6.99 (t, J=5.09 Hz, 1 H), 7.14 (d, J=9.04 Hz, 1 H), 7.38 (t, J=8.48 Hz, 1 H). MS m/z: Calcd. for C$_{26}$H$_{38}$N$_4$O$_6$ 502.28 [M]$^+$, found 503.9 [M+H]$^+$.

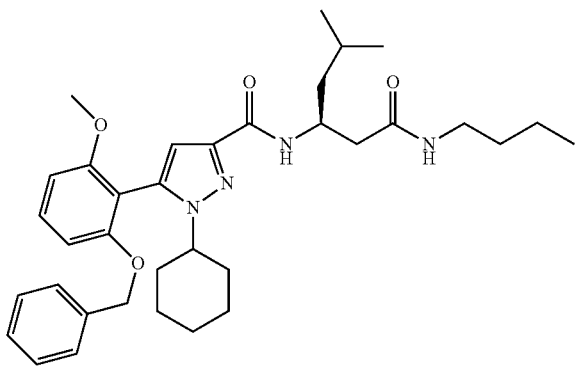 [SMILES: CCCCNC(=O)C[C@H](CC(C)C)NC(=O)c1cc(-c2c(OC)cccc2OCc2ccccc2)n(C2CCCCC2)n1]

133: 5-(2-(Benzyloxy)-6-methoxyphenyl)-N-((S)-1-(butylamino)-5-methyl-1-oxohexan-3-yl)-1-cyclohexyl-1H-pyrazole-3-carboxamide: 66% yield; $^1$H NMR (CDCl$_3$, 300 MHz) δ 0.85 (t, J=6.35 Hz, 3 H), 0.96 (dd, J=6.40, 1.88 Hz, 6 H), 1.08-1.33 (m, 5 H), 1.38-1.53 (m, 4 H), 1.63-1.96 (m, 5 H), 2.55 (d, J=6.10 Hz, 2 H), 3.17-3.29 (m, 2 H), 3.62-3.72 (m, 4 H), 3.74 (s, 3 H), 4.34-4.49 (m, 1 H), 5.05 (s, 2 H), 6.55-6.66 (m, 3 H), 6.68 (s, 1 H), 7.08 (d, J=9.42 Hz, 1 H), 7.16-7.23 (m, 2 H), 7.24-7.34 (m, 4 H). MS m/z: Calcd. for C$_{35}$H$_{48}$N$_4$O$_4$ 588.37 [M]$^+$, found 589.5 [M+H]$^+$.

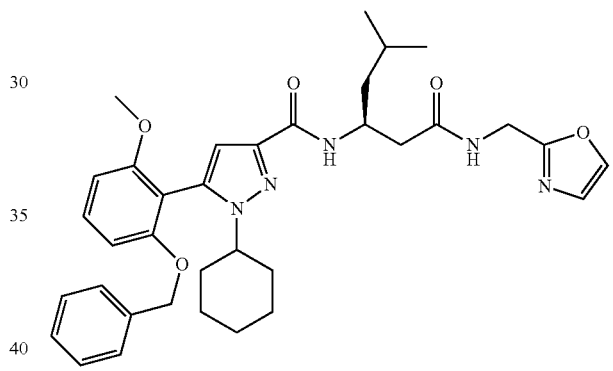

134: 5-(2-(Benzyloxy)-6-methoxyphenyl)-1-cyclohexyl-N-((S)-5-methyl-1-((oxazol-2-ylmethyl)amino)-1-oxohexan-3-yl)-1H-pyrazole-3-carboxamide: 72% yield; $^1$H NMR (CDCl$_3$, 300 MHz) δ 0.93-0.99 (m, 6 H), 1.12-1.23 (m, 3 H), 1.45-1.56 (m, 1 H), 1.62-1.72 (m, 2 H), 1.73-1.80 (m, 4 H), 1.81-1.92 (m, 4 H), 2.65-2.72 (m, 2 H), 3.74 (s, 3 H), 4.43-4.53 (m, 1 H), 4.53-4.64 (m, 2 H), 5.06 (d, J=3.91 Hz, 2 H), 6.61-6.69 (m, 3 H), 6.93 (s, 1 H), 7.16-7.23 (m, 3 H), 7.25-7.36 (m, 5 H), 7.45 (s, 1 H). MS m/z: Calcd. for C$_{35}$H$_{43}$N$_5$O$_5$ 613.33 [M]$^+$, found 614.7 [M+H]$^+$.

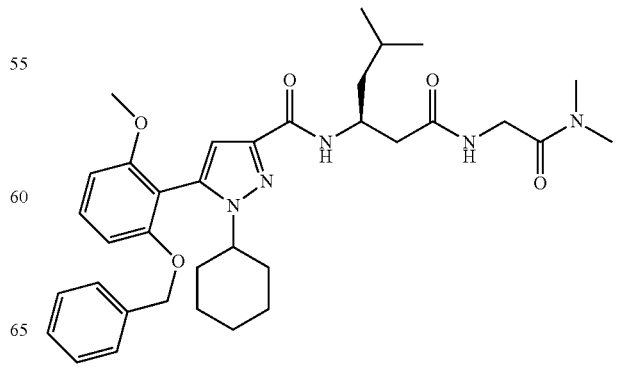

136: 5-(2-(Benzyloxy)-6-methoxyphenyl)-1-cyclohexyl-N-((S)-1-((2-(dimethylamino)-2-oxoethyl)amino)-5-methyl-1-oxohexan-3-yl)-1H-pyrazole-3-carboxamide: 46% yield; $^1$H NMR (CDCl$_3$, 500 MHz) δ 0.93-0.96 (m, 3 H), 0.97 (dd, J=7.32, 2.44 Hz, 3 H), 1.12-1.30 (m, 3 H), 1.40-1.50 (m, 2 H), 1.61-1.71 (m, 1 H), 1.72-1.82 (m, 3 H), 1.83-1.97 (m, 4 H), 2.58-2.63 (m, 2 H), 2.98 (s, 3 H), 2.97 (d, J=8.10, 3 H), 3.66-3.71 (m, 1 H), 3.73 (s, 3 H), 4.05-4.12 (m, 2 H), 4.50-4.58 (m, 1 H), 5.05 (s, 2 H), 6.61 (d, J=5.10, 2 H), 6.69 (s, 1 H), 6.82 (br. s., 1 H), 7.17-7.26 (m, 2 H), 7.27-7.34 (m, 4 H), 7.38-7.45 (m, 1 H). MS m/z: Calcd. for C$_{35}$H$_{47}$N$_5$O$_5$ 617.36 [M]$^+$, found 616.7 [M–H]$^+$.

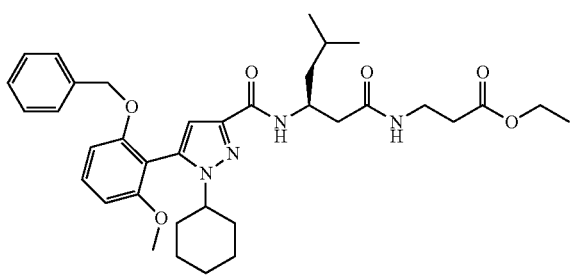 [SMILES: CCOC(=O)CCNC(=O)C[C@H](CC(C)C)NC(=O)c1cc(-c2c(OC)cccc2OCc2ccccc2)n(C2CCCCC2)n1]

138: Ethyl 3-((3S)-3-(5-(2-(benzyloxy)-6-methoxyphenyl)-1-cyclohexyl-1H-pyrazole-3-carboxamido)-5-methylhexanamido)propanoate: 65% yield; $^1$H NMR (CDCl$_3$, 300 MHz) δ 0.95 (d, J=6.78 Hz, 6 H), 1.10-1.33 (m, 4 H), 1.08-1.18 (m, 2 H), 1.24 (t, J=7.16 Hz, 3 H), 1.39-1.53 (m, 1 H), 1.62-1.81 (m, 4 H), 1.82-1.97 (m, 2 H), 2.46-2.58 (m, 3 H), 3.44-3.61 (m, 3 H), 3.63-3.75 (m, 1 H), 3.73 (s, 3 H), 4.05-4.16 (m, 2 H), 4.34-4.49 (m, 1 H), 5.05 (s, 2 H), 6.63 (dd, J=8.48, 1.32 Hz, 1 H), 6.68 (s, 1 H), 6.76 (d, J=6.03 Hz, 1 H), 7.10-7.24 (m, 3 H), 7.24-7.42 (m, 5 H). MS m/z: Calcd. for C$_{36}$H$_{48}$N$_4$O$_6$ 632.36 [M]$^+$, found 631.6 [M–H]$^+$.

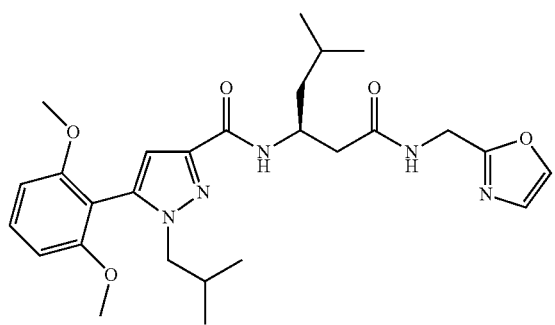 [SMILES: COc1cccc(OC)c1-c1cc(C(=O)N[C@H](CC(=O)NCc2ncco2)CC(C)C)nn1CC(C)C]

140: (S)-5-(2,6-Dimethoxyphenyl)-1-isobutyl-N-(5-methyl-1-((oxazol-2-ylmethyl)amino)-1-oxohexan-3-yl)-1H-pyrazole-3-carboxamide: 36% yield; $^1$H NMR (CDCl$_3$, 300 MHz) δ 0.73 (d, J=6.78 Hz, 6 H), 0.95 (d, J=6.40 Hz, 6 H), 1.40-1.53 (m, 1 H), 1.61-1.84 (m, 2 H), 2.02-2.18 (m, 1 H), 2.64 (d, J=6.03 Hz, 2 H), 3.62 (d, J=7.54 Hz, 2 H), 3.74 (s, 6 H), 4.41-4.50 (m, 1 H), 4.55-4.63 (m, 2 H), 6.63 (d, J=8.29 Hz, 2 H), 6.66 (s, 1 H), 7.00 (s, 1 H), 7.14 (d, J=7.91 Hz, 2 H), 7.38 (t, J=8.48 Hz, 1 H), 7.49 (s, 1 H). MS m/z: Calcd. for C$_{27}$H$_{37}$N$_5$O$_5$ 511.28 [M]$^+$, found 512.3 [M+H]$^+$.

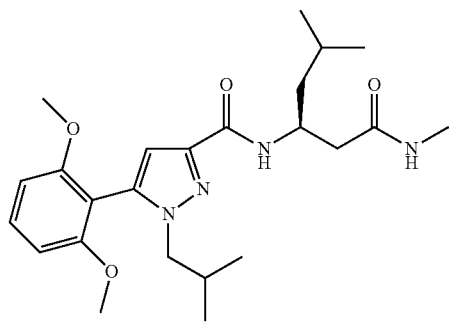 [SMILES: CNC(=O)C[C@H](CC(C)C)NC(=O)c1cc(-c2c(OC)cccc2OC)n(CC(C)C)n1]

141: (S)-5-(2,6-Dimethoxyphenyl)-1-isobutyl-N-(5-methyl-1-(methylamino)-1-oxohexan-3-yl)-1H-pyrazole-3-carboxamide: 61% yield; $^1$H NMR (CDCl$_3$, 300 MHz) δ 0.74 (d, J=6.78 Hz, 6 H), 0.94 (d, J=6.40 Hz, 6 H), 1.37-1.51 (m, 1 H), 1.60-1.82 (m, 2 H), 2.07-2.20 (m, 1 H), 2.54 (d, J=6.03 Hz, 2 H), 2.80 (d, J=4.90 Hz, 3 H), 3.63 (d, J=7.16 Hz, 2 H), 3.74 (s, 6 H), 4.34-4.49 (m, 1 H), 6.62 (d, J=8.67 Hz, 2 H), 6.68 (s, 2 H), 7.07 (d, J=9.42 Hz, 1 H), 7.38 (t, J=8.29 Hz, 1 H). MS m/z: Calcd. for C$_{24}$H$_{36}$N$_4$O$_4$ 444.27 [M]$^+$, found 445.5 [M+H]$^+$.

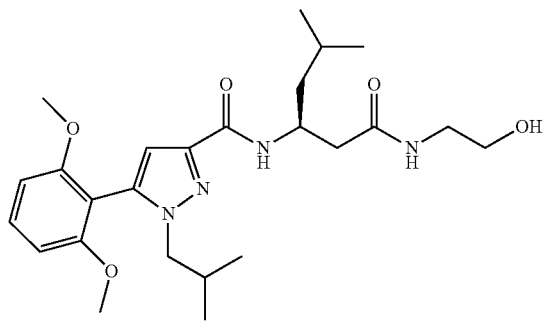 [SMILES: COc1cccc(OC)c1-c1cc(C(=O)N[C@H](CC(=O)NCCO)CC(C)C)nn1CC(C)C]

142: (S)-5-(2,6-Dimethoxyphenyl)-N-(1-((2-hydroxyethyl)amino)-5-methyl-1-oxohexan-3-yl)-1-isobutyl-1H-pyrazole-3-carboxamide: 61% yield; $^1$H NMR (CDCl$_3$, 300 MHz) δ 0.75 (d, J=6.78 Hz, 3 H), 0.74 (d, J=6.78 Hz, 3 H), 0.96 (d, J=6.40 Hz, 6 H), 1.38-1.50 (m, 1 H), 1.60-1.83 (m, 2 H), 2.05-2.19 (m, 1 H), 2.45-2.68 (m, 3 H), 3.21-3.31 (m, 1 H), 3.47-3.62 (m, 2 H), 3.64 (dd, J=7.16, 1.51 Hz, 2 H), 3.74 (s, 6 H), 4.43-4.57 (m, 1 H), 6.62 (d, J=8.29 Hz, 2 H), 6.68 (s, 1 H), 6.88-7.11 (m, 2 H), 7.38 (t, J=8.29 Hz, 1 H). MS m/z: Calcd. for C$_{25}$H$_{38}$N$_4$O$_5$ 474.38 [M]$^+$, found 475.7 [M+H]$^+$.

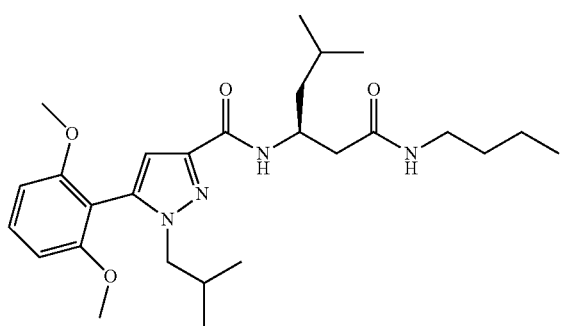 [SMILES: CCCCNC(=O)C[C@H](CC(C)C)NC(=O)c1cc(-c2c(OC)cccc2OC)n(CC(C)C)n1]

143: (S)-N-(1-(Butylamino)-5-methyl-1-oxohexan-3-yl)-5-(2,6-dimethoxyphenyl)-1-isobutyl-1H-pyrazole-3-carboxamide: 71% yield; $^1$H NMR (CDCl$_3$, 300 MHz) δ 0.74 (dd, J=6.78, 2.26 Hz, 6 H), 0.87 (t, J=7.16 Hz, 3 H), 0.94 (d, J=6.40 Hz, 6 H), 1.22-1.36 (m, 2 H), 1.41-1.53 (m, 3 H), 1.60-1.81 (m, 2 H), 2.07-2.19 (m, 1 H), 2.54 (d, J=6.03 Hz, 2 H), 3.19-3.28 (m, 2 H), 3.63 (d, J=7.16 Hz, 2 H), 3.73 (s, 3 H), 3.74 (s, 3 H), 4.34-4.46 (m, 1 H), 6.51 (br. s., 1 H), 6.62 (d, J=8.29 Hz, 2 H), 6.67 (s, 1 H), 7.06 (d, J=8.67 Hz, 1 H), 7.37 (t, J=8.48 Hz, 1 H). MS m/z: Calcd. for C$_{27}$H$_{42}$N$_4$O$_4$ 486.65 [M]$^+$, found 487.6 [M+H]$^+$.

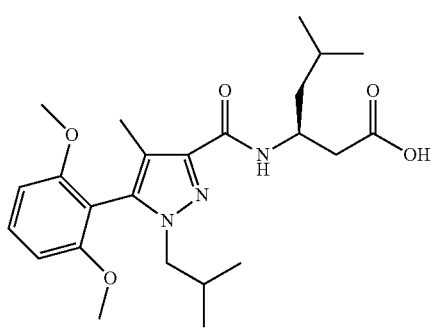 [SMILES: COc1cccc(OC)c1-c1c(C)c(C(=O)N[C@H](CC(=O)O)CC(C)C)nn1CC(C)C]

150: (S)-3-(5-(2,6-Dimethoxyphenyl)-1-isobutyl-4-methyl-1H-pyrazole-3-carboxamido)-5-methylhexanoic acid: 67% yield; $^1$H NMR (CDCl$_3$, 300 MHz) δ 0.72 (d, J=6.78 Hz, 6 H), 0.97 (d, J=6.40 Hz, 6 H), 1.46-1.55 (m, 1 H), 1.62-1.84 (m, 2 H), 1.98-2.11 (m, 1 H), 2.08 (s, 3H), 2.64-2.79 (m, 2 H), 3.61 (d, J=7.54 Hz, 2 H), 3.75 (s, 6 H), 4.33-4.49 (m, 1 H), 6.63 (d, J=8.29 Hz, 2 H), 7.30 (d, J=8.29 Hz, 1 H), 7.39 (t, J=8.48 Hz, 1 H). MS m/z: Calcd. for C$_{24}$H$_{35}$N$_3$O$_5$ 445.26 [M]$^+$, found 444.7 [M–H]$^+$.

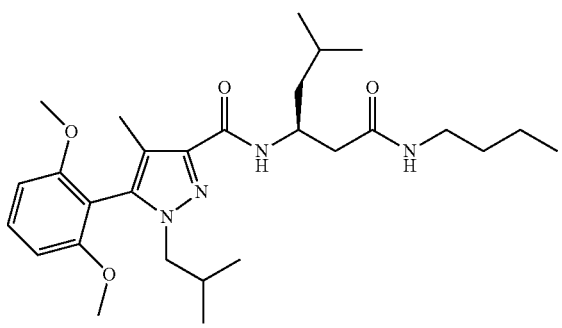 [SMILES: CCCCNC(=O)C[C@H](CC(C)C)NC(=O)c1nn(CC(C)C)c(-c2c(OC)cccc2OC)c1C]

151: (S)—N-(1-(Butylamino)-5-methyl-1-oxohexan-3-yl)-5-(2,6-dimethoxyphenyl)-1-isobutyl-4-methyl-1H-pyrazole-3-carboxamide: 80% yield; $^1$H NMR (CDCl$_3$, 300 MHz) δ 0.72 (dd, J=6.78, 3.39 Hz, 6 H), 0.86 (t, J=7.16 Hz, 3 H), 0.95 (d, J=6.78 Hz, 6 H), 1.24-1.36 (m, 3 H), 1.40-1.52 (m, 2 H), 1.60-1.69 (m, 1 H), 1.69-1.83 (m, 1 H), 1.98-2.12 (m, 1 H), 2.08 (s, 3 H), 2.54 (d, J=6.40 Hz, 2 H), 3.15-3.33 (m, 2 H), 3.59 (d, J=7.16 Hz, 2 H), 3.74 (s, 6 H), 4.35-4.47 (m, 1 H), 6.62-6.74 (m, 3 H), 7.04 (d, J=9.04 Hz, 1 H), 7.39 (t, J=8.29 Hz, 1 H). MS m/z: Calcd. for C$_{28}$H$_{44}$N$_4$O$_4$ 500.34 [M]$^+$, found 501.8 [M+H]$^+$.

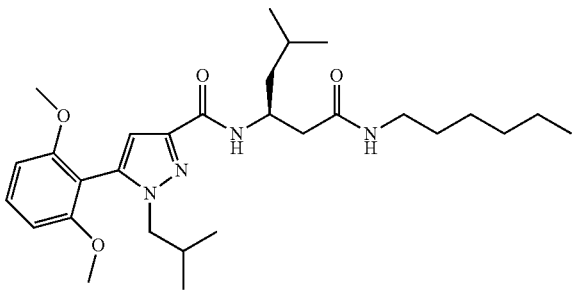 [SMILES: CCCCCCNC(=O)C[C@H](CC(C)C)NC(=O)c1cc(-c2c(OC)cccc2OC)n(CC(C)C)n1]

154: (S)-5-(2,6-Dimethoxyphenyl)-N-(1-(hexylamino)-5-methyl-1-oxohexan-3-yl)-1-isobutyl-1H-pyrazole-3-carboxamide: 64% yield; $^1$H NMR (CDCl$_3$, 300 MHz) δ 0.74 (d, J=6.40 Hz, 6 H), 0.85 (t, J=7.35 Hz, 3 H), 0.94 (d, J=6.78 Hz, 6 H), 1.21-1.34 (m, 6 H), 1.40-1.54 (m, 3 H), 1.61-1.82 (m, 2 H), 2.05-2.19 (m, 1 H), 2.53 (d, J=6.03 Hz, 2 H), 3.18-3.27 (m, 2 H), 3.63 (d, J=7.54 Hz, 2 H), 3.74 (s, 6 H), 4.35-4.45 (m, 1 H), 6.54 (br. s., 1 H), 6.62 (d, J=8.29 Hz, 2 H), 6.67 (s, 1 H), 7.09 (d, J=9.04 Hz, 1 H), 7.38 (t, J=8.29 Hz, 1 H). MS m/z: Calcd. for C$_{29}$H$_{46}$N$_4$O$_4$ 514.35 [M]$^+$, found 515.6 [M+H]$^+$.

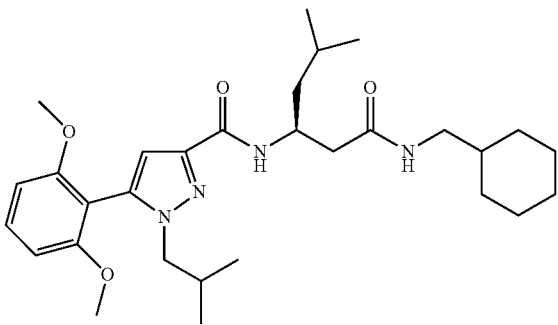 [SMILES: COc1cccc(OC)c1-c1cc(C(=O)N[C@H](CC(=O)NCC2CCCCC2)CC(C)C)nn1CC(C)C]

155: (S)—N-(1-(((Cyclohexylmethyl)amino)-5-methyl-1-oxohexan-3-yl)-5-(2,6-dimethoxyphenyl)-1-isobutyl-1H-pyrazole-3-carboxamide: 71% yield; $^1$H NMR (CDCl$_3$, 300 MHz) δ 0.75 (d, J=3.77 Hz, 3 H), 0.72 (d, J=3.39 Hz, 3 H), 0.80-0.92 (m, 2 H), 0.94 (d, J=6.40 Hz, 6 H), 1.05-1.27 (m, 4 H), 1.38-1.54 (m, 3 H), 1.62-1.79 (m, 5 H), 2.06-2.19 (m, 1 H), 2.55 (d, J=6.03 Hz, 2 H), 3.01-3.16 (m, 2 H), 3.63 (d, J=7.16 Hz, 2 H), 3.72 (s, 3 H), 3.74 (s, 3 H), 4.37-4.47 (m, 1 H), 6.53-6.73 (m, 4 H), 7.07 (d, J=8.67 Hz, 1 H), 7.37 (t, J=8.29 Hz, 1 H). MS m/z: Calcd for C$_{30}$H$_{46}$N$_4$O$_4$ 526.35 [M]$^+$, found 527.5 [M+H]$^+$.

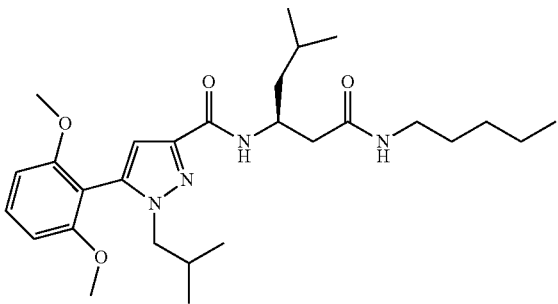 [SMILES: CCCCCNC(=O)C[C@H](CC(C)C)NC(=O)c1cc(-c2c(OC)cccc2OC)n(CC(C)C)n1]

156: (S)-5-(2,6-Dimethoxyphenyl)-1-isobutyl-N-(5-methyl-1-oxo-1-(pentylamino)hexan-3-yl)-1H-pyrazole-3-carboxamide: 83% yield; $^1$H NMR (CDCl$_3$, 300 MHz) δ 0.74 (dd, J=6.78, 1.13 Hz, 6 H), 0.86 (t, J=7.35 Hz, 3 H), 0.94 (d, J=6.40 Hz, 6 H), 1.21-1.35 (m, 4H), 1.39-1.53 (m, 3 H), 1.62-1.83 (m, 2 H), 2.04-2.20 (m, 1 H), 2.53 (d, J=6.03 Hz, 2 H), 3.19-3.26 (m, 2 H), 3.63 (d, J=7.54 Hz, 2 H), 3.73 (s, 3 H), 3.74 (s, 3 H), 4.34-4.48 (m, 1 H), 6.55 (br. s., 1 H), 6.62 (d, J=8.29 Hz, 2 H), 6.67 (s, 1 H), 7.08 (d, J=8.67 Hz, 1 H), 7.38 (t, J=8.29 Hz, 1 H). MS m/z: Calcd for C$_{28}$H$_{44}$N$_4$O$_4$ 500.67 [M]$^+$, found 501.8 [M+H]$^+$.

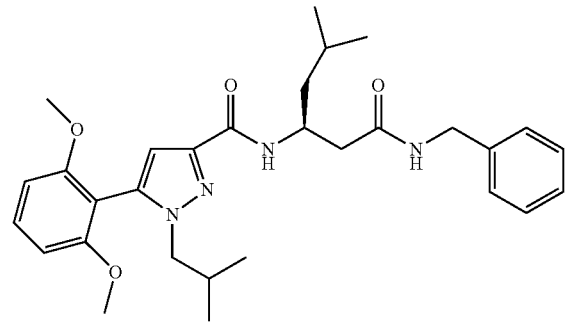

160: (S)—N-(1-(Benzylamino)-5-methyl-1-oxohexan-3-yl)-5-(2,6-dimethoxyphenyl)-1-isobutyl-1H-pyrazole-3-carboxamide: 66% yield; $^1$H NMR (CDCl$_3$, 300 MHz) δ 0.74 (d, J=6.78 Hz, 6 H), 0.94 (d, J=6.40 Hz, 6 H), 1.37-1.52 (m, 1 H), 1.63-1.80 (m, 2 H), 2.03-2.19 (m, 1 H), 2.60 (d, J=6.40 Hz, 2 H), 3.64 (d, J=7.54 Hz, 2 H), 3.72 (s, 3 H), 3.75 (s, 3 H), 4.37-4.51 (m, 3 H), 6.62 (s, 1 H), 6.65 (d, J=6.40 Hz, 2 H), 7.11 (d, J=9.04 Hz, 1 H), 7.17-7.25 (m, 6 H), 7.38 (t, J=8.29 Hz, 1 H). MS m/z: Calcd. for C$_{30}$H$_{40}$N$_4$O$_4$ 520.30 [M]$^+$, found 521.6 [M+H]$^+$.

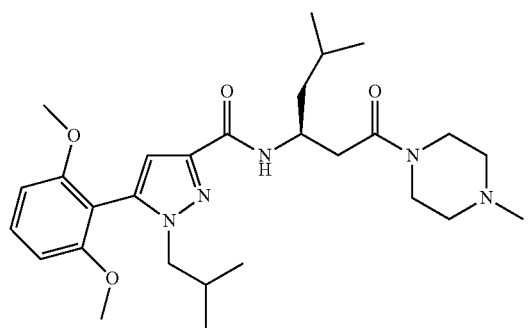 [SMILES: COc1cccc(OC)c1-c1cc(C(=O)N[C@H](CC(=O)N2CCN(C)CC2)CC(C)C)nn1CC(C)C]

158: (S)-5-(2,6-Dimethoxyphenyl)-1-isobutyl-N-(5-methyl-1-(4-methylpiperazin-1-yl)-1-oxohexan-3-yl)-1H-pyrazole-3-carboxamide: 72% yield; $^1$H NMR (CDCl$_3$, 300 MHz) δ 0.74 (d, J=6.78 Hz, 6 H), 0.95 (dd, J=6.40, 1.51 Hz, 6 H), 1.46-1.57 (m, 1 H), 1.67-1.82 (m, 2 H), 2.05-2.20 (m, 1 H), 2.29 (s, 3 H), 2.32-2.55 (m, 4 H), 2.89 (dd, J=14.51, 3.96 Hz, 1 H), 3.45-3.60 (m, 3 H), 3.63 (d, J=7.54 Hz, 2 H), 3.73 (s, 6 H), 3.68-3.80 (m, 2 H), 4.32-4.44 (m, 1 H), 6.62 (d, J=8.29 Hz, 2 H), 6.67 (s, 1 H), 7.18 (d, J=8.67 Hz, 1 H), 7.37 (t, J=8.29 Hz, 1 H). MS m/z: Calcd. for C$_{28}$H$_{43}$N$_5$O$_4$ 513.33 [M]$^+$, found 514.5 [M+H]$^+$.

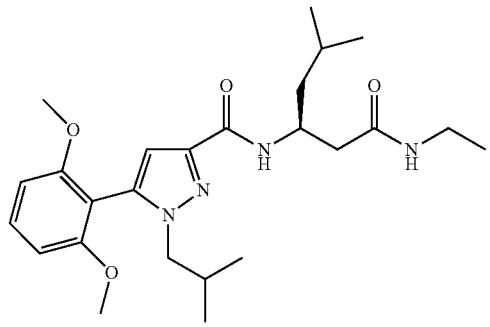

161: (S)-5-(2,6-Dimethoxyphenyl)-N-(1-(ethylamino)-5-methyl-1-oxohexan-3-yl)-1-isobutyl-1H-pyrazole-3-carboxamide: 69% yield; $^1$H NMR (CDCl$_3$, 300 MHz) δ 0.74 (d, J=6.78 Hz, 6 H), 0.95 (d, J=6.40 Hz, 6 H), 1.10 (t, J=7.35 Hz, 3 H), 1.40-1.51 (m, 1 H), 1.60-1.82 (m, 2 H), 2.08-2.19 (m, 1 H), 2.53 (d, J=6.03 Hz, 2 H), 3.23-3.32 (quin, J=6.78 Hz, 2 H), 3.63 (d, J=7.54 Hz, 2 H), 3.74 (s, 6 H), 4.34-4.46 (m, 1 H), 6.50 (br. s., 1 H), 6.62 (d, J=8.67 Hz, 2 H), 6.68 (s, 1 H), 7.07 (d, J=9.04 Hz, 1 H), 7.37 (t, J=8.48 Hz, 1 H). MS m/z: Calcd. for C$_{25}$H$_{38}$N$_4$O$_4$ 458.29 [M]$^+$, found 459.5 [M+H]$^+$.

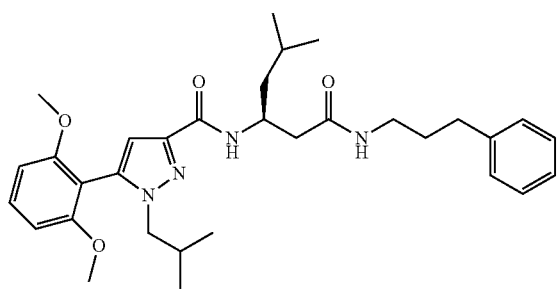 [SMILES: COc1cccc(OC)c1-c1cc(C(=O)N[C@H](CC(=O)NCCCc2ccccc2)CC(C)C)nn1CC(C)C]

159: (S)-5-(2,6-Dimethoxyphenyl)-1-isobutyl-N-(5-methyl-1-oxo-1-((3-phenylpropyl)amino)hexan-3-yl)-1H-pyrazole-3-carboxamide: 68% yield; $^1$H NMR (CDCl$_3$, 300 MHz) δ 0.73 (dd, J=6.78, 1.13 Hz, 6 H), 0.95 (d, J=6.40 Hz, 6 H), 1.40-1.52 (m, 1 H), 1.61-1.75 (m, 1 H), 1.76-1.88 (m, 3 H), 2.05-2.18 (m, 1 H), 2.52 (d, J=6.03 Hz, 2 H), 2.62 (t, J=7.15 Hz, 2 H), 3.24-3.30 (m, 2 H), 3.62 (d, J=7.16 Hz, 2 H), 3.68 (s, 3 H), 3.73 (s, 3 H), 4.35-4.48 (m, 1 H), 6.61 (dd, J=8.29, 1.51 Hz, 2 H), 6.65-6.71 (m, 1 H), 6.68 (s, 1 H), 7.07 (d, J=9.04 Hz, 1 H), 7.12-7.20 (m, 3 H), 7.21-7.24 (m, 2 H), 7.37 (t, J=8.48 Hz, 1 H). MS m/z: Calcd. for C$_{32}$H$_{44}$N$_4$O$_4$ 548.34 [M]$^+$, found 549.6 [M+H]$^+$.

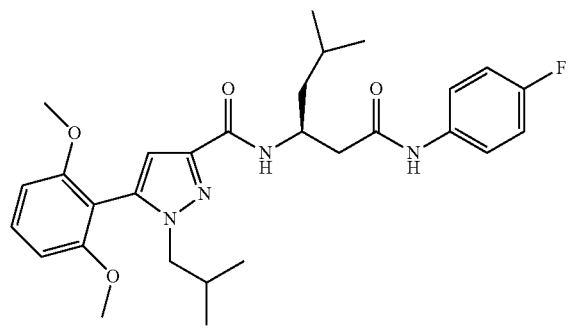 [SMILES: COc1cccc(OC)c1-c1cc(C(=O)N[C@H](CC(=O)Nc2ccc(F)cc2)CC(C)C)nn1CC(C)C]

163: (S)-5-(2,6-Dimethoxyphenyl)-N-(1-((4-fluorophenyl)amino)-5-methyl-1-oxohexan-3-yl)-1-isobutyl-1H-pyrazole-3-carboxamide: 10% yield; $^1$H NMR (CDCl$_3$, 300 MHz) δ 0.74 (dd, J=6.78, 1.88 Hz, 6 H), 0.97 (d, J=6.40 Hz, 6 H), 1.46-1.55 (m, 1 H), 1.63-1.73 (m, 1 H), 1.73-1.84 (m, 1 H), 2.06-2.18 (m, 1 H), 2.72 (d, J=5.65 Hz, 2 H), 3.63 (d, J=7.54 Hz, 2 H), 3.73 (s, 3 H), 3.75 (s, 3 H), 4.43-4.59 (m, 1 H), 6.62 (dd, J=8.29, 1.51 Hz, 2 H), 6.72 (s, 1 H), 6.97 (t, J=8.85 Hz, 2 H), 7.05 (d, J=8.67 Hz, 1 H), 7.38 (t, J=8.48 Hz, 1 H), 7.58 (dd, J=9.04, 4.90 Hz, 2 H), 9.11 (s, 1 H). MS m/z: Calcd. for C$_{29}$H$_{37}$FN$_4$O$_4$ 524.28 [M]$^+$, found 525.6 [M+H]$^+$.

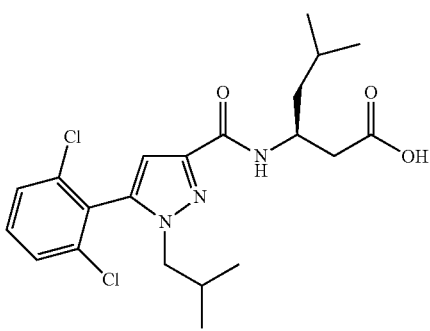 [SMILES: CC(C)C[C@@H](CC(=O)O)NC(=O)c1cc(-c2c(Cl)cccc2Cl)n(CC(C)C)n1]

165: (S)-3-(5-(2,6-Dichlorophenyl)-1-isobutyl-1H-pyrazole-3-carboxamido)-5-methylhexanoic acid: 71% yield; $^1$H NMR (CDCl$_3$, 300 MHz) δ 0.81 (d, J=6.40 Hz, 6 H), 0.98 (dd, J=6.22, 3.20 Hz, 6 H), 1.45-1.56 (m, 1 H), 1.65-1.82 (m, 2 H), 2.08-2.22 (m, 1 H), 2.73 (d, J=5.27 Hz, 2 H), 3.67 (d, J=7.54 Hz, 2 H), 4.45-4.56 (m, 1 H), 6.81 (s, 1 H), 7.22-7.24 (m, 1 H), 7.32-7.40 (m, 1 H), 7.43 (s, 1 H), 7.45 (d, J=1.88 Hz, 1 H). MS m/z: Calcd. for C$_{21}$H$_{27}$Cl$_2$N$_3$O$_3$ 439.14 [M]$^+$, found 440.3 [M+H]$^+$.

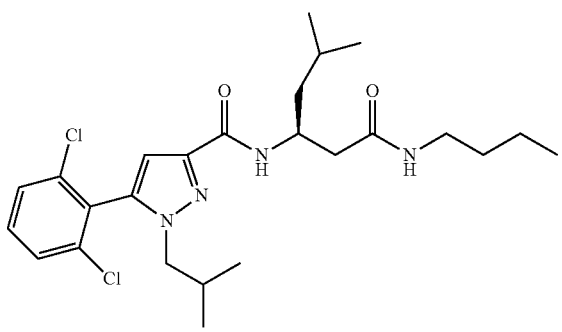 [SMILES: CCCCNC(=O)C[C@H](CC(C)C)NC(=O)c1cc(-c2c(Cl)cccc2Cl)n(CC(C)C)n1]

166: (S)—N-(1-(Butylamino)-5-methyl-1-oxohexan-3-yl)-5-(2,6-dichlorophenyl)-1-isobutyl-1H-pyrazole-3-carboxamide: 85% yield; $^1$H NMR (CDCl$_3$, 300 MHz) δ 0.81 (d, J=6.40 Hz, 6 H), 0.87 (t, J=7.35 Hz, 3 H), 0.96 (dd, J=6.40, 2.26 Hz, 6 H), 1.23-1.37 (m, 2 H), 1.40-1.51 (m, 3 H), 1.64-1.79 (m, 2 H), 2.12-2.23 (m, 1 H), 2.48-2.62 (m, 2 H), 3.24 (q, J=6.66 Hz, 2 H), 3.66 (d, J=7.54 Hz, 2 H), 4.35-4.48 (m, 1 H), 6.31 (br. s., 1 H), 6.78 (s, 1 H), 7.19 (d, J=9.04 Hz, 1 H), 7.32-7.40 (m, 1 H), 7.41-7.49 (m, 1 H). MS m/z: Calcd. for C$_{25}$H$_{36}$Cl$_2$N$_4$O$_2$ 494.22 [M]$^+$, found 495.4 [M+H]$^+$.

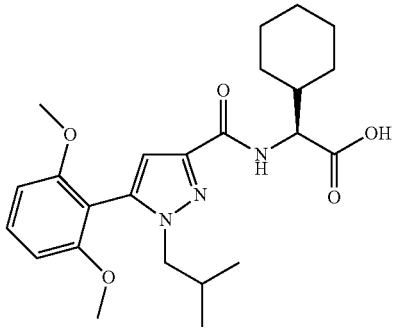 [SMILES: COc1cccc(OC)c1-c1cc(C(=O)N[C@H](C(=O)O)C2CCCCC2)nn1CC(C)C]

169: (S)-2-Cyclohexyl-2-(5-(2,6-dimethoxyphenyl)-1-isobutyl-1H-pyrazole-3-carboxamido)acetic acid: 94% yield; $^1$H NMR (CDCl$_3$, 300 MHz) δ 0.76 (d, J=6.78 Hz, 3 H), 0.74 (d, J=6.78 Hz, 3 H), 1.09-1.39 (m, 6 H), 1.63-1.91 (m, 5 H), 1.99-2.19 (m, 2 H), 3.69 (dd, J=7.16, 3.01 Hz, 2 H), 3.73 (s, 3 H), 3.75 (s, 3 H), 4.55-4.64 (m, 1 H), 6.62 (d, J=8.67 Hz, 2 H), 6.72 (s, 1 H), 7.38 (t, J=8.48 Hz, 1 H), 7.43 (d, J=8.67 Hz, 1 H). MS m/z: Calcd. for C$_{24}$H$_{33}$N$_3$O$_5$ 443.24 [M]$^+$, found 442.7 [M−H]$^+$.

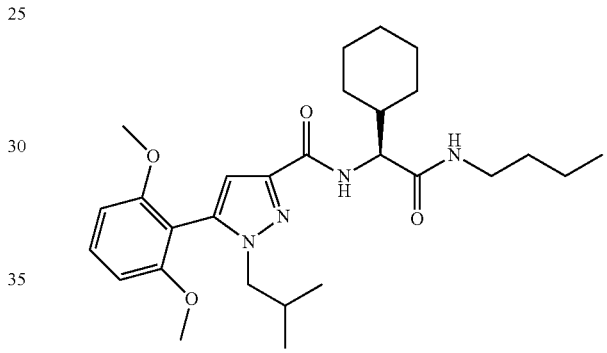

170: (S)—N-(2-(Butylamino)-1-cyclohexyl-2-oxoethyl)-5-(2,6-dimethoxyphenyl)-1-isobutyl-1H-pyrazole-3-carboxamide: 65% yield; $^1$H NMR (CDCl$_3$, 300 MHz) δ 0.75 (t, J=6.78 Hz, 6 H), 0.91 (t, J=7.35 Hz, 3 H), 1.02-1.19 (m, 3 H), 1.20-1.40 (m, 5 H), 1.44-1.54 (m, 2 H), 1.68-1.90 (m, 4 H), 1.93-2.08 (m, 1 H), 2.10-2.21 (m, 1 H), 3.19-3.34 (m, 2 H), 3.58-3.67 (m, 2 H), 3.73 (s, 3 H), 3.74 (s, 3 H), 4.29-4.36 (m, 1 H), 6.06-6.10 (m, 1 H), 6.62 (d, J=8.67 Hz, 2 H), 6.68 (s, 1 H), 7.29-7.42 (m, 2 H). MS m/z: Calcd. for C$_{28}$H$_{42}$N$_4$O$_4$ 498.32 [M]$^+$, found 499.9 [M+H]$^+$.

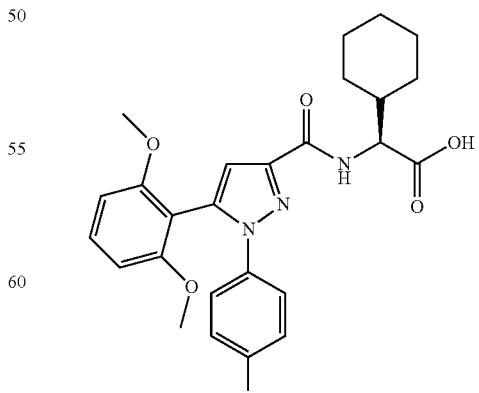

NTRC-1 (EC$_{50}$ = ~4 μM)

TABLE 1

| CP# | STRUCTURE | M.W. |
|---|---|---|
| 26 | 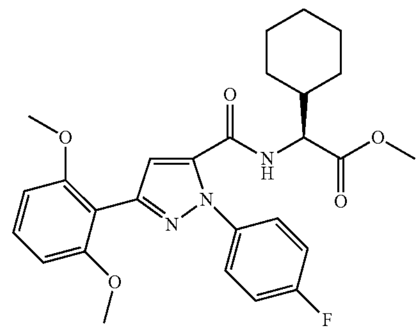 [SMILES: COC(=O)[C@@H](NC(=O)c1cc(-c2c(OC)cccc2OC)nn1-c1ccc(F)cc1)C1CCCCC1] | 509.57 |
| 27 | 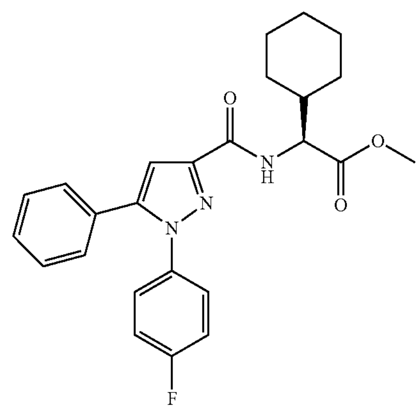 [SMILES: COC(=O)[C@@H](NC(=O)c1cc(-c2ccccc2)n(-c2ccc(F)cc2)n1)C1CCCCC1] | 435.49 |
| 28 | 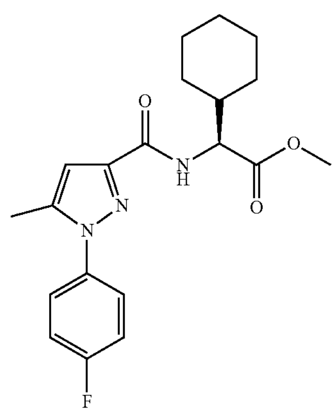 | 373.42 |
| 29 | 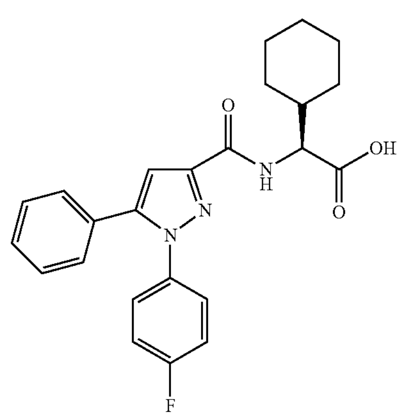 [SMILES: O=C(N[C@H](C(=O)O)C1CCCCC1)c1cc(-c2ccccc2)n(-c2ccc(F)cc2)n1] | 421.18 |

TABLE 1-continued

| CP# | STRUCTURE | M.W. |
|---|---|---|
| 30 | 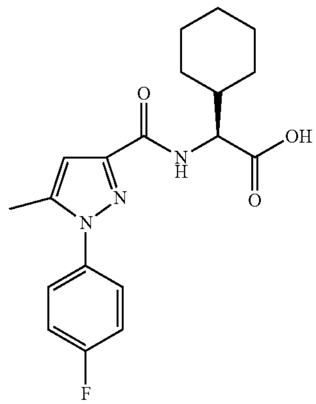 [SMILES: Cc1cc(C(=O)N[C@H](C(=O)O)C2CCCCC2)nn1-c1ccc(F)cc1] | 359.39 |
| 31 | 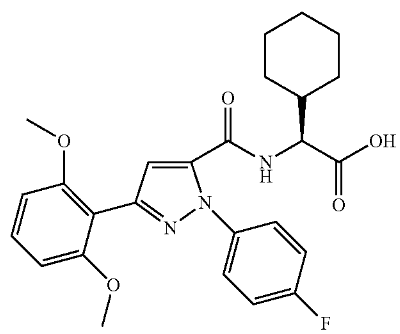 [SMILES: COc1cccc(OC)c1-c1cc(C(=O)N[C@H](C(=O)O)C2CCCCC2)n(-c2ccc(F)cc2)n1] | 481.52 |
| 32 | 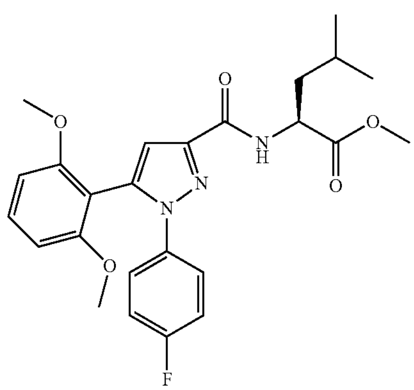 [SMILES: COC(=O)[C@H](CC(C)C)NC(=O)c1cc(-c2c(OC)cccc2OC)n(-c2ccc(F)cc2)n1] | 469.50 |
| 33 | 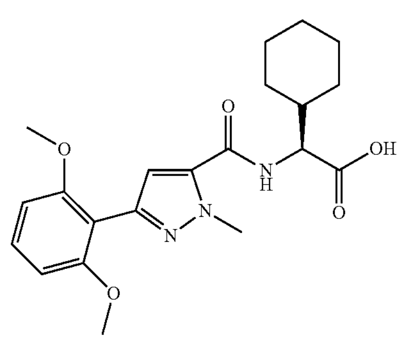 [SMILES: COc1cccc(OC)c1-c1cc(C(=O)N[C@H](C(=O)O)C2CCCCC2)n(C)n1] | 401.45 |

TABLE 1-continued

| CP# | STRUCTURE | M.W. |
|---|---|---|
| 34 | 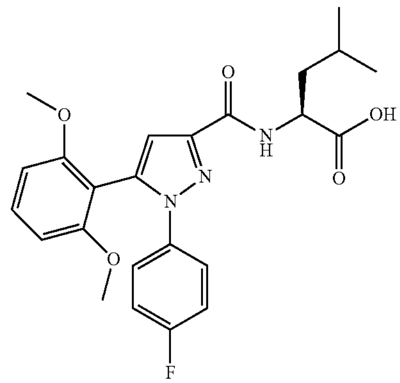 [SMILES: COc1cccc(OC)c1-c1cc(C(=O)N[C@@H](CC(C)C)C(=O)O)nn1-c1ccc(F)cc1] | 455.48 |
| 35 | 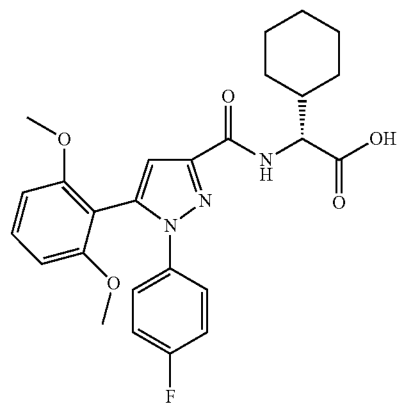 [SMILES: COc1cccc(OC)c1-c1cc(C(=O)N[C@@H](C(=O)O)C2CCCCC2)nn1-c1ccc(F)cc1] | 481.51 |
| 36 | 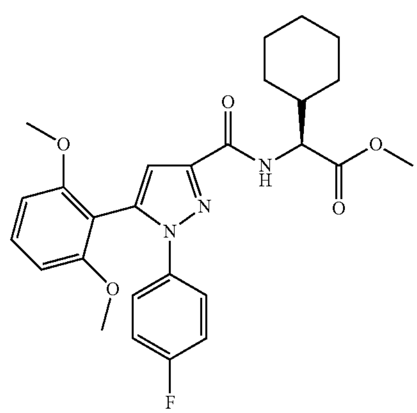 [SMILES: COC(=O)[C@@H](NC(=O)c1cc(-c2c(OC)cccc2OC)n(-c2ccc(F)cc2)n1)C1CCCCC1] | 495.54 |
| 37 | 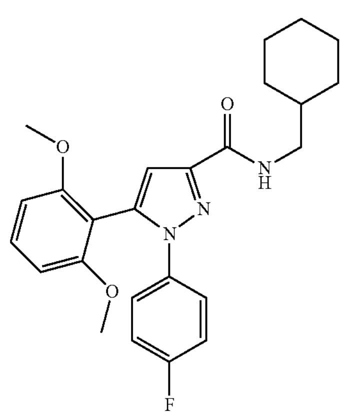 [SMILES: COc1cccc(OC)c1-c1cc(C(=O)NCC2CCCCC2)nn1-c1ccc(F)cc1] | 437.50 |

TABLE 1-continued
| CP# | STRUCTURE | M.W. |
|---|---|---|
| 38 | 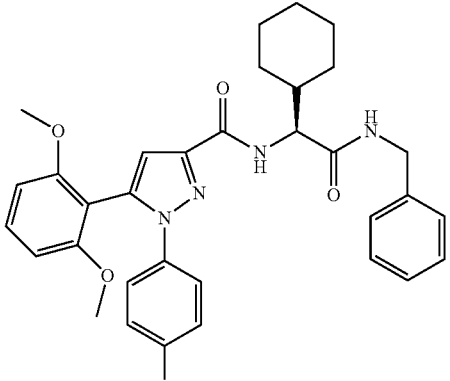 | 570.65 |
| 39 | 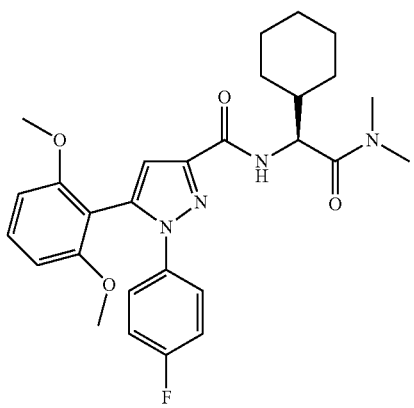 [SMILES: COc1cccc(OC)c1-c1cc(C(=O)N[C@H](C(=O)N(C)C)C2CCCCC2)nn1-c1ccc(F)cc1] | 508.58 |
| 40 | 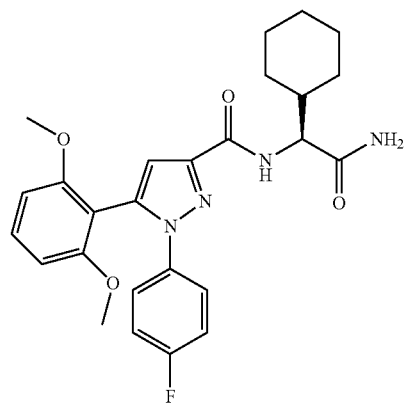 [SMILES: COc1cccc(OC)c1-c1cc(C(=O)N[C@H](C(N)=O)C2CCCCC2)nn1-c1ccc(F)cc1] | 480.53 |

TABLE 1-continued
| CP# | STRUCTURE | M.W. |
|---|---|---|
| 41 | 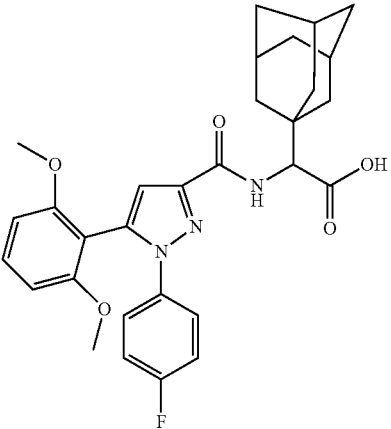 [SMILES: COc1cccc(OC)c1-c1cc(C(=O)NC(C(=O)O)C23CC4CC(CC(C4)C2)C3)nn1-c1ccc(F)cc1] | 533.59 |
| 42 | 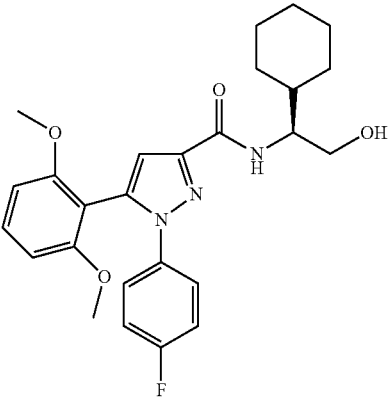 [SMILES: COc1cccc(OC)c1-c1cc(C(=O)N[C@H](CO)C2CCCCC2)nn1-c1ccc(F)cc1] | 467.53 |
| 43 | 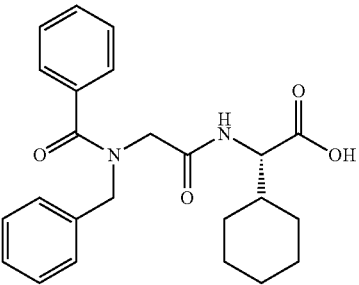 [SMILES: O=C(CN(Cc1ccccc1)C(=O)c1ccccc1)N[C@H](C(=O)O)C1CCCCC1] | 408.49 |
| 44 | 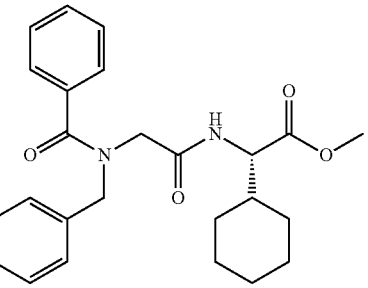 | 422.52 |

TABLE 1-continued
| CP# | STRUCTURE | M.W. |
|---|---|---|
| 45 | 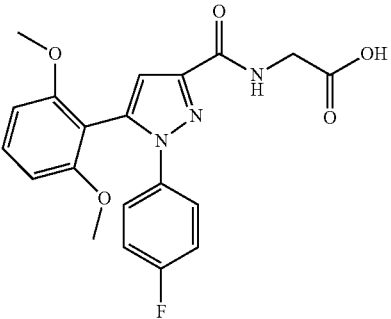 [SMILES: COc1cccc(OC)c1-c1cc(C(=O)NCC(=O)O)nn1-c1ccc(F)cc1] | 399.12 |
| 46 | 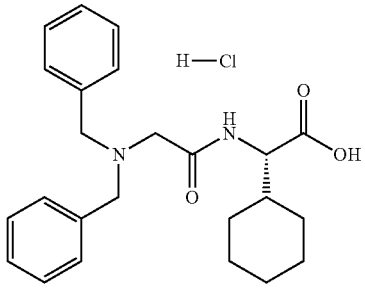 [SMILES: O=C(CN(Cc1ccccc1)Cc1ccccc1)N[C@H](C(=O)O)C1CCCCC1 ; Cl] | 430.97 |
| 47 | 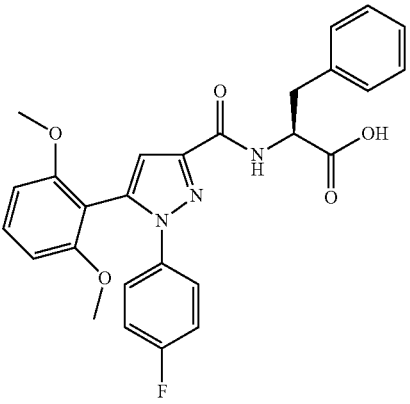 [SMILES: COc1cccc(OC)c1-c1cc(C(=O)N[C@@H](Cc2ccccc2)C(=O)O)nn1-c1ccc(F)cc1] | 489.49 |
| 48 | 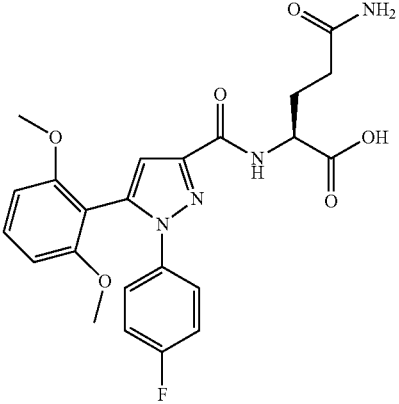 [SMILES: COc1cccc(OC)c1-c1cc(C(=O)N[C@@H](CCC(N)=O)C(=O)O)nn1-c1ccc(F)cc1] | 470.45 |

TABLE 1-continued

| CP# | STRUCTURE | M.W. |
|---|---|---|
| 34P | 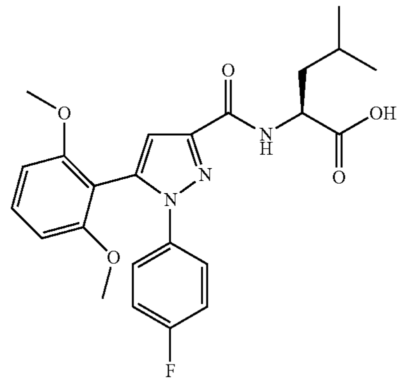 [SMILES: COc1cccc(OC)c1-c1cc(C(=O)N[C@@H](CC(C)C)C(=O)O)nn1-c1ccc(F)cc1] | 455.48 |
| 49 | 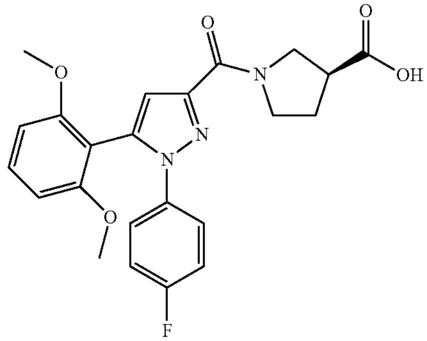 [SMILES: COc1cccc(OC)c1-c1cc(C(=O)N2CC[C@H](C(=O)O)C2)nn1-c1ccc(F)cc1] | 439.44 |
| 50 | 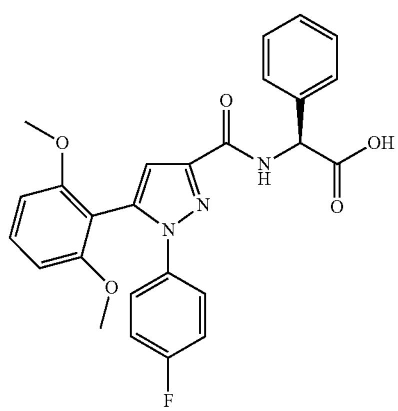 [SMILES: COc1cccc(OC)c1-c1cc(C(=O)N[C@H](C(=O)O)c2ccccc2)nn1-c1ccc(F)cc1] | 475.47 |
| 51 | 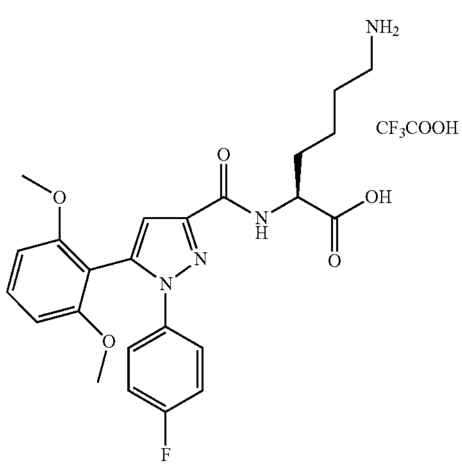 [SMILES: COc1cccc(OC)c1-c1cc(C(=O)N[C@@H](CCCCN)C(=O)O)nn1-c1ccc(F)cc1 ; "CF3COOH"] | 584.52 |

TABLE 1-continued

| CP# | STRUCTURE | M.W. |
|---|---|---|
| 52 | 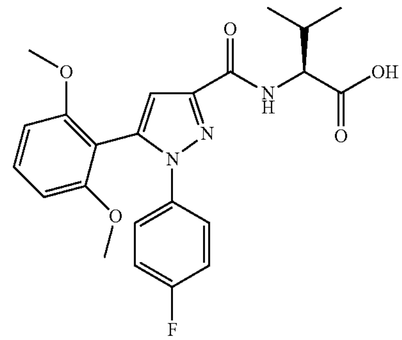 [SMILES: COc1cccc(OC)c1-c1cc(C(=O)N[C@H](C(=O)O)C(C)C)nn1-c1ccc(F)cc1] | 441.45 |
| 53 | 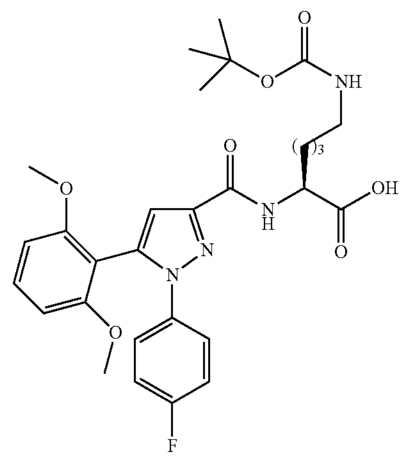 | 570.60 |
| 54 | 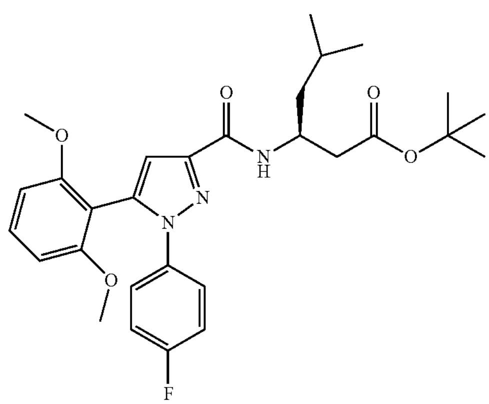 [SMILES: COc1cccc(OC)c1-c1cc(C(=O)N[C@H](CC(=O)OC(C)(C)C)CC(C)C)nn1-c1ccc(F)cc1] | 525.61 |
| 55 | 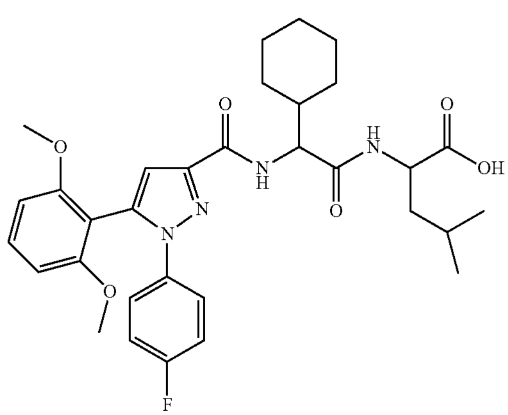 [SMILES: COc1cccc(OC)c1-c1cc(C(=O)NC(C(=O)NC(CC(C)C)C(=O)O)C2CCCCC2)nn1-c1ccc(F)cc1] | 594.67 |

TABLE 1-continued

| CP# | STRUCTURE | M.W. |
|---|---|---|
| 56 | 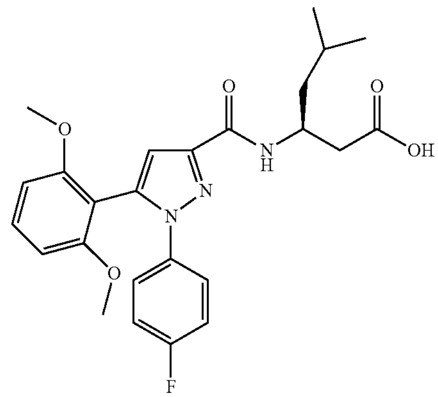 [SMILES: COc1cccc(OC)c1-c1cc(C(=O)N[C@H](CC(=O)O)CC(C)C)nn1-c1ccc(F)cc1] | 469.51 |
| 57 | 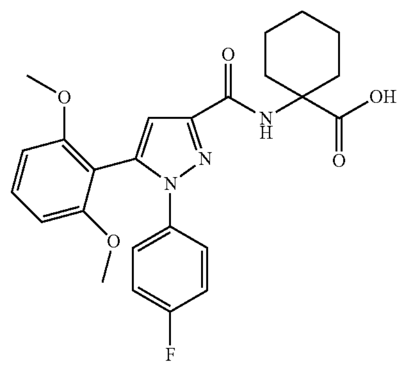 [SMILES: COc1cccc(OC)c1-c1cc(C(=O)NC2(C(=O)O)CCCCC2)nn1-c1ccc(F)cc1] | 467.49 |
| 58 | 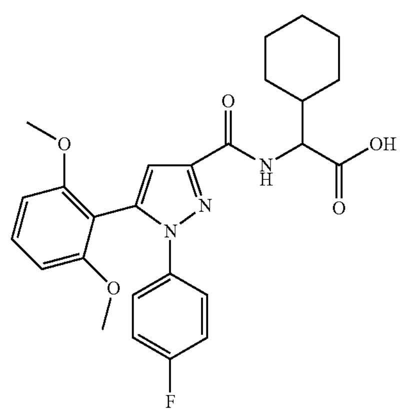 [SMILES: COc1cccc(OC)c1-c1cc(C(=O)NC(C(=O)O)C2CCCCC2)nn1-c1ccc(F)cc1] | 467.49 |
| 59 | 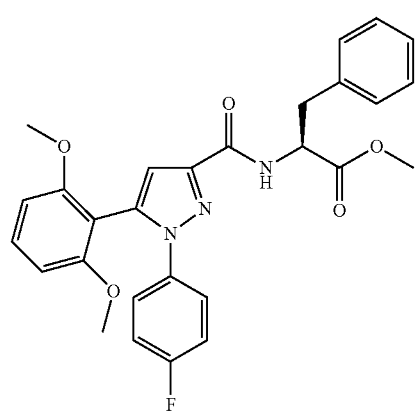 [SMILES: COC(=O)[C@H](Cc1ccccc1)NC(=O)c1cc(-c2c(OC)cccc2OC)n(-c2ccc(F)cc2)n1] | 503.52 |

TABLE 1-continued

| CP# | STRUCTURE | M.W. |
|---|---|---|
| 60 | 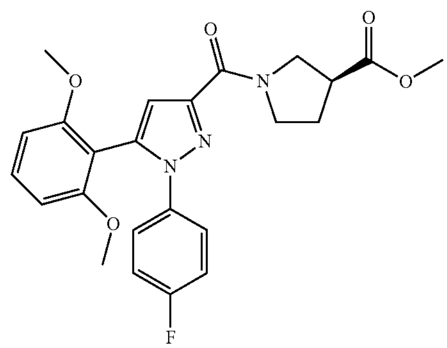 [SMILES: COC(=O)[C@H]1CCN(C(=O)c2cc(-c3c(OC)cccc3OC)n(-c3ccc(F)cc3)n2)C1] | 453.46 |
| 61 | 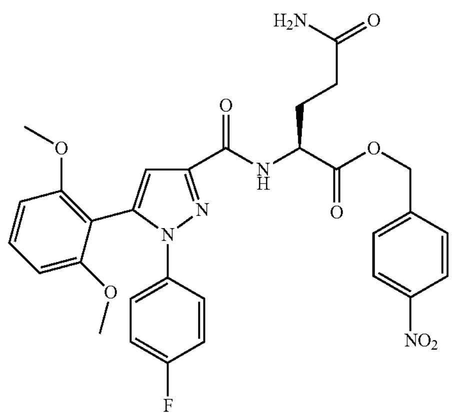 [SMILES: COc1cccc(OC)c1-c1cc(C(=O)N[C@@H](CCC(N)=O)C(=O)OCc2ccc([N+](=O)[O-])cc2)nn1-c1ccc(F)cc1] | 605.57 |
| 62 | 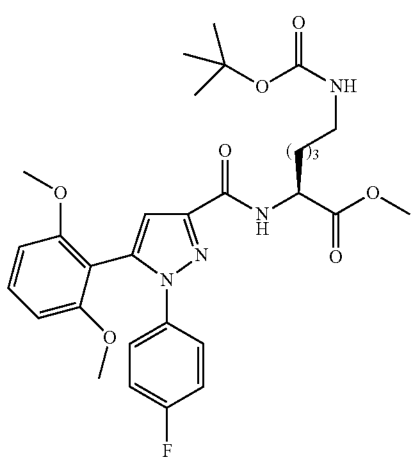 | 584.63 |
| 63 | 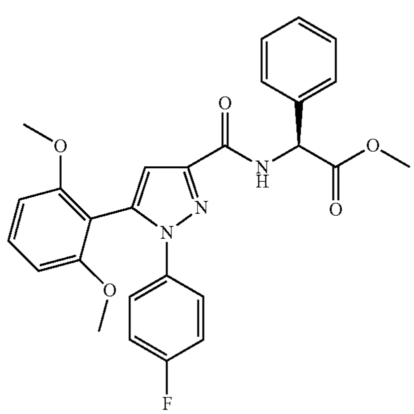 [SMILES: COC(=O)[C@@H](NC(=O)c1cc(-c2c(OC)cccc2OC)n(-c2ccc(F)cc2)n1)c1ccccc1] | 489.49 |

TABLE 1-continued

| CP# | STRUCTURE | M.W. |
|---|---|---|
| 64 | 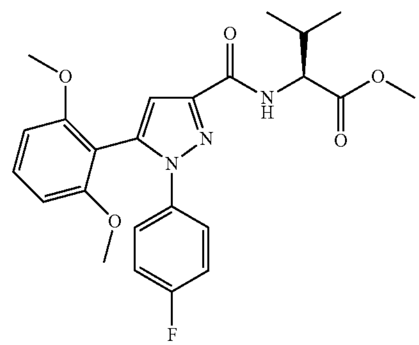 [SMILES: COC(=O)[C@@H](NC(=O)c1cc(-c2c(OC)cccc2OC)n(-c2ccc(F)cc2)n1)C(C)C] | 455.48 |
| 65 | 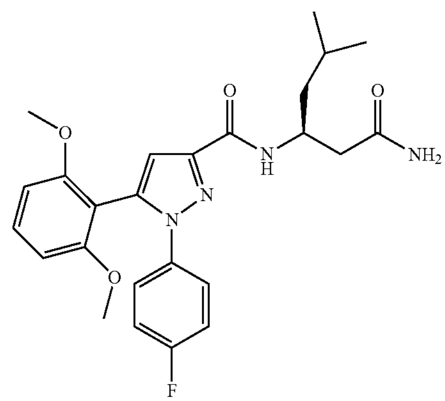 [SMILES: COc1cccc(OC)c1-c1cc(C(=O)N[C@H](CC(N)=O)CC(C)C)nn1-c1ccc(F)cc1] | 468.52 |
| 66 | 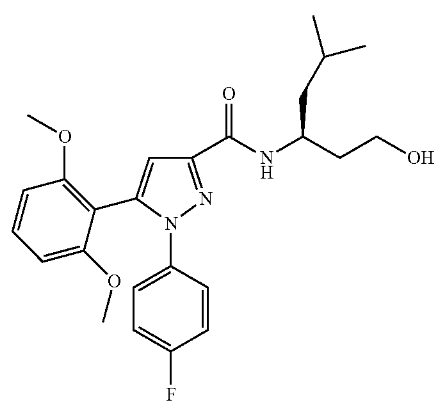 [SMILES: COc1cccc(OC)c1-c1cc(C(=O)N[C@H](CCO)CC(C)C)nn1-c1ccc(F)cc1] | 455.52 |
| 67 | 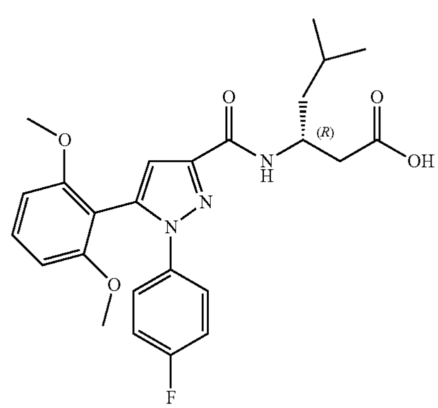 | 469.51 |

TABLE 1-continued

| CP# | STRUCTURE | M.W. |
|---|---|---|
| 68 | 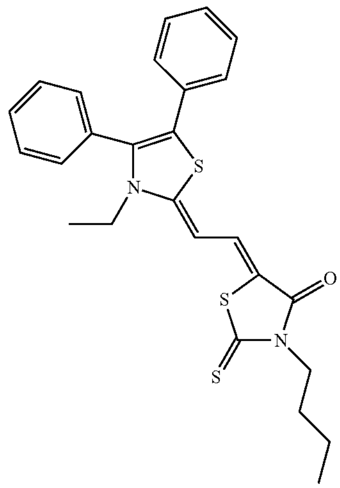 [SMILES: CCCCN1C(=O)/C(=C/C=C2\SC(c3ccccc3)=C(c3ccccc3)N2CC)SC1=S] | 478.69 |
| 69 | 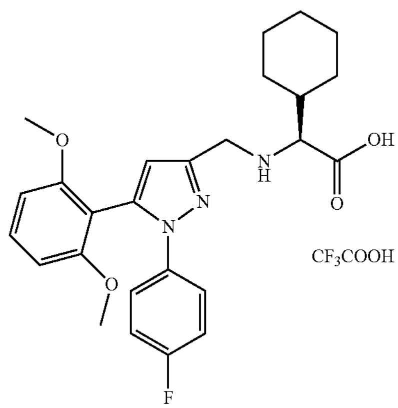 [SMILES: COc1cccc(OC)c1-c1cc(CN[C@H](C(=O)O)C2CCCCC2)nn1-c1ccc(F)cc1 ; "CF3COOH"] | 581.56 |
| 70 | 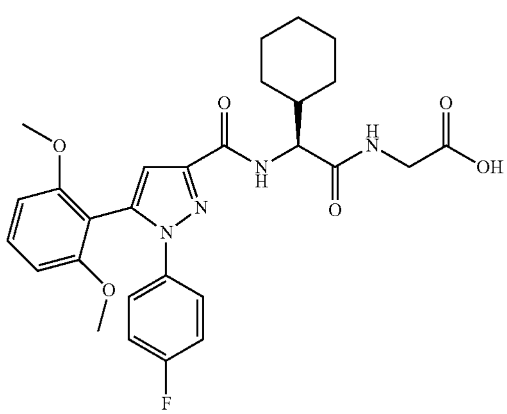 [SMILES: COc1cccc(OC)c1-c1cc(C(=O)N[C@H](C(=O)NCC(=O)O)C2CCCCC2)nn1-c1ccc(F)cc1] | 538.57 |

TABLE 1-continued

| CP# | STRUCTURE | M.W. |
|---|---|---|
| 71 | 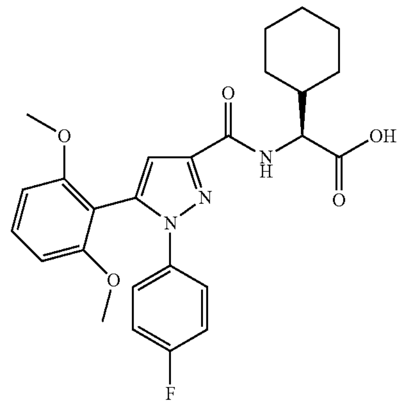 [SMILES: COc1cccc(OC)c1-c1cc(C(=O)N[C@H](C(=O)O)C2CCCCC2)nn1-c1ccc(F)cc1] | 481.52 |
| 35P | 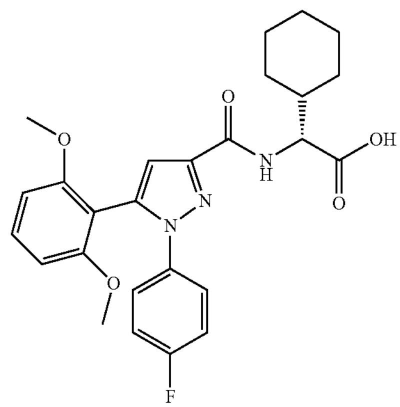 [SMILES: COc1cccc(OC)c1-c1cc(C(=O)N[C@@H](C(=O)O)C2CCCCC2)nn1-c1ccc(F)cc1] | 481.52 |
| 72 | 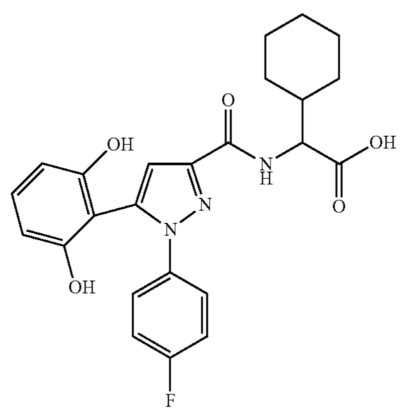 [SMILES: O=C(NC(C(=O)O)C1CCCCC1)c1cc(-c2c(O)cccc2O)n(-c2ccc(F)cc2)n1] | 453.46 |
| 42P | 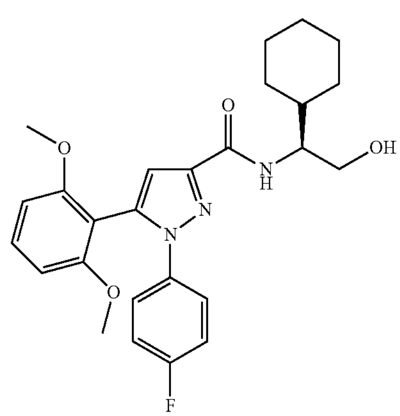 [SMILES: COc1cccc(OC)c1-c1cc(C(=O)N[C@H](CO)C2CCCCC2)nn1-c1ccc(F)cc1] | 467.53 |

TABLE 1-continued

| CP# | STRUCTURE | M.W. |
|---|---|---|
| 73 | 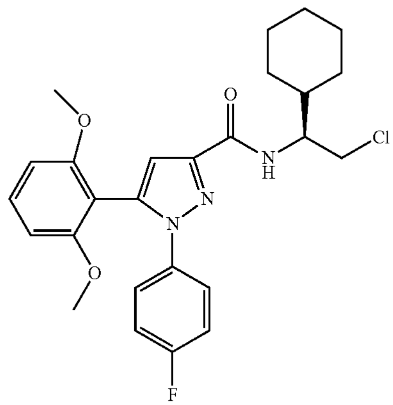 [SMILES: COc1cccc(OC)c1-c1cc(C(=O)N[C@H](CCl)C2CCCCC2)nn1-c1ccc(F)cc1] | 485.98 |
| 74 | 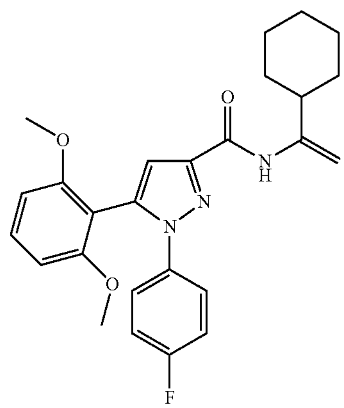 [SMILES: C=C(NC(=O)c1cc(-c2c(OC)cccc2OC)n(-c2ccc(F)cc2)n1)C1CCCCC1] | 449.53 |
| 75 | 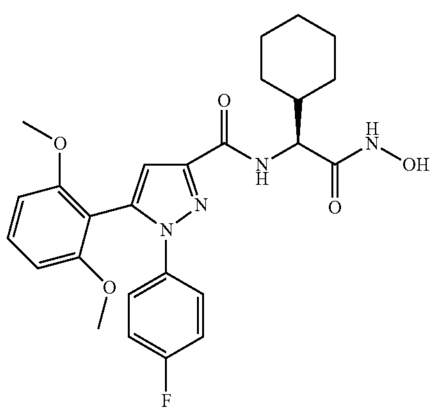 [SMILES: COc1cccc(OC)c1-c1cc(C(=O)N[C@H](C(=O)NO)C2CCCCC2)nn1-c1ccc(F)cc1] | 496.53 |
| 76 | 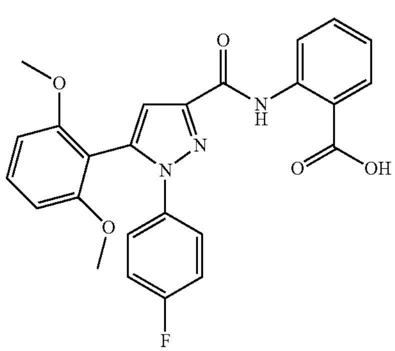 [SMILES: COc1cccc(OC)c1-c1cc(C(=O)Nc2ccccc2C(=O)O)nn1-c1ccc(F)cc1] | 461.44 |

TABLE 1-continued

| CP# | STRUCTURE | M.W. |
|---|---|---|
| 77 | 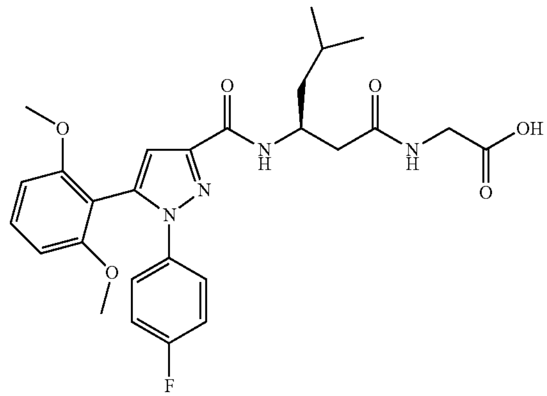 [SMILES: COc1cccc(OC)c1-c1cc(C(=O)N[C@H](CC(=O)NCC(=O)O)CC(C)C)nn1-c1ccc(F)cc1] | 526.56 |
| 78 | 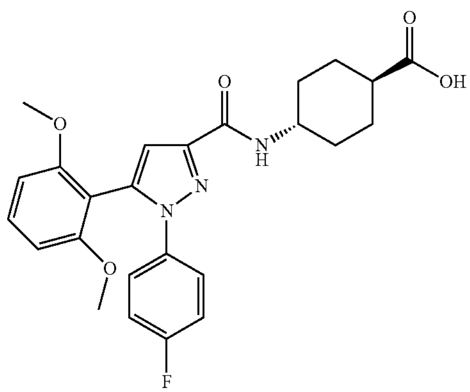 [SMILES: COc1cccc(OC)c1-c1cc(C(=O)N[C@H]2CC[C@H](C(=O)O)CC2)nn1-c1ccc(F)cc1] | 467.49 |
| 79 | 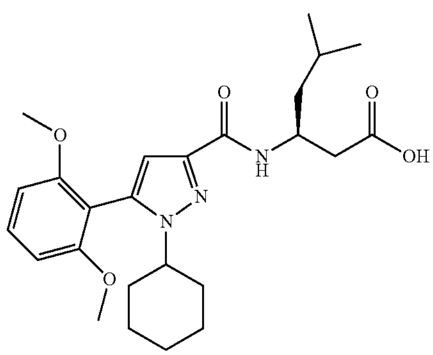 [SMILES: COc1cccc(OC)c1-c1cc(C(=O)N[C@H](CC(=O)O)CC(C)C)nn1C1CCCCC1] | 457.56 |
| 80 | 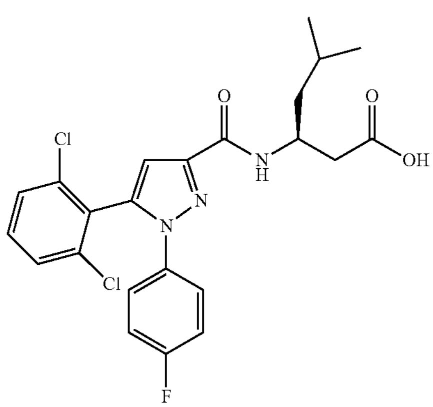 [SMILES: CC(C)C[C@@H](CC(=O)O)NC(=O)c1cc(-c2c(Cl)cccc2Cl)n(-c2ccc(F)cc2)n1] | 478.34 |

TABLE 1-continued

| CP# | STRUCTURE | M.W. |
|---|---|---|
| 81 | 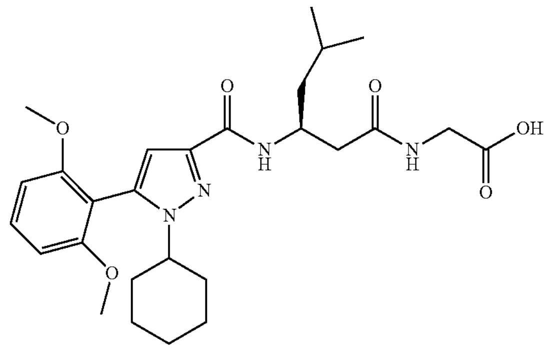 [SMILES: COc1cccc(OC)c1-c1cc(C(=O)N[C@H](CC(=O)NCC(=O)O)CC(C)C)nn1C1CCCCC1] | 514.61 |
| 82 | 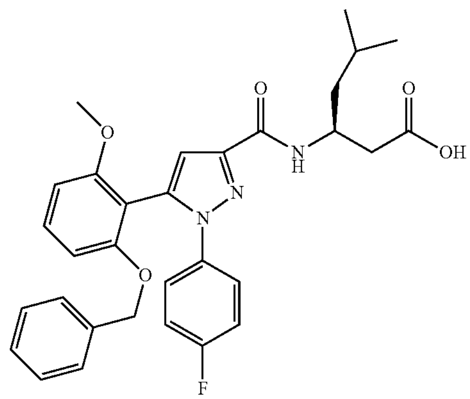 [SMILES: COc1cccc(OCc2ccccc2)c1-c1cc(C(=O)N[C@H](CC(=O)O)CC(C)C)nn1-c1ccc(F)cc1] | 454.60 |
| 83 | 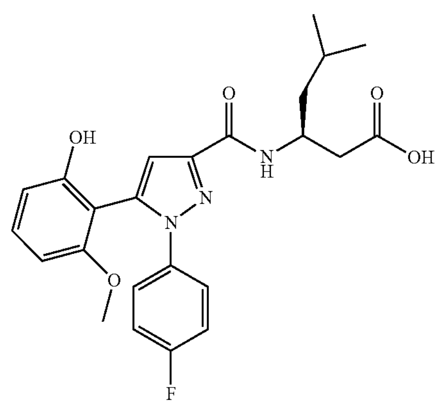 [SMILES: COc1cccc(O)c1-c1cc(C(=O)N[C@H](CC(=O)O)CC(C)C)nn1-c1ccc(F)cc1] | 455.48 |
| 84 | 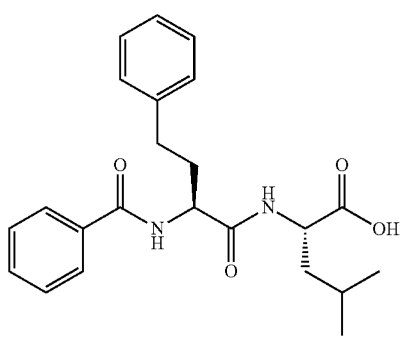 [SMILES: CC(C)C[C@H](NC(=O)[C@H](CCc1ccccc1)NC(=O)c1ccccc1)C(=O)O] | 396.48 |

TABLE 1-continued

| CP# | STRUCTURE | M.W. |
|---|---|---|
| 85 | 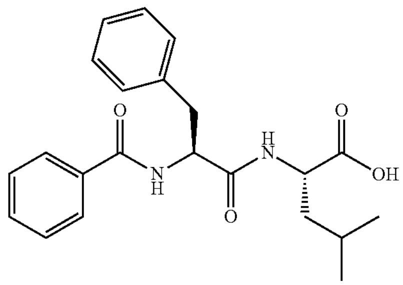 [SMILES: CC(C)C[C@H](NC(=O)[C@H](Cc1ccccc1)NC(=O)c1ccccc1)C(=O)O] | 382.45 |
| 86 | 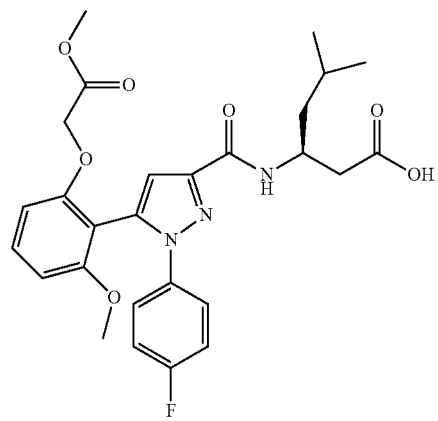 [SMILES: COC(=O)COc1cccc(OC)c1-c1cc(C(=O)N[C@H](CC(=O)O)CC(C)C)nn1-c1ccc(F)cc1] | 527.54 |
| 87 | 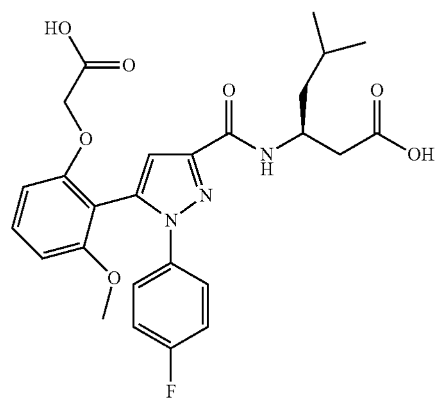 [SMILES: COc1cccc(OCC(=O)O)c1-c1cc(C(=O)N[C@H](CC(=O)O)CC(C)C)nn1-c1ccc(F)cc1] | 513.51 |
| 88 | 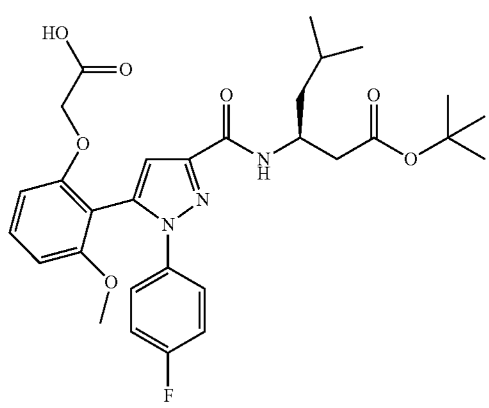 [SMILES: COc1cccc(OCC(=O)O)c1-c1cc(C(=O)N[C@H](CC(=O)OC(C)(C)C)CC(C)C)nn1-c1ccc(F)cc1] | 569.62 |

TABLE 1-continued

| CP# | STRUCTURE | M.W. |
|---|---|---|
| 89 | 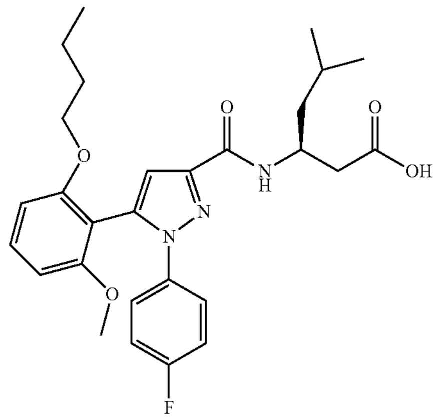 [SMILES: CCCCOc1cccc(OC)c1-c1cc(C(=O)N[C@H](CC(=O)O)CC(C)C)nn1-c1ccc(F)cc1] | 511.59 |
| 90 | 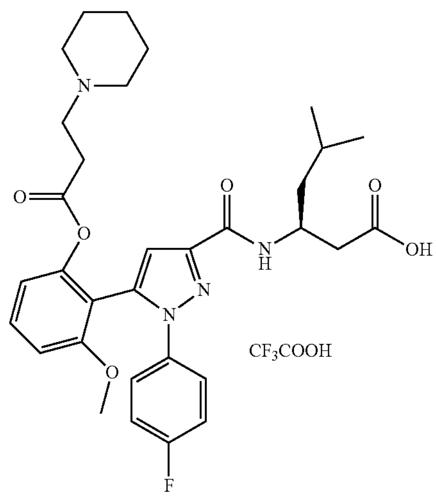 [SMILES: COc1cccc(OC(=O)CCN2CCCCC2)c1-c1cc(C(=O)N[C@H](CC(=O)O)CC(C)C)nn1-c1ccc(F)cc1 ; "CF3COOH"] | 708.70 |
| 91 | 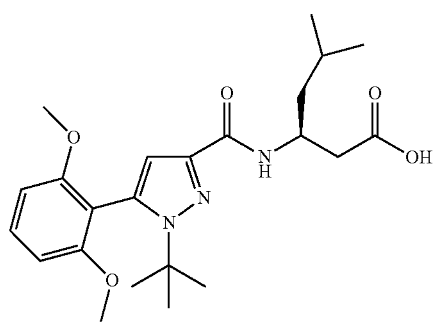 [SMILES: COc1cccc(OC)c1-c1cc(C(=O)N[C@H](CC(=O)O)CC(C)C)nn1C(C)(C)C] | 431.53 |
| 92 | 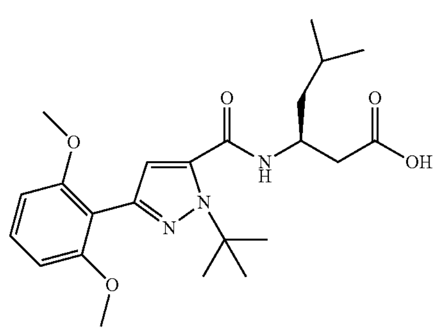 [SMILES: COc1cccc(OC)c1-c1cc(C(=O)N[C@H](CC(=O)O)CC(C)C)n(C(C)(C)C)n1] | 431.53 |

TABLE 1-continued

| CP# | STRUCTURE | M.W. |
|---|---|---|
| 93 | 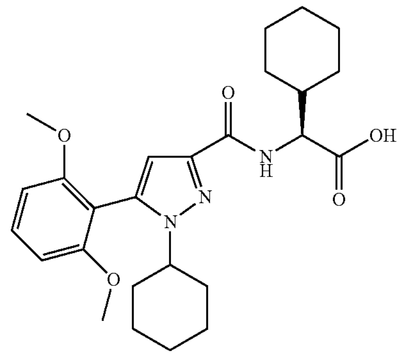 [SMILES: COc1cccc(OC)c1-c1cc(C(=O)N[C@H](C(=O)O)C2CCCCC2)nn1C1CCCCC1] | 469.57 |
| 94 | 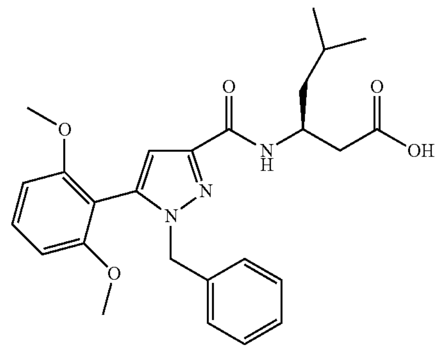 [SMILES: COc1cccc(OC)c1-c1cc(C(=O)N[C@H](CC(=O)O)CC(C)C)nn1Cc1ccccc1] | 465.54 |
| 95 | 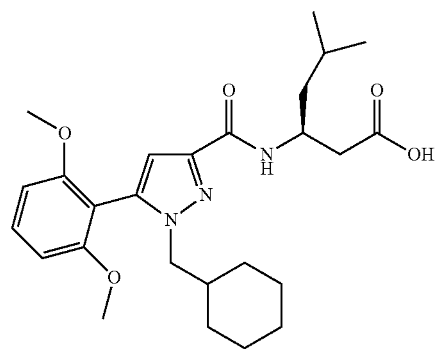 [SMILES: COc1cccc(OC)c1-c1cc(C(=O)N[C@H](CC(=O)O)CC(C)C)nn1CC1CCCCC1] | 471.59 |
| 96 | 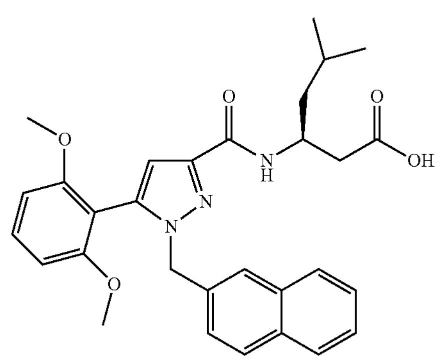 [SMILES: COc1cccc(OC)c1-c1cc(C(=O)N[C@H](CC(=O)O)CC(C)C)nn1Cc1ccc2ccccc2c1] | 515.60 |

TABLE 1-continued

| CP# | STRUCTURE | M.W. |
|---|---|---|
| 97 | 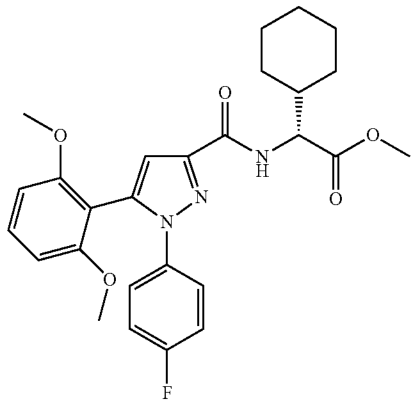 [SMILES: COC(=O)[C@H](NC(=O)c1cc(-c2c(OC)cccc2OC)n(-c2ccc(F)cc2)n1)C1CCCCC1] | 495.54 |
| 98 | 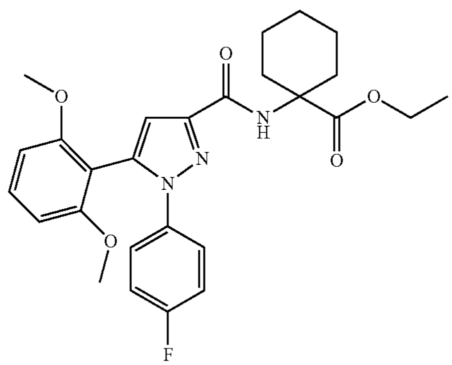 [SMILES: CCOC(=O)C1(NC(=O)c2cc(-c3c(OC)cccc3OC)n(-c3ccc(F)cc3)n2)CCCCC1] | 495.54 |
| 99 | 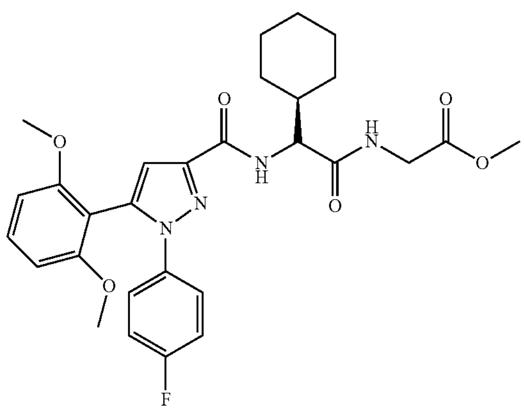 | 552.59 |
| 100 | 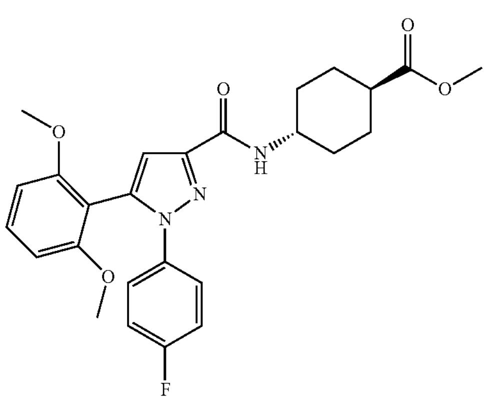 [SMILES: COc1cccc(OC)c1-c1cc(C(=O)N[C@H]2CC[C@H](C(=O)OC)CC2)nn1-c1ccc(F)cc1] | 481.52 |

TABLE 1-continued

| CP# | STRUCTURE | M.W. |
|---|---|---|
| 101 | 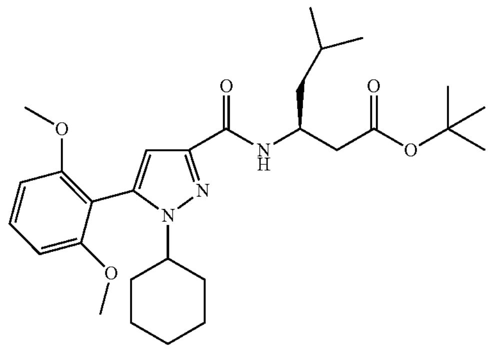 [SMILES: COc1cccc(OC)c1-c1cc(C(=O)N[C@H](CC(=O)OC(C)(C)C)CC(C)C)nn1C1CCCCC1] | 513.67 |
| 102 | 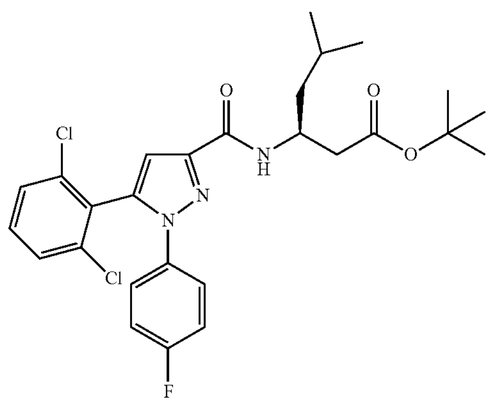 [SMILES: CC(C)C[C@@H](CC(=O)OC(C)(C)C)NC(=O)c1cc(-c2c(Cl)cccc2Cl)n(-c2ccc(F)cc2)n1] | 534.45 |
| 103 | 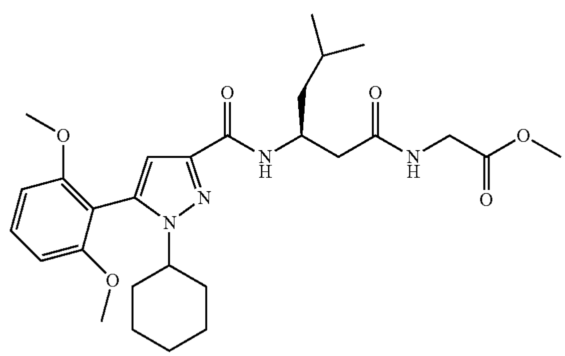 [SMILES: COC(=O)CNC(=O)C[C@H](CC(C)C)NC(=O)c1cc(-c2c(OC)cccc2OC)n(C2CCCCC2)n1] | 528.64 |
| 104 | 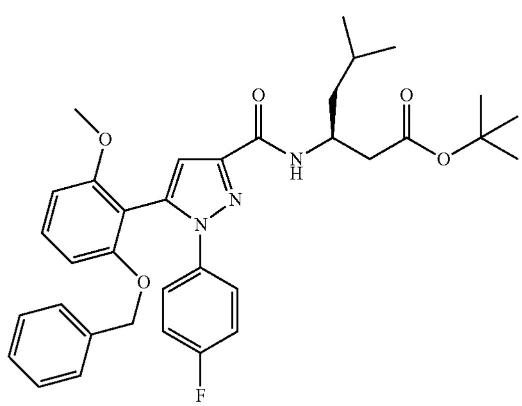 [SMILES: COc1cccc(OCc2ccccc2)c1-c1cc(C(=O)N[C@H](CC(=O)OC(C)(C)C)CC(C)C)nn1-c1ccc(F)cc1] | 601.71 |

TABLE 1-continued

| CP# | STRUCTURE | M.W. |
|---|---|---|
| 105 | 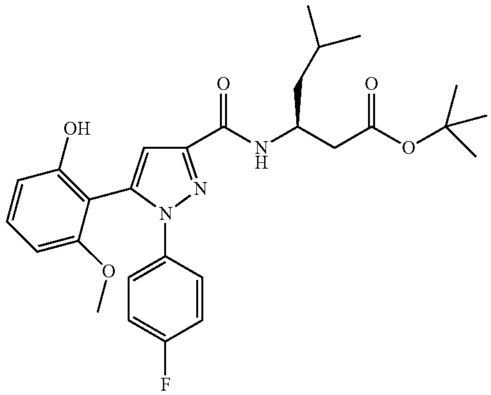 [SMILES: COc1cccc(O)c1-c1cc(C(=O)N[C@H](CC(=O)OC(C)(C)C)CC(C)C)nn1-c1ccc(F)cc1] | 511.59 |
| 106 | 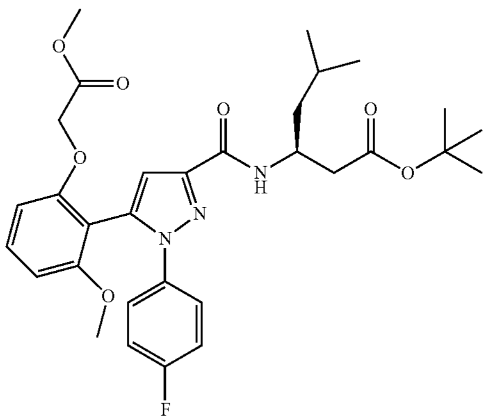 [SMILES: COC(=O)COc1cccc(OC)c1-c1cc(C(=O)N[C@H](CC(=O)OC(C)(C)C)CC(C)C)nn1-c1ccc(F)cc1] | 583.65 |
| 107 | 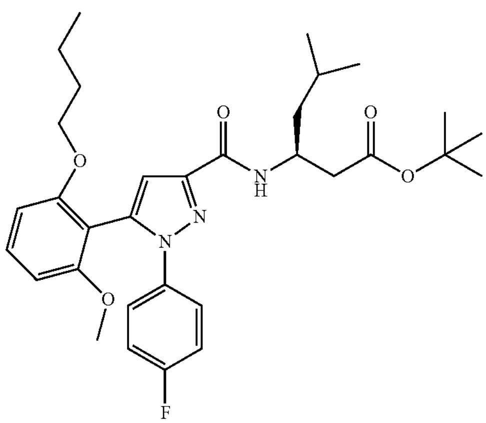 [SMILES: CCCCOc1cccc(OC)c1-c1cc(C(=O)N[C@H](CC(=O)OC(C)(C)C)CC(C)C)nn1-c1ccc(F)cc1] | 567.69 |
| 108 | 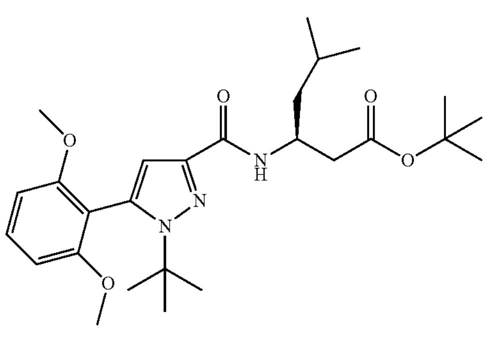 [SMILES: COc1cccc(OC)c1-c1cc(C(=O)N[C@H](CC(=O)OC(C)(C)C)CC(C)C)nn1C(C)(C)C] | 487.63 |

TABLE 1-continued

| CP# | STRUCTURE | M.W. |
|---|---|---|
| 109 | 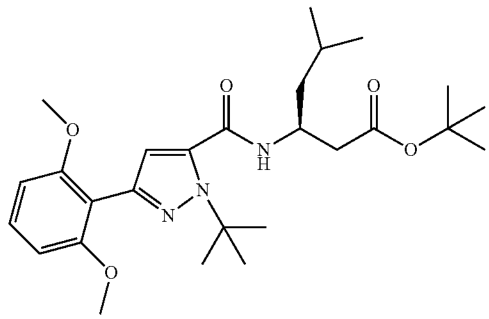 [SMILES: COc1cccc(OC)c1-c1cc(C(=O)N[C@H](CC(=O)OC(C)(C)C)CC(C)C)n(C(C)(C)C)n1] | 487.63 |
| 110 | 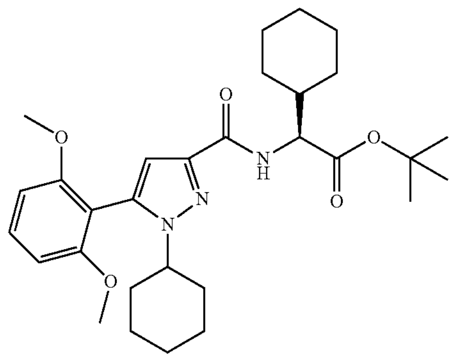 [SMILES: COc1cccc(OC)c1-c1cc(C(=O)N[C@H](C(=O)OC(C)(C)C)C2CCCCC2)nn1C1CCCCC1] | 525.68 |
| 111 | 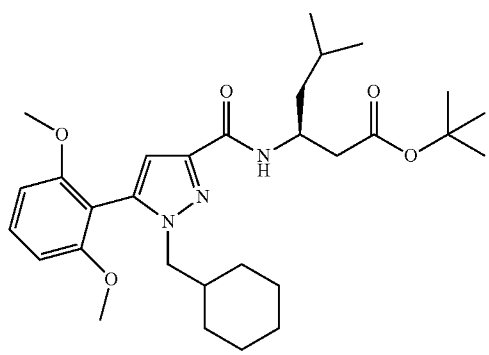 [SMILES: COc1cccc(OC)c1-c1cc(C(=O)N[C@H](CC(=O)OC(C)(C)C)CC(C)C)nn1CC1CCCCC1] | 527.70 |
| 112 | 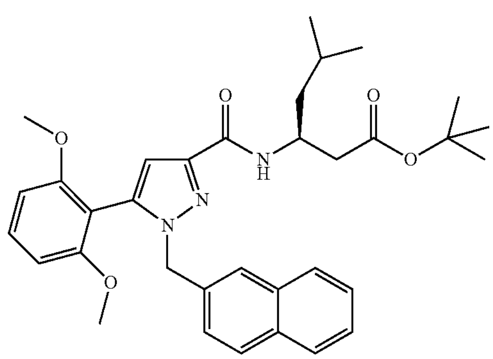 [SMILES: COc1cccc(OC)c1-c1cc(C(=O)N[C@H](CC(=O)OC(C)(C)C)CC(C)C)nn1Cc1ccc2ccccc2c1] | 571.30 |

TABLE 1-continued
| CP# | STRUCTURE | M.W. |
|---|---|---|
| 113 | 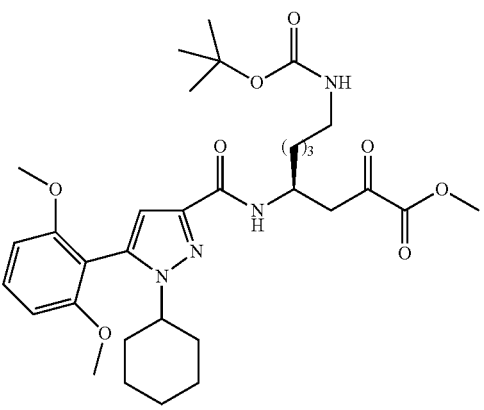 | 572.69 |
| 114 | 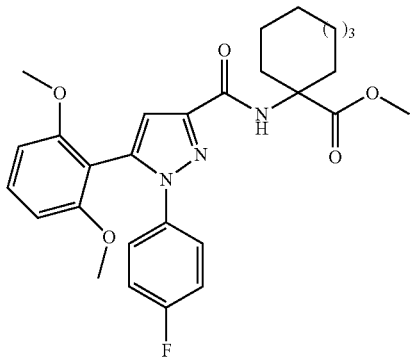 | 509.57 |
| 115 | 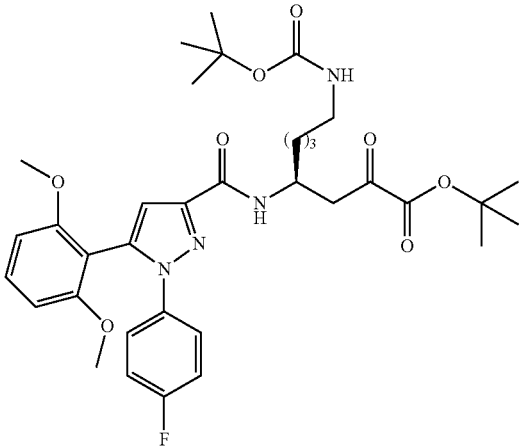 | 626.72 |

TABLE 1-continued

| CP# | STRUCTURE | M.W. |
|---|---|---|
| 116 | 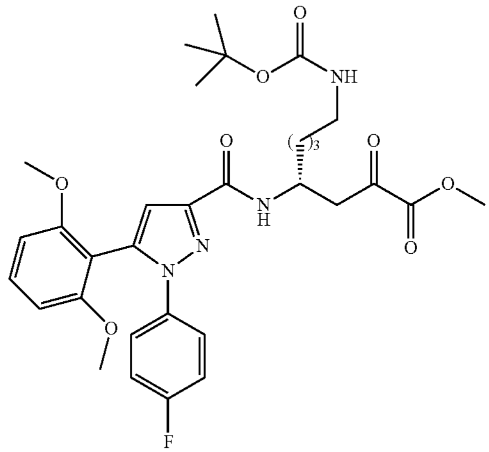 | 584.63 |
| 117 | 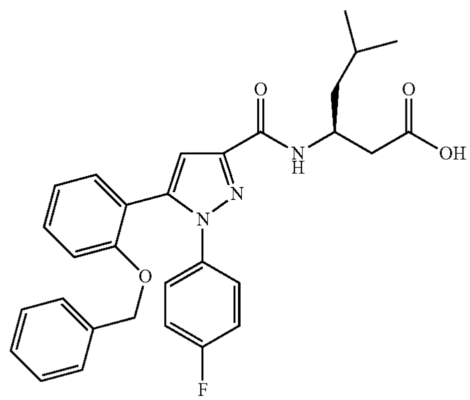 [SMILES: CC(C)C[C@@H](CC(=O)O)NC(=O)c1cc(-c2ccccc2OCc2ccccc2)n(-c2ccc(F)cc2)n1] | 515.58 |
| 118 | 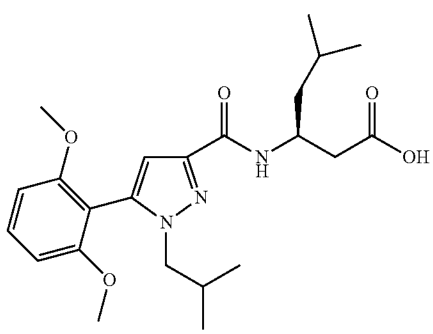 [SMILES: COc1cccc(OC)c1-c1cc(C(=O)N[C@H](CC(=O)O)CC(C)C)nn1CC(C)C] | 431.53 |
| 119 | 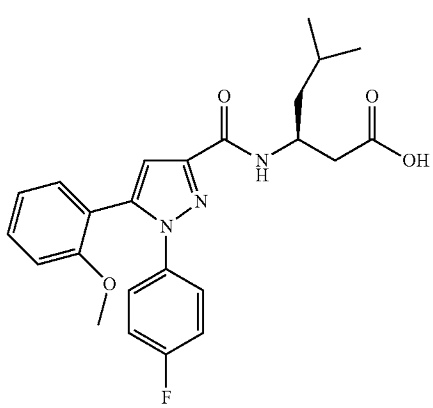 [SMILES: COc1ccccc1-c1cc(C(=O)N[C@H](CC(=O)O)CC(C)C)nn1-c1ccc(F)cc1] | 439.48 |

| CP# | STRUCTURE | M.W. |
|---|---|---|
| 120 | 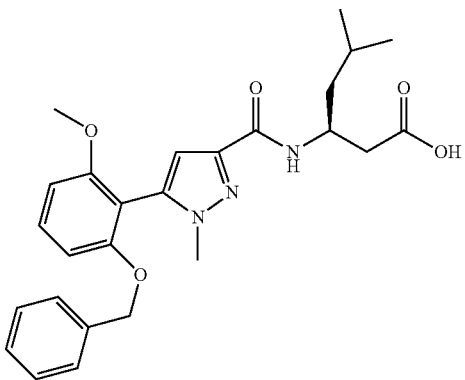 [SMILES: COc1cccc(OCc2ccccc2)c1-c1cc(C(=O)N[C@H](CC(=O)O)CC(C)C)nn1C] | 465.54 |
| 121 | 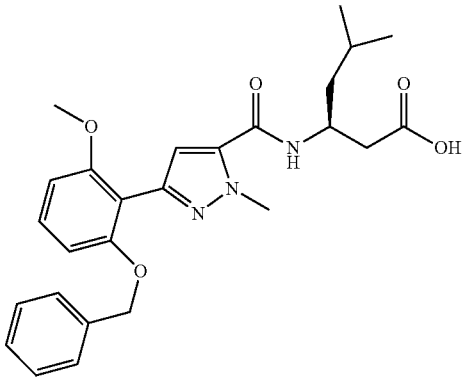 [SMILES: COc1cccc(OCc2ccccc2)c1-c1cc(C(=O)N[C@H](CC(=O)O)CC(C)C)n(C)n1] | 465.54 |
| 122 | 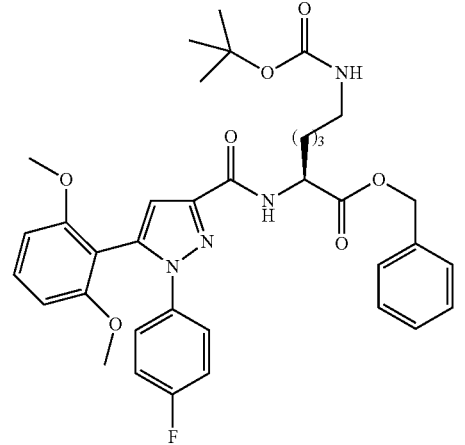 | 660.73 |

TABLE 1-continued

| CP# | STRUCTURE | M.W. |
|---|---|---|
| 123 | 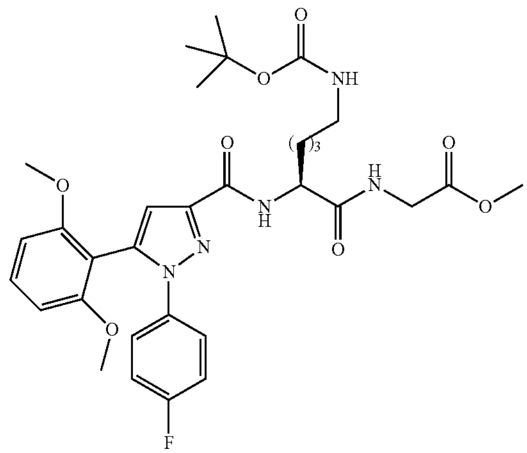 | 641.69 |
| 124 | 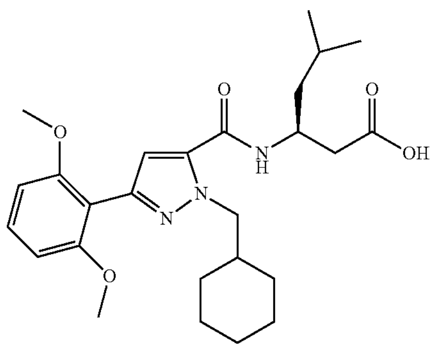 [SMILES: COc1cccc(OC)c1-c1cc(C(=O)N[C@H](CC(=O)O)CC(C)C)n(CC2CCCCC2)n1] | 471.59 |
| 125 | 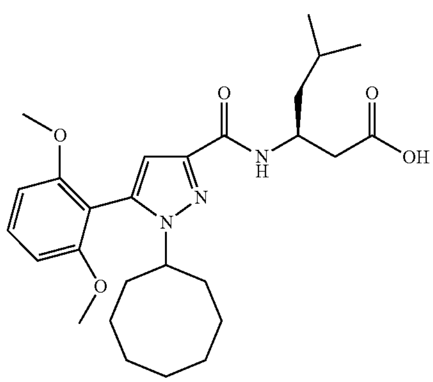 [SMILES: COc1cccc(OC)c1-c1cc(C(=O)N[C@H](CC(=O)O)CC(C)C)nn1C1CCCCCCC1] | 485.62 |
| 126 | 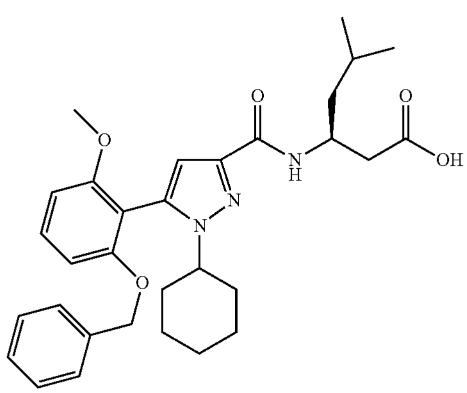 [SMILES: COc1cccc(OCc2ccccc2)c1-c1cc(C(=O)N[C@H](CC(=O)O)CC(C)C)nn1C1CCCCC1] | 533.66 |

TABLE 1-continued

| CP# | STRUCTURE | M.W. |
|---|---|---|
| 127 | 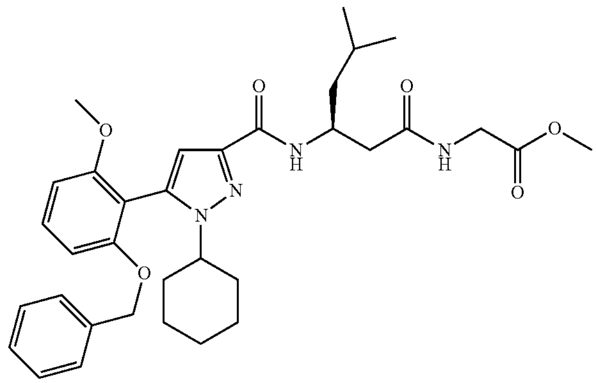 [SMILES: COC(=O)CNC(=O)C[C@H](CC(C)C)NC(=O)c1cc(-c2c(OC)cccc2OCc2ccccc2)n(C2CCCCC2)n1] | 604.74 |
| 128 | 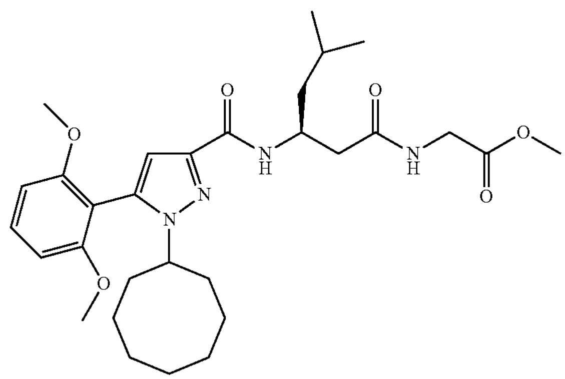 [SMILES: COC(=O)CNC(=O)C[C@H](CC(C)C)NC(=O)c1cc(-c2c(OC)cccc2OC)n(C2CCCCCCC2)n1] | 556.69 |
| 129 | 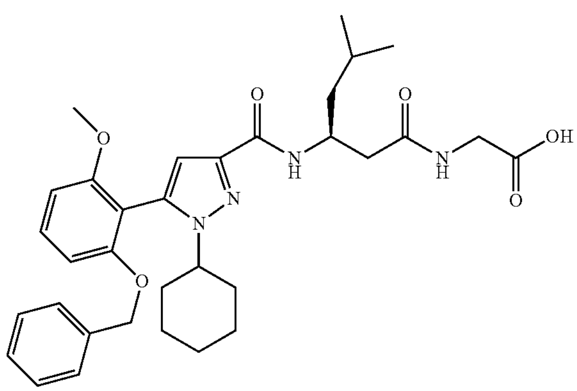 [SMILES: COc1cccc(OCc2ccccc2)c1-c1cc(C(=O)N[C@H](CC(=O)NCC(=O)O)CC(C)C)nn1C1CCCCC1] | 590.71 |
| 130 | 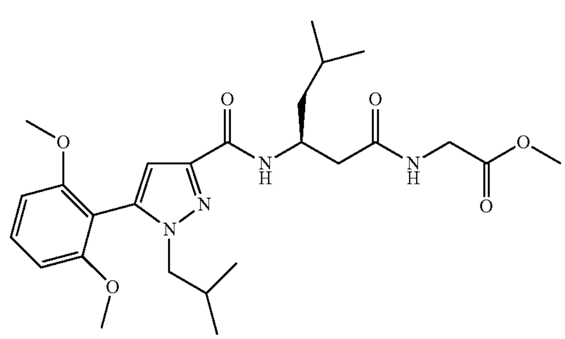 [SMILES: COC(=O)CNC(=O)C[C@H](CC(C)C)NC(=O)c1cc(-c2c(OC)cccc2OC)n(CC(C)C)n1] | 502.60 |

TABLE 1-continued
| CP# | STRUCTURE | M.W. |
|---|---|---|
| 131 | 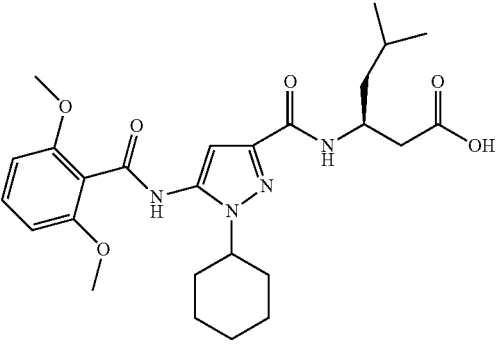 [SMILES: COc1cccc(OC)c1C(=O)Nc1cc(C(=O)N[C@H](CC(=O)O)CC(C)C)nn1C1CCCCC1] | 500.59 |
| 132 | 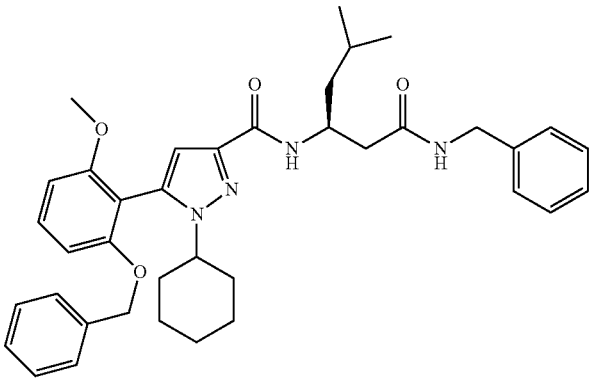 [SMILES: COc1cccc(OCc2ccccc2)c1-c1cc(C(=O)N[C@H](CC(=O)NCc2ccccc2)CC(C)C)nn1C1CCCCC1] | 622.80 |
| 133 | 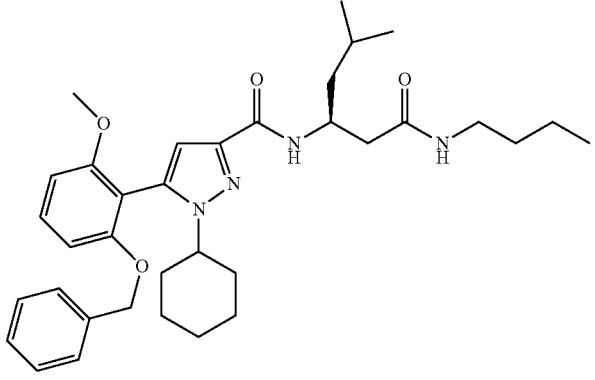 [SMILES: CCCCNC(=O)C[C@H](CC(C)C)NC(=O)c1cc(-c2c(OC)cccc2OCc2ccccc2)n(C2CCCCC2)n1] | 588.78 |
| 134 | 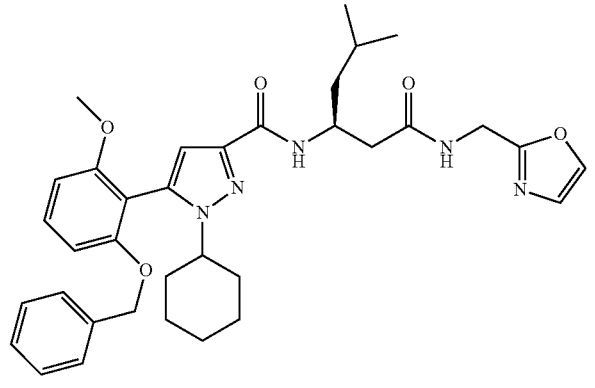 [SMILES: COc1cccc(OCc2ccccc2)c1-c1cc(C(=O)N[C@H](CC(=O)NCc2ncco2)CC(C)C)nn1C1CCCCC1] | 613.75 |

TABLE 1-continued
| CP# | STRUCTURE | M.W. |
|---|---|---|
| 135 | 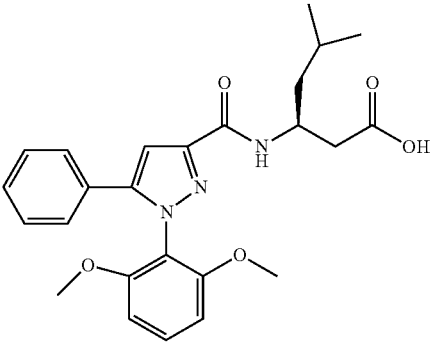 [SMILES: COc1cccc(OC)c1-n1nc(C(=O)N[C@H](CC(=O)O)CC(C)C)cc1-c1ccccc1] | 451.51 |
| 136 | 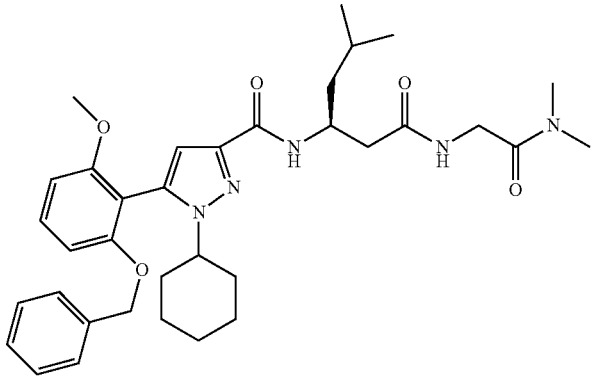 [SMILES: COc1cccc(OCc2ccccc2)c1-c1cc(C(=O)N[C@H](CC(=O)NCC(=O)N(C)C)CC(C)C)nn1C1CCCCC1] | 617.78 |
| 137 | 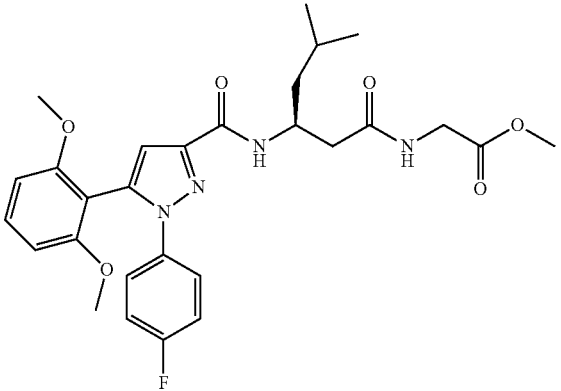 [SMILES: COC(=O)CNC(=O)C[C@H](CC(C)C)NC(=O)c1cc(-c2c(OC)cccc2OC)n(-c2ccc(F)cc2)n1] | 540.58 |
| 138 | 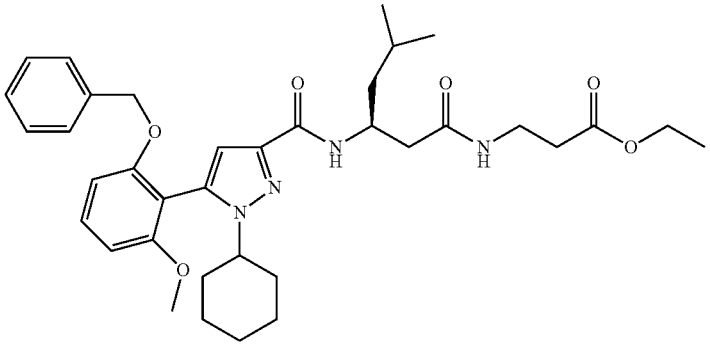 [SMILES: CCOC(=O)CCNC(=O)C[C@H](CC(C)C)NC(=O)c1cc(-c2c(OC)cccc2OCc2ccccc2)n(C2CCCCC2)n1] | 632.79 |

TABLE 1-continued
| CP# | STRUCTURE | M.W. |
|---|---|---|
| 139 | 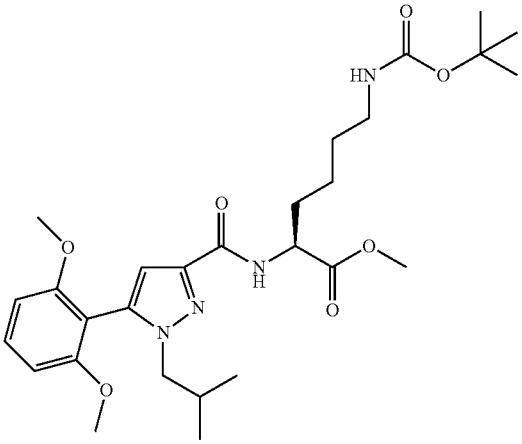 [SMILES: COC(=O)[C@H](CCCCNC(=O)OC(C)(C)C)NC(=O)c1cc(-c2c(OC)cccc2OC)n(CC(C)C)n1] | 546.66 |
| 140 | 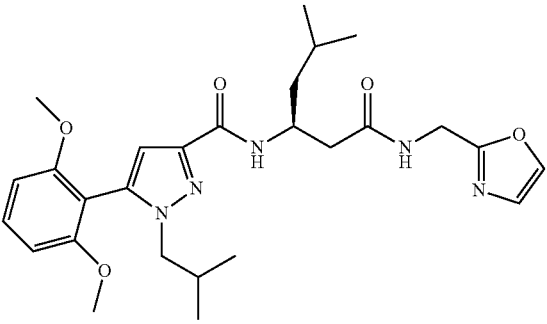 [SMILES: COc1cccc(OC)c1-c1cc(C(=O)N[C@H](CC(=O)NCc2ncco2)CC(C)C)nn1CC(C)C] | 511.61 |
| 141 | 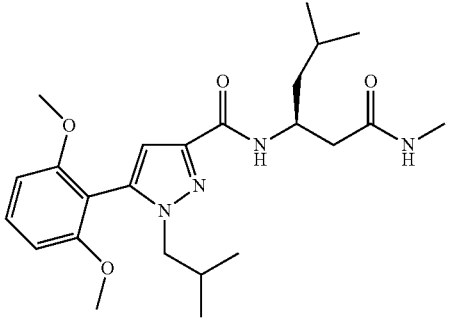 [SMILES: CNC(=O)C[C@H](CC(C)C)NC(=O)c1cc(-c2c(OC)cccc2OC)n(CC(C)C)n1] | 444.57 |
| 142 | 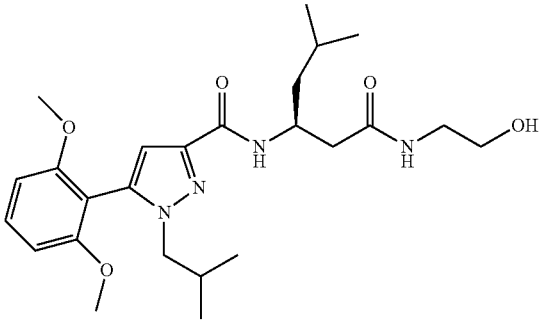 [SMILES: COc1cccc(OC)c1-c1cc(C(=O)N[C@H](CC(=O)NCCO)CC(C)C)nn1CC(C)C] | 474.59 |

TABLE 1-continued
| CP# | STRUCTURE | M.W. |
|---|---|---|
| 143 | 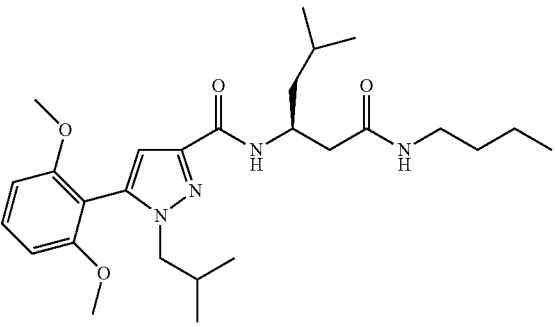 [SMILES: CCCCNC(=O)C[C@H](CC(C)C)NC(=O)c1cc(-c2c(OC)cccc2OC)n(CC(C)C)n1] | 486.65 |
| 144 | 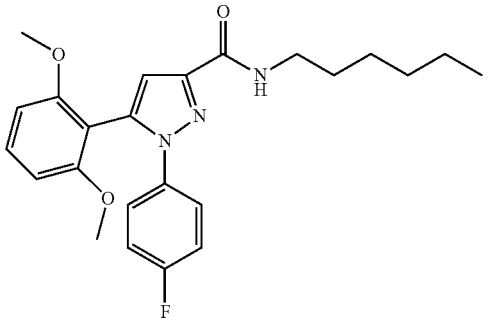 [SMILES: CCCCCCNC(=O)c1cc(-c2c(OC)cccc2OC)n(-c2ccc(F)cc2)n1] | 425.50 |
| 145 | 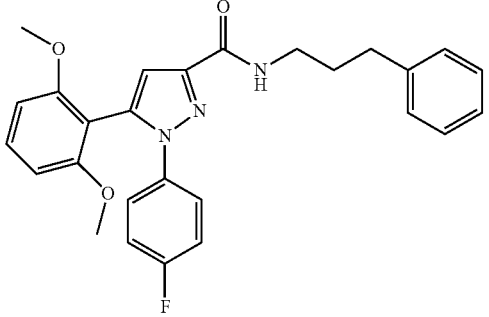 [SMILES: COc1cccc(OC)c1-c1cc(C(=O)NCCCc2ccccc2)nn1-c1ccc(F)cc1] | 459.51 |
| 146 | 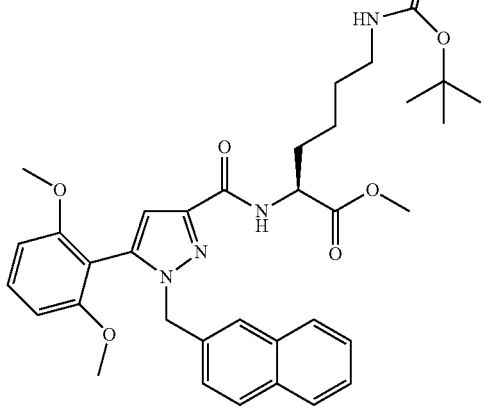 | 630.73 |

| CP# | STRUCTURE | M.W. |
|---|---|---|
| 147 | 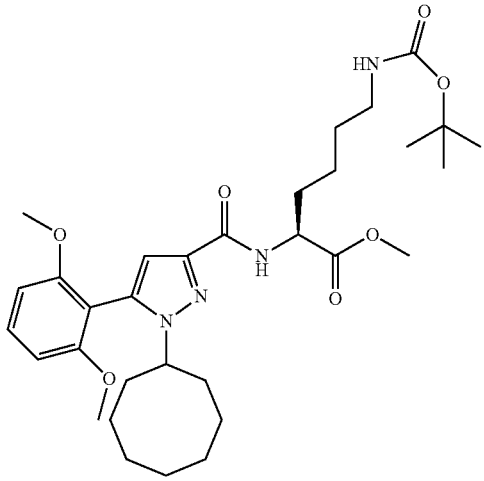 [SMILES: COC(=O)[C@H](CCCCNC(=O)OC(C)(C)C)NC(=O)c1cc(-c2c(OC)cccc2OC)n(C2CCCCCCC2)n1] | 600.75 |
| 148 | 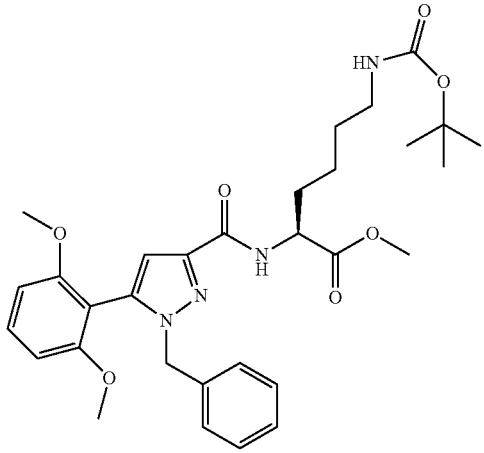 [SMILES: COC(=O)[C@H](CCCCNC(=O)OC(C)(C)C)NC(=O)c1cc(-c2c(OC)cccc2OC)n(Cc2ccccc2)n1] | 580.67 |
| 149 | 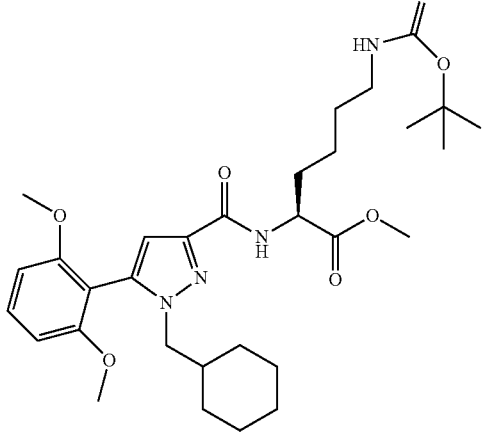 | 586.72 |

TABLE 1-continued

| CP# | STRUCTURE | M.W. |
|---|---|---|
| 150 | 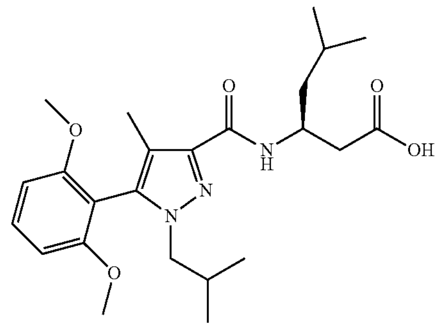 [SMILES: COc1cccc(OC)c1-c1c(C)c(C(=O)N[C@H](CC(=O)O)CC(C)C)nn1CC(C)C] | 445.55 |
| 151 | 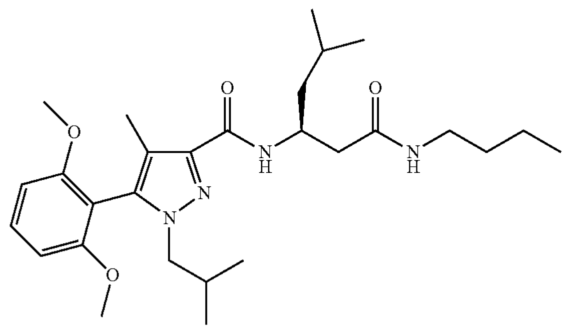 [SMILES: CCCCNC(=O)C[C@H](CC(C)C)NC(=O)c1nn(CC(C)C)c(-c2c(OC)cccc2OC)c1C] | 500.67 |
| 152 | 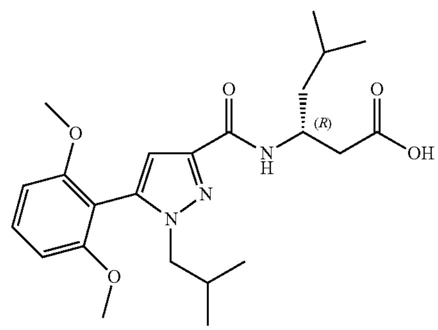 | 431.53 |
| 153 | 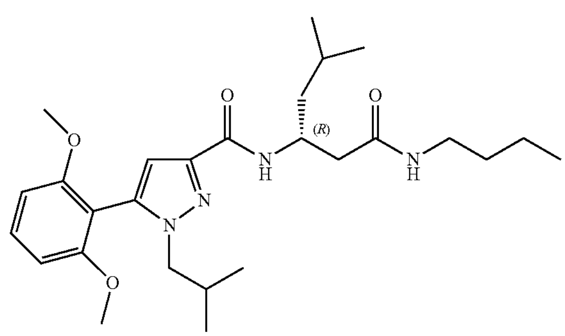 | 486.65 |

TABLE 1-continued
| CP# | STRUCTURE | M.W. |
|---|---|---|
| 154 | 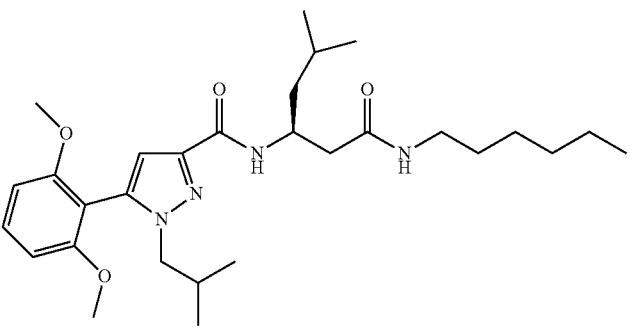 [SMILES: CCCCCCNC(=O)C[C@H](CC(C)C)NC(=O)c1cc(-c2c(OC)cccc2OC)n(CC(C)C)n1] | 514.70 |
| 155 | 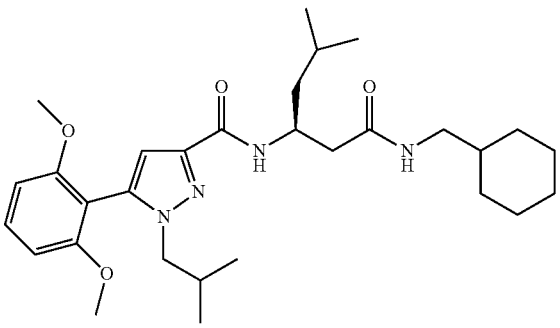 [SMILES: COc1cccc(OC)c1-c1cc(C(=O)N[C@H](CC(=O)NCC2CCCCC2)CC(C)C)nn1CC(C)C] | 526.71 |
| 156 | 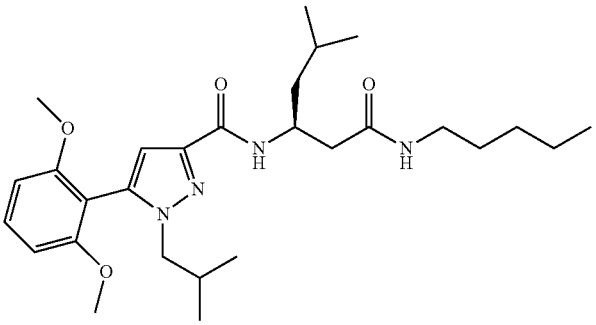 [SMILES: CCCCCNC(=O)C[C@H](CC(C)C)NC(=O)c1cc(-c2c(OC)cccc2OC)n(CC(C)C)n1] | 500.67 |
| 157 | 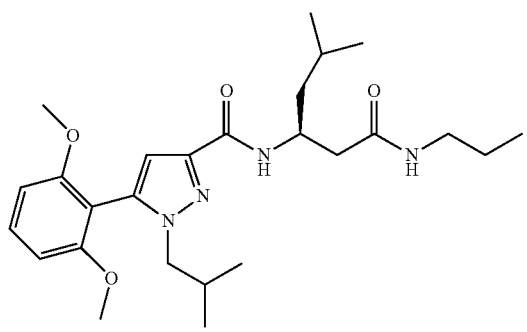 [SMILES: CCCNC(=O)C[C@H](CC(C)C)NC(=O)c1cc(-c2c(OC)cccc2OC)n(CC(C)C)n1] | 472.62 |

TABLE 1-continued
| CP# | STRUCTURE | M.W. |
|---|---|---|
| 158 | 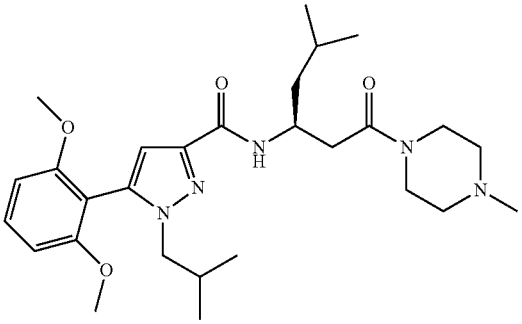 [SMILES: COc1cccc(OC)c1-c1cc(C(=O)N[C@H](CC(=O)N2CCN(C)CC2)CC(C)C)nn1CC(C)C] | 513.67 |
| 159 | 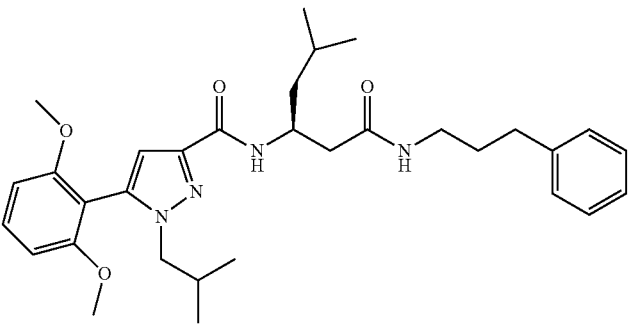 [SMILES: COc1cccc(OC)c1-c1cc(C(=O)N[C@H](CC(=O)NCCCc2ccccc2)CC(C)C)nn1CC(C)C] | 548.72 |
| 160 | 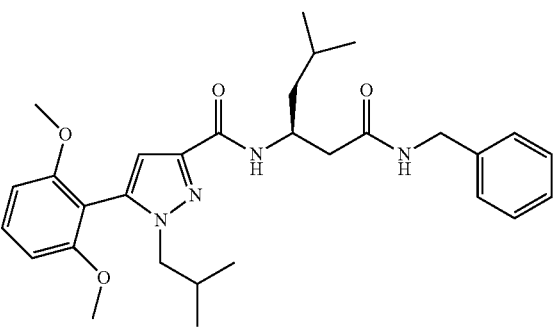 [SMILES: COc1cccc(OC)c1-c1cc(C(=O)N[C@H](CC(=O)NCc2ccccc2)CC(C)C)nn1CC(C)C] | 520.66 |
| 161 | 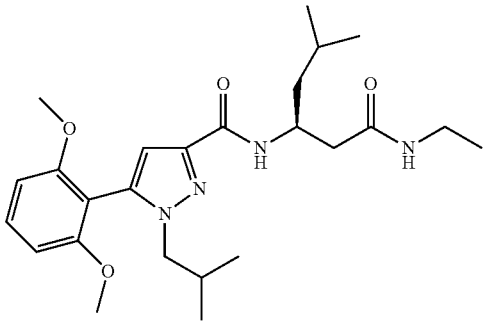 [SMILES: CCNC(=O)C[C@H](CC(C)C)NC(=O)c1cc(-c2c(OC)cccc2OC)n(CC(C)C)n1] | 458.59 |

TABLE 1-continued

| CP# | STRUCTURE | M.W. |
|---|---|---|
| 162 | 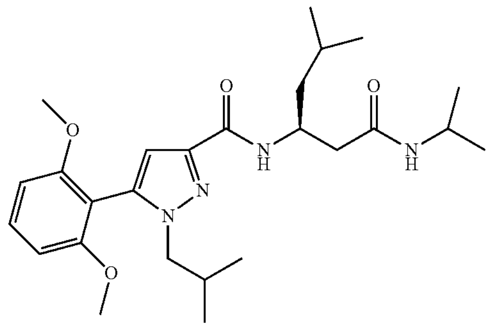 [SMILES: COc1cccc(OC)c1-c1cc(C(=O)N[C@H](CC(=O)NC(C)C)CC(C)C)nn1CC(C)C] | 472.62 |
| 163 | 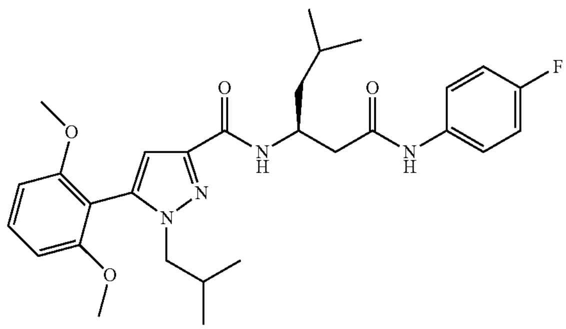 [SMILES: COc1cccc(OC)c1-c1cc(C(=O)N[C@H](CC(=O)Nc2ccc(F)cc2)CC(C)C)nn1CC(C)C] | 524.63 |
| 164 | 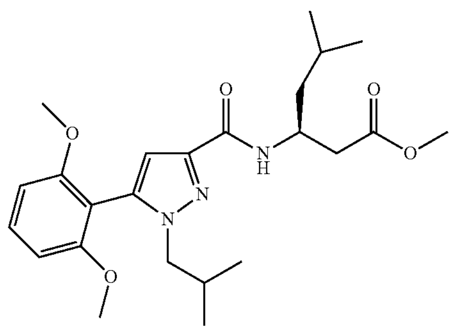 [SMILES: COC(=O)C[C@H](CC(C)C)NC(=O)c1cc(-c2c(OC)cccc2OC)n(CC(C)C)n1] | 445.55 |
| 165 | 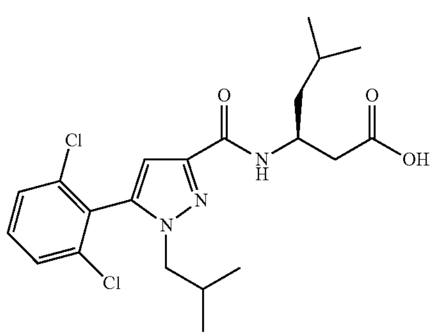 [SMILES: CC(C)C[C@@H](CC(=O)O)NC(=O)c1cc(-c2c(Cl)cccc2Cl)n(CC(C)C)n1] | 440.36 |

TABLE 1-continued
| CP# | STRUCTURE | M.W. |
|---|---|---|
| 166 | 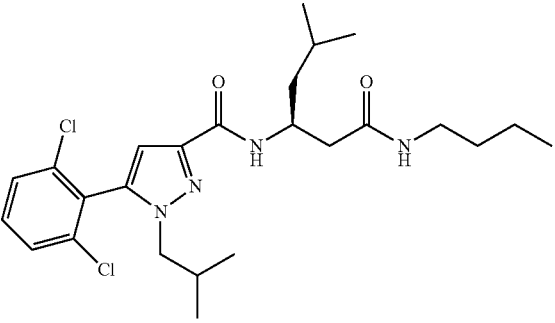 [SMILES: CCCCNC(=O)C[C@H](CC(C)C)NC(=O)c1cc(-c2c(Cl)cccc2Cl)n(CC(C)C)n1] | 495.48 |
| 167 | 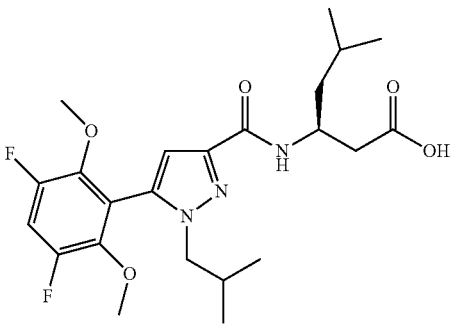 [SMILES: COc1c(F)cc(F)c(OC)c1-c1cc(C(=O)N[C@H](CC(=O)O)CC(C)C)nn1CC(C)C] | 467.51 |
| 168 | 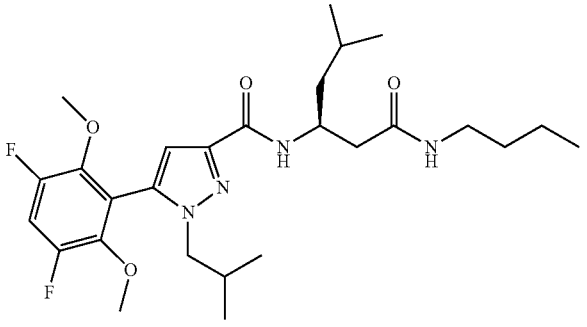 [SMILES: CCCCNC(=O)C[C@H](CC(C)C)NC(=O)c1cc(-c2c(OC)c(F)cc(F)c2OC)n(CC(C)C)n1] | 522.63 |
| 169 | 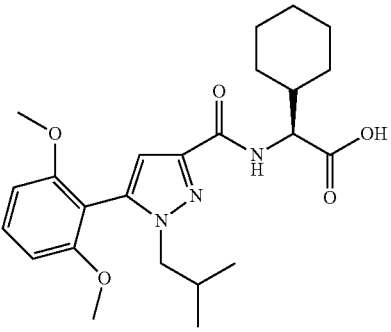 [SMILES: COc1cccc(OC)c1-c1cc(C(=O)N[C@H](C(=O)O)C2CCCCC2)nn1CC(C)C] | 443.54 |

TABLE 1-continued
| CP# | STRUCTURE | M.W. |
|---|---|---|
| 170 | 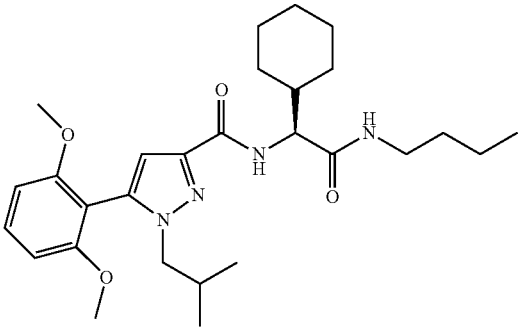 [SMILES: CCCCNC(=O)[C@@H](NC(=O)c1cc(-c2c(OC)cccc2OC)n(CC(C)C)n1)C1CCCCC1] | 498.66 |
| 171 | 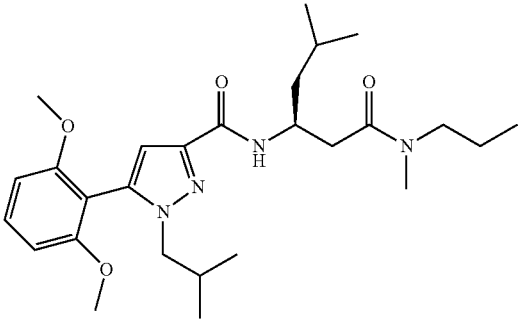 [SMILES: CCCN(C)C(=O)C[C@H](CC(C)C)NC(=O)c1cc(-c2c(OC)cccc2OC)n(CC(C)C)n1] | 486.65 |
| 172 | 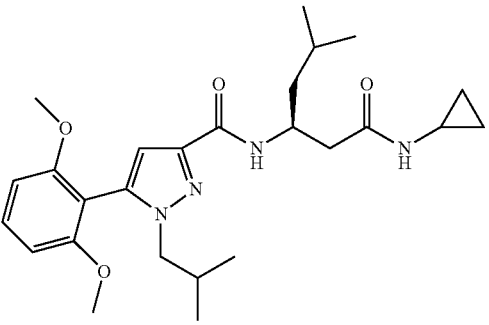 [SMILES: COc1cccc(OC)c1-c1cc(C(=O)N[C@H](CC(=O)NC2CC2)CC(C)C)nn1CC(C)C] | 470.60 |
| 173 | 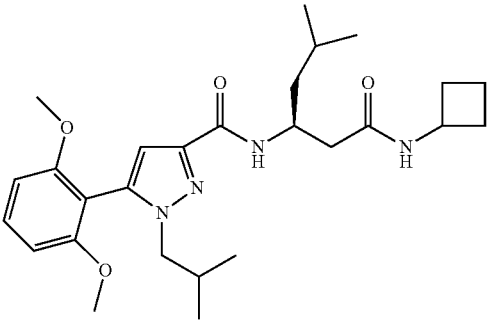 [SMILES: COc1cccc(OC)c1-c1cc(C(=O)N[C@H](CC(=O)NC2CCC2)CC(C)C)nn1CC(C)C] | 484.63 |

TABLE 1-continued

| CP# | STRUCTURE | M.W. |
|---|---|---|
| 174 | 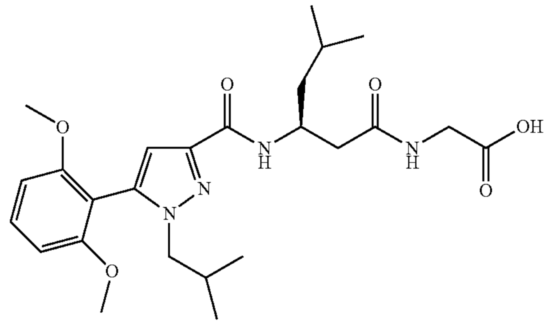 [SMILES: COc1cccc(OC)c1-c1cc(C(=O)N[C@H](CC(=O)NCC(=O)O)CC(C)C)nn1CC(C)C] | 488.58 |
| 175 | 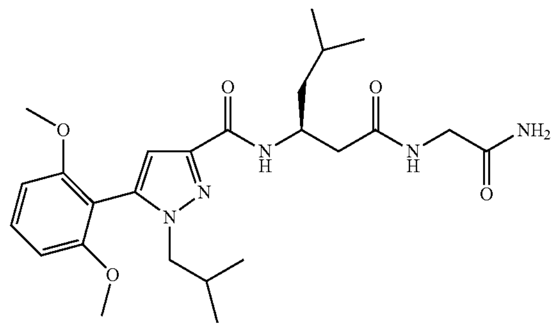 [SMILES: COc1cccc(OC)c1-c1cc(C(=O)N[C@H](CC(=O)NCC(N)=O)CC(C)C)nn1CC(C)C] | 487.59 |
| 176 | 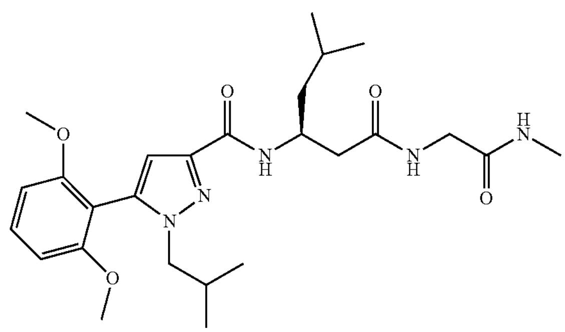 [SMILES: CNC(=O)CNC(=O)C[C@H](CC(C)C)NC(=O)c1cc(-c2c(OC)cccc2OC)n(CC(C)C)n1] | 501.62 |
| 177 | 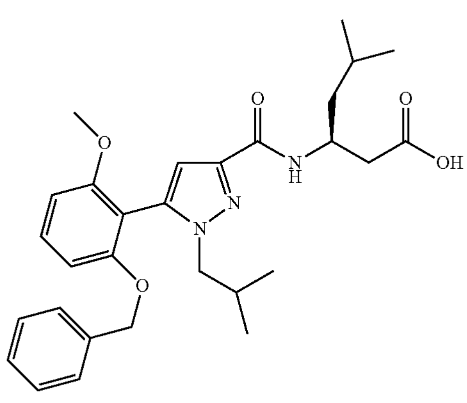 [SMILES: COc1cccc(OCc2ccccc2)c1-c1cc(C(=O)N[C@H](CC(=O)O)CC(C)C)nn1CC(C)C] | 507.62 |

TABLE 1-continued

| CP# | STRUCTURE | M.W. |
|---|---|---|
| 178 | 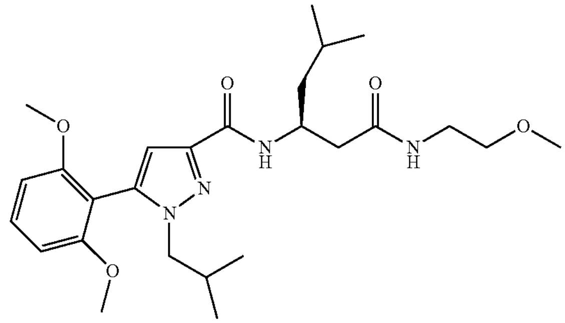 [SMILES: COCCNC(=O)C[C@H](CC(C)C)NC(=O)c1cc(-c2c(OC)cccc2OC)n(CC(C)C)n1] | 488.62 |
| 179 | 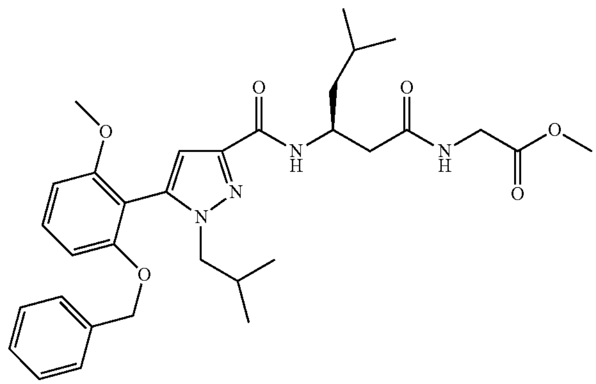 [SMILES: COC(=O)CNC(=O)C[C@H](CC(C)C)NC(=O)c1cc(-c2c(OC)cccc2OCc2ccccc2)n(CC(C)C)n1] | 578.70 |
| 180 | 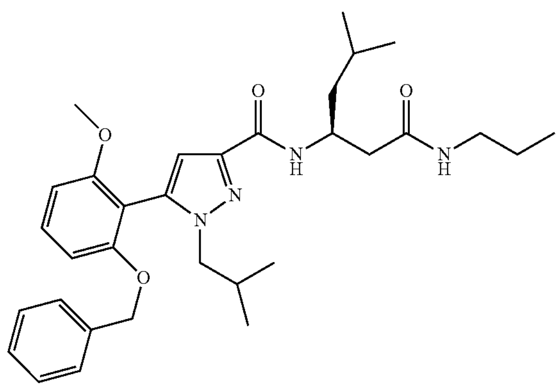 [SMILES: CCCNC(=O)C[C@H](CC(C)C)NC(=O)c1cc(-c2c(OC)cccc2OCc2ccccc2)n(CC(C)C)n1] | 548.72 |
| 181 | 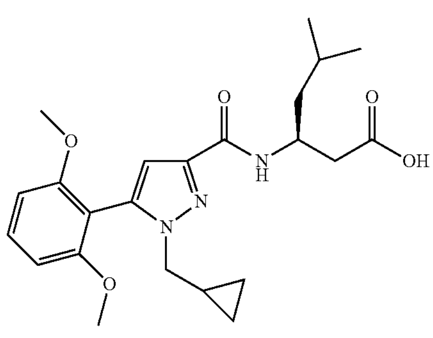 [SMILES: COc1cccc(OC)c1-c1cc(C(=O)N[C@H](CC(=O)O)CC(C)C)nn1CC1CC1] | 429.51 |

| CP# | STRUCTURE | M.W. |
|---|---|---|
| 182 | 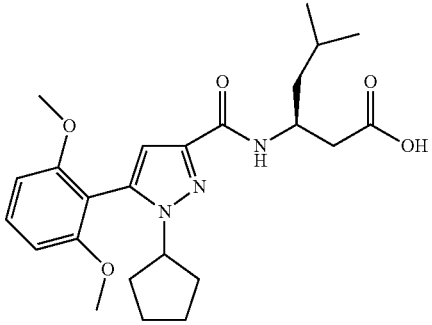 [SMILES: COc1cccc(OC)c1-c1cc(C(=O)N[C@H](CC(=O)O)CC(C)C)nn1C1CCCC1] | 443.54 |
| 183 | 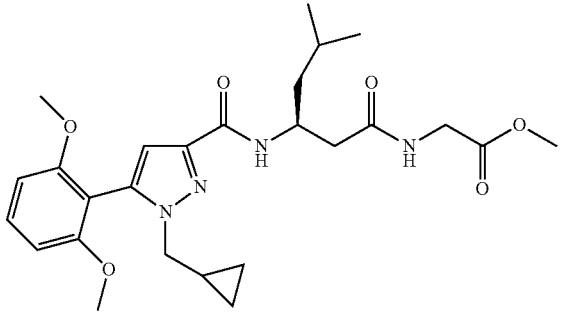 [SMILES: COC(=O)CNC(=O)C[C@H](CC(C)C)NC(=O)c1cc(-c2c(OC)cccc2OC)n(CC2CC2)n1] | 500.59 |
| 184 | 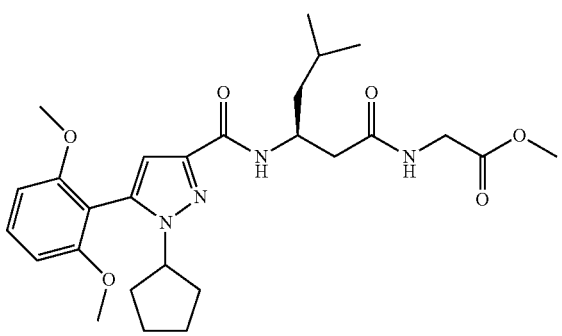 [SMILES: COC(=O)CNC(=O)C[C@H](CC(C)C)NC(=O)c1cc(-c2c(OC)cccc2OC)n(C2CCCC2)n1] | 514.61 |
| 185 | 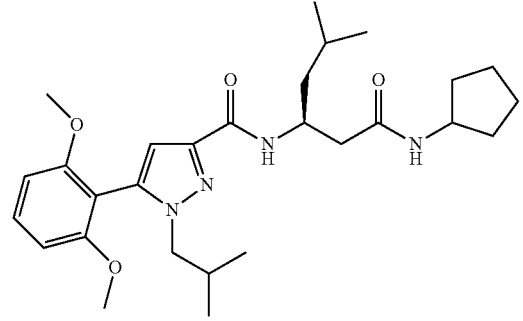 [SMILES: COc1cccc(OC)c1-c1cc(C(=O)N[C@H](CC(=O)NC2CCCC2)CC(C)C)nn1CC(C)C] | 498.66 |

TABLE 1-continued
| CP# | STRUCTURE | M.W. |
|---|---|---|
| 186 | 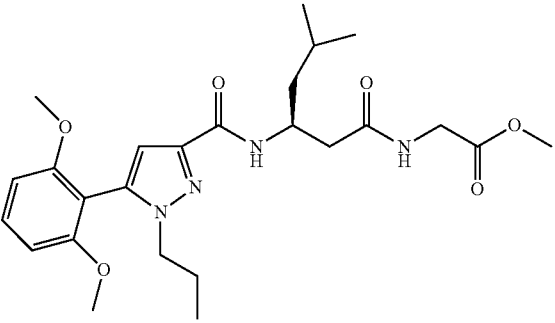 [SMILES: CCCn1nc(C(=O)N[C@H](CC(=O)NCC(=O)OC)CC(C)C)cc1-c1c(OC)cccc1OC] | 488.58 |
| 187 | 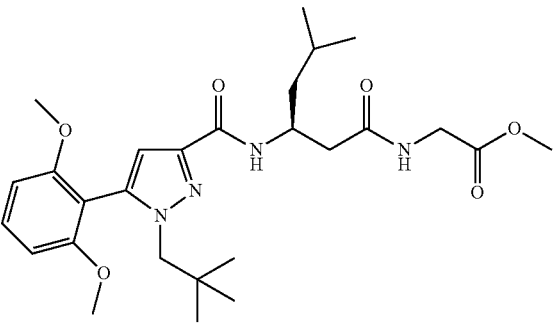 [SMILES: COC(=O)CNC(=O)C[C@H](CC(C)C)NC(=O)c1cc(-c2c(OC)cccc2OC)n(CC(C)(C)C)n1] | 516.63 |
| 188 | 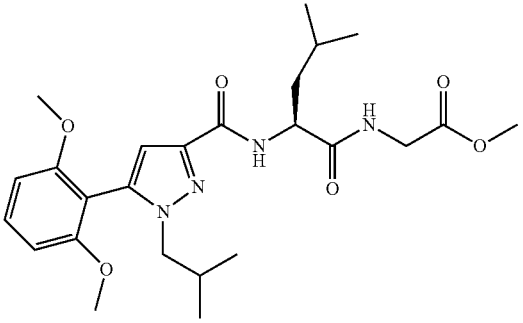 [SMILES: COC(=O)CNC(=O)[C@H](CC(C)C)NC(=O)c1cc(-c2c(OC)cccc2OC)n(CC(C)C)n1] | 488.58 |
| 189 | 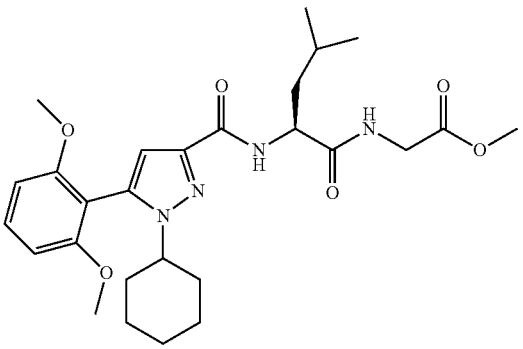 [SMILES: COC(=O)CNC(=O)[C@H](CC(C)C)NC(=O)c1cc(-c2c(OC)cccc2OC)n(C2CCCCC2)n1] | 514.61 |

US 10,377,718 B2
255
256
TABLE 1-continued
| CP# | STRUCTURE | M.W. |
|---|---|---|
| 190 | 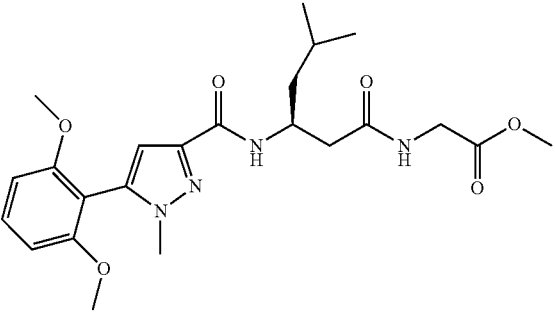 [SMILES: COC(=O)CNC(=O)C[C@H](CC(C)C)NC(=O)c1cc(-c2c(OC)cccc2OC)n(C)n1] | 460.52 |
| 191 | 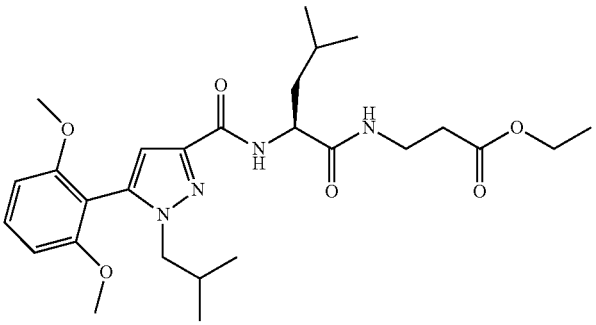 [SMILES: CCOC(=O)CCNC(=O)[C@H](CC(C)C)NC(=O)c1cc(-c2c(OC)cccc2OC)n(CC(C)C)n1] | 516.63 |
| 193 | 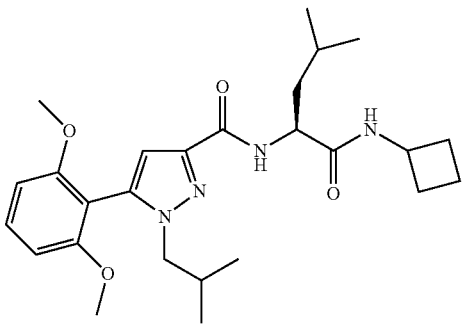 [SMILES: COc1cccc(OC)c1-c1cc(C(=O)N[C@@H](CC(C)C)C(=O)NC2CCC2)nn1CC(C)C] | 470.60 |
| 197 | 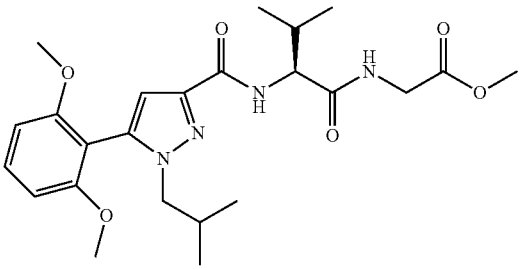 [SMILES: COC(=O)CNC(=O)[C@@H](NC(=O)c1cc(-c2c(OC)cccc2OC)n(CC(C)C)n1)C(C)C] | 474.55 |
| 198 | 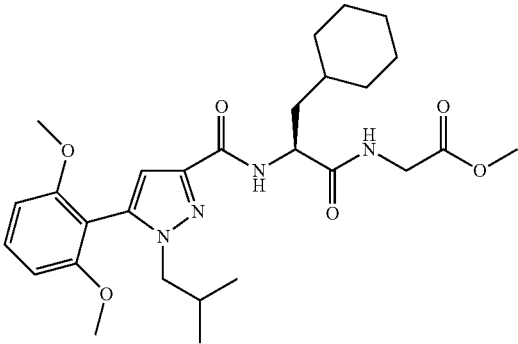 [SMILES: COC(=O)CNC(=O)[C@H](CC1CCCCC1)NC(=O)c1cc(-c2c(OC)cccc2OC)n(CC(C)C)n1] | 528.64 |

TABLE 1-continued
| CP# | STRUCTURE | M.W. |
|---|---|---|
| 204 | 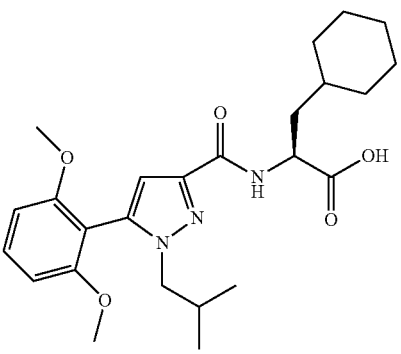 [SMILES: COc1cccc(OC)c1-c1cc(C(=O)N[C@@H](CC2CCCCC2)C(=O)O)nn1CC(C)C] | 457.56 |
| 205 | 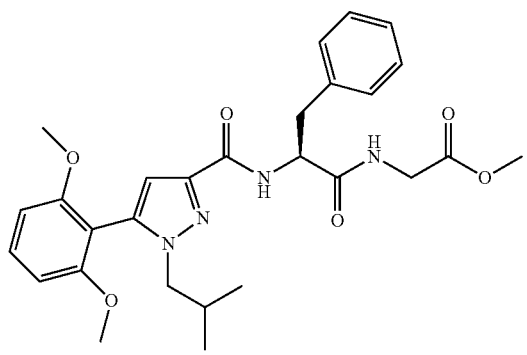 [SMILES: COC(=O)CNC(=O)[C@H](Cc1ccccc1)NC(=O)c1cc(-c2c(OC)cccc2OC)n(CC(C)C)n1] | 522.59 |
| 206 | 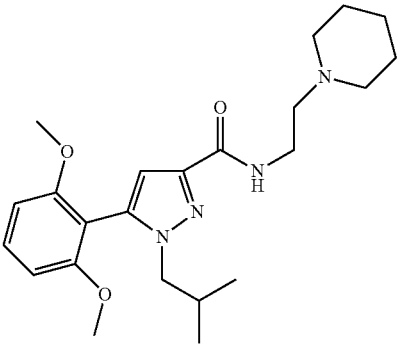 [SMILES: COc1cccc(OC)c1-c1cc(C(=O)NCCN2CCCCC2)nn1CC(C)C] | 414.54 |
| 207 | 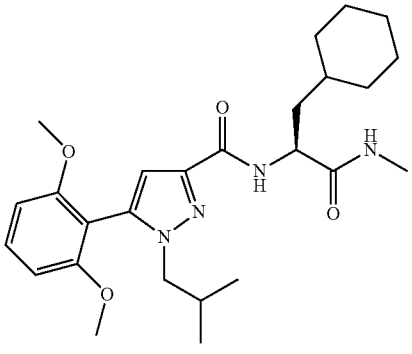 [SMILES: CNC(=O)[C@H](CC1CCCCC1)NC(=O)c1cc(-c2c(OC)cccc2OC)n(CC(C)C)n1] | 470.60 |

TABLE 1-continued

| CP# | STRUCTURE | M.W. |
|---|---|---|
| 208 | 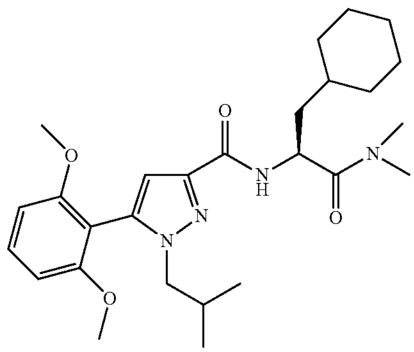 [SMILES: COc1cccc(OC)c1-c1cc(C(=O)N[C@@H](CC2CCCCC2)C(=O)N(C)C)nn1CC(C)C] | 484.63 |
| 209 | 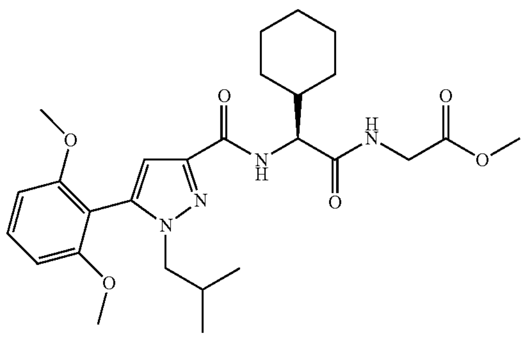 [SMILES: COC(=O)CNC(=O)[C@@H](NC(=O)c1cc(-c2c(OC)cccc2OC)n(CC(C)C)n1)C1CCCCC1] | 514.61 |
| 210 | 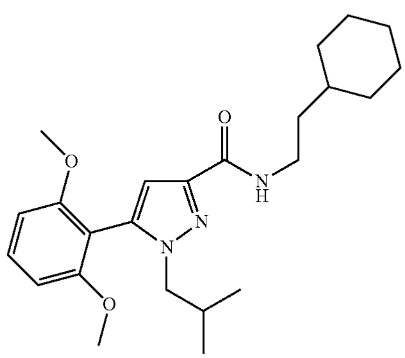 [SMILES: COc1cccc(OC)c1-c1cc(C(=O)NCCC2CCCCC2)nn1CC(C)C] | 413.55 |
| 211 | 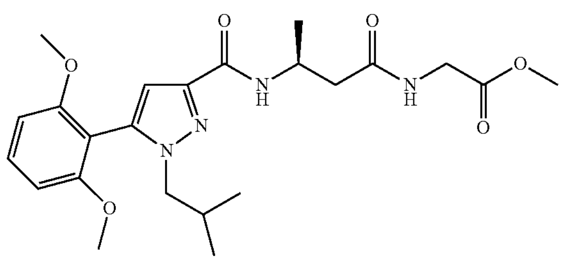 [SMILES: COC(=O)CNC(=O)C[C@H](C)NC(=O)c1cc(-c2c(OC)cccc2OC)n(CC(C)C)n1] | 460.52 |

TABLE 1-continued

| CP# | STRUCTURE | M.W. |
|---|---|---|
| 212 | 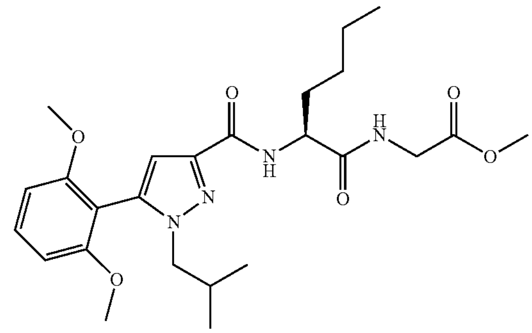 [SMILES: CCCC[C@H](NC(=O)c1cc(-c2c(OC)cccc2OC)n(CC(C)C)n1)C(=O)NCC(=O)OC] | 488.58 |
| 213 | 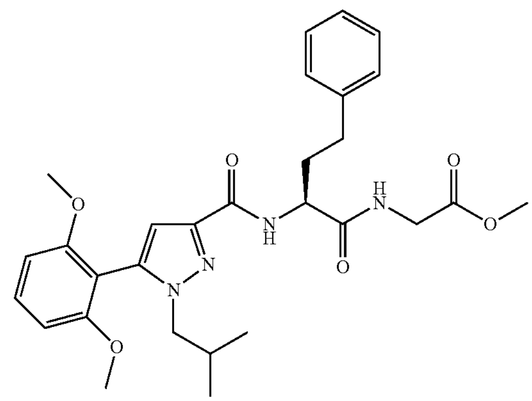 [SMILES: COC(=O)CNC(=O)[C@H](CCc1ccccc1)NC(=O)c1cc(-c2c(OC)cccc2OC)n(CC(C)C)n1] | 536.62 |
| 214 | 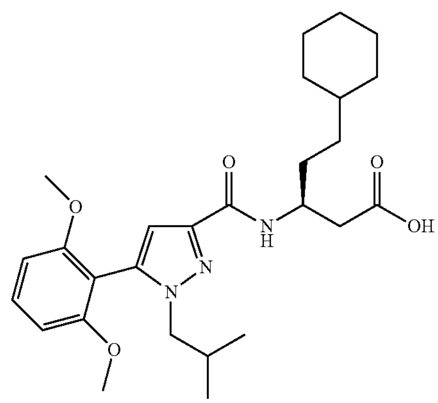 [SMILES: COc1cccc(OC)c1-c1cc(C(=O)N[C@@H](CCC2CCCCC2)CC(=O)O)nn1CC(C)C] | 485.62 |
| 215 | 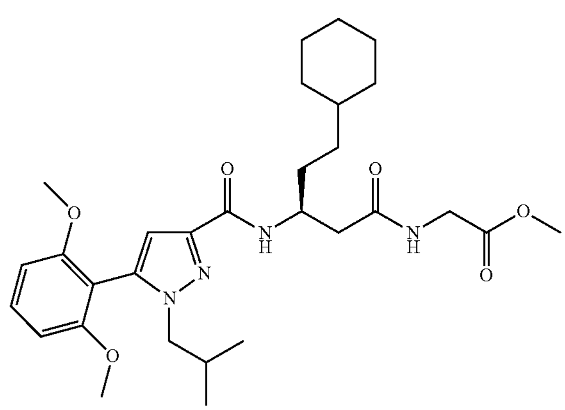 [SMILES: COC(=O)CNC(=O)C[C@H](CCC1CCCCC1)NC(=O)c1cc(-c2c(OC)cccc2OC)n(CC(C)C)n1] | 556.69 |

TABLE 1-continued
| CP# | STRUCTURE | M.W. |
|---|---|---|
| 216 | 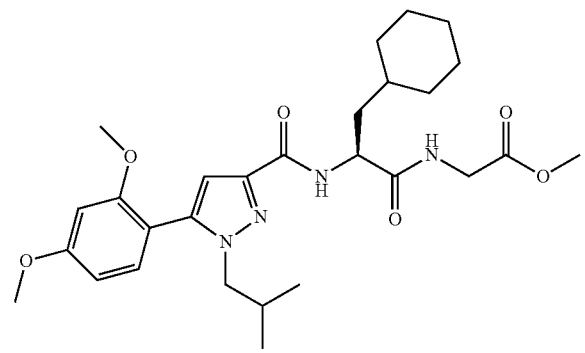 | 528.64 |
| 217 | 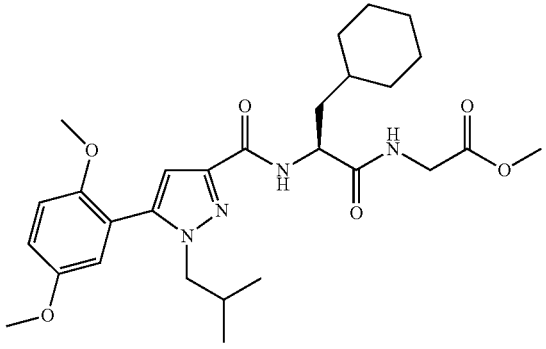 | 528.64 |
| 218 | 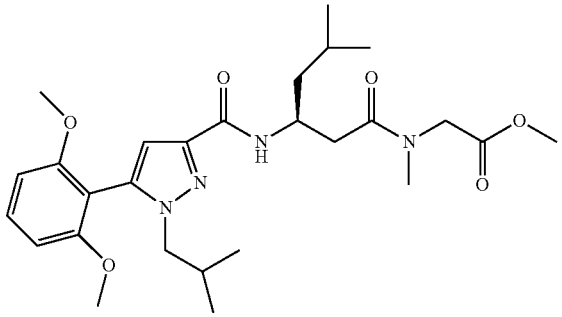 [SMILES: COC(=O)CN(C)C(=O)C[C@H](CC(C)C)NC(=O)c1cc(-c2c(OC)cccc2OC)n(CC(C)C)n1] | 516.63 |
| 219 | 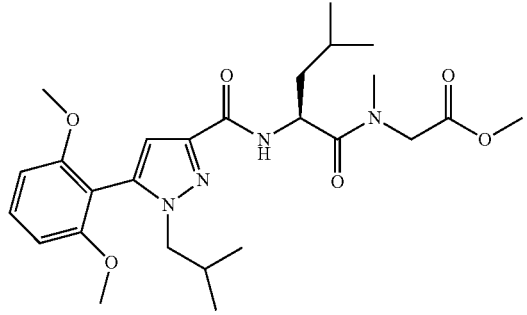 [SMILES: COC(=O)CN(C)C(=O)[C@H](CC(C)C)NC(=O)c1cc(-c2c(OC)cccc2OC)n(CC(C)C)n1] | 502.60 |

TABLE 1-continued
| CP# | STRUCTURE | M.W. |
|---|---|---|
| 220 | 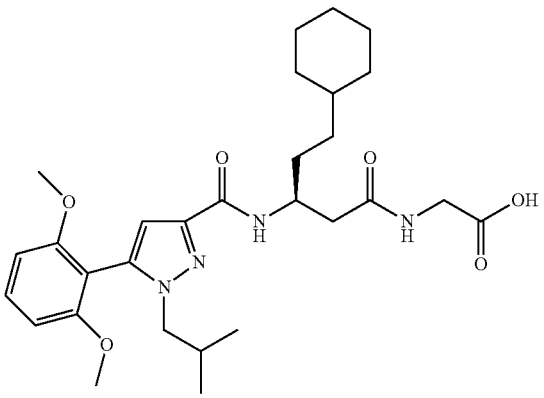 [SMILES: COc1cccc(OC)c1-c1cc(C(=O)N[C@@H](CCC2CCCCC2)CC(=O)NCC(=O)O)nn1CC(C)C] | 542.67 |
| 221 | 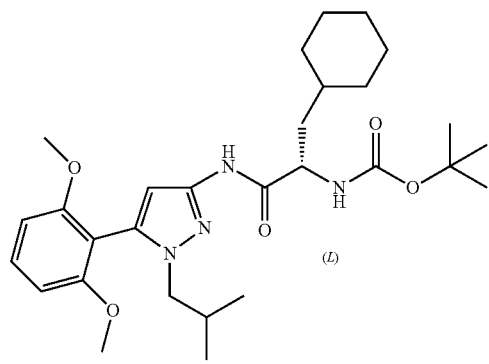 [SMILES: COc1cccc(OC)c1-c1cc(NC(=O)[C@H](CC2CCCCC2)NC(=O)OC(C)(C)C)nn1CC(C)C] (L) | 528.68 |
| 222 | 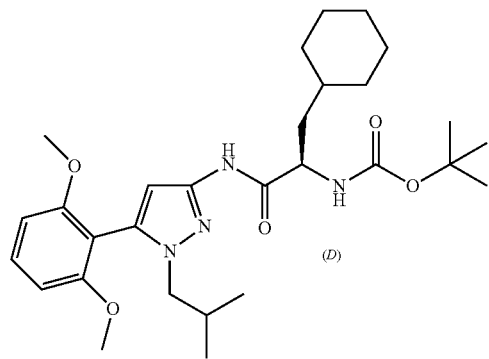 [SMILES: COc1cccc(OC)c1-c1cc(NC(=O)[C@@H](CC2CCCCC2)NC(=O)OC(C)(C)C)nn1CC(C)C ; "(D)"] (D) | 528.68 |
| 223 | 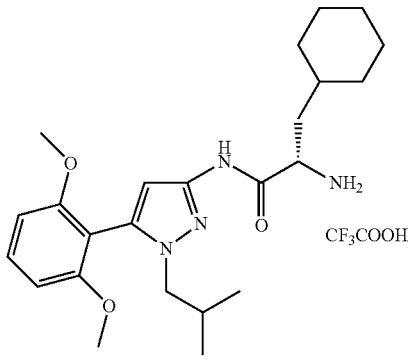 [SMILES: COc1cccc(OC)c1-c1cc(NC(=O)[C@@H](N)CC2CCCCC2)nn1CC(C)C ; "CF3COOH"] | 542.59 |

TABLE 1-continued
| CP# | STRUCTURE | M.W. |
|---|---|---|
| 224 | 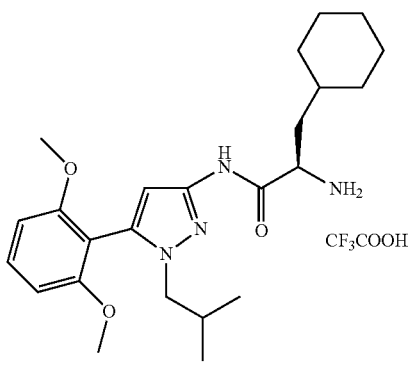 [SMILES: COc1cccc(OC)c1-c1cc(NC(=O)[C@H](N)CC2CCCCC2)nn1CC(C)C ; "CF3COOH"] | 542.59 |
| 225 | 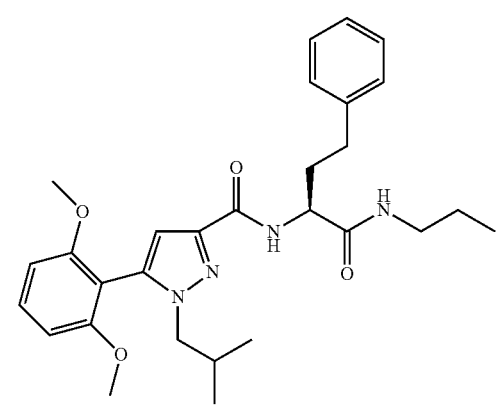 [SMILES: CCCNC(=O)[C@H](CCc1ccccc1)NC(=O)c1cc(-c2c(OC)cccc2OC)n(CC(C)C)n1] | 506.64 |
| 226 | 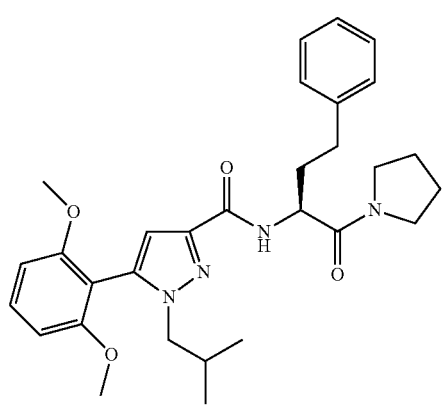 [SMILES: COc1cccc(OC)c1-c1cc(C(=O)N[C@@H](CCc2ccccc2)C(=O)N2CCCC2)nn1CC(C)C] | 518.65 |
| 227 | 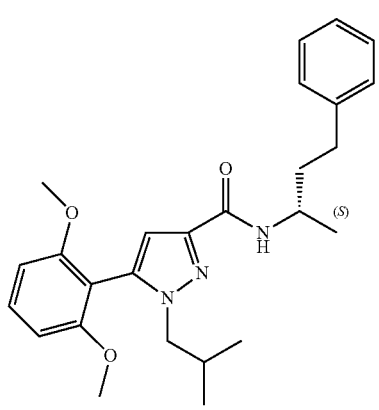 | 435.56 |

TABLE 1-continued
| CP# | STRUCTURE | M.W. |
|---|---|---|
| 228 | 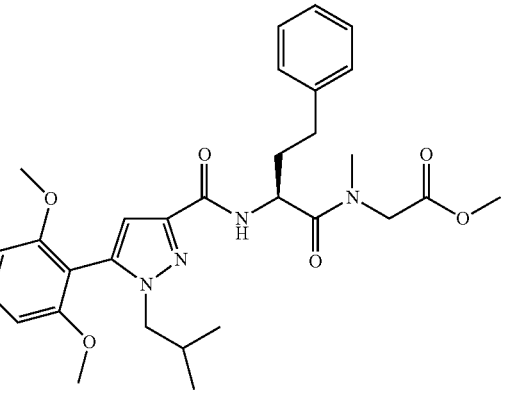 | 550.65 |
| 229 | 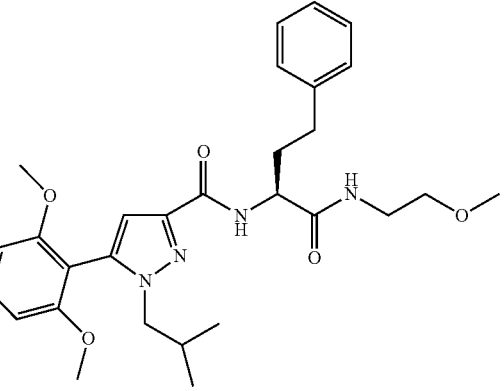 | 522.64 |
| 230 | 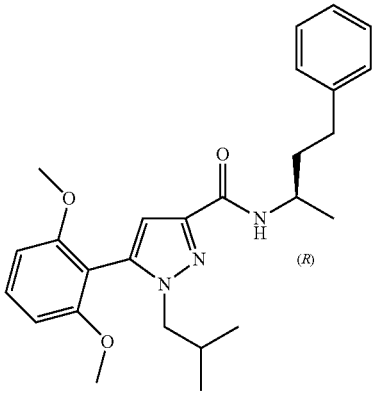 | 435.56 |
| 231 | 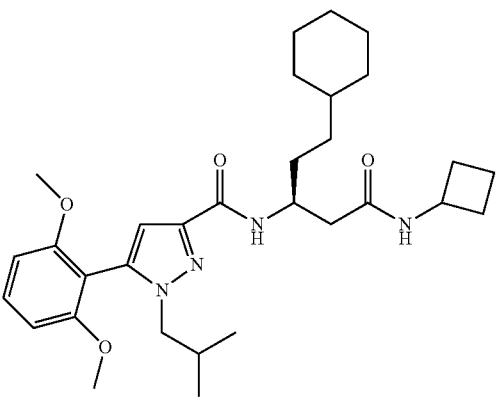 [SMILES: COc1cccc(OC)c1-c1cc(C(=O)N[C@@H](CCC2CCCCC2)CC(=O)NC2CCC2)nn1CC(C)C] | 538.72 |

TABLE 1-continued

| CP# | STRUCTURE | M.W. |
|---|---|---|
| 232 | 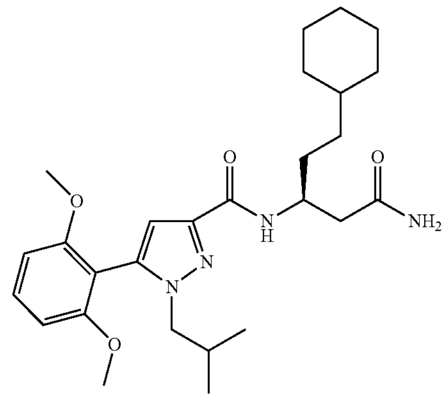 [SMILES: COc1cccc(OC)c1-c1cc(C(=O)N[C@@H](CCC2CCCCC2)CC(N)=O)nn1CC(C)C] | 484.63 |
| 233 | 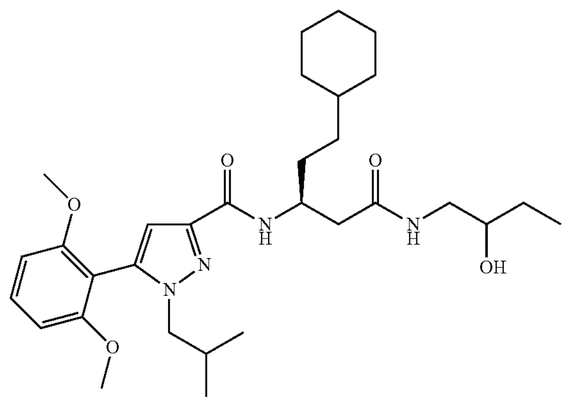 [SMILES: CCC(O)CNC(=O)C[C@H](CCC1CCCCC1)NC(=O)c1cc(-c2c(OC)cccc2OC)n(CC(C)C)n1] | 556.74 |
| 234 | 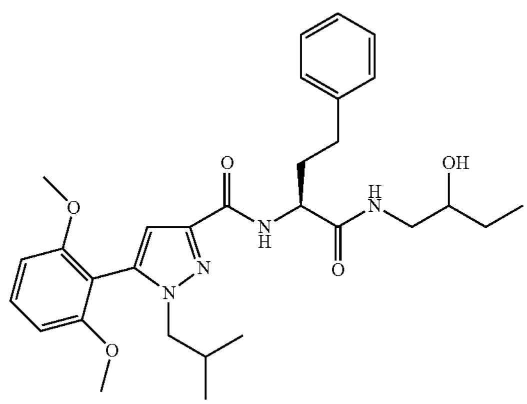 [SMILES: CCC(O)CNC(=O)[C@H](CCc1ccccc1)NC(=O)c1cc(-c2c(OC)cccc2OC)n(CC(C)C)n1] | 536.66 |
| 235 | 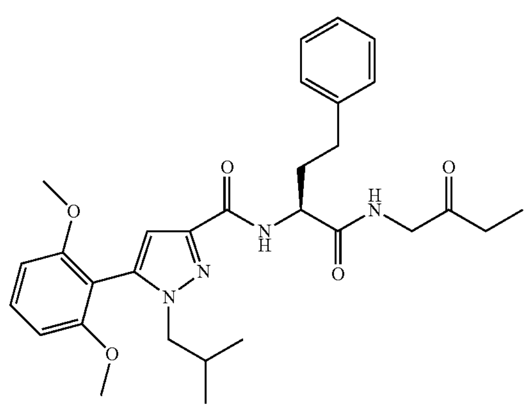 [SMILES: CCC(=O)CNC(=O)[C@H](CCc1ccccc1)NC(=O)c1cc(-c2c(OC)cccc2OC)n(CC(C)C)n1] | 534.65 |

TABLE 1-continued

| CP# | STRUCTURE | M.W. |
|---|---|---|
| 236 | 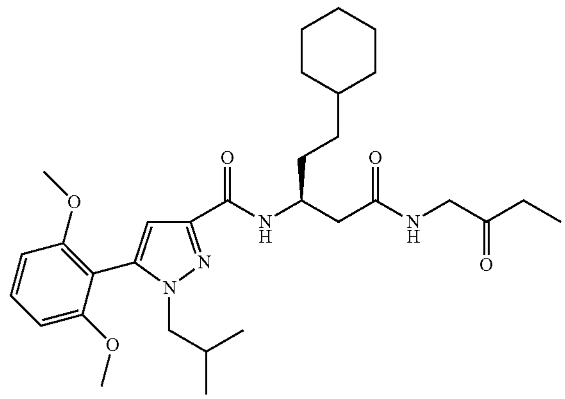 [SMILES: CCC(=O)CNC(=O)C[C@H](CCC1CCCCC1)NC(=O)c1cc(-c2c(OC)cccc2OC)n(CC(C)C)n1] | 554.72 |
| 237 | 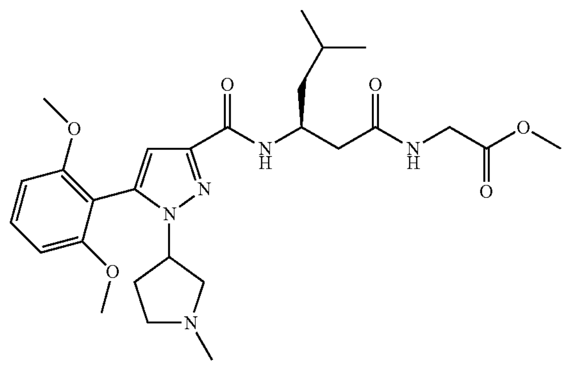 [SMILES: COC(=O)CNC(=O)C[C@H](CC(C)C)NC(=O)c1cc(-c2c(OC)cccc2OC)n(C2CCN(C)C2)n1] | 529.63 |
| 238 | 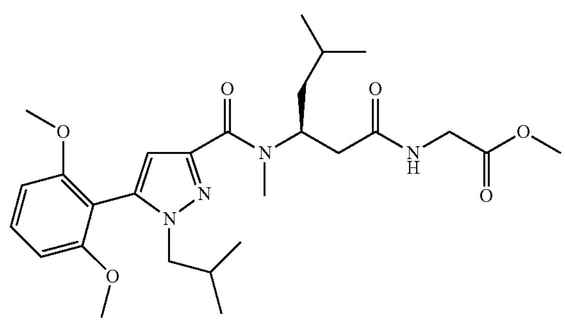 [SMILES: COC(=O)CNC(=O)C[C@H](CC(C)C)N(C)C(=O)c1cc(-c2c(OC)cccc2OC)n(CC(C)C)n1] | 516.63 |
| 239 | 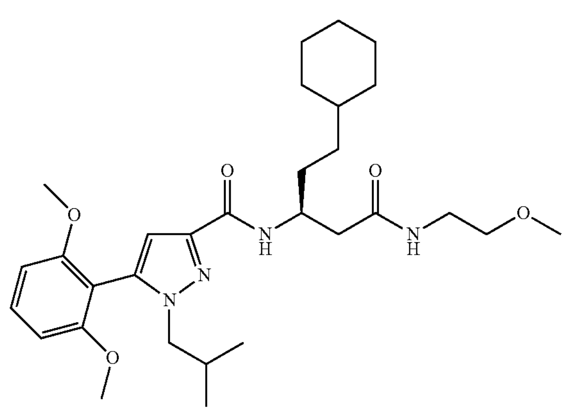 [SMILES: COCCNC(=O)C[C@H](CCC1CCCCC1)NC(=O)c1cc(-c2c(OC)cccc2OC)n(CC(C)C)n1] | 542.71 |

TABLE 1-continued

| CP# | STRUCTURE | M.W. |
|---|---|---|
| 240 | 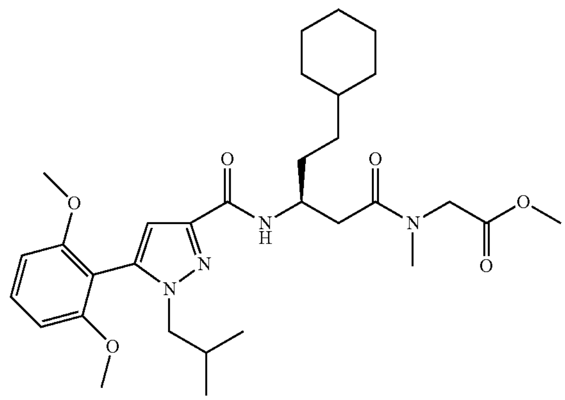 [SMILES: COC(=O)CN(C)C(=O)C[C@H](CCC1CCCCC1)NC(=O)c1cc(-c2c(OC)cccc2OC)n(CC(C)C)n1] | 570.72 |
| 241 | 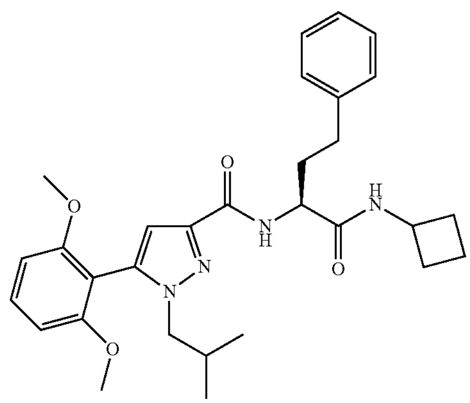 [SMILES: COc1cccc(OC)c1-c1cc(C(=O)N[C@@H](CCc2ccccc2)C(=O)NC2CCC2)nn1CC(C)C] | 518.65 |
| 242 | 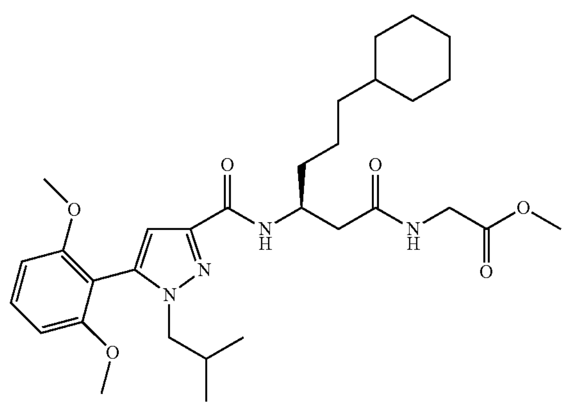 [SMILES: COC(=O)CNC(=O)C[C@H](CCCC1CCCCC1)NC(=O)c1cc(-c2c(OC)cccc2OC)n(CC(C)C)n1] | 570.72 |
| 243 | 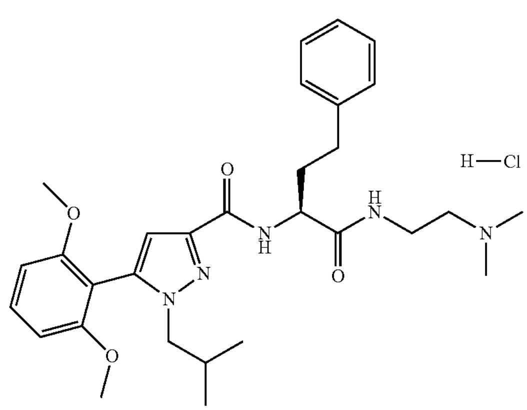 | 572.14 |

TABLE 1-continued

| CP# | STRUCTURE | M.W. |
|---|---|---|
| 244 | 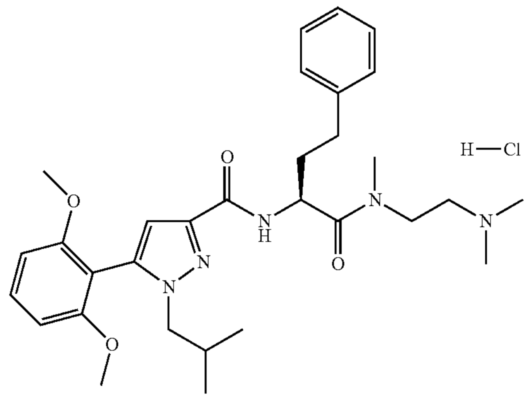 | 586.17 |
| 245 | 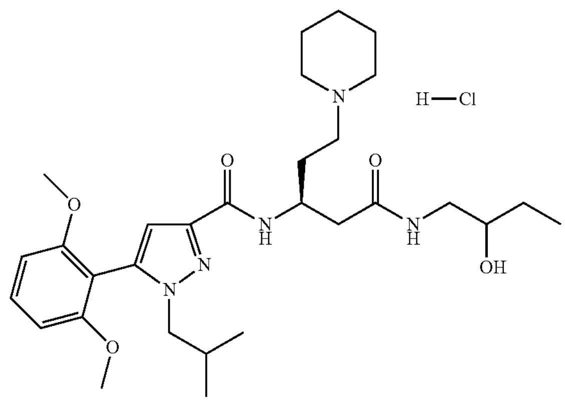 | 594.19 |
| 246 | 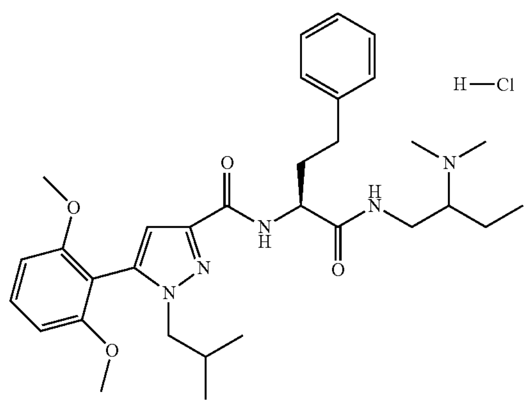 [SMILES: CCC(CNC(=O)[C@H](CCc1ccccc1)NC(=O)c1cc(-c2c(OC)cccc2OC)n(CC(C)C)n1)N(C)C ; Cl] | 600.19 |
| 247 | 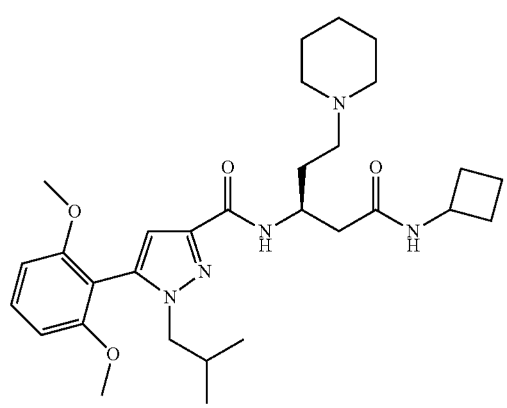 [SMILES: COc1cccc(OC)c1-c1cc(C(=O)N[C@@H](CCN2CCCCC2)CC(=O)NC2CCC2)nn1CC(C)C] | 539.71 |

TABLE 1-continued

| CP# | STRUCTURE | M.W. |
|---|---|---|
| 247 HCl | 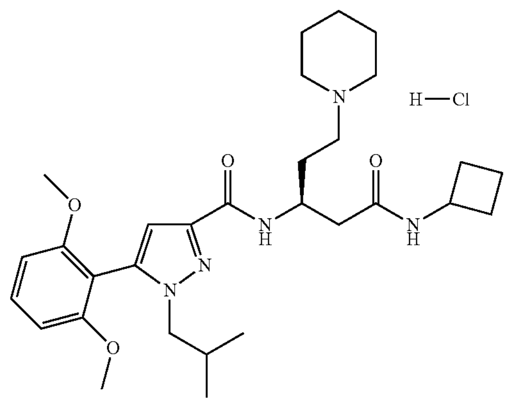 | 576.17 |
| 248 | 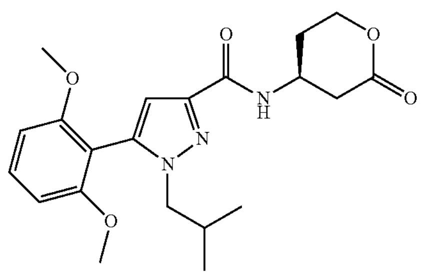 [SMILES: COc1cccc(OC)c1-c1cc(C(=O)N[C@H]2CCOC(=O)C2)nn1CC(C)C] | 401.46 |
| 249 | 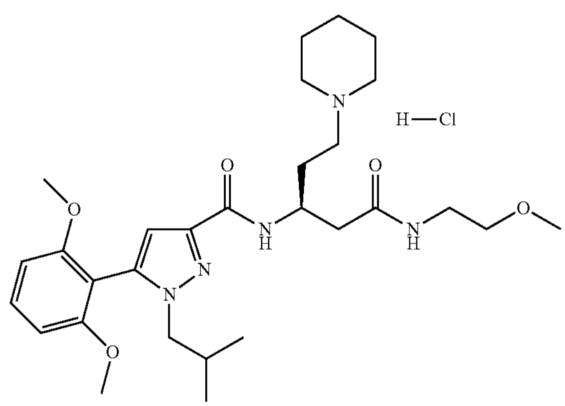 | 580.16 |
| 250 | 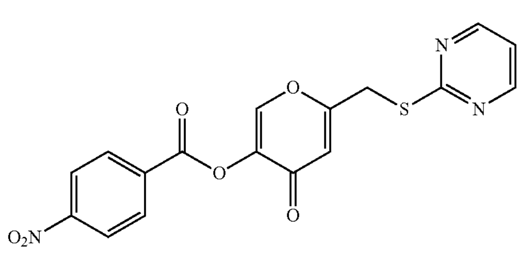 [SMILES: O=C(Oc1coc(CSc2ncccn2)cc1=O)c1ccc([N+](=O)[O-])cc1] | 385.35 |

TABLE 1-continued
| CP# | STRUCTURE | M.W. |
|---|---|---|
| 251 | 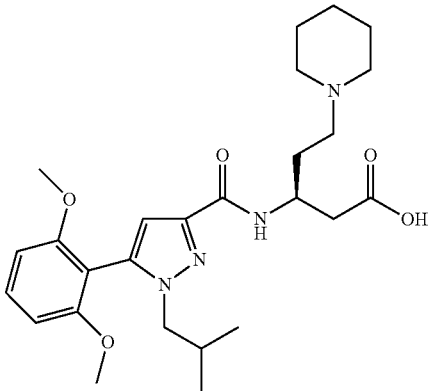 [SMILES: COc1cccc(OC)c1-c1cc(C(=O)N[C@@H](CCN2CCCCC2)CC(=O)O)nn1CC(C)C] | 486.60 |
| 252 | 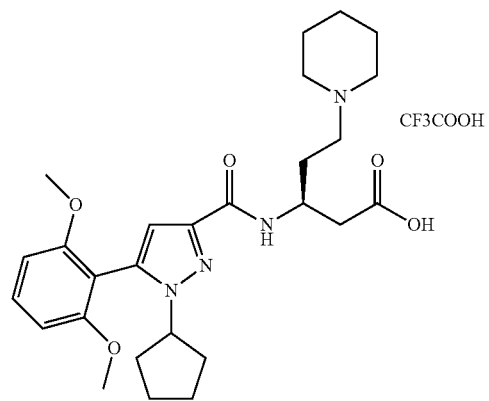 CF3COOH | 612.64 |
| 253 | 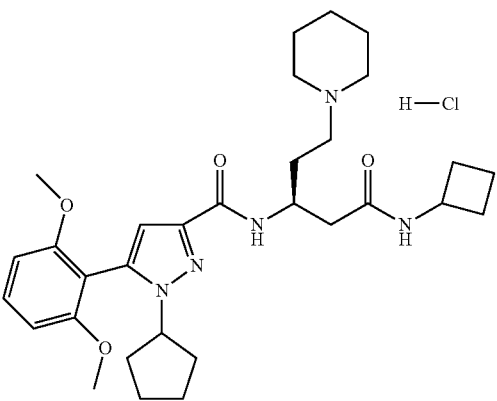 H—Cl | 587.32 |
| 254 | 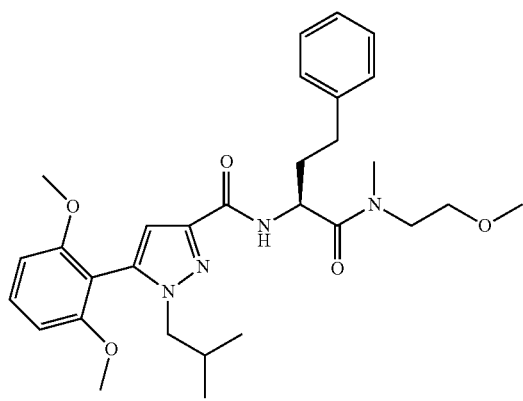 [SMILES: COCCN(C)C(=O)[C@H](CCc1ccccc1)NC(=O)c1cc(-c2c(OC)cccc2OC)n(CC(C)C)n1] | 536.66 |

TABLE 1-continued

| CP# | STRUCTURE | M.W. |
|-----|-----------|------|
| 255 | 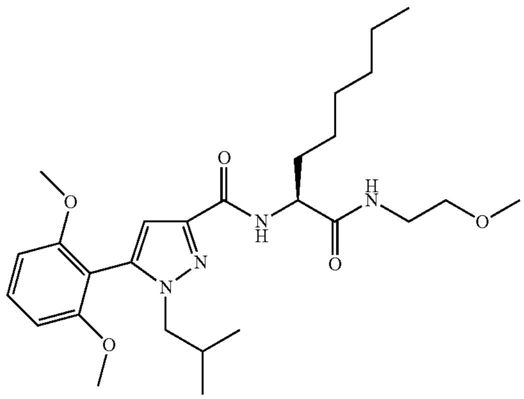 [SMILES: CCCCCC[C@H](NC(=O)c1cc(-c2c(OC)cccc2OC)n(CC(C)C)n1)C(=O)NCCOC] | 502.65 |
| 256 | 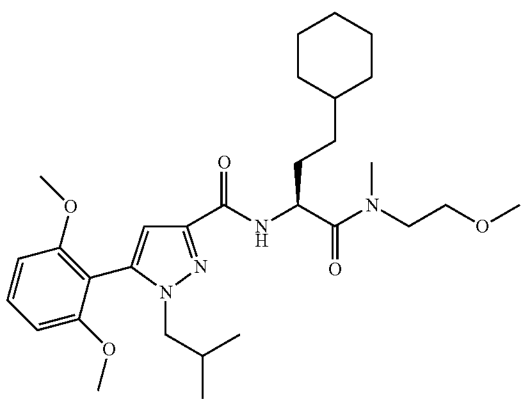 [SMILES: COCCN(C)C(=O)[C@H](CCC1CCCCC1)NC(=O)c1cc(-c2c(OC)cccc2OC)n(CC(C)C)n1] | 542.71 |
| 257 | 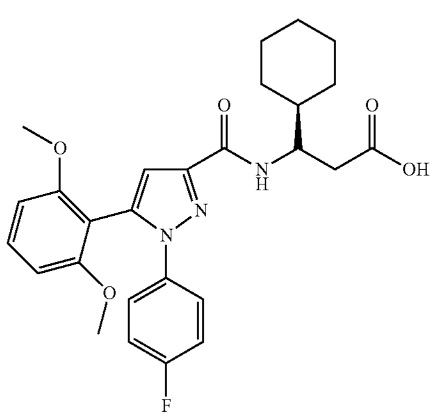 | 495.54 |

TABLE 1-continued

| CP# | STRUCTURE | M.W. |
|---|---|---|
| 258 | 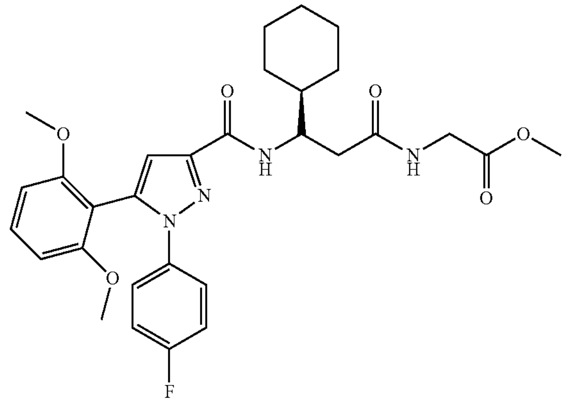 | 566.62 |
| 259 | 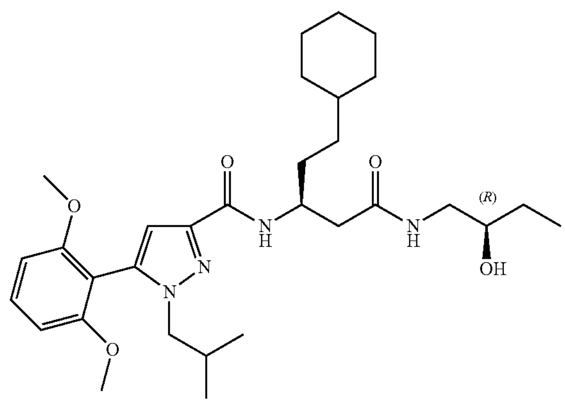 | 556.74 |
| 260 | 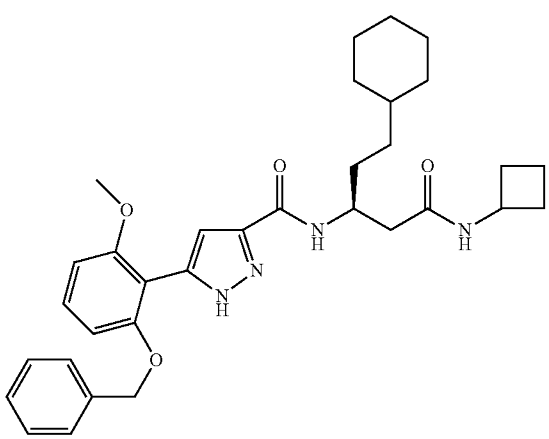 [SMILES: COc1cccc(OCc2ccccc2)c1-c1cc(C(=O)N[C@@H](CCC2CCCCC2)CC(=O)NC2CCC2)n[nH]1] | 558.71 |

TABLE 1-continued

| CP# | STRUCTURE | M.W. |
|---|---|---|
| 261 | 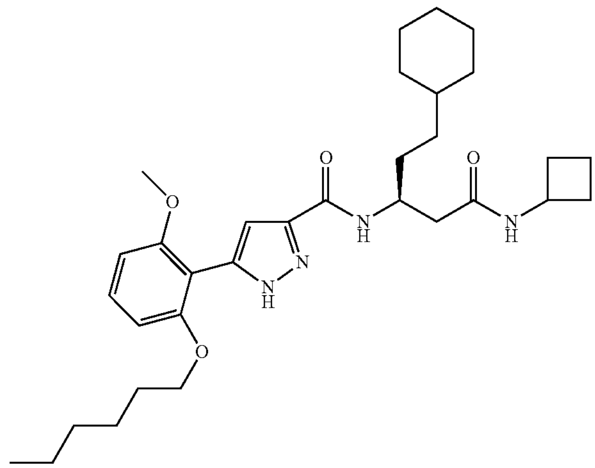 [SMILES: CCCCCCOc1cccc(OC)c1-c1cc(C(=O)N[C@@H](CCC2CCCCC2)CC(=O)NC2CCC2)n[nH]1] | 552.75 |
| 262 | 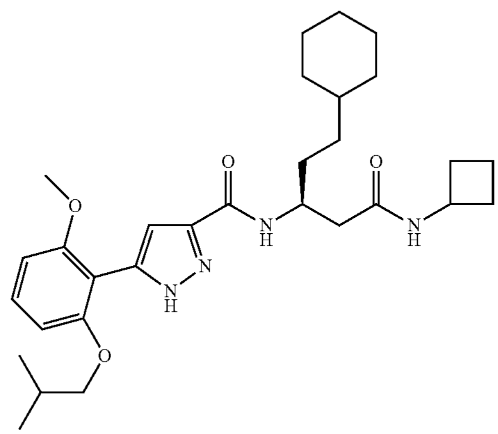 [SMILES: COc1cccc(OCC(C)C)c1-c1cc(C(=O)N[C@@H](CCC2CCCCC2)CC(=O)NC2CCC2)n[nH]1] | 524.69 |
| 263 | 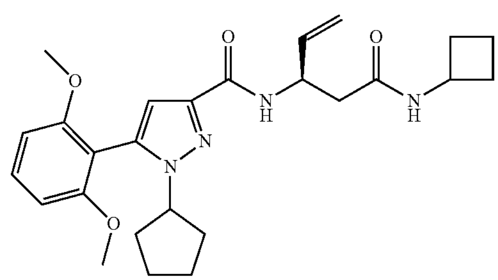 [SMILES: C=C[C@@H](CC(=O)NC1CCC1)NC(=O)c1cc(-c2c(OC)cccc2OC)n(C2CCCC2)n1] | 466.57 |
| 264 | 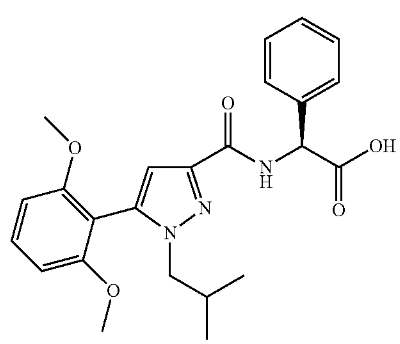 [SMILES: COc1cccc(OC)c1-c1cc(C(=O)N[C@H](C(=O)O)c2ccccc2)nn1CC(C)C] | 437.49 |

TABLE 1-continued
| CP# | STRUCTURE | M.W. |
|---|---|---|
| 265 | 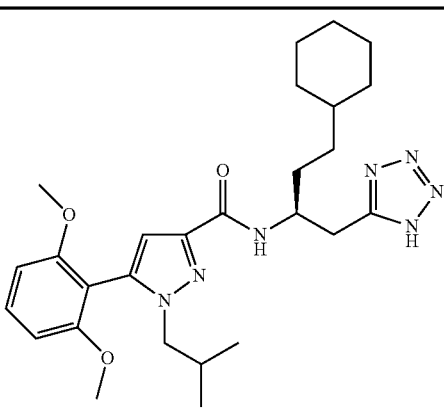 | 509.64 |
| 266 | 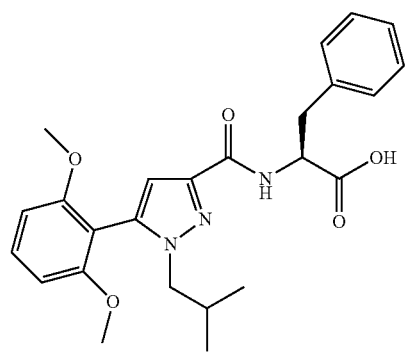 [SMILES: COc1cccc(OC)c1-c1cc(C(=O)N[C@@H](Cc2ccccc2)C(=O)O)nn1CC(C)C] | 451.51 |
| 267 | 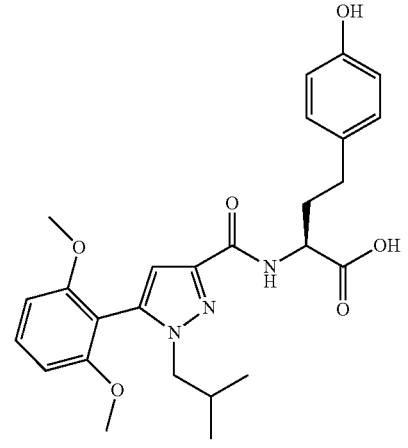 [SMILES: COc1cccc(OC)c1-c1cc(C(=O)N[C@@H](CCc2ccc(O)cc2)C(=O)O)nn1CC(C)C] | 481.54 |
| 268 | 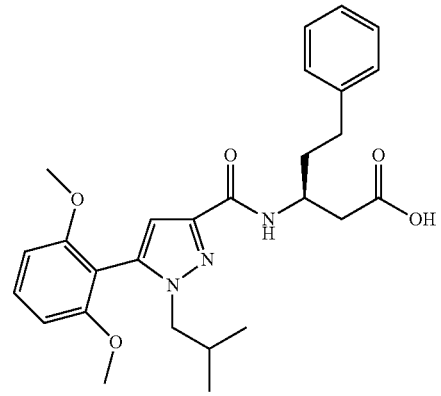 [SMILES: COc1cccc(OC)c1-c1cc(C(=O)N[C@@H](CCc2ccccc2)CC(=O)O)nn1CC(C)C] | 479.57 |

6.2. Characterization of the Apelin Agonist Activity of the Compounds

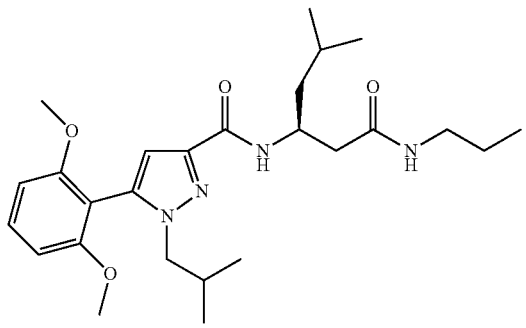 [SMILES: CCCNC(=O)C[C@H](CC(C)C)NC(=O)c1cc(-c2c(OC)cccc2OC)n(CC(C)C)n1]

The compounds above were studied for their in vitro activity as apelin agonists using the methods described by Giddings et al. Giddings et al., 2010 Int J High Thro Screen. 1:39-47, the contents of which are hereby incorporated by reference in its entirety. Using the methods described in Giddings et al. and Apelin-13 as a positive control, compounds with the following numbers had agonist activity (EC50) of <10 μM 34, 56, 65, 67, 70, 71, 77, 79, 81, 82, 86, 93, 95, 103, 118, 126, 127, 129, 130, 132, 133, 134, 136, 137, 138, 140, 141, 142, 143, 153, 154, 155, 156, 157, 161, 162, 163, 164, 167, 168, 169, 171, 172, 173, 174, 175, 176, 181, 182, 183, 184, 185, 186, 187, 188, 189, 191, 198, 204, 205, 212, 213, 214, 215, 217, 218, 219, 220, 225, 226, 228, 229, 231, 232, 233, 234, 235, 236, 238, 239, 240, 241, 242, 245, 247, 249, 251, 252, 253, 256, 257, 258, 259, 263 and 265. Based on three runs, compound no. 198 had a mean activity of 53 nM.

6.3. In vivo Blood Pressure Lowering Activity of the Compounds

The compounds were also assayed for blood pressure activity using C57BL/6 mice and the procedure described by Tatemoto et al. The novel peptide apelin lowers blood pressure via a nitric oxide-dependent mechanism. Regul Pept. 2001; 99: 87-92. The compounds were synthesized and characterized using the in vitro assays described above. Studies have been published citing reductions in blood pressure occur following peptide apelin administration. Apelin-13 was used as a positive control.

Knockout C57BL/6 mice lacking APJ have cardiovascular deficiencies. The sequence of apelin-13, the positive control compound, is identical between rodents and humans. Charo et al. Am J Physiol Heart Circ Physiol. 2009 November 297(5):H1904-13; Carpene et al. J Physiol Biochem. 2007 December; 63(4):359-73. Blood pressure measurements in these species of mice have been reported in the literature. Tiemann et al. Am J Physiol Heart Circ Physiol. 2003 February; 284(2):H464-74.

On the first day of the study, 11 animals were treated with apelin-13, 11 with vehicle alone, and 11 as sham controls. The two later groups were used to determine effects (if any) of the vehicle or injection alone on blood pressure (BP). The experiment was conducted as follows: The animals were restrained and a baseline measurement taken for 5 min. Animals were injected and immediately monitored for 15 minutes. The effect of test agents should be apparent within this time. Tatemoto et al. reported that the effects of Apelin-13 were apparent within minutes. Tatemoto et al. 2001 Immediately following dosing, blood pressure (diastolic, systolic and mean pressure) and heart rate for each animal was recorded for up to 15 minutes using a Kent Scientific CODA Non-Invasive Blood Pressure System. The apelin-13 control animals were dosed by IP injection with apelin-13 as a positive control at 10 nmol/kg (5 mL/kg dose volume) prepared in injection grade water. On day 2-5 a similar protocol was used in increasing doses. The animals were randomized daily in three groups of 11 to receive either of the two experimental compounds by IP injection. The 22 animals were randomly assigned daily to either compound treatment group were dosed with compound 143 or173 for 4 successive days by IP injection in a dose-escalation design at dose levels of 1, 3, 10 and 30 mg/kg. At the end of the 5-day dosing period, all animals were humanely euthanized.

Apelin-13 at 0.4 nmol/kg lowers blood pressure by ~10%. Table 3 below shows that the compounds described herein lower blood pressure in a dose escalating manner. At the highest doses the compounds lowered blood pressure by a mean of 9%.

TABLE 2

Dosing protocol

| | |
|---|---|
| Route of administration: | IP(intraperitoneal) |
| Dosage: | Concentration(s) 0.2, 0.6, 2 and 6 mg/mL |
| Dosing volume in ml/kg | 5 mL/kg |
| Dose(s) in mg/kg | 1, 3, 10 and 30 mg/kg |
| Vehicle | 20% dimethylacetamide in sesame oil |
| Frequency of administration: | once per day |
| Number of days of the dosing period: | 1 (baseline and positive control) + 4 (test) |

TABLE 3

In Vivo Blood Pressure Results

| | | Day 2 | 1 mg/kg | | Day 3 | 3 mg/kg | |
|---|---|---|---|---|---|---|---|
| | | Vehicle | #143 | #173 | Vehicle | #143 | #173 |
| | Group | 1 | 2 | 3 | 1 | 2 | 3 |
| Diastolic | Baseline | 130 | 127 | 114 | 120 | 132 | 127 |
| | Postdose | 123 | 129 | 118 | 126 | 127 | 129 |
| % | | −5 | 1 | 3 | 5 | −4 | 2 |
| Systolic | Baseline | 163 | 161 | 151 | 155 | 163 | 156 |
| | Postdose | 155 | 160 | 149 | 156 | 158 | 159 |
| % | | −5 | −1 | −1 | 0 | −3 | 2 |
| Mean | Baseline | 141 | 138 | 126 | 132 | 142 | 136 |
| | Postdose | 134 | 139 | 128 | 136 | 137 | 139 |
| % | | −5 | 0 | 1 | 3 | −4 | 2 |
| HR | Baseline | 729 | 706 | 681 | 685 | 665 | 661 |
| | Postdose | 718 | 727 | 716 | 736 | 763 | 738 |
| % | | −2 | 3 | 5 | 8 | 15 | 12 |

| | | Day 4 | 10 mg/Kg | | Day 5 | 30 mg/Kg | |
|---|---|---|---|---|---|---|---|
| | | Vehicle | #143 | #173 | Vehicle | #143 | #173 |
| | Group | 1 | 2 | 3 | 1 | 2 | 3 |
| Diastolic | Baseline | 119.5 | 131.3 | 114.9 | 125.4 | 130 | 122.2 |
| | Postdose | 126.3 | 124.2 | 119.3 | 125.4 | 118.8 | 117.5 |
| % | | 6 | −5 | 4 | 0 | −9 | −4 |
| Systolic | Baseline | 150 | 167.5 | 150.5 | 156.3 | 164.1 | 155.7 |
| | Postdose | 156.6 | 157.1 | 150 | 154.7 | 150.2 | 148.2 |
| % | | 4 | −6 | 0 | −1 | −8 | −5 |
| Mean | Baseline | 129.3 | 143 | 126.3 | 135.4 | 141 | 133 |
| | Postdose | 136.1 | 134.8 | 129.2 | 134.8 | 128.9 | 127.4 |
| % | | 5 | −6 | 2 | 0 | −9 | −4 |
| HR | Baseline | 740.4 | 669.3 | 682.5 | 686.3 | 733.9 | 701.1 |
| | Postdose | 761.6 | 745 | 749.4 | 735.1 | 722.8 | 721.7 |
| % | | 3 | 11 | 10 | 7 | −2 | 3 |

It is to be understood that, while the disclosure has been described in conjunction with the detailed description, thereof, the foregoing description is intended to illustrate and not limit the scope of the disclosure. Other aspects, advantages, and modifications of the disclosure are within the scope of the claims set forth below. All publications, patents, and patent applications cited in this specification are herein incorporated by reference as if each individual publication or patent application was specifically and individually indicated to be incorporated by reference.

We claim:
1. A compound represented by the Formula I:

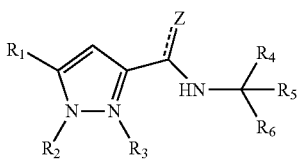

or a pharmaceutically acceptable salt, a prodrug, or a salt of a prodrug thereof, wherein
$R_1$ is represented by the formula:

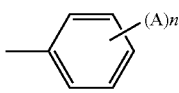

each A is independently $C_{1-8}$ alkoxy, $C_{1-8}$ alkoxy-$C_{5-12}$ aryl, halogen, or $O(CH_2)_xCO_2R_7$;
$R_7$ and $R_8$
$R_7$ and $R_8$ are independently optionally substituted $C_{5-12}$ aryl, optionally substituted $C_{1-8}$ alkyl, optionally substituted $C_{3-8}$ cycloalkyl, hydroxyl, or H; or
$R_7$ and $R_8$ together make an optionally substituted 3-8 member ring, which may be substituted with one or more heteroatoms selected from O, N, or S;
n is 1, 2, 3, or 4;
wherein the first A is substituted ortho to the point of attachment from the depicted pyrazole;
each x is independently 1, 2, 3, or 4;
$R_2$ is substituted $C_{5-12}$ aryl, optionally substituted $C_{1-8}$ alkyl, optionally substituted $C_{2-8}$ alkyl-substituted $C_{5-12}$ aryl, optionally substituted $C_{2-8}$ alkyl-optionally substituted $C_{3-8}$ cycloalkyl, or optionally substituted $C_{3-8}$ cycloalkyl;
$R_3$ is absent;
$R_4$ is $C_{2-8}$ alkyl, $C_{2-8}$ alkenyl, $C_{3-8}$ cycloalkyl, $C_{2-8}$ alkyl-$C_{5-12}$ aryl, $C_{1-8}$ alkyl-$C_{3-8}$ cycloalkyl, $C_{1-8}$ alkyl-5 to 7 membered heteroaryl, $(CH_2)_xNR_7R_8$, or $C_{1-8}$ alkyl-substituted $C_{5-12}$ aryl where the $C_{5-12}$ aryl is substituted either meta or para from the $C_{1-8}$ alkylene linker;
$R_5$ is optionally substituted $C_{1-8}$ alkyl, $C_{5-12}$ aryl, $C_{1-8}$ alkyl-$C_{5-12}$ aryl, $C_{1-8}$ alkyl-$C_{3-8}$ cycloalkyl, $C_{1-8}$ alkyl-5 to 7 membered heteroaryl, $C_{3-8}$ cycloalkyl, $(CH_2)_xNR_7R_8$, $(CH_2)_xNHCOR_7$, $(CH_2)_xNHCO_2R_7$, $(CH_2)_xCONR_7R_8$, $(CH_2)_xCONR_7(CH_2)_yCO_2R_9$, $(CH_2)_xCONR_7(CH_2)_yCONR_7R_8$, $(CH_2)_xCONR_7(CH_2)_yR_9$, $(CH_2)_xCOR_7$, $(CH_2)_xCO_2R_7$, $CHR_7COR_9$, $CHR_7CONHCHR_8COR_9$, or $CONR_7R_8$;
$R_6$ is H;
or $R_4$ and $R_5$ together make a 4-8 member ring which may be substituted with one or more heteroatoms selected from O, N, or S, and may be further substituted with one or more of $C_{1-8}$ alkoxy, $C_{1-8}$ alkyl, H, isoxazolyl, or hydroxyl;
$R_9$ is $C_{1-8}$ alkoxy, $C_{1-8}$ alkyl, H, isoxazolyl, or hydroxyl;
each y is independently 1, 2, or 3;
and Z is =O, where the depicted dashed line to Z is a double bond,
wherein substituted refers to substitution with one or more of $C_{1-8}$ alkyl, halogen, $C_{1-8}$ haloalkyl, $C_{1-8}$ alkoxy, hydroxyl, carbonyl, $CO_2R_9$, $C_{5-12}$ aryl, 5 to 7 membered heteroaryl, $C_{3-8}$ cycloalkyl, $C_{1-8}$ alkyl-$C_{5-12}$ aryl, $C_{1-8}$ alkyl-5 to 7 membered heteroaryl, $C_{1-8}$ alkyl-$C_{3-8}$ cycloalkyl, $NO_2$, $N_3$, $NH_2$, $N(CH_3)_2$, $SO_{(1-3)}H$, or SH.

2. The compound of claim 1, wherein
n is 4;
each A is independently $C_{1-4}$ alkoxy, $C_{1-4}$ alkoxy-$C_{5-12}$ aryl, or halogen;
$R_2$ is $C_{5-12}$ aryl, $C_{1-8}$ alkyl, or $C_{3-8}$ cycloalkyl;
$R_4$ is $C_{2-8}$ alkyl, $C_{2-8}$ alkyl-$C_{5-12}$ aryl, $C_{1-8}$ alkyl-$C_{3-8}$ cycloalkyl, or $(CH_2)_xNR_7R_8$;
$R_5$ is $(CH_2)_xNHCOR_7$, $(CH_2)_xNHCO_2R_7$, $(CH_2)_xCONR_7R_8$, $(CH_2)_xCONR_7(CH_2)_yCO_2R_9$, $(CH_2)_xCONR_7(CH_2)_yCONR_7R_8$, $(CH_2)_xCONR_7(CH_2)_yR_9$, $(CH_2)_xCOR_7$, $(CH_2)_xCO_2R_7$, $CHR_7COR_9$, $CHR_7CONHCHR_8COR_9$, or $CONR_7R_8$;
$R_6$ is H;
$R_9$ is $C_{1-8}$ alkyl, H, or an oxazole;
each x independently is 1, 2, 3, or 4;
each y independently is 1, 2, or 3; and
Z is =O.

3. The compound of claim 2, wherein
n is 4;
each A is independently $C_1$ alkoxy, $C_1$ alkoxy-$C_{5-12}$ aryl, or halogen;
$R_2$ is $C_{5-12}$ aryl, $C_4$ alkyl or $C_6$ cycloalkyl;
$R_4$ is $C_{2-4}$ alkyl, $C_{2-8}$ alkyl($C_{5-12}$ aryl), $C_{1-8}$ alkyl-$C_{3-8}$ cycloalkyl, or $(CH_2)_xNR_7R_8$;
$R_5$ is $(CH_2)_xNHCOR_7$, $(CH_2)_xNHCO_2R_7$, $(CH_2)_xCONR_7R_8$, $(CH_2)_xCONR_7(CH_2)_yCO_2R_9$, $(CH_2)_xCONR_7(CH_2)_yCONR_7R_8$, $(CH_2)_xCONR_7(CH_2)_yR_9$, $(CH_2)_xCOR_7$, $(CH_2)_xCO_2R_7$, $CHR_7COR_9$, $CHR_7CONHCHR_8COR_9$, or $CONR_7R_8$;
$R_6$ is H;
$R_8$ is $C_{1-4}$ alkyl or H;
$R_9$ is $C_{1-8}$ alkyl, H, or an oxazole;
each x independently is 1, 2, 3, or 4;
each y independently is 1, 2, or 3; and
Z is =O.

4. The compound of claim 3, wherein
n is 4;
each A is independently $C_1$ alkoxy, $C_1$ alkoxy-$C_{5-12}$ aryl, or fluorine;
$R_2$ is $C_{5-12}$ aryl, $C_4$ alkyl or $C_6$ cycloalkyl;
$R_4$ is $C_{2-4}$ alkyl, $C_{2-4}$ alkyl-$C_{5-12}$ aryl, $C_{1-4}$ alkyl-$C_{5-8}$ cycloalkyl, or $(CH_2)_xNR_7R_8$;
$R_5$ is $(CH_2)_xNHCOR_7$, $(CH_2)_xNHCO_2R_7$, $(CH_2)_xCONR_7R_8$, $(CH_2)_xCONR_7(CH_2)_yCO_2R_9$, $(CH_2)_xCONR_7(CH_2)_yCONR_7R_8$, $(CH_2)_xCONR_7(CH_2)_yR_9$, $(CH_2)_xCOR_7$, $(CH_2)_xCO_2R_7$, $CHR_7COR_9$, $CHR_7CONHCHR_8COR_9$, or $CONR_7R_8$;
$R_6$ is H;
$R_8$ is $C_{1-4}$ alkyl or H;
$R_9$ is $C_{1-8}$ alkyl, H, or an oxazole;
each x independently is 1, 2, 3, or 4; and
each y independently is 1, 2, or 3.

5. The compound of claim 4, wherein
n is 4;
each A is independently $C_1$ alkoxy, $C_1$ alkoxy-$C_{5-12}$ aryl, or fluorine;
$R_2$ is $C_{5-12}$ aryl, $C_4$ alkyl, or $C_6$ cycloalkyl;
$R_4$ is $C_{2-4}$ alkyl, $C_{2-4}$ alkyl($C_{5-12}$ aryl), $C_{1-4}$ alkyl-$C_{5-8}$ cycloalkyl, or $(CH_2)_xNR_7R_8$;
$R_5$ is $(CH_2)_xNHCOR_7$, $(CH_2)_xNHCO_2R_7$, $(CH_2)_xCONR_7R_8$, $(CH_2)_xCONR_7(CH_2)_yCO_2R_9$, $(CH_2)_xCONR_7(CH_2)_yCONR_7R_8$, $(CH_2)_xCONR_7(CH_2)_yR_9$, $(CH_2)_xCOR_7$, $(CH_2)_xCO_2R_7$, $CHR_7COR_9$, $CHR_7CONHCHR_8COR_9$, or $CONR_7R_8$;
$R_6$ is H;
$R_8$ is H;
$R_9$ is $C_{1-8}$ alkyl, H, or an oxazole;
each x independently is 1, 2, 3, or 4; and
each y independently is 1, 2, or 3.

6. The compound of claim 1, wherein
n is 2;
each A is independently $C_{1-4}$ alkoxy, or $C_{1-4}$ alkoxy-$C_{5-12}$ aryl;
$R_2$ is $C_{5-12}$ aryl, $C_{1-8}$ alkyl or $C_{3-8}$ cycloalkyl;
$R_4$ is $C_{2-4}$ alkyl, $C_{2-8}$ alkyl($C_{5-12}$ aryl), $C_{1-8}$ alkyl-$C_{3-8}$ cycloalkyl, or $(CH_2)_xNR_7R_8$;
$R_5$ is $(CH_2)_xNHCOR_7$, $(CH_2)_xNHCO_2R_7$, $(CH_2)_xCONR_7R_8$, $(CH_2)_xCONR_7(CH_2)_yCO_2R_9$, $(CH_2)_xCONR_7(CH_2)_yCONR_7R_8$, $(CH_2)_xCONR_7(CH_2)_yR_9$, $(CH_2)_xCOR_7$, $(CH_2)_xCO_2R_7$, $CHR_7COR_9$, $CHR_7CONHCHR_8COR_9$, or $CONR_7R_8$;
$R_6$ is H;
$R_9$ is $C_{1-8}$ alkyl, H, or an oxazole;
each x independently is 1, 2, 3, or 4;
each y independently is 1, 2, or 3; and
Z is =O.

7. The compound of claim 6, wherein
n is 2;
each A is independently $C_1$ alkoxy, or $C_1$ alkoxy-$C_{5-12}$ aryl;
$R_2$ is $C_{5-12}$ aryl, $C_4$ alkyl or $C_6$ cycloalkyl;
$R_4$ is $C_{2-8}$ alkyl, $C_{2-8}$ alkyl-$C_{5-12}$ aryl, $C_{1-8}$ alkyl-$C_{3-8}$ cycloalkyl, or $(CH_2)_xNR_7R_8$;
$R_5$ is $(CH_2)_xNHCOR_7$, $(CH_2)_xNHCO_2R_7$, $(CH_2)_xCONR_7R_8$, $(CH_2)_xCONR_7(CH_2)_yCO_2R_9$, $(CH_2)_xCONR_7(CH_2)_yCONR_7R_8$, $(CH_2)_xCONR_7(CH_2)_yR_9$, $(CH_2)_xCOR_7$, $(CH_2)_xCO_2R_7$, $CHR_7COR_9$, $CHR_7CONHCHR_8COR_9$, or $CONR_7R_8$;
$R_6$ is H;
$R_8$ is $C_{1-4}$ alkyl or H;
$R_9$ is $C_{1-8}$ alkyl, H, or an oxazole;
each x independently is 1, 2, 3, or 4;
each y independently is 1, 2, or 3; and
Z is =O.

8. The compound of claim 7, wherein
n is 2;
each A is independently $C_1$ alkoxy, or $C_1$ alkoxy-$C_{5-12}$ aryl;
$R_2$ is $C_{5-12}$ aryl, $C_4$ alkyl or $C_6$ cycloalkyl;
$R_4$ is $C_{2-4}$ alkyl, $C_{2-4}$ alkyl-$C_{5-12}$ aryl, $C_{1-4}$ alkyl-$C_{5-8}$ cycloalkyl, or $(CH_2)_xNR_7R_8$;
$R_5$ is $(CH_2)_xNHCOR_7$, $(CH_2)_xNHCO_2R_7$, $(CH_2)_xCONR_7R_8$, $(CH_2)_xCONR_7(CH_2)_yCO_2R_9$, $(CH_2)_xCONR_7(CH_2)_yCONR_7R_8$, $(CH_2)_xCONR_7(CH_2)_yR_9$, $(CH_2)_xCOR_7$, $(CH_2)_xCO_2R_7$, $CHR_7COR_9$, $CHR_7CONHCHR_8COR_9$, or $CONR_7R_8$;
$R_6$ is H;
$R_8$ is $C_{1-4}$ alkyl or H;
$R_9$ is $C_{1-8}$ alkyl, H, or an oxazole;
each x independently is 1, 2, 3, or 4;
each y independently is 1, 2, or 3; and
Z is =O.

9. The compound of claim 8, wherein
n is 2;
each A is independently $C_1$ alkoxy, or $C_1$ alkoxy-$C_{5-12}$ aryl;
$R_2$ is $C_{5-12}$ aryl, $C_4$ alkyl or $C_6$ cycloalkyl;
$R_4$ is $C_{2-4}$ alkyl, $C_{2-4}$ alkyl-$C_{5-12}$ aryl, $C_{1-4}$ alkyl-$C_{5-8}$ cycloalkyl, or $(CH_2)_xNR_7R_8$;
$R_5$ is $(CH_2)_xNHCOR_7$, $(CH_2)_xNHCO_2R_7$, $(CH_2)_xCONR_7R_8$, $(CH_2)_xCONR_7(CH_2)_yCO_2R_9$, $(CH_2)_xCONR_7(CH_2)_yCONR_7R_8$, $(CH_2)_xCONR_7(CH_2)_yR_9$, $(CH_2)_xCOR_7$, $(CH_2)_xCO_2R_7$, $CHR_7COR_9$, $CHR_7CONHCHR_8COR_9$, or $CONR_7R_8$;
$R_6$ is H;
$R_8$ is H;
$R_9$ is $C_{1-8}$ alkyl, H, or an oxazole;
each x independently is 1, 2, 3, or 4;
each y independently is 1, 2, or 3; and
Z is =O.

10. The compound of claim 1, wherein $R_5$ is $C_{1-8}$ alkyl-5 to 7membered heteroaryl, and the $C_{1-8}$ alkyl-5 to 7 membered heteroaryl is a $C_{1-8}$ alkyl-tetrazole.

11. A compound selected from:
(2S)-2-{[5-(2,6-dimethoxyphenyl)-1-(4-fluorophenyl)-1H-pyrazol-3-yl]formamido}-4-methylpentanoic acid;
(3S)-3-{[5-(2,6-dimethoxyphenyl)-1-(4-fluorophenyl)-1H-pyrazol-3-yl]formamido}-5-methylhexanoic acid;
(3S)-3-{[5-(2,6-dimethoxyphenyl)-1-(4-fluorophenyl)-1H-pyrazol-3-yl]formamido}-5-methylhexanamide;
(3R)-3-{[5-(2,6-dimethoxyphenyl)-1-(4-fluorophenyl)-1H-pyrazol-3-yl]formamido}-5-methylhexanoic acid;
2-(2-cyclohexyl-2-{[5-(2,6-dimethoxyphenyl)-1-(4-fluorophenyl)-1H-pyrazol-3-yl]formamido}acetamido) acetic acid;
2-[(3S)-3-{[5-(2,6-dimethoxyphenyl)-1-(4-fluorophenyl)-1H-pyrazol-3-yl]formamido}-5-methylhexanamido]acetic acid;
(3S)-3-{[1-cyclohexyl-5-(2,6-dimethoxyphenyl)-1H-pyrazol-3-yl]formamido}-5-methylhexanoic acid;
2-[(3S)-3-{[1-cyclohexyl-5-(2,6-dimethoxyphenyl)-1H-pyrazol-3-yl]formamido}-5-methylhexanamido]acetic acid;
(3S)-3-({5-[2-(benzyloxy)-6-methoxyphenyl]-1-(4-fluorophenyl)-1H-pyrazol-3-yl}formamido)-5-methylhexanoic acid;
(3S)-3-{[1-(4-fluorophenyl)-5-[2-methoxy-6-(2-methoxy-2-oxoethoxy)phenyl]-1H-pyrazol-3-yl]formamido}-5-methylhexanoic acid;
2-cyclohexyl-2-{[1-cyclohexyl-5-(2,6-dimethoxyphenyl)-1H-pyrazol-3-yl]formamido}acetic acid;
(3S)-3-{[1-(cyclohexylmethyl)-5-(2,6-dimethoxyphenyl)-1H-pyrazol-3-yl]formamido}-5-methylhexanoic acid;
methyl 2-[(3S)-3-{[1-cyclohexyl-5-(2,6-dimethoxyphenyl)-1H-pyrazol-3-yl]formamido}-5-methylhexanamido]acetate;
(3S)-3-{[5-(2,6-dimethoxyphenyl)-1-(2-methylpropyl)-1H-pyrazol-3-yl]formamido}-5-methylhexanoic acid;
(3S)-3-({5-[2-(benzyloxy)-6-methoxyphenyl]-1-cyclohexyl-1H-pyrazol-3-yl}formamido)-5-methylhexanoic acid;
methyl 2[(3S)-3-({5-[2(benzyloxy)-6-methoxyphenyl]-1-cyclohexyl-1H-pyrazol-3-yl}formamido)-5-methylhexanamido]acetate;

2-[(3S)-3-({5-[2(benzyloxy)-6-methoxyphenyl]-1-cyclohexyl-1H-pyrazol-3-yl}formamido)-5-methylhexanamido]acetic acid;

methyl 2[(3S)-3-{[5-(2,6-dimethoxyphenyl)-1-(2methylpropyl)-1H-pyrazol-3-yl]formamido}-5-methylhexanamido]acetate;

(3S)-N-benzyl-3-({5-[2-(benzyloxy)-6-methoxyphenyl]-1-cyclohexyl-1H-pyrazol-3-yl}formamido)-5-methylhexanamide;

(3S)-3-({5-[2(benzyloxy)-6-methoxyphenyl]-1-cyclohexyl-1H-pyrazol-3-yl}formamido)-N-butyl-5-methylhexanamide;

(3S)-3-({5-[2(benzyloxy)-6-methoxyphenyl]-1-cyclohexyl-1H-pyrazol-3-yl}formamido)-5-methyl-N-(1,3-oxazol-2ylmethyl)hexanamide;

(3S)-3-({5-[2(benzyloxy)-6-methoxyphenyl]-1-cyclohexyl-1H-pyrazol-3-yl}formamido)-N-[(dimethylcarbamoyl)methyl]-5-methylhexanamide;

methyl 2-[(3S)-3-{[5-(2,6-dimethoxyphenyl)-1-(4-fluorophenyl)-1H-pyrazol-3-yl]formamido}-5-methylhexanamido]acetate;

ethyl 3-[(3S)-3-({5-[2(benzyloxy)-6-methoxyphenyl]-1-cyclohexyl-1H-pyrazol-3-yl}formamido)-5-methylhexanamido]propanoate;

(3S)-3-{[5-(2,6-dimethoxyphenyl)-1-(2methylpropyl)-1H-pyrazol-3-yl]formamido}-5-methyl-N-(1,3-oxazol-2ylmethyl)hexanamide;

(3S)-3-{[5-(2,6-dimethoxyphenyl)-1-(2methylpropyl)-1H-pyrazol-3-yl]formamido}-N,5-dimethylhexanamide;

(3S)-3-{[5-(2,6-dimethoxyphenyl)-1-(2methylpropyl)-1H-pyrazol-3-yl]formamido}-N-(2-hydroxyethyl)-5-methylhexanamide;

(3S)-N-butyl-3-{[5-(2,6-dimethoxyphenyl)-1-(2methylpropyl)-1H-pyrazol-3-yl]formamido}-5-methylhexanamide;

(3R)-N-butyl-3-{[5-(2,6-dimethoxyphenyl)-1-(2methylpropyl)-1H-pyrazol-3-yl]formamido}-5-methylhexanamide;

(3S)-3-{[5-(2,6-dimethoxyphenyl)-1-(2methylpropyl)-1H-pyrazol-3-yl]formamido}-N-hexyl-5-methylhexanamide;

(3S)-N-(cyclohexylmethyl)-3-{[5-(2,6-dimethoxyphenyl)-1-(2methylpropyl)-1H-pyrazol-3-yl]formamido}-5-methylhexanamide;

(3S)-3-{[5-(2,6-dimethoxyphenyl)-1-(2methylpropyl)-1H-pyrazol-3-yl]formamido}-5-methyl-N-pentylhexanamide;

(3S)-3-{[5-(2,6-dimethoxyphenyl)-1-(2methylpropyl)-1H-pyrazol-3-yl]formamido}-5-methyl-N-propylhexanamide;

(3S)-3-{[5-(2,6-dimethoxyphenyl)-1-(2methylpropyl)-1H-pyrazol-3-yl]formamido}-N-ethyl-5-methylhexanamide;

(3S)-3-{[5-(2,6-dimethoxyphenyl)-1-(2methylpropyl)-1H-pyrazol-3-yl]formamido}-5-methyl-N-(propan-2yl)hexanamide;

(3S)-3-{[5-(2,6-dimethoxyphenyl)-1-(2methylpropyl)-1H-pyrazol-3-yl]formamido}-N-(4-fluorophenyl)-5-methylhexanamide;

methyl (3S)-3-{[5-(2,6-dimethoxyphenyl)-1-(2methylpropyl)-1H-pyrazol-3-yl]formamido}-5-methylhexanoate;

(3S)-3-{[5-(3,5-difluoro-2,6-dimethoxyphenyl)-1-(2methylpropyl)-1H-pyrazol-3-yl]formamido}-5-methylhexanoic acid;

(3S)-N-butyl-3-{[5-(3,5-difluoro-2,6-dimethoxyphenyl)-1-(2methylpropyl)-1H-pyrazol-3-yl]formamido}-5-methylhexanamide;

(2S)-2cyclohexyl-2-{[5-(2,6-dimethoxyphenyl)-1-(2methylpropyl)-1H-pyrazol-3-yl]formamido}acetic acid;

(3S)-3-{[5-(2,6-dimethoxyphenyl)-1-(2methylpropyl)-1H-pyrazol-3-yl]formamido}-N,5-dimethyl-N-propylhexanamide;

(3S)-N-cyclopropyl-3-{[5-(2,6-dimethoxyphenyl)-1-(2methylpropyl)-1H-pyrazol-3-yl]formamido}-5-methylhexanamide;

(3S)-N-cyclobutyl-3-{[5-(2,6-dimethoxyphenyl)-1-(2methylpropyl)-1H-pyrazol-3-yl]formamido}-5-methylhexanamide;

2-[(3S)-3-{[5-(2,6-dimethoxyphenyl)-1-(2methylpropyl)-1H-pyrazol-3-yl]formamido}-5-methylhexanamido]acetic acid;

(3S)-N-(carbamoylmethyl)-3-{[5-(2,6-dimethoxyphenyl)-1-(2methylpropyl)-1H-pyrazol-3-yl]formamido}-5-methylhexanamide;

(3S)-3-{[5-(2,6-dimethoxyphenyl)-1-(2methylpropyl)-1H-pyrazol-3-yl]formamido}-5-methyl-N-[(methylcarbamoyl)methyl]hexanamide;

(3S)-3-{[1-(cyclopropylmethyl)-5-(2,6-dimethoxyphenyl)-1H-pyrazol-3-yl]formamido}-5-methylhexanoic acid;

(3S)-3-{[1-cyclopentyl-5-(2,6-dimethoxyphenyl)-1H-pyrazol-3-yl]formamido}-5-methylhexanoic acid;

methyl 2-[(3S)-3-{[1-(cyclopropylmethyl)-5-(2,6-dimethoxyphenyl)-1H-pyrazol-3-yl]formamido}-5-methylhexanamido]acetate;

methyl 2-[(3S)-3-{[1-cyclopentyl-5-(2,6-dimethoxyphenyl)-1H-pyrazol-3-yl]formamido}-5-methylhexanamido]acetate;

(3S)-N-cyclopentyl-3-{[5-(2,6-dimethoxyphenyl)-1-(2methylpropyl)-1H-pyrazol-3-yl]formamido}-5-methylhexanamide;

methyl 2-[(3S)-3-{[5-(2,6-dimethoxyphenyl)-1-propyl-1H-pyrazol-3-yl]formamido}-5-methylhexanamido]acetate;

methyl 2-[(3S)-3-{[5-(2,6-dimethoxyphenyl)-1-(2,2dimethylpropyl)-1H-pyrazol-3-yl]formamido}-5-methylhexanamido]acetate;

methyl 2-[(2S)-2-{[5-(2,6-dimethoxyphenyl)-1-(2methylpropyl)-1H-pyrazol-3-yl]formamido}-4-methylpentanamido]acetate;

methyl 2-[(2S)-2-{[1-cyclohexyl-5-(2,6-dimethoxyphenyl)-1H-pyrazol-3-yl]formamido}-4-methylpentanamido]acetate;

ethyl 3-[(2S)-2-{[5-(2,6-dimethoxyphenyl)-1-(2methylpropyl)-1H-pyrazol-3-yl]formamido}-4-methylpentanamido]propanoate;

methyl 2-[(2S)-3-cyclohexyl-2-{[5-(2,6-dimethoxyphenyl)-1-(2methylpropyl)-1H-pyrazol-3-yl]formamido}propanamido]acetate;

(2S)-3-cyclohexyl-2-{[5-(2,6-dimethoxyphenyl)-1-(2methylpropyl)-1H-pyrazol-3-yl]formamido}propanoic acid;

methyl 2-[(2S)-2-{[5-(2,6-dimethoxyphenyl)-1-(2methylpropyl)-1H-pyrazol-3-yl]formamido}-3-phenylpropanamido]acetate;

methyl 2-[(2S)-2-{[5-(2,6-dimethoxyphenyl)-1-(2methylpropyl)-1H-pyrazol-3-yl]formamido}hexanamido]acetate;

methyl 2-[(2S)-2-{[5-(2,6-dimethoxyphenyl)-1-(2methylpropyl)-1H-pyrazol-3-yl]formamido}-4-phenylbutanamido]acetate;
(3S)-5-cyclohexyl-3-{[5-(2,6-dimethoxyphenyl)-1-(2methylpropyl)-1H-pyrazol-3-yl]formamido}pentanoic acid;
methyl 2-[(3S)-5-cyclohexyl-3-{[5-(2,6-dimethoxyphenyl)-1-(2methylpropyl)-1H-pyrazol-3-yl]formamido}pentanamido]acetate;
methyl 2-[(2S)-3-cyclohexyl-2-{[5-(2,5-dimethoxyphenyl)-1-(2methylpropyl)-1H-pyrazol-3-yl]formamido}propanamido]acetate;
methyl 2-[(3S)-3-{[5-(2,6-dimethoxyphenyl)-1-(2methylpropyl)-1H-pyrazol-3-yl]formamido}-N,5-dimethylhexanamido]acetate;
methyl 2-[(2S)-2-{[5-(2,6-dimethoxyphenyl)-1-(2methylpropyl)-1H-pyrazol-3-yl]formamido}-N,4-dimethylpentanamido]acetate;
2-[(3S)-5-cyclohexyl-3-{[5-(2,6-dimethoxyphenyl)-1-(2methylpropyl)-1H-pyrazol-3-yl]formamido}pentanamido]acetic acid;
(2S)-2-{[5-(2,6-dimethoxyphenyl)-1-(2methylpropyl)-1H-pyrazol-3-yl]formamido}-4-phenyl-N-propylbutanamide;
5-(2,6-dimethoxyphenyl)-1-(2methylpropyl)-N-[(2S)-1-oxo-4-phenyl-1-(pyrrolidin-1-yl)butan-2yl]-1H-pyrazole-3-carboxamide;
methyl 2-[(2S)-2-{[5-(2,6-dimethoxyphenyl)-1-(2methylpropyl)-1H-pyrazol-3-yl]formamido}-N-methyl-4-phenylbutanamido]acetate;
(2S)-2-{[5-(2,6-dimethoxyphenyl)-1-(2methylpropyl)-1H-pyrazol-3-yl]formamido}-N-(2-methoxyethyl)-4-phenylbutanamide;
(3S)-N-cyclobutyl-5-cyclohexyl-3-{[5-(2,6-dimethoxyphenyl)-1-(2methylpropyl)-1H-pyrazol-3-yl]formamido}pentanamide;
(3S)-5-cyclohexyl-3-{[5-(2,6-dimethoxyphenyl)-1-(2methylpropyl)-1H-pyrazol-3-yl]formamido}pentanamide;
(3S)-5-cyclohexyl-3-{[5-(2,6-dimethoxyphenyl)-1-(2methylpropyl)-1H-pyrazol-3-yl]formamido}-N-(2hydroxybutyl)pentanamide;
(2S)-2-{[5-(2,6-dimethoxyphenyl)-1-(2methylpropyl)-1H-pyrazol-3-yl]formamido}-N-(2-hydroxybutyl)-4-phenylbutanamide;
(2S)-2-{[5-(2,6-dimethoxyphenyl)-1-(2methylpropyl)-1H-pyrazol-3-yl]formamido}-N-(2-oxobutyl)-4-phenylbutanamide;
(3S)-5-cyclohexyl-3-{[5-(2,6-dimethoxyphenyl)-1-(2methylpropyl)-1H-pyrazol-3-yl]formamido}-N-(2oxobutyl)pentanamide;
methyl 2-[(3S)-3-{1-[5-(2,6-dimethoxyphenyl)-1-(2methylpropyl)-1H-pyrazol-3-yl]-N-methylformamido}-5-methylhexanamido]acetate;
(3S)-5-cyclohexyl-3-{[5-(2,6-dimethoxyphenyl)-1-(2methylpropyl)-1H-pyrazol-3-yl]formamido}-N-(2methoxyethyl)pentanamide;
methyl 2-[(3S)-5-cyclohexyl-3-{[5-(2,6-dimethoxyphenyl)-1-(2methylpropyl)-1H-pyrazol-3-yl]formamido}-N-methylpentanamido]acetate;
(2S)-N-cyclobutyl-2-{[5-(2,6-dimethoxyphenyl)-1-(2methylpropyl)-1H-pyrazol-3-yl]formamido}-4-phenylbutanamide;
methyl 2-[(3S)-6-cyclohexyl-3-{[5-(2,6-dimethoxyphenyl)-1-(2methylpropyl)-1H-pyrazol-3-yl]formamido}hexanamido]acetate;
(3S)-3-{[5-(2,6-dimethoxyphenyl)-1-(2methylpropyl)-1H-pyrazol-3-yl]formamido}-N-(2-hydroxybutyl)-5-(piperidin-1-yl)pentanamide;
(3S)-N-cyclobutyl-3-{[5-(2,6-dimethoxyphenyl)-1-(2methylpropyl)-1H-pyrazol-3-yl]formamido}-5-(piperidin-1yl)pentanamide;
(3S)-3-{[5-(2,6-dimethoxyphenyl)-1-(2methylpropyl)-1H-pyrazol-3-yl]formamido}-N-(2-methoxyethyl)-5-(piperidin-1-yl)pentanamide;
(3S)-3-{[5-(2,6-dimethoxyphenyl)-1-(2methylpropyl)-1H-pyrazol-3-yl]formamido}-5-(piperidin-1-yl)pentanoic acid;
(3S)-3-{[1-cyclopentyl-5-(2,6-dimethoxyphenyl)-1H-pyrazol-3-yl]formamido}-5-(piperidin-1yl)pentanoic acid;
(3S)-N-cyclobutyl-3-{[1-cyclopentyl-5-(2,6-dimethoxyphenyl)-1H-pyrazol-3-yl]formamido}-5-(piperidin-1yl)pentanamide;
(2S)-4-cyclohexyl-2-{[5-(2,6-dimethoxyphenyl)-1-(2methylpropyl)-1H-pyrazol-3-yl]formamido}-N-(2methoxyethyl)-N-methylbutanamide;
(3R)-3-cyclohexyl-3-{[5-(2,6-dimethoxyphenyl)-1-(4-fluorophenyl)-1H-pyrazol-3-yl]formamido}propanoic acid;
methyl 2(3-cyclohexyl-3-{[5-(2,6-dimethoxyphenyl)-1-(4-fluorophenyl)-1H-pyrazol-3-yl]formamido}propanamido)acetate;
(3S)-5-cyclohexyl-3-{[5-(2,6-dimethoxyphenyl)-1-(2methylpropyl)-1H-pyrazol-3-yl]formamido}-N-[(2R)-2hydroxybutyl]pentanamide;
(3R)-N-cyclobutyl-3-{[1-cyclopentyl-5-(2,6-dimethoxyphenyl)-1H-pyrazol-3-yl]formamido}pent-4-enamide; or
N-[2S)-4-cyclohexyl-1-(1H-1,2,3,4-tetrazol-5-yl)butan-2yl]-5-(2,6-dimethoxyphenyl)-1-(2methylpropyl)-1H-pyrazole-3-carboxamide, or a pharmaceutically acceptable salt, prodrug, or salt of a prodrug thereof.

12. A pharmaceutical composition comprising at least one pharmaceutically acceptable excipient and a therapeutically effective amount of the compound of claim 1.

13. The pharmaceutical composition of claim 12, wherein the therapeutically effective amount is an amount effective for lowering blood pressure.

14. The pharmaceutical composition of claim 12, wherein the therapeutically effective amount is an amount effective for the treatment of asthma, cardiomyopathy, diabetes, dyslipidemia, hypertension, inflammation, liver disease, metabolic disorder, neurodegenerative disease, obesity, preeclampsia, or renal dysfunction.

15. The pharmaceutical composition of claim 14, wherein the hypertension is pulmonary arterial hypertension.

16. The pharmaceutical composition of claim 14, wherein the liver disease is alcoholic liver disease, toxicant-induced liver disease, or viral-induced liver disease.

17. The pharmaceutical composition of claim 14, wherein the renal dysfunction is polycystic kidney disease.

18. The pharmaceutical composition of claim 12, wherein the therapeutically effective amount is an amount effective to treat a vein-related disorder.

19. The pharmaceutical composition of claim 18, wherein the therapeutically effective amount is an amount effective to treat an angioma, a venous insufficiency, a stasis or a thrombosis.

20. The pharmaceutical composition of claim 12, wherein the therapeutically effective amount is an amount effective to reduce the likelihood of HIV-related neurodegeneration.

21. A pharmaceutical composition comprising at least one pharmaceutically acceptable excipient and a therapeutically effective amount of a compound of claim 11.

22. The pharmaceutical composition of claim 21, wherein the therapeutically effective amount is an amount effective for lowering blood pressure.

23. The pharmaceutical composition of claim 21, wherein the therapeutically effective amount is an amount effective for the treatment of asthma, cardiomyopathy, diabetes, dyslipidemia, hypertension, inflammation, liver disease, metabolic disorder, neurodegenerative disease, obesity, preeclampsia, or renal dysfunction.

24. The pharmaceutical composition of claim 23, wherein the hypertension is pulmonary arterial hypertension.

25. The pharmaceutical composition of claim 23, wherein the liver disease is alcoholic liver disease, toxicant-induced liver disease, or viral-induced liver disease.

26. The pharmaceutical composition of claim 23, wherein the renal dysfunction is polycystic kidney disease.

27. The pharmaceutical composition of claim 23, wherein the therapeutically effective amount is an amount effective to treat a vein-related disorder.

28. The pharmaceutical composition of claim 27, wherein the vein-related disorder is an angioma, a venous insufficiency, a stasis or a thrombosis.

29. The pharmaceutical composition of claim 23, wherein the therapeutically effective amount is an amount effective to reduce the likelihood of HIV-related neurodegeneration.

\* \* \* \* \*